(12) United States Patent
Bembenek et al.

(10) Patent No.: US 7,935,725 B2
(45) Date of Patent: May 3, 2011

(54) ARYL-SUBSTITUTED BRIDGED OR FUSED DIAMINES AS MODULATORS OF LEUKOTRIENE A₄ HYDROLASE

(75) Inventors: Scott D. Bembenek, San Diego, CA (US); Wendy Eccles, San Diego, CA (US); Laurent Gomez, San Diego, CA (US); Cheryl A. Grice, Carlsbad, CA (US); Aaron M. Kearney, Lakeside, CA (US); Adrienne M. Landry-Bayle, Carlsbad, CA (US); Taraneh Mirzadegan, San Diego, CA (US); Alejandro Santillán, Jr., San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 31 days.

(21) Appl. No.: 12/291,018

(22) Filed: Oct. 30, 2008

(65) Prior Publication Data

US 2009/0111794 A1    Apr. 30, 2009

Related U.S. Application Data

(60) Provisional application No. 60/984,126, filed on Oct. 31, 2007.

(51) Int. Cl.
*A61K 31/38* (2006.01)
(52) U.S. Cl. ........ 514/443; 544/111; 546/113; 546/122; 546/268.1; 548/159; 548/247; 548/335.1; 548/453; 548/950; 549/59; 549/356; 549/429; 549/505
(58) Field of Classification Search .............. 514/443; 544/111; 546/113, 122, 268.1; 548/159, 548/247, 335.1, 453, 450; 549/59, 356, 429, 549/505
See application file for complete search history.

(56) References Cited

U.S. PATENT DOCUMENTS

| | | | |
|---|---|---|---|
| 5,585,492 | A | 12/1996 | Chandrakumar et al. |
| 5,700,816 | A | 12/1997 | Isakson et al. |
| 5,719,306 | A | 2/1998 | Chandrakumar et al. |
| 5,723,492 | A | 3/1998 | Chandrakumar et al. |
| 6,407,140 | B1 | 6/2002 | Gregory et al. |
| 6,506,876 | B1 | 1/2003 | Chandrakumar et al. |
| 6,559,140 | B2 | 5/2003 | Bennani et al. |
| 2003/0004191 | A1 | 1/2003 | Gregory et al. |
| 2005/0043355 | A1 | 2/2005 | Gregory et al. |
| 2005/0043378 | A1 | 2/2005 | Bembenek et al. |
| 2005/0043379 | A1 | 2/2005 | Bembenek et al. |
| 2006/0074121 | A1 | 4/2006 | Chen et al. |
| 2007/0079078 | A1 | 4/2007 | Fujita et al. |
| 2007/0155726 | A1* | 7/2007 | Arnaiz et al. .............. 514/218 |

FOREIGN PATENT DOCUMENTS

| | | |
|---|---|---|
| EP | 0266576 | 5/1988 |
| WO | WO 01/81347 | 1/2001 |
| WO | WO 2004/103959 | 12/2004 |
| WO | WO 2006/004475 | 1/2006 |
| WO | WO 2007/007069 | 1/2007 |
| WO | WO 2007/079078 | 7/2007 |

OTHER PUBLICATIONS

Wang, S. et al. A Novel Hepatointestinal Leukotriene B4 Receptor. Cloning and Functional Characterization. J. Biol. Chem. 2000, 275(52), 40686-40694.
Weiner, H.L., et al. Inflammation and Therapeutic Vaccination in CNS Diseases. Nature (London) 2002, 420(6917), 879-884.
Willemsen M.A. et al. Clinical and biochemical effects of zileuton in patients with the Sjogren-Larsson syndrome. Eur J Pediatr. 2001,160, 711-717.
Woodmansee D.P. et al. Simon RA. A pilot study examining the role of zileuton in atopic dermatitis. Ann Allergy Asthma Immunol. 1999, 83, 548-552.
Yokomizo, T. et al. Leukotriene A4 Hydrolase and Leukotriene B4 Metabolism. J. Lipid Mediat. Cell Signal. 1995, 12(2-3), 321-332.
Yokomizo, T. et al. A Second Leukotriene B4 Receptor, BLT2: A New Therapeutic Target in Inflammation and Immunological Disorders. J. Exp. Med. 2000, 192(3), 421-431.
Yokomizo, T. et al. Co-expression of two LTB4 Receptors in Human Mononuclear Cells. Life Sci. 2001, 68(19-20), 2207-2212.
Yokomizo, T. et al. Leukotriene B4: Metabolism and Signal Transduction. Arch. Biochem. Biophys. 2001, 385(2), 231-241.
Zhu, Y.I. et al. Preview of Potential Therapeutic Applications of Leukotriene B4 Inhibitors in Dermatology. Skin Pharmacol. Appl. Skin Physiol. 2000, 13(5), 235-245.
Zhu, L. et al. A convenient synthesis of 2-mercapto and 2-chlorobenzothiazoies, J. Heterocyclic Chem. 2005, 42, 727-730.
Zouboulis, Ch.C. et al. Zileuton, an Oral 5-Lipoxygenase Inhibitor, Directly Reduces Sebum Production. Dermatology 2005, 210(1), 36-38.
Zouboulis, Ch.C. et al. A new concept for acne therapy: a pilot study with zileuton, an oral 5-lipoxygenase inhibitor. Arch. Dermatol. 2003, 139(5), 668-670.
Cohen, J. The Immunopathogenesis of Sepsis. Nature (London) 2002, 420(6917), 885-891.
Coussens, L.M. et al. Inflammation and Cancer. Nature (London) 2002, 420(6917), 860-867.
Crooks, S.W. and R.A. Stockley. Leukotriene B₄. Int. J. Biochem. Cell Biol. 1998, 30(2), 173-178.
Cunha, J.M. et al. The critical role of leukotriene B4 in antigen-induced mechanical hyperalgesia in immunised rats. Br. J. Pharmacol. 2003, 139(6), 1135-1145.
Ellis, C.N. et al. Cost of atopic dermatitis and eczema in the United States. J. Am. Acad. Dermatol. 2002, 46, 361-370.
Emingil, G. et al. Levels of leukotriene B4 in gingival crevicular fluid and gingival tissue in specific periodontal diseases. J. Periodontol. 2001, 72(8), 1025-1031.

(Continued)

Primary Examiner — James O Wilson
Assistant Examiner — Douglas M Willis

(57) ABSTRACT

Aryl-substituted bridged or fused diamine compounds, pharmaceutical compositions containing them, and methods of using the compounds and the pharmaceutical compositions for leukotriene A₄ hydrolase (LTA₄H or LTA4H) modulation and for the treatment of disease states, disorders, and conditions mediated by LTA₄H activity, such as allergy, asthma, autoimmune diseases, pruritis, inflammatory bowel disease, ulcerative colitis, and cardiovascular disease, including atherosclerosis and prevention of myocardial infarction.

16 Claims, 1 Drawing Sheet

OTHER PUBLICATIONS

Fitzpatrick, F.A. et al. Effects of Leukotriene $A_4$ on Neutrophil Activation. Ann. N. Y. Acad. Sci. 1994, 714, 64-74.

Ford-Hutchinson, A.W. et al. 5-Lipoxygenase. Ann. Rev. Biochem. 1994, 63, 383-417.

Fleisher, D. et al. Improved oral drug delivery: solubility limitations overcome by the use of prodrugs. Advanced Drug Delivery Reviews, 1996, 19, 115-130.

Friedrich E.B. et al. Mechanisms of leukotriene $B_4$-triggered monocyte adhesion. Arterioscler Thromb Vasc Biol 2003, 23, 1761-1767.

Funk et al. Molecular Cloning and Amino Acid Sequence of Leukotriene A4 Hydrolase. PNAS 1987, 84, 6677-6681.

Gelfand, E.W. et al. CD8+ T lymphocytes and leukotriene B4: novel interactions in the persistence and progression of asthma. J. Allergy Clin. Immunol. 2006, 117(3), 577-582.

Gierse et al. High level Experssion and Purification of Human Leukotriene A4 Hydrolase from Insect Cells Infected with a Baculovirus Vector. Protein Expression and Purification, 1993, 4, 358-366.

Gompertz, S. et al. Changes in bronchial inflammation during acute exacerbations of chronic bronchitis. Eur. Respir. J. 2001, 17(6), 1112-1119.

Goodarzi, K. et al. Leukotriene B4 and BLT1 Control Cytotoxic Effector T Cell Recruitment to Inflamed Tissues. Nat. Immunol. 2003) 4(10), 965-973.

Griffiths, R.J. et al. Leukotriene $B_4$ Plays a Critical Role in the Progression of Collagen-Induced Arthritis. PNAS 1995, 92(2), 517-521.

Hakonarson, H. et al. Effects of a 5-lipoxygenase-activating protein inhibitor on biomarkers associated with risk of myocardial infarction. A randomized trial. JAMA 2005, 293(18), 2245-2256.

Hanifin, J.M. et al. Guidelines of care for atopic dermatitis, developed in accordance with the American Academy of Dermatology (AAD)/ American Academy of Dermatology Association Administrative Regulations for Evidence-Based Clinical Practice Guidelines. J. Am. Acad. Dermatol. 2004, 50, 391-404.

Helgadottir, A. et al. The Gene Encoding 5-Lipoxygenase Activating Protein Confers Risk of Myocardial Infarction and Stroke. Nat. Genet. 2004, 36(3), 233-239.

Helgadottir A. et al. A variant of the gene encoding leukotriene A4 hydrolase confers ethnicity-specific risk of myocardial infarction. Nat Genet. 2006, 38, 68-74.

Huang L, et al. Molecular and Biological Characterization of the Murine Leukotriene B4 Receptor Expressed on Eosinophils. J. Exp. Med. 1998, 188(6), 1063-1074.

Hwang, S.W. et al. Direct activation of capsaicin receptors by products of lipoxygenases: endogenous capsaicin-like substances. Proc. Natl. Acad. Sci. USA 2000, 97(11), 6155-6160.

Ikai, K. Psoriasis and the Arachidonic Acid Cascade, Jour. Of Derm. Sci., 1999, 21, 135-146.

Jala, V.R. et al. Leukotrienes and Atherosclerosis: New Role for Old Mediators. Trends Immunol. 2004, 25(6), 315-322.

Kachur, J.F. et al. Pharmacological Characterization of SC-57461A (3-[Methyl[3-[4-(phenylmethyl)phenoxy]propyl]amino]propanoic acid HCl), a Potent and Selective Inhibitor of Leukotriene $A_4$ Hydrolase II: In Vivo Studies. J. Pharmacol. Exp. Ther. 2002, 300(2), 583-587.

Klein, A. et al. Stem Cell Factor Plays a Major Role in the Recruitment of Eosinophils in Allergic Pleurisy in Mice via the Production of Leukotriene $B_4$. J. Immunol. 2000, 164(8), 4271-4276.

Laughter, D. et al. The prevalence of atopic dermatitis in Oregon schoolchildren. J. Am. Acad. Dermatol. 2000, 43, 649-655.

Liao, T. et al. Blockade of the interaction of leukotriene B4 with its receptor prevents development of autoimmune uveitis. Invest. Ophthalmol. Vis. Sci. 2006, 47(4), 1543-1549.

Libby, P. Inflammation in Atherosclerosis. Nature (London) 2002, 420(6917), 868-874.

Miyahara N. et al. Role of the LTB4/BLT1 pathway in allergen-induced airway hyperresponsiveness and inflammation. Allergy Intl. 2006, 55(2), 91-97.

Munafo, D.A. et al. Leukotriene A4 Hydrolase in Human Bronchoalveolar Lavage Fluid. J. Clin. Invest. 1994, 93(3), 1042-1050.

Nakae, H. et al. Relationship between cytokines and leukotriene B4 in sepsis. Res. Commun. Chem. Pathol. Pharmacol. 1994, 83(2), 151-156.

Nathan, C. Points of Control in Inflammation. Nature (London) 2002, 420(6917), 846-852.

Alestas, T. et al. Enzymes involved in the biosynthesis of leukotriene B4 and prostaglandin E2 are active in sebaceous glands. J. Mol. Med. 2006, 84(1), 75-87.

Andoh, T. et al. Intradermal leukotriene B4, but not prostaglandin E2, induces itch-associated responses in mice. Eur. J. Pharmacol. 1998, 353(1), 93-96.

Andoh, T. et al. Involvement of blockade of leukotriene B4 action in anti-pruritic effects of emedastine in mice. Eur. J. Pharmacol. 2000, 406(1), 149-152.

Andoh, T. et al. Involvement of leukotriene B4 in substance P-induced itch-associated response in mice. J. Investigativ. Dermatol. 2001, 117(6), 1621-1626.

Andoh, T. et al. Intradermal nociceptin elicits itch-associated responses through leukotriene B4 in mice. J. Investigativ. Dermatol. 2004, 123(1), 196-201.

Andoh, T. et al. Suppression by bepotastine besilate of substance P-induced itch-associated responses through the inhibition of the leukotriene B4 action in mice. Eur. J. Pharmacol. 2006, 547(1-3), 59-64.

Barnes, P.J. Future Advances in COPD Therapy. Respiration 2001, 68(5), 441-448.

Bagshawe et al. Antibody-Directed Enzyme Prodrug Therapy: A Review Drug Dev. Res. 1995, 34, 220-230.

Barone, F.C. et al. Time-related changes in myeloperoxidase activity and leukotriene B4 receptor binding reflect leukocyte influx in cerebral focal stroke. Mol. Chem. Neuropathol. 1995, 24(1), 13-30.

Benoist, C. and D. Mathis. Mast Cells in Autoimmune Disease. Nature 2002, 420(6917), 875-878.

Berge et al. Pharmaceutical Salts Journal of Pharmaceutical Sciences 1977, 66(1), 1-19.

Bertolini et al. A New Rational Hypothesis for the Pharmacophore of the Active Metabolite of Leflunomide, A Potent Immunosuppressive Drug. J Med Chem 1997, 40, 2011-2016.

Bodor et al. Novel Approaches to the Design of Safer Drugs: Soft Drugs and Site-Specific Chemical Delivery Systems Advances in Drug Research 1984, 13, 224-331.

Byrum, R.S. et al. Determination of the Contribution of Cysteinyl Leukotrienes and Leukotriene $B_4$ in Acute Inflammatory Responses Using 5-Lipoxygenase- and Leukotriene $A_4$ Hydrolase-Deficient Mice. J. Immunol. 1999, 163(12), 6810-6819.

Camp, R.D.R. et al. Responses of Human Skin to Intradermal Injection of Leukotrienes $C_4$, $D_4$ and $B_4$. Br. J. Pharmacol. 1983, 80(3), 497-502.

Camp, R. et al. Production of Intraepidermal Microabscesses by Topical Application of Leukotriene $B_4$. J. Invest. Dermatol. 1984, 82(2), 202-204.

Carpagnano, G.E. et al. Increased leukotrien B4 and interleukin-6 in exhaled breath condensate in cystic fibrosis. Am. J. Respir. Crit. Care Med. 2003, 167(8), 1109-1112.

Chen, X. et al. Leukotriene A4 hydrolase in rat and human esophageal adenocarcinomas and inhibitory effects of bestatin. J. Natl. Cancer Inst. 2003, 95(14), 1053-1061.

Chen, X. et al. Leukotriene A4 hydrolase as a target for cancer prevention and therapy. Curr. Cancer Drug Targets 2004, 4(3), 267-283.

Cohen, J. The Immunopathogenesis of Sepsis. Nature (London) 2002, 420(6917), 885-891.

Coussens, L.M. and Werb, Z. Inflammation and Cancer. Nature (London) 2002, 420(6917), 860-867.

International Search Report dated Jan. 13, 2009 for International Appln. No. PCT/US08/12339.

Ott, V.L. et al. Cell-Dependent Migration of Effector CD8+ T Cells Through Production of Leukotriene B4. Nat. Immunol. 2003, 4(10), 974-981.

Penning, T.D. Inhibitor of Leukotriene A4 (LTA4) Hydrolase as Potential Anti-Inflammatory Agents. Curr. Pharm. Des. 2001, 7(3), 163-179.

Reid, G.K. et al. Correlation Between Expression of 5-Lipoxygenase-Activating Protein, 5-Lipoxygenase, and Cellular Leukotriene Synthesis. J. Biol. Chem. 1990, 265(32), 19818-19823.

Robinson, R. et al. Discovery of the Hemifumarate and (α-L-Alanyloxy) methyl Ether as Prodrugs of an Antirheumatic Oxindole: Prodrugs for the Enolic OH Group. J. Med. Chem. 1996, 39, 10-18.

Samuelsson, B. et al. Leukotrienes: Mediators of Immediate Hypersensitivity Reactions and Inflammation. Science (Washington, D.C.) 1983, 220 (4597), 568-575.

Samuelsson, B et al. Enzymes Involved in the Biosynthesis of Leukotriene B4. J. Biol. Chem. 1989, 264(33), 19469-19472.

Shan et al. Prodrug strategies based on intramolecular cyclization reactions. Journal of Pharmaceutical Sciences 1997, 86(7), 765-767.

Sharon, P. et al. Enhanced Synthesis of Leukotriene B4 by Colonic Mucosa in Inflammatory Bowel Disease. Gastroenterology 1984, 86(3), 453-460.

Sidbury, R. et al. Old, new, and emerging therapies for atopic dermatitis. Dermatol. Clin. 2000, 18(1), 1-11.

Steinberg, D. Atherogenesis in Perspective: Hypercholesterolemia and Inflammation as Partners in Crime. Nat. Med. 2002, 8(11), 1211-1217.

Su, J.C. et al. Atopic eczema: its impact on the family and financial cost. Arch. Dis. Child 1997, 76, 159-162.

Subbarao, K. et al. Role of Leukotriene B4 Receptors in the Development of Atherosclerosis: Potential Mechanisms. Arterioscler. Thromb. Vasc. Biol. 2004, 24, 369-375.

Tager, A.M. et al. Leukotriene B4 Receptor BLT1 Mediates Early Effector T Cell Recruitment. Nat. Immunol. 2003, 4(10), 982-990.

Takakuwa, T. et al. Relationships between plasma levels of type-II phospholipase A2, PAF-acetylhydrolase, leukotriene B4, complements, endothelin-1 and thrombomodulin in patients with sepsis. Res. Commun. Chem. Pathol. Pharmacol. 1994, 84(3), 271-281.

Terawaki K. et al. Absence of leukotriene $B_4$ receptor 1 confers resistance to airway hyperresponsiveness and Th2-type immune responses. J Immunol. 2005, 17(7), 4217-4225.

Tracey, K.J. The Inflammatory Reflex. Nature (London) 2002, 420(6917), 853-859.

Tsuji F. et al. Involvement of Leukotriene B4 in Arthritis Models. Life Sci. 1998, 64(3), L51-L56.

* cited by examiner

ARYL-SUBSTITUTED BRIDGED OR FUSED DIAMINES AS MODULATORS OF LEUKOTRIENE A₄ HYDROLASE

This application claims the benefit of U.S. provisional patent application Ser. No. 60/984,126, filed Oct. 31, 2007, which is incorporated herein by reference.

FIELD OF THE INVENTION

The present invention relates to certain aryl-substituted bridged or fused diamine compounds, pharmaceutical compositions containing them, and methods of using the compounds and pharmaceutical compositions for leukotriene $A_4$ hydrolase ($LTA_4H$ or LTA4H) modulation and for the treatment of disease states, disorders, and conditions mediated by $LTA_4H$.

BACKGROUND OF THE INVENTION

Inflammation is normally an acute response by the immune system to invasion by microbial pathogens, chemicals or physical injury. In some cases, however, the inflammatory response can progress to a chronic state, and be the cause of inflammatory disease. Therapeutic control of this chronic inflammation in diverse diseases is a major medical need.

Leukotrienes (LT) are biologically active metabolites of arachidonic acid (B. Samuelsson, Science 1983, 220(4597): 568-575) that have been implicated in inflammatory diseases, including asthma (D. A. Munafo et al., J. Clin. Invest. 1994, 93(3):1042-1050; N. Miyahara, et al., Allergol Int., 2006, 55(2): 91-7; E. W. Gelfand, et al., J. Allergy Clin. Immunol. 2006, 117(3): 577-82; K. Terawaki, et al., J. Immunol. 2005, 175(7): 4217-25), inflammatory bowel disease (IBD) (P. Sharon and W. F. Stenson, Gastroenterology 1984, 86(3): 453-460), chronic obstructive pulmonary disease (COPD) (P. J. Barnes, Respiration 2001, 68(5): 441-448), arthritis (R. J. Griffiths et al., Proc. Natl. Acad. Sci. U.S.A. 1995, 92(2): 517-521; F. Tsuji et al., Life Sci. 1998, 64(3): L51-L56), psoriasis (K. Ikai, J. Dermatol. Sci. 1999, 21(3): 135-146; Y. I. Zhu and M. J. Stiller, Skin Pharmacol. Appl. Skin Physiol. 2000, 13(5):235-245) and atherosclerosis (Friedrich, E. B. et al. *Arterioscler Thromb Vasc Biol* 23, 1761-7 (2003); Subbarao, K. et al. *Arterioscler Thromb Vasc Biol* 24, 369-75 (2004); Helgadottir, A. et al. *Nat Genet* 36, 233-9 (2004); Jala, V. R. et al *Trends in Immun.* 25, 315-322 (2004)). The synthesis of leukotrienes is initiated by the conversion of arachidonic acid to an unstable epoxide intermediate, leukotriene A4 (LTA4), by 5-lipoxygenase (5-LO) (A. W. Ford-Hutchinson et al., Annu. Rev. Biochem. 1994, 63: 383-347). This enzyme is expressed predominantly by cells of myeloid origin, particularly neutrophils, eosinophils, monocytes/macrophages and mast cells (G. K. Reid et al., J. Biol. Chem. 1990, 265(32): 19818-19823). LTA4 can either be conjugated with glutathione by leukotriene C4 (LTC4) synthase to produce the cysteinyl leukotriene, LTC4, or hydrolyzed to the diol, leukotriene B4 (LTB4) (B. Samuelsson, Science 1983, 220(4597): 568-575). LTC4 and its metabolites, LTD4 and LTE4, induce smooth muscle contraction, broncho-constriction and vascular permeability, while LTB4 is a potent chemo-attractant and activator of neutrophils.

The stereospecific hydrolysis of LTA4 to LTB4 is catalyzed by leukotriene A4 hydrolase ($LTA_4H$), a zinc-containing, cytosolic enzyme. This enzyme is ubiquitously expressed, with high levels in small intestinal epithelial cells, lung, and aorta (B. Samuelsson and C. D. Funk, J. Biol. Chem. 1989, 264(33): 19469-19472). Moderate expression of $LTA_4H$ is observed in leukocytes, particularly neutrophils (T. Yokomizo et al., J. Lipid Mediators Cell Signaling 1995, 12(2,3): 321-332).

Leukotriene B4 is a key pro-inflammatory mediator, able to recruit inflammatory cells, such as neutrophils and eosinophils, as well as activate neutrophils (F. A. Fitzpatrick et al., Ann. N. Y. Acad. Sci. 1994, 714: 64-74; S. W. Crooks and R. A. Stockley, Int. J. Biochem. Cell Biol. 1998, 30(2): 173-178; A. Klein et al., J. Immunol. 2000, 164: 4271-4276). LTB4 mediates its pro-inflammatory effects by binding to G protein-coupled receptors, leukotriene B4 receptor 1 (BLT1) and leukotriene B4 receptor 2 (BLT2) (T. Yokomizo et al., Arch. Biochem. Biophys. 2001, 385(2): 231-241). The receptor first identified, BLT1, binds LTB4 with high affinity, leading to intracellular signaling and chemotaxis. BLT1 is expressed mainly in peripheral leukocytes, particularly neutrophils, eosinophils, macrophages (Huang, W. W. et al. *J Exp Med* 188, 1063-74 (1998)) and monocytes (Yokomizo, T., Izumi, T. & Shimizu, T. *Life Sci* 68, 2207-12 (2001)). The murine receptor is also expressed on effector T cells and was recently shown to mediate LTB4-dependent migration of effector $CD8^+$ T cells (Goodarzi, K., Goodarzi, M., Tager, A. M., Luster, A. D. & von Andrian, U. H. *Nat Immunol* 4, 965-73 (2003); Ott, V. L., Cambier, J. C., Kappler, J., Marrack, P. & Swanson, B. J. *Nat Immunol* 4, 974-81 (2003)), early effector $CD4^+$ T helper type 1 ($T_H1$) and $T_H2$ chemotaxis and adhesion to endothelial cells, as well as early effector $CD4^+$ and $CD8^+$ T cell recruitment in an asthma animal model (Tager, A. M. et al., *Nat Immunol* 4, 982-90 (2003)). LTB4 receptor BLT2 (S. Wang et al., J. Biol. Chem. 2000, 275(52): 40686-40694; T. Yokomizo et al., J. Exp. Med. 2000, 192(3): 421-431) shares 42% amino acid homology with BLT1, but is more broadly expressed, including in peripheral tissues such as the spleen, ovary and liver, as well as in leukocytes. BLT2 binds LTB4 with lower affinity than BLT1 does, mediates chemotaxis at higher concentrations of LTB4, and differs from BLT1 in its affinity for certain antagonists. While LTB4 receptor antagonists may differ in their affinity for BLT1 versus BLT2, blocking the production of LTB4 using $LTA_4H$ inhibitors would be expected to inhibit the downstream events mediated through both BLT1 and BLT2.

Studies have shown that introduction of exogenous LTB4 into normal tissues can induce inflammatory symptoms (R. D. R. Camp et al., Br. J. Pharmacol. 1983, 80(3): 497-502; R. Camp et al., J. Invest. Dermatol. 1984, 82(2): 202-204). Elevated levels of LTB4 have been observed in a number of inflammatory diseases including IBD, COPD, psoriasis, rheumatoid arthritis (RA), cystic fibrosis and asthma (S. W. Crooks and R. A. Stockley, Int. J. Biochem. Cell Biol. 1998, 30(2): 173-178). Therefore, reduction of LTB4 production by an inhibitor of $LTA_4H$ activity would be predicted to have therapeutic potential in a wide range of diseases.

This idea is supported by a study of $LTA_4H$-deficient mice that, while otherwise healthy, exhibited markedly decreased neutrophil influx in arachidonic acid-induced ear inflammation and zymosan-induced peritonitis models (R. S. Byrum et al., J. Immunol. 1999, 163(12): 6810-6819). $LTA_4H$ inhibitors have been shown to be effective anti-inflammatory agents in pre-clinical studies. For example, oral administration of $LTA_4H$ inhibitor SC57461 caused inhibition of ionophore-induced LTB4 production in mouse blood ex vivo, and in rat peritoneum in vivo (J. K. Kachur et al., J. Pharm. Exp. Ther. 2002, 300(2), 583-587). Eight weeks of treatment with the same inhibitor compound significantly improved colitis symptoms in cotton top tamarins (T. D. Penning, Curr. Pharm. Des. 2001, 7(3): 163-179). The spontaneous colitis that develops in these animals is very similar to human IBD. The results therefore indicate that $LTA_4H$ inhibitors would have therapeutic utility in this and other human inflammatory diseases.

Events that elicit the inflammatory response include the formation of the pro-inflammatory mediator leukotriene B4. Hydrolase $LTA_4H$ catalyzes the formation of this mediator, and $LTA_4H$ inhibitors block the production of the pro-inflammatory mediator LTB4, thus, providing the ability to prevent and/or treat leukotriene-mediated conditions, such as inflammation. The inflammatory response is characterized by pain, increased temperature, redness, swelling, or reduced function, or by a combination of two or more of these symptoms. Regarding the onset and evolution of inflammation, inflammatory diseases or inflammation-mediated diseases or conditions include, but are not limited to, acute inflammation, allergic inflammation, and chronic inflammation.

Atopic dermatitis (AD) is a chronic inflammatory skin disease that usually occurs in individuals with a personal or family history of atopy. The major features are pruritus and chronic or relapsing eczematous lesions. Complications include bacterial, fungal and viral infections as well as ocular disease. Atopic dermatitis is the most common inflammatory skin disease in children and affects more than 15% of children in the US (Laughter, D., et al., J. Am. Acad. Dermatol. 2000, 43, 649-655). Atopic dermatitis may persist in 60% of adults who were affected as children (Sidbury, R., et al., Dermatol. Clin. 2000, 18(1), 1-11).

Atopic dermatitis has significant societal impact. The family stress related to caring for children with moderate to severe AD may be comparable to the stress seen in families of children with type I diabetes mellitus (Su, J. C., et al., Arch. Dis. Child 1997, 76, 159-162). In the US, the annual cost of medical services and prescription drugs for the treatment of AD/eczema is similar to those for emphysema, psoriasis and epilepsy (Ellis, C. N., et al., J. Am. Acad. Dermatol. 2002, 46, 361-370).

Topical corticosteroids and emollients are the standard of care in the treatment of AD. However, topical steroids are associated with cutaneous complications such as striae, atrophy and telangeictasia that limit the long-term use of these agents (Hanifin, J. M., et al., J. Am. Acad. Dermatol. 2004, 50, 391-404). Emollients have a steroid-sparing effect and are useful for both prevention and maintenance therapy. Crude coal tar and preparations containing coal tar derivatives have also been used for many years in the treatment of AD and have significant cosmetic disadvantages that influence compliance (Hanifin, et al., 2004). Topical doxepin may be a useful short-term adjunctive therapy for the relief of pruritus but sedation and contact dermatitis may complicate its use (Hanifin, et al., 2004).

The topical calcineurin inhibitors tacrolimus (Protopic®) and pimecrolimus (Elidel®) have been shown to reduce the extent, severity and symptoms of AD in adults and children and are approved for use as second-line therapy of AD. However, the recent addition of boxed warnings to the product labels regarding rare cases of malignancy reported in patients treated with topical calcineurin inhibitors limits long term use of these agents in the treatment of AD (Food and Drug Administration [FDA]/Center for Drug Evaluation and Research [CDER] resources page).

Antibiotics are used in the treatment of *Staphylococcus aureus* infections in patients with AD but have a minimal effect on the dermatitis (Hanifin, et al., 2004). Although sedating antihistamines may be useful if sleep disruption is present, oral antihistamines are generally not effective in treating AD-associated pruritus (Hanifin, et al., 2004). Ultraviolet (UV) phototherapy, including photochemotherapy with psoralen is well established in the treatment of AD but relapse upon cessation of therapy frequently occurs (Hanifin, et al., 2004).

Systemic immunomodulatory therapy with cyclosporine and corticosteroids is effective but can be associated with severe side effects and is generally reserved for patients with severe disease. Systemic corticosteroids are associated with growth retardation in children, avascular necrosis of bone, osteopenia, increased risk of infection, poor wound healing, cataracts, hyperglycemia and hypertension. Cyclosporine is nephrotoxic in a majority of patients and is associated with tremor, hirsutism, hypertension, hyperlipidemia and gum hyperplasia.

While AD that is mild to moderate in severity generally responds to topical therapy, correct use of these therapies and compliance remain a major issue in the clinic. An oral or topical agent lacking the risks associated with corticosteroids and the calcineurin inhibitors would be a welcome addition to the armamentarium of treatments for AD that is mild to moderate in severity. An effective oral or topical therapy with fewer side effects than systemic immunomodulatory therapies and potent topical corticosteroids would fill an unmet medical need in the treatment of AD.

$LTB_4$ is a potent pro-inflammatory lipid mediator derived from arachidonic acid via the 5-lipoxygenase (5-LO) pathway. $LTB_4$ is known to be a chemotactic factor and activator of leukocytes, particularly granulocytes and T-cells, and has been implicated in several allergic and inflammatory diseases.

$LTB_4$ plays a role in AD. $LTB_4$ levels are elevated in skin lesions and plasma in AD. Reported in vivo and in vitro studies have shown that leukotrienes, especially $LTB_4$, contribute to the inflammation of the skin in AD through their chemotactic effect on inflammatory cells. $LTB_4$ receptors are expressed on mast cells, T cells, eosinophils, dendritic cells and macrophages, all of which accumulate in AD lesions. $LTB_4$ itself is a pruritic agent, and has also been shown to mediate substance P- and nociceptin-induced pruritus, a key component of the itching in AD. $LTB_4$ also induces proliferation of keratinocytes, an effect which is further potentiated by substance P. Recent reports indicate a role for $LTB_4$ in development of a Th2 immune response and IgE production. The role of $LTB_4$ in AD is further supported by beneficial effects of the 5-lipoxygenase inhibitor, zileuton, in a small open-label trial in AD (Woodmansee, D. P., et al., Ann. Allergy Asthma Immunol. 1999, 83, 548-552) and in relieving the pruritus in Sjögren-Larsson syndrome patients who have elevated $LTB_4$ levels due to an impairment in its degradation (Willemsen, M. A., et al., Eur. J. Pediatr. 2001, 160, 711-717).

Embodiments of this invention have shown dose-dependent inhibition of dermal inflammation and pruritus in a number of preclinical models, as well as inhibition of Th2 responses and IgE production. Oral administration of embodiments of this invention inhibited arachidonic-acid-induced ear inflammation (neutrophil influx and edema) in mice. In a mouse model of cutaneous contact hypersensitivity (CHS), dosing of embodiments of this invention around sensitization decreased IgE production and skin edema upon antigen challenge, while dosing prior to challenge decreased pruritus. Oral dosing of embodiments of this invention was also efficacious in reducing pruritus in mice induced by compound 48/80, substance P or IgE-antigen interaction in the skin.

$LTA_4H$ inhibitors are hypothesized to specifically block the production of $LTB_4$ from $LTA_4$, without affecting the biosynthesis of lipoxins, which are also produced from $LTA_4$. Increasing or maintaining lipoxin $A_4$ ($LXA_4$) production may have beneficial therapeutic effects in dermal inflammation as it has been reported that topical application of a stable lipoxin analogue inhibits edema, granulocyte infiltration and epidermal hyperproliferation in murine skin inflammation models. 5-LO inhibitors block the pathway upstream of $LTA_4$. This would be expected to lead to a block in not only synthesis of $LTA_4$, $LTB_4$ and cysteinyl leukotrienes, but also $LXA_4$.

Embodiments of this invention have been studied in a number of in vivo skin (and peritoneal) inflammation models including arachidonic acid-induced ear inflammation, zymosan-induced peritonitis, fluorescein isothiocyanate (FITC)-induced cutaneous contact hypersensitivity (CHS), and cutaneous itch induced by substance P, compound 48/80 and IgE/antigen interaction. Pharmacology models were also performed with embodiments of this invention to assess their effects on the development of Th2 immune responses and allergic lung inflammation, including ovalbumin (OVA) sensitization model and OVA sensitization and airway challenge models. Additional pharmacological profiling demonstrated efficacy in models of acute and chronic TNBS-induced colitis and collagen-induced arthritis.

An allergy is an abnormal reaction to an allergen (an ordinarily harmless substance) that triggers an abnormal response in a sensitized individual. Allergic rhinitis is an inflammation of the mucus membranes of the nose that occurs in response to an airborne antigen (allergen). Allergic rhinitis, also called allergic rhinoconjunctivitis, is characterized by frequent or repetitive sneezing, runny or congested nose, and pruritus of the nose, eyes and throat. It may also be associated with other symptoms such as headache, impaired smell, postnasal drip, conjunctival symptoms (e.g., itchy watery eyes), sinusitis and other complicating respiratory symptoms. Depending upon the time of exposure, allergic rhinitis can be classified as perennial, seasonal or occupational.

Embodiments of this invention have shown dose-dependent inhibition of lung inflammation in a number of preclinical models, as well as inhibition of Th2 responses and IgE production. In addition, embodiments of this invention inhibit pruritus induced by allergen/IgE interaction.

Based upon the well-described leukotriene biosynthesis pathway (FIG. 1), $LTA_4H$ inhibitors are hypothesized to specifically block the production of $LTB_4$ from $LTA_4$, without affecting the biosynthesis of lipoxins, which are also produced from $LTA_4$. Lipoxins, such as $LXA_4$, have been the focus of intense study and are known to play a key role as natural anti-inflammatory agents and key mediators of the natural process of resolving an inflammatory response. Furthermore, production of endogenous $LXA_4$ has been described in a variety of inflammatory diseases and lower levels of $LXA_4$ have been found in patients with severe versus moderate asthma. These data are consistent with the proposition that $LXA_4$ plays an important role in resolution of acute inflammation. Unlike $LTA_4$ inhibitors, 5-LO inhibitors block this pathway upstream of $LTA_4$. This would lead to a block in not only synthesis of $LTA_4$, $LTB_4$ and cysteinyl leukotrienes, but also $LXA_4$. Furthermore, there is a possibility that $LTA_4H$ inhibitors result in a buildup of $LTA_4$, and pathway shunting to pro-inflammatory cysteinyl leukotrienes, although to date there is no known data to support this possibility. Embodiments of this invention have shown in a model of zymosan-induced peritonitis that inhibition of $LTB_4$ production leads to an increase in $LXA_4$ production.

Neutrophil infiltration is a prominent feature of severe asthma. Zileuton (Zyflo®) has been suggested to be efficacious is severe asthma patients, while CysLT antagonists (i.e., Montelukast/Singulair®) are not. Embodiments of this invention inhibit Th2 T cell responses and IgE production in animal models of asthma.

Embodiments of this invention inhibited sensitization to antigen and reduced inflammatory responses to airway allergen challenge in sensitized mice, leading to dose-dependent decreases in airway hyperreactivity, airway recruitment of inflammatory cells, and reductions in inteleukin (IL)-5, IL-13, and antigen-specific IgE production.

In trinitrobenzene sulfonic acid (TNBS)-induced colitis in rats, embodiments of this invention had significant inhibitory effects on colonic inflammation, including macroscopic colonic injury, inflammatory cell content, and levels of tumor necrosis factor alpha (TNF-α), $LTB_4$, and IL-6. $LTA_4H$ inhibition by embodiments of this invention also significantly attenuated the joint inflammation and swelling associated with the destruction of collagen in murine models of arthritis.

Embodiments of this invention are expected to find utility in treating skin burns, such as those due to sunburn or some other agent.

Embodiments of this invention are expected to find utility in treating also any one or a combination of atopic dermatitis, contact dermatitis, acne (T. Alestas, et al., *J. Mol. Med.* 2006, 84(1): 75-87; Ch. C. Zouboulis, et al., *Dermatology,* 2005, 210(1): 36-8; *Arch. Dermatol.* 2003, 139(5): 668-70), myocardial infarction (A. Helgadottir, et al., *Nat. Genet.* 2006, 38(1): 68-74; *Nat. Genet.* 2004, 36(3): 233-9; H. Hakonarson, et al., *JAMA* 2005, 293(18): 2245-56), stroke (A. Helgadottir, et al., *Nat. Genet.* 2004, 36(3): 233-9; F. C. Barone, et al., *Mol. Chem. Neuropathol.* 1995, 24(1): 13-30), pain (J. M. Cunha, et al., *Br. J. Pharmacol.* 2003, 139(6): 1135-45; S. W. Hwang, et al., *Proc. Natl. Acad. Sci. USA* 2000, 97(11): 6155-60), itch (T. Andoh, et al., *Eur. J. Pharmacol.* 2006, 547(1-3): 59-64, 2000, 406(1): 149-152, 1998, 353(1): 93-96); *J. Investigativ. Dermatol.* 2004, 123(1): 196-201, 2001, 117(6): 1621-26; gingivitis (G. Emingil, et al., *J. Periodontol.* 2001, 72(8): 1025-31), uveitis (T. Liao, et al., *Invest. Ophthalmol. Vis. Sci.* 2006, 47(4): 1543-9), bronchitis (S. Gompertz, et al., *Eur. Respir. J.* 2001, 17(6): 1112-9), allergic rhinitis, cystic fibrosis (G. E. Carpagnano, et al., *Am. J. Respir. Crit. Care Med.* 2003, 167(8): 1109-12), upper grastrointestinal cancer (X. Chen, et al., *Curr. Cancer Drug Targets* 2004, 4(3): 267-83; *J. natl. cancer inst.* 2003, 95(14): 1053-61), and sepsis (H. Nakae, et al., *Res. Commun. Chem. Pathol. Pharmacol.* 1994, 83(2): 151-6, 84(3): 271-81), and skin burns.

Examples of textbooks on the subject of inflammation include: 1) Gallin, J. I.; Snyderman, R., *Inflammation: Basic Principles and Clinical Correlates,* 3rd ed.; Lippincott Williams & Wilkins: Philadelphia, 1999; 2) Stvrtinova, V., et al., *Inflammation and Fever. Pathophysiology Principles of Diseases* (Textbook for Medical Students); Academic Press: New York, 1995; 3) Cecil; et al. *Textbook Of Medicine,* 18th ed.; W.B. Saunders Co., 1988; and 4) Stedman's Medical Dictionary.

Background and review material on inflammation and conditions related with inflammation can be found in articles such as the following: C. Nathan, Points of control in inflammation, *Nature* 2002, 420: 846-852; K. J. Tracey, The inflammatory reflex, *Nature* 2002, 420: 853-859; L. M. Coussens and Z. Werb, Inflammation and cancer, *Nature* 2002, 420: 860-867; P. Libby, Inflammation in atherosclerosis, *Nature* 2002, 420: 868-874; C. Benoist and D. Mathis, Mast cells in autoimmune disease, *Nature* 2002, 420: 875-878; H. L. Weiner and D. J. Selkoe, Inflammation and therapeutic vaccination in CNS diseases, *Nature* 2002, 420: 879-884; J. Cohen, The immunopathogenesis of sepsis, *Nature* 2002, 420: 885-891; D. Steinberg, Atherogenesis in perspective:

Hypercholesterolemia and inflammation as partners in crime, *Nature Medicine* 2002, 8(11): 1211-1217.

Inflammation is due to or associated with any one of a plurality of conditions, such as asthma, chronic obstructive pulmonary disease (COPD), atherosclerosis, rheumatoid arthritis, multiple sclerosis, inflammatory bowel diseases (including Crohn's disease and ulcerative colitis), psoriasis, atopic dermatitis, contact dermatitis, acne, myocardial infarction, stroke, pain, itch (pruritus), gingivitis, uveitis, bronchitis, allergic rhinitis, cystic fibrosis, upper gastrointestinal cancer, sepsis, and skin burns, which are each characterized by excessive or prolonged inflammation at some stage of the disease.

Aryl-substituted bridged or fused diamines are disclosed in U.S. Patent Appl. Publ. Nos. US2003/004191, US2005/043355, and US2006/074121 and in U.S. Pat. Nos. 6,559,140, 5,700,816, 5,585,492, 5,719,306, 6,506,876, 5,723,492, and 6,407,140. Benzothiazole and benzoxazole $LTA_4H$ modulators have been described in U.S. Patent Appl. Publ. Nos. US2005/0043378 and US2005/0043379. In addition, diamine derivatives are described as $LTA_4H$ inhibitors in U.S. Patent Appl. Publ. Nos. 2007/0155726 and 2007/079078. However, there remains a need for potent $LTA_4H$ modulators with desirable pharmaceutical properties. Certain aryl-substituted bridged or fused diamine derivatives have been found in the context of this invention to have $LTA_4H$-modulating activity.

SUMMARY OF THE INVENTION

In one aspect the invention relates to chemical entities selected from compounds of Formula (I), pharmaceutically acceptable salts of compounds of Formula (I), pharmaceutically acceptable prodrugs of compounds of Formula (I), and pharmaceutically active metabolites of compounds of Formula (I):

(I)

wherein $R^1$ is H; —$CH_2CO_2H$; —$(CH_2)_{1-3}CO_2C_{1-4}$alkyl; —$CH_2$-aryl substituted with $CO_2R^a$; —C(O)$C_{1-4}$alkyl; —C(O)C($R^a$)($R^b$)—OH; —C(O)C($R^a$)($R^b$)—F; —C(O)C($R^a$)($R^b$)—$CF_3$; —C(O)C($R^a$)($R^b$)—O$C_{1-4}$alkyl; —C(O)C($R^a$)($R^b$)—N($R^c$)$R^d$; —C(O)N($R^c$)($R^d$); —C(O)-cycloalkyl; —C(O)—(monocyclic heteroaryl) optionally substituted with methyl; —C(O)-(monocyclic heterocycloalkyl) optionally substituted with methyl or —$CO_2C_{1-4}$alkyl; —$SO_2C_{1-4}$alkyl; —$SO_2NH_2$; —$SO_2$-cycloalkyl; or —$SO_2$-(monocyclic heteroaryl) optionally substituted with methyl;

where $R^a$ and $R^b$ are each independently H or methyl; or $R^a$ and $R^b$ taken together with the carbon to which they are attached form a saturated monocyclic cycloalkyl or heterocycloalkyl, optionally substituted with one or two methyl groups;

$R^c$ is H; and $R^d$ is H, $C_{1-4}$alkyl, —$CO_2C_{1-4}$alkyl, —C(O)$CF_3$, or —$(CH_2)_{0-1}$-monocyclic heteroaryl optionally substituted with one or two methyl groups;

X is N or >CHN$R^e$—;

where $R^e$ is H or methyl;

Z is N or >CHN$R^f$—;

where $R^f$ is H or methyl; and at least one of X and Z is N;

m, n, p, and q are independently 0, 1, or 2 wherein the sum (m+n+p+q) may not exceed 6; and provided that when the sum of m, n, p, and q is 2, then Y is a bond, —$CH_2$—, or —$CH_2CH_2$—; and when the sum of m, n, p, and q is 4, 5 or 6, then Y is a bond;

Q is O or $CH_2$, and said Q is linked at the "a" or "b" position of the phenyl ring;

D is O or S;

$R^2$ is H, $CH_3$, $OCH_3$, halo, OH, $NH_2$, or CN;

$R^3$ is H or F; and

A is —$CH_2$—, —$CH_2CH_2$—, or —$OCH_2CH_2$—.

In certain embodiments, the compound of Formula (I) is a compound selected from those species described or exemplified in the detailed description below.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I). Pharmaceutical compositions according to the invention may further comprise a pharmaceutically acceptable excipient.

In another aspect, the chemical entities of the invention are useful as $LTA_4H$ modulators. Thus, the invention is directed to a method for modulating $LTA_4H$ activity, comprising exposing $LTA_4H$ to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit $LTA_4H$ activity.

In another aspect, the invention is directed to a method of treating a subject suffering from or diagnosed with a disease, disorder, or medical condition mediated by $LTA_4H$ activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND ITS PREFERRED EMBODIMENTS

Figure 1:
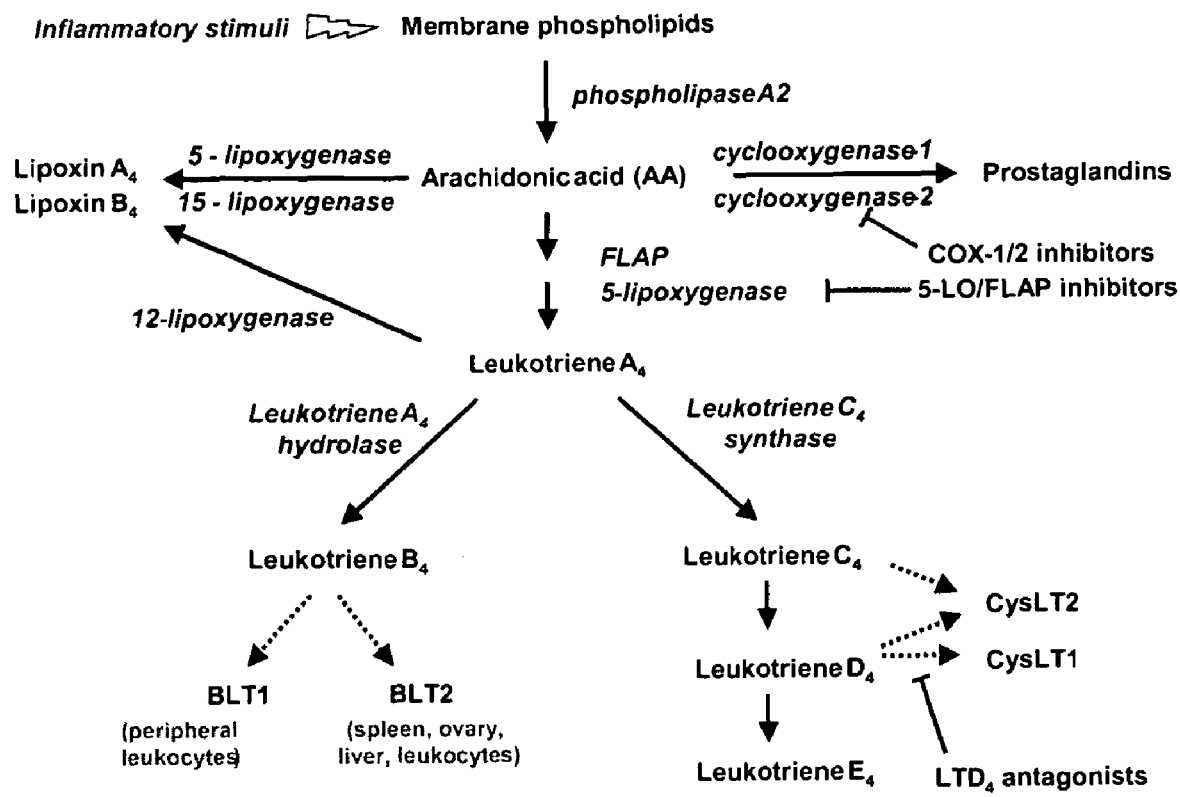
FIG. 1 depicts a schematic representation of some features of the leukotriene synthesis pathway.

For the sake of brevity, the disclosures of the publications, including patents and patent applications, cited anywhere in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a / symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

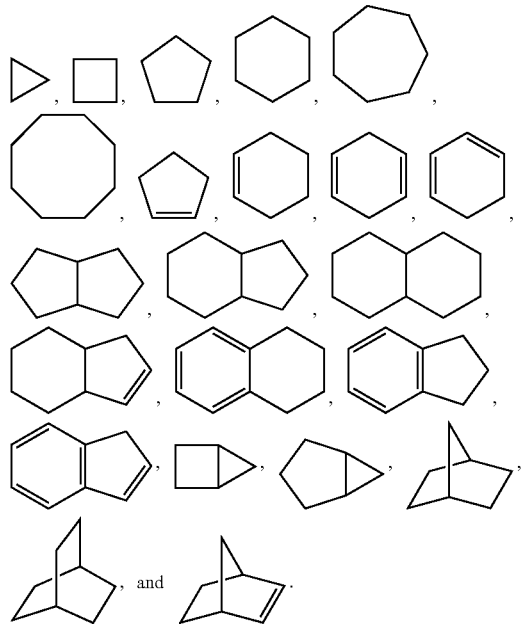

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

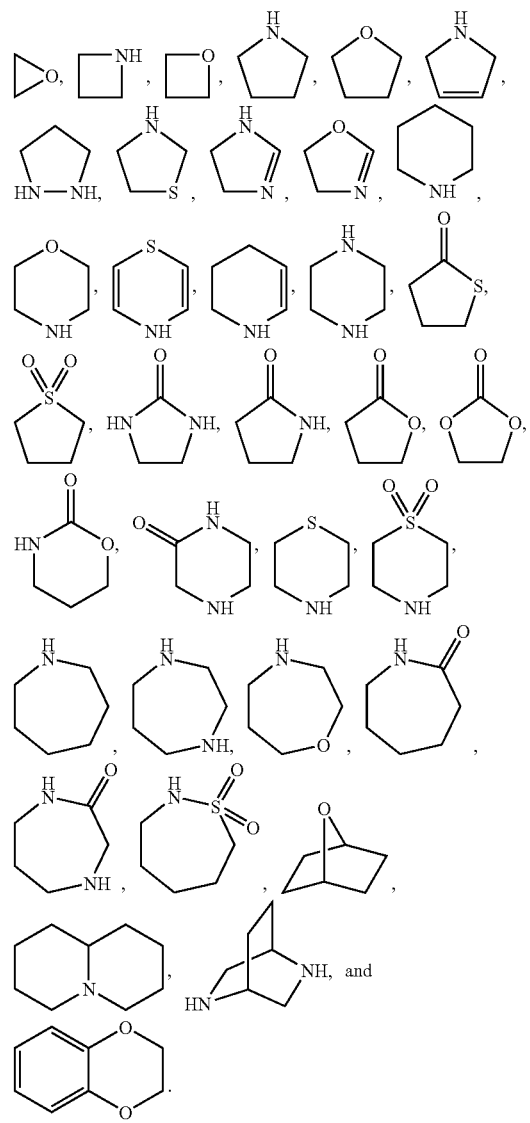

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

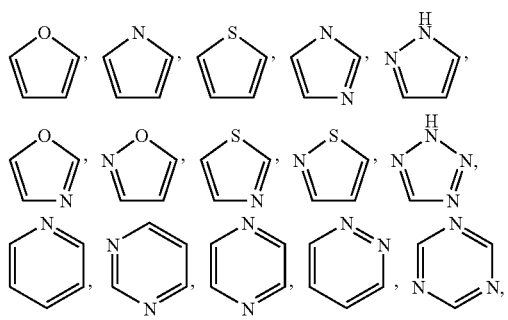

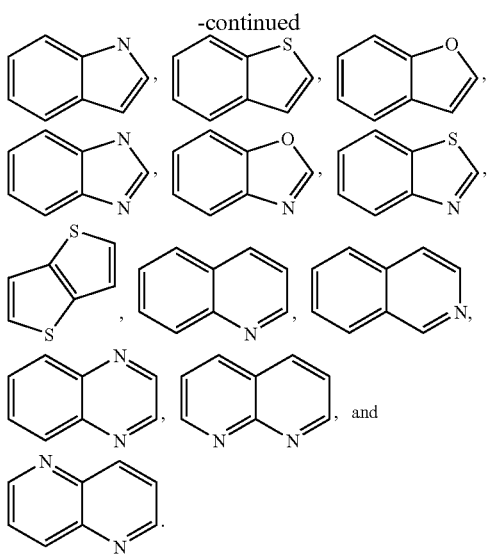

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, unless otherwise indicated, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Certain formulae given herein are meso compounds, which are compounds that possess asymmetric centers (in this case, asymmetric carbons), but which are achiral molecules. Such compounds are named herein as meso compounds. In some cases, meso compounds are depicted and named herein with a specific stereochemical configuration. However, one skilled in the art will recognize the meso nature of such compounds. Examples include meso-endo-(8-Methanesulfonyl-8-aza-bicyclo[3.2.1]oct-3-yl)-{2-[4-(6-methyl-benzothiazol-2-yloxy)-phenoxy]-ethyl}-amine and meso-endo-3-{2-[4-(4-Chloro-benzothiazol-2-yloxy)-phenoxy]-ethylamino}-8-aza-bicyclo[3.2.1]octane-8-carboxylic acid amide.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}Cl$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-2}$, A, D, Q, X, Y, Z, m, n, p, and q, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-2}$, A, D, Q, X, Y, Z, m, n, p, and q, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments, $R^1$ is H; —$CH_2CO_2H$; —$(CH_2)_{1-3}CO_2C_{1-4}$alkyl; —$CH_2$ aryl substituted with $CO_2R^a$; —$C(O)C_{1-4}$alkyl; —$C(O)C(R^a)(R^b)$—OH; —$C(O)C(R^a)(R^b)$—F; —$C(O)C(R^a)(R^b)$—$CF_3$; —$C(O)C(R^a)(R^b)$—$OC_{1-4}$alkyl; —$C(O)C(R^a)(R^b)$—$N(R^c)R^d$; —$C(O)N(R^c)(R^d)$; —C(O)-cycloalkyl; —C(O)-(monocyclic heteroaryl) optionally substituted with methyl; —C(O)-(monocyclic heterocycloalkyl) optionally substituted with methyl or —$CO_2C_{1-4}$alkyl; —$SO_2C_{1-4}$alkyl; —$SO_2NH_2$; —$SO_2$-cycloalkyl; or —$SO_2$-(monocyclic heteroaryl) optionally substituted with methyl. In some embodiments, $R^a$ and $R^b$ are each independently H or methyl; or $R^a$ and $R^b$ taken together with the carbon to which they are attached form a saturated monocyclic cycloalkyl or heterocycloalkyl ring, optionally substituted with one or two methyl groups.

In some embodiments, $R^1$ is H; —CH$_2$CO$_2$H; —(CH$_2$)$_{1-3}$CO$_2$C$_{1-4}$alkyl; —CH$_2$-aryl substituted with CO$_2$R$^a$; —C(O)C$_{1-4}$alkyl; —C(O)C(R$^a$)(R$^b$)—OH; —C(O)C(R$^a$)(R$^b$)—F; —C(O)C(R$^a$)(R$^b$)—CF$_3$; —C(O)C(R$^a$)(R$^b$)—OC$_{1-4}$alkyl; —C(O)C(R$^a$)(R$^b$)—N(R$^c$)R$^d$; —C(O)NH$_2$; —C(O)-cycloalkyl; —C(O)-(monocyclic heteroaryl) optionally substituted with methyl; —C(O)-(monocyclic heterocycloalkyl) optionally substituted with methyl or —CO$_2$C$_{1-4}$alkyl; —SO$_2$C$_{1-4}$alkyl; —SO$_2$NH$_2$; —SO$_2$-cycloalkyl; or —SO$_2$-(monocyclic heteroaryl) optionally substituted with methyl. In some embodiments, $R^a$ and $R^b$ are each independently H or methyl; or $R^a$ and $R^b$ taken together with the carbon to which they are attached form a saturated monocyclic cycloalkyl.

In some embodiments, $R^1$ is H; —CH$_2$-aryl substituted with CO$_2$R$^a$; —C(O)C$_{1-4}$alkyl; —C(O)C(R$^a$)(R$^b$)—OH; —C(O)C(R$^a$)(R$^b$)—F; —C(O)C(R$^a$)(R$^b$)—CF$_3$; —C(O)C(R$^a$)(R$^b$)—OC$_{1-4}$alkyl; —C(O)C(R$^a$)(R$^b$)—N(R$^c$)R$^d$; —C(O)N(R$^c$)(R$^d$); —C(O)-cycloalkyl; —C(O)-(monocyclic heteroaryl) optionally substituted with methyl; —C(O)-(monocyclic heterocycloalkyl) optionally substituted with methyl or —CO$_2$C$_{1-4}$alkyl; —SO$_2$C$_{1-4}$alkyl; —SO$_2$NH$_2$; —SO$_2$-cycloalkyl; or —SO$_2$-(monocyclic heteroaryl) optionally substituted with methyl.

In some embodiments of Formula (I), $R^1$ is H, acetyl, 2-hydroxyacetyl, 2-fluoro-acetyl, carboxymethyl, 3,3,3-trifluoro-propionyl, 1-hydroxycyclopropane-carbonyl, 2-hydroxy-2-methyl-propionyl, tetrahydro-furan-3-carbonyl, tetrahydro-furan-2-carbonyl, tetrahydro-pyran-4-carbonyl, 2-tert-butoxycarbonylamino-acetyl, 2-methoxy-acetyl, 2-amino-acetyl, carbamoyl, methanesulfonyl, tert-butoxycarbonylmethyl, 1H-pyrrole-2-carbonyl, 1-methyl-1H-pyrrole-2-carbonyl, 1-methyl-1H-pyrrole-3-carbonyl, 1-tert-butoxycarbonylamino-cyclopropanecarbonyl, 1-tert-butoxycarbonyl-azetidine-3-carbonyl, 2-(2,2,2-trifluoroacetylamino)-acetyl, azetidine-3-carbonyl, cyclobutanecarbonyl, furan-2-carbonyl, furan-3-carbonyl, pyrazine-2-carbonyl, thiophene-2-carbonyl, thiophene-3-carbonyl, cyclopropanecarbonyl, isoxazole-5-carbonyl, morpholine-4-carbonyl, sulfamoyl, pyridine-3-sulfonyl, furan-2-sulfonyl, 1-methyl-1H-imidazole-2-sulfonyl, 1-methyl-1H-pyrrole-2-sulfonyl, thiophene-2-sulfonyl, thiophene-3-sulfonyl, cyclopropanesulfonyl, formamidyl, N-furan-2-ylmethyl-formamidyl, N-pyridin-4-yl-formamidyl, N-(3,5-dimethyl-isoxazol-4-yl)-formamidyl,

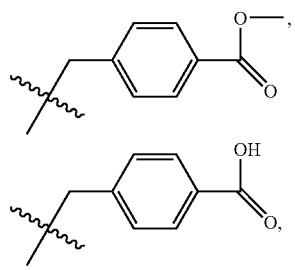

methoxycarbonylmethyl, ethoxycarbonylmethyl, or 3-methoxycarbonyl-propyl.

In further embodiments, $R^1$ is acetyl or carbamoyl.

In some embodiments

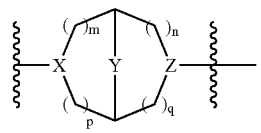

is 2,5-diaza-bicyclo[2.2.1]heptane, 8-aza-bicyclo[3.2.1]oct-3-ylamine, 3,8-diaza-bicyclo[3.2.1]octane, octahydro-pyrrolo[3,4-b]pyrrole, octahydro-pyrrolo[3,4-c]pyrrole, octahydro-pyrrolo[3,4-c]pyridine, decahydro-[1,6]naphthyridine, or 3-Aza-bicyclo[3.1.0]hex-6-ylamine.

In further embodiments,

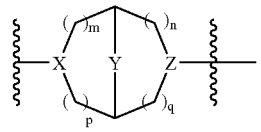

is (S,S)-2,5-diaza-bicyclo[2.2.1]heptane, (R,R)-2,5-diaza-bicyclo[2.2.1]heptane, or endo-3,8-aza-bicyclo[3.2.1]oct-3-yl-amine.

In some embodiments, A is —CH$_2$—, —CH$_2$CH$_2$—, or —OCH$_2$CH$_2$—.

In some embodiments, $R^3$ is H. In other embodiments, $R^3$ is fluoro.

In some embodiments, Q is O or CH$_2$ and is linked at the "a" or "b" position of the phenyl ring. In certain embodiments, Q is O and is linked to the a position. In certain embodiments, Q is O and is linked to the b position. In certain embodiments, Q is CH$_2$ and is linked to the a position. In certain embodiments, Q is CH$_2$ and is linked to the b position.

In some embodiments, D is O. In other embodiments, D is S.

In some embodiments, $R^2$ is H, CH$_3$, OCH$_3$, halo, OH, NH$_2$, or CN. In certain embodiments, $R_2$ is H. In further embodiments $R_2$ is a halo. In further embodiments $R_2$ is CH$_3$.

The invention includes also pharmaceutically acceptable salts of the compounds represented by Formula (I), preferably of those described above and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluene-sulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "active agents") of the present invention are useful as $LTA_4H$ modulators in the methods of the invention. Such methods for modulating $LTA4H$ activity comprise exposing LTA4H to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit $LTA_4H$ activity.

In some embodiments, the $LTA_4H$ is in a subject with a disease, disorder, or medical condition mediated by $LTA_4H$ activity, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through $LTA_4H$ activity, such as inflammation. Active agents according to the invention may therefore be used as anti-inflammatory agent(s).

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with an $LTA_4H$ modulating agent include inflammation due to any one of a plurality of conditions such as allergy, asthma, nasal polyps, allergic rhinitis, nasal itch, ocular inflammation (e.g., post-surgical ocular inflammation), conjunctivitis, uveitis, dry eye, psoriasis, pruritis, itch, itchy skin, atopic dermatitis, urticaria (hives), contact dermatitis, scleroderma, skin burns, acne, inflammatory bowel diseases (including colitis, Crohn's disease and ulcerative colitis), chronic obstructed pulmonary disease (COPD), atherosclerosis, arthritis (including rheumatoid arthritis), multiple sclerosis, myocardial infarction, stroke, pain, gingivitis, bronchitis, cystic fibrosis, upper gastrointestinal cancer, sepsis, autoimmune thyroid diseases, and immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis treatable with an $LTA_4H$-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, asthma, autoimmune diseases, pruritis, inflammatory bowel disease, ulcerative colitis, or cardiovascular disease, including atherosclerosis and prevention of myocardial infarction.

Thus, the active agents may be used to treat subjects diagnosed with or suffering from a disease, disorder, or condition mediated through $LTA_4H$ activity. The term "treat" or "treating" as used herein is intended to refer to administration of an active agent or composition of the invention to a subject for the purpose of effecting a therapeutic or prophylactic benefit through modulation of $LTA_4H$ activity. Treating includes reversing, ameliorating, alleviating, inhibiting the progress of, lessening the severity of, or preventing a disease, disorder, or condition, or one or more symptoms of such disease, disorder or condition mediated through modulation of $LTA_4H$ activity. The term "subject" refers to a mammalian patient in need of such treatment, such as a human. "Modulators" include both inhibitors and activators, where "inhibitors" refer to compounds that decrease, prevent, inactivate, desensitize or down-regulate $LTA_4H$ expression or activity, and "activators" are compounds that increase, activate, facilitate, sensitize, or up-regulate $LTA_4H$ expression or activity. Embodiments of chemical entities according to this invention are $LTA_4H$-modulating chemical entities.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. When referring to modulating the target receptor, an "effective amount" means an amount sufficient to at least affect the activity of such receptor. Measuring the activity of the target receptor may be performed by routine analytical methods. Target receptor modulation is useful in a variety of settings, including assays.

In addition, effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by $LTA_4H$ activity, such as another $LTA_4H$ modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

Other embodiments of this invention further comprise the administration of at least one CysLT antagonist and/or at least one CysLT synthesis inhibitor. In some embodiments of this invention, such $LTA_4H$ modulator and CysLT antagonist and/ or CysLT synthesis inhibitor are coadministered. Examples of CysLT antagonists are CysLT1 and CysLT2 antagonists.

The active agents of the invention are used, alone or in combination with one or more additional active ingredients, to formulate pharmaceutical compositions of the invention. A pharmaceutical composition of the invention comprises an effective amount of at least one active agent in accordance with the invention. Such compositions may further comprise a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to the most generic form of Formula (I).

SCHEME A

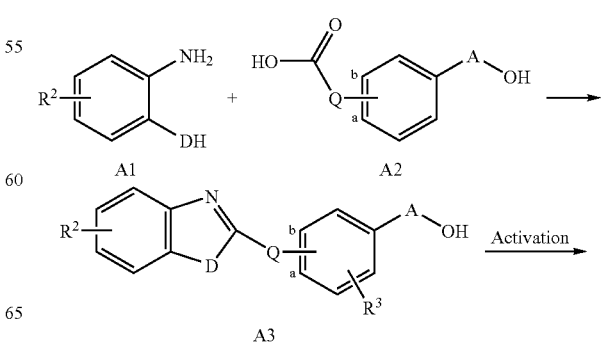

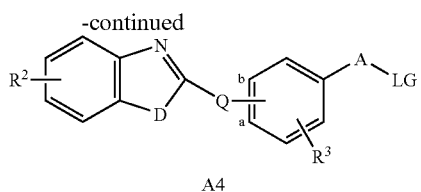

A4

Intermediates of formula A4, where Q is —CH$_2$— are prepared according to Scheme A. Amines A1, where D is O or S, are condensed with phenylacetic acid compounds A2, with heating, to provide fused thiazoles or oxazoles A3. Where D is O, reactions are performed in the presence of an activating agent such as carbonyldiimidazole. The free hydroxyl group is activated using methods known in the art to give compounds A4, where LG is a suitable leaving group (such as chloro, bromo, iodo, tosyl, or mesyl). Preferably, thionyl chloride in CH$_2$Cl$_2$ is used to provide compounds A4 where LG is chloro. Analogs of A4 where Q is O are known in the literature or are prepared according to methods described in U.S. Patent Appl. Publ. Nos. US2005/0043378 and US2005/0043379.

SCHEME B

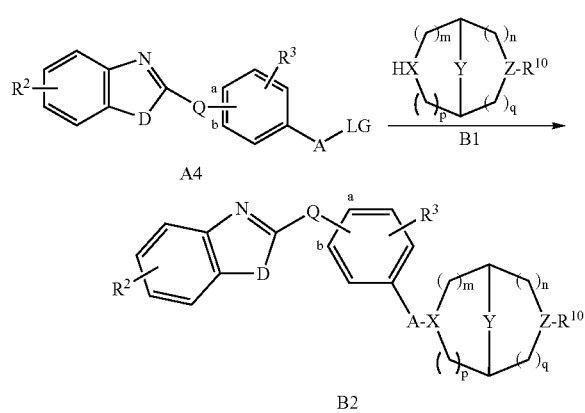

In one embodiment, compounds of Formula (I) where D is S are prepared according to Scheme B. Compounds A4, where D is S and LG is a suitable leaving group (such as halo, tosyl, or mesyl), are reacted with amines B1 in the presence of a suitable base (such as Et$_3$N), in a polar solvent (such as acetonitrile) to give compounds of formula B2, where D is S. Amines B1, where R$^{10}$ is R$^1$ or a suitable nitrogen protecting group, are commercially available or are prepared using methods in the art or methods described in EP 0266576 or WO 01/81347. Where R$^{10}$ is R$^1$, one skilled in the art will recognize compounds B2 are embodiments of Formula (I).

SCHEME C

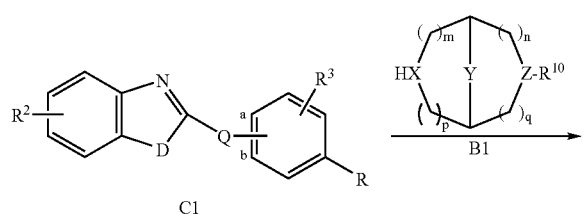

Compounds of formula B2, where D is S, are also prepared by reductive amination protocols. Aldehydes C1, where D is S and R is —CHO or —CH$_2$CHO, are commercially available or are prepared using methods in the art or methods described in U.S. Patent Appl. Publ. Nos. US2005/0043378 and US2005/0043379. Aldehydes C1 may also be used or purified in a protected form, such as a bisulfite complex. Reaction of aldehydes C1 with amines B1 in the presence of a suitable reducing agent (such as NaCNBH$_3$ or NaB(OAc)$_3$H) in a solvent such as 1,2-dichloroethane (DCE), CH$_2$Cl$_2$, methanol, or ethanol, and optionally employing an acid catalyst (such as acetic acid or ZnCl$_2$) provides compounds B2, where D is S.

SCHEME D

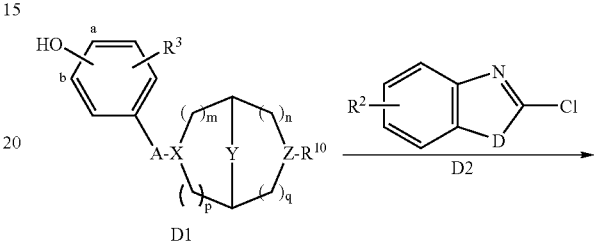

Alternatively, phenols D1 (prepared using methods analogous to those in the preceding reaction schemes) are reacted with chlorides D2 (where D is S or O) to form compounds B2 where D is S. Compounds of formula D2 are commercially available or are prepared using methods in the art or methods described in Intl. Pat. Appl. No. WO 2006/04475 and L. Zhu, et al. *J. Heterocyclic Chem.* 2005, 42, 727-730.

SCHEME E

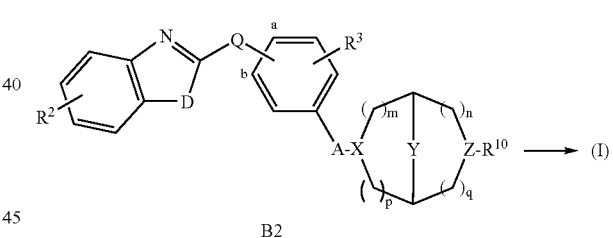

Compounds B2, where D is S or O and R$^{10}$ is a suitable protecting group (such as tert-butylcarbamoyl group), are converted to compounds of Formula (I) according to Scheme E. Where R$^{10}$ is a suitable protecting group, deprotection is effected using generally known methods. For example, where R$^{10}$ is a Boc group, deprotection is accomplished using an acid such as HCl or TFA, in a solvent such as Et$_2$O, dioxane, or CH$_2$Cl$_2$. Substituents R$^1$ are installed by acylation, sulfonylation, reductive amination, or alkylation protocols using methods known in the art to give compounds of Formula (I).

Compounds of Formula (I) may be converted to their corresponding salts using methods described in the art. For example, an amine of Formula (I) is treated with trifluoroacetic acid, HCl, or citric acid in a solvent such as Et$_2$O, CH$_2$Cl$_2$, THF, or MeOH to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry Methods

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Analytical reversed-phase HPLC was performed on an Agilent 1100 Series instrument using one of the following gradients: 1 to 99% acetonitrile/water (0.05% trifluoroacetic acid) over 5.0 min or 7.0 min with a flow rate of 1 mL/min (Waters XTerra MS C18 (5 µm, 4.6×100 mm) column or Phenomenex Synergi max-RP (4 µm, 4.6×150 mm) column) or 1 to 99% acetonitrile/water (20 mM $NH_4OH$) over 5.0 min or 7.0 min with a flow rate of 1.5 mL/min (Phenomenex Gemeni C18 (5 µm, 3.0×150 mm) column). Analytical reversed phase LC/MS was performed either on an Agilent 1100 Series instrument using 5 to 99% acetonitrile/water (0.05% trifluoroacetic acid) over 5.0 min or 7.0 min with a flow rate of 0.6 mL/min (Waters XTerra RP18 (5 µm, 3.0×100 mm) column) or on a Waters 2790 instrument using 5 to 99% acetonitrile/water (0.1% formic acid) over 5.0 min with a flow rate of 0.6 mL/min (Waters XTerra RP18 (5 µm, 3.0×100 mm) column).

Preparative reversed phase HPLC was performed on a Dionex APS2000 LC/MS or HPLC with a Phenomenex Gemini C18 (5 µm, 30×100 mm) column or a Waters XBridge C18 (5 µm, 30×100 mm) column and variable gradients of acetonitrile/water (20 mM $NH_4OH$) at a flow rate of 30 mL/min. Alternatively, the purification was performed with a Phenomenex Gemini C18 (5 µm, 50×100 mm) column or a Waters XBridge C18 (5 µm, 50×100 mm) column and variable gradients of acetonitrile/water (20 mM $NH_4OH$) at a flow rate of 80 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration). NMR interpretation was performed using MestReC or MestReNova software to assign chemical shift and multiplicity. In cases where 2 adjacent peaks of equal or unequal height were observed, these 2 peaks may be labeled either as a multiplet or as a doublet. In the case of a doublet a coupling constant using this software may be assigned. In any given example, one or more protons may not be reported due to obscurity by water and/or solvent peaks.

Chemical names were typically generated using ChemDraw Version 6.0.2 (CambridgeSoft, Cambridge, Mass.) or ACD/Name Version 9 (Advanced Chemistry Development, Toronto, Ontario, Canada).

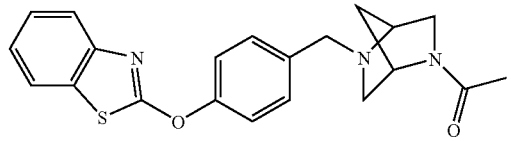

Example 1

(S,S)-1-{5-[4-(Benzothiazol-2-yloxy)-benzyl]-2,5-diaza-bicyclo[2.2.1]hept-2-yl}-ethanone Step A: (S,S)-5-[4-(Benzothiazol-2-yloxy)-benzyl]-2,5-diaza-bicyclo[2.2.1]heptane-2-carboxylic acid tert-butyl ester. To a stirred solution of 2-(4-chloromethyl-phenoxy)-benzothiazole (15.3 g, 55.3 mmol) and (S,S)-2,5-diaza-bicyclo[2.2.1]heptane-2-carboxylic acid tert-butyl ester (13.2 g, 66.4 mmol) in $CH_3CN$ (200 mL) was added triethylamine ($Et_3N$) (11.5 mL, 82.9 mmol). The resulting solution was stirred at rt for 24 h and then concentrated. The crude residue was then partitioned between $CH_2Cl_2$ (800 mL) and saturated (satd.) aqueous (aq.) $NaHCO_3$ (200 mL). The organic layer was separated, dried ($Na_2SO_4$), filtered and concentrated. Purification by silica gel flash chromatography (10% to 40% ethyl acetate (EtOAc) in hexanes) afforded the title compound as a white foam (17.2 g, 71%). MS (ESI): mass calcd. for $C_{24}H_{27}N_3O_3S$, 437.18; m/z found, 438.2 $[M+H]^+$. $^1H$ NMR (500 MHz, $CDCl_3$, mixture of rotamers): 7.73 (d, J=7.1 Hz, 1H), 7.66 (d, J=7.1 Hz, 1H), 7.42 (d, J=8.1 Hz, 2H), 7.38 (m, 1H), 7.32-7.24 (br m, 3H), 4.40 (br m, 0.5H), 4.26 (br m, 0.5H), 3.76 (br d, J=9.7 Hz, 2H), 3.63 (br d, J=10.5 Hz, 0.5H), 3.50 (br m, 1H), 3.46 (m, 0.5H), 3.18 (br m, 1H), 2.93 (br d, J=8.8 Hz, 0.5H), 2.88 (br d, J=9.4 Hz, 0.5H), 2.73 (br d, J=9.2 Hz, 0.5H), 2.55 (br d, J=9.2 Hz, 0.5H), 1.87 (br t, J=8.8 Hz, 1H), 1.74 (br d, J=9.3 Hz, 0.5H), 1.68 (br d, J=9.3 Hz, 0.5H), 1.47 (s, 9H).

Step B: (S,S)-2-[4-(2,5-Diaza-bicyclo[2.2.1]hept-2-ylmethyl)-phenoxy]-benzothiazole hydrochloride. To a stirred solution of (S,S)-5-[4-(benzothiazol-2-yloxy)-benzyl]-2,5-diaza-bicyclo[2.2.1]heptane-2-carboxylic acid tert-butyl ester (8.2 g, 18.7 mmol) in $CH_2Cl_2$ (200 mL) was added HCl (4.0 N in 1,4-dioxane, 46 mL, 187 mmol). The resulting white suspension was stirred at rt for 4 h and then concentrated affording the title compound as a white solid (5.4 g, 70%). MS (ESI): mass calcd. for $C_{19}H_{19}N_3OS$, 337.12; m/z found, 338.2 $[M+H]^+$. $^1H$ NMR (500 MHz, $CD_3OD$): 7.84 (m, 3H), 7.64 (d, J=8.3 Hz, 1H), 7.55 (m, 2H), 7.44 (m, 1H), 7.34 (m, 1H), 4.67 (br m, 3H), 4.55 (br m, 1H), 4.05 (br m, 1H), 3.84 (br d, J=13.2 Hz, 1H), 3.60 (dd, J=13.7, 2.7 Hz, 3H), 2.79 (br m, 1H), 2.34 (br d, J=12.7 Hz, 1H).

Step C: (S,S)-1-{5-[4-(Benzothiazol-2-yloxy)-benzyl]-2,5-diaza-bicyclo[2.2.1]hept-2-yl}-ethanone. To a stirred solution of (S,S)-2-[4-(2,5-diaza-bicyclo[2.2.1]hept-2-ylmethyl)-phenoxy]-benzothiazole hydrochloride (109 mg, 0.27 mmol) and $Et_3N$ (150 µL, 1.1 mmol) in $CH_2Cl_2$ (4 mL) was added acetic anhydride (40 µL, 0.4 mmol), and the resulting solution was then stirred at rt for 18 h. The resulting white suspension was partitioned between CH$_2$Cl$_2$ (150 mL) and satd. aq. NaHCO$_3$ (50 mL). The organic layer was separated, dried (Na$_2$SO$_4$), filtered and concentrated. Purification by silica gel flash chromatography (0% to 5% CH$_3$OH in CH$_2$Cl$_2$) afforded the title compound as a viscous, colorless oil (93 mg, 92%). MS (ESI): mass calcd. for C$_{21}$H$_{21}$N$_3$O$_2$S, 379.14; m/z found, 380.2 [M+H]$^+$. $^1$H NMR (500 MHz, CDCl$_3$, mixture of rotamers): 7.73 (d, J=7.5 Hz, 1H), 7.66 (d, J=8.0 Hz, 1H), 7.44-7.36 (m, 3H), 7.33-7.24 (m, 3H), 4.78 (br m, 0.5H), 4.23 (m, 0.5H), 3.78-3.73 (br m, 2.5H), 3.56 (m, 1.5H), 3.32 (dd, J=9.3, 2.2 Hz, 0.5H), 3.27 (dd, J=11.4, 2.3 Hz, 0.5H), 3.01 (dd, J=9.1, 2.2 Hz, 0.5H), 2.84 (dd, J=9.7, 2.1 Hz, 0.5H), 2.77 (br d, J=9.9 Hz, 0.5H), 2.56 (dd, J=9.9, 1.2 Hz, 0.5H), 2.08 (s, 1.5H), 2.00 (s, 1.5H), 1.98 (br m, 0.5H), 1.91 (br m, 0.5H), 1.80 (br m, 0.5H), 1.66 (br m, 0.5H).

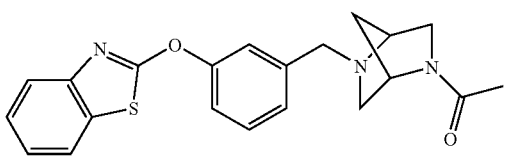

Example 2

(S,S)-1-{5-[3-(Benzothiazol-2-yloxy)-benzyl]-2,5-diaza-bicyclo[2.2.1]hept-2-yl}-ethanone This compound was prepared using the methods outlined in Example 1, substituting the appropriate chloromethyl phenoxy-benzothiazole. MS (ESI): mass calcd. for C$_{21}$H$_{21}$N$_3$O$_2$S, 379.14; m/z found, 380.1 [M+H]$^+$. $^1$H NMR (500 MHz, CDCl$_3$, mixture of rotamers): 7.73 (d, J=8.1 Hz, 1H), 7.67 (m, 1H), 7.42-7.36 (m, 3H), 7.30-7.23 (m, 3H), 4.77 (br m, 0.5H), 4.22 (m, 0.5H), 3.80 (br m, 1H), 3.77 (s, 1H), 3.74 (dd, J=11.5, 2.2 Hz, 0.5H), 3.56 (m, 1.5H), 3.31 (dd, J=9.4, 2.1 Hz, 0.5H), 3.26 (dd, J=11.5, 2.2 Hz, 0.5H), 3.03 (dd, J=9.4, 2.2 Hz, 0.5H), 2.83 (dd, J=9.8, 2.2 Hz, 0.5H), 2.76 (br d, J=10.3 Hz, 0.5H), 2.55 (dd, J=9.8, 1.2 Hz, 0.5H), 2.07 (s, 1.5H), 1.98 (s, 1.5H), 1.97 (br m, 0.5H), 1.89 (br m, 0.5H), 1.79 (br m, 0.5H), 1.65 (br m, 0.5H).

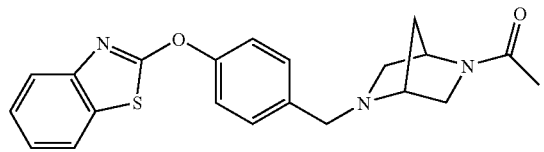

Example 3

(R,R)-1-{5-[4-(Benzothiazol-2-yloxy)-benzyl]-2,5-diaza-bicyclo[2.2.1]hept-2-yl}-ethanone Step A: (4S,2R)-4-Methanesulfonyloxy-2-methanesulfonyloxymethyl-pyrrolidine-1-carboxylic acid tert-butyl ester. To a solution of 4-hydroxy-2-hydroxymethyl-pyrrolidine-1-carboxylic acid tert-butyl ester (10.85 g, 50.0 mmol) in pyridine (50 mL) was added methanesulfonyl chloride (10.8 mL, 140 mmol) over a period of 20 min. After stirring for 16 h, the reaction mixture was concentrated to dryness, diluted with satd. aq. Na$_2$CO$_3$ and extracted with EtOAc (2×). The combined organic layers were dried (MgSO$_4$), filtered and concentrated to provide the title compound as an oil that slowly solidified (14.4 g, 84%). $^1$H NMR (400 MHz, CDCl$_3$): 5.24-5.20 (m, 1H), 4.72-4.47 (m, 1H), 4.32-4.17 (m, 2H), 4.01-3.75 (m, 1H), 3.63-3.48 (m, 1H), 3.04 (s, 3H), 3.01 (s, 3H), 2.60-2.25 (m, 2H), 1.48 (s, 9H).

Step B: (2R,5R)-2,5-Diaza-bicyclo[2.2.1]heptane-2-carboxylic acid tert-butyl ester. A heterogeneous mixture of (4S,2R)-4-methanesulfonyloxy-2-methanesulfonyloxymethyl-pyrrolidine-1-carboxylic acid tert-butyl ester (1 g, 2.7 mmol) in ammonium hydroxide (27 wt % solution in water, 10 mL) was warmed to 65° C. in a sealed tube for 16 h during which time the mixture became homogeneous. The aqueous was extracted with CH$_2$Cl$_2$ (2×) and the combined organics were dried over Na$_2$SO$_4$, filtered, and concentrated to provide the title compound as a yellow solid that was used directly in subsequent steps (350 mg, 66%). MS (ESI): mass calcd. for C$_{10}$H$_{18}$N$_2$O$_2$, 198.1; m/z found, 199.0 [M+H]$^+$. $^1$H NMR (400 MHz, CDCl$_3$): 4.48-4.27 (m, 1H), 3.70 (s, 1H), 3.41-3.30 (m, 1H), 3.22-3.11 (m, 1H), 3.08-2.95 (m, 2H), 1.80-1.65 (m, 2H), 1.48 (s, 9H).

Step C. The title compound was prepared using the methods analogous to those outlined in Example 1, Steps B and C. MS (ESI): mass calcd. for C$_{21}$H$_{21}$N$_3$O$_2$S, 379.14; m/z found, 380.2 [M+H]$^+$. $^1$H NMR (400 MHz, CDCl$_3$, mixture of rotamers): 7.76-7.72 (m, 1H), 7.69-7.66 (m, 1H), 7.45-7.36 (m, 3H), 7.34-7.25 (m, 3H), 4.79 (br s, 0.5H), 4.24, (br s, 0.5H), 3.80-3.72 (m, 2.5H), 3.60-3.54 (m, 1.5H), 3.33 (dd, J=9.3, 2.3 Hz, 0.5H), 3.28 (dd, J=11.4, 2.0 Hz, 0.5H), 3.02 (dd, J=11.4, 2.0 Hz, 0.5H), 2.87-2.75 (m, 1H), 2.56 (dd, J=9.5, 1.1 Hz, 0.5H), 2.09 (s, 1.5H), 2.01 (s, 1.5H), 2.01-1.64 (m, 2H).

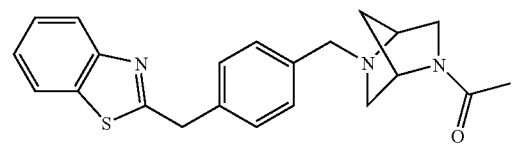

Example 4

(S,S)-1-[5-(4-Benzothiazol-2-ylmethyl-benzyl)-2,5-diaza-bicyclo[2.2.1]hept-2-yl]-ethanone Step A: (4-Benzothiazol-2-ylmethyl-phenyl)-methanol. To (4-hydroxymethyl-phenyl)-acetic acid (2 g, 12 mmol) was added 2-amino-benzenethiol (13.2 g, 12 mmol) and the mixture was heated at 160° C. for 48 h. The crude residue was then partitioned between EtOAc (200 mL) and 1 N NaOH (200 mL). The organic layer was separated, washed with satd. aq. NaCl (200 mL), dried (MgSO$_4$), filtered and concentrated. Purification by silica gel flash chromatography (0% to 80% EtOAc in hexanes) afforded the title compound as a colorless oil (0.42 g, 14%). MS (ESI): mass calcd. for C$_{15}$H$_{13}$NOS, 255.34; m/z found, 456.1 [M+H]$^+$. $^1$H NMR (500 MHz, CDCl$_3$): 8.00 (d, J=8.1 Hz, 1H), 7.80 (d, J=8.1 Hz, 1H), 7.48-7.45 (m, 1H), 7.39-7.28 (m, 5H), 4.71 (s, 2H), 4.44 (s, 2H).

Step B: 2-(4-Chloromethyl-benzyl)-benzothiazole. To a solution of (4-benzothiazol-2-ylmethyl-phenyl)-methanol (2.1 g, 8.1 mmol) in CH$_2$Cl$_2$ (90 mL) was added thionyl chloride (0.65 mL, 8.9 mmol) and the mixture was stirred at rt for 4 h. The reaction mixture was concentrated to afford the title compound as a tan solid (2.6 g, 100%). MS (ESI): mass calcd. for C$_{15}$H$_{12}$ClNS, 273.04; m/z found, 274.0 [M+H]$^+$.

$^1$H NMR (500 MHz, CDCl$_3$): 8.34 (d, J=8.2 Hz, 1H), 7.89 (d, J=8.2 Hz, 1H), 7.71-7.67 (m, 1H), 7.61-7.58 (m, 1H), 7.50-7.48 (m, 2H), 7.45-7.44 (m, 2H), 4.84 (s, 2H), 4.60 (s, 2H).

Step C: 5-(4-Benzothiazol-2-ylmethyl-benzyl)-2,5-diaza-bicyclo[2.2.1]heptane-2-carboxylic acid tert-butyl ester. To a solution of 2-(4-chloromethyl-benzyl)-benzothiazole (1.0 g, 3.7 mmol) and (S,S)-2,5-diaza-bicyclo[2.2.1]heptane-2-carboxylic acid tert-butyl ester (0.9 g, 4.4 mmol) in CH$_3$CN (36 mL) was added Et$_3$N (0.77 mL, 5.5 mmol) and the resulting solution was stirred at rt for 24 h. The reaction mixture was then concentrated and the crude residue was then partitioned between CH$_2$Cl$_2$ (200 mL) and satd. aq. NaHCO$_3$ (200 mL). The organic layer was separated, dried (MgSO$_4$), filtered and concentrated. Purification by silica gel flash chromatography (0% to 10% CH$_3$OH in CH$_2$Cl$_2$) afforded the title compound as clear oil (0.88 g, 55%). MS (ESI): mass calcd. for C$_{25}$H$_{29}$N$_3$O$_2$S, 435.59; m/z found, 436.2 [M+H]$^+$. $^1$H NMR (500 MHz, CDCl$_3$, mixture of rotamers): 8.01 (d, J=8.2 Hz, 1H), 7.81 (d, J=8.0 Hz, 1H), 7.48-7.45 (m, 1H), 7.37-7.34 (m, 5H), 4.44 (s, 2H), 4.40 (br s, 0.5H), 4.25 (br s, 0.5H), 3.75-3.75 (m, 2H), 3.64-3.44 (m, 2H), 3.17 (t, J=11.3 Hz, 1H), 2.90 (dd, J=25.2, 9.5 Hz, 1H), 2.74 (d, J=9.6 Hz, 0.5H), 2.55 (d, J=9.4 Hz, 0.5H), 1.88-1.86 (br m, 1H), 1.73-1.65 (br m, 1H), 1.48 (s, 9H).

Step D: (S,S)-2-[4-(2,5-Diaza-bicyclo[2.2.1]hept-2-ylmethyl)-benzyl]-benzothiazole dihydrochloride. To a solution of 5-(4-benzothiazol-2-ylmethyl-benzyl)-2,5-diaza-bicyclo[2.2.1]heptane-2-carboxylic acid tert-butyl ester (0.82 g, 1.9 mmol) in CH$_2$Cl$_2$ (19 mL) was added HCl (4.0 N in 1,4-dioxane, 7 mL) and the resulting white suspension was stirred at rt for 4 h. The reaction mixture was concentrated affording the title compound as a white solid (0.9 g, 100%). MS (ESI): mass calcd. for free amine C$_{20}$H$_{21}$N$_3$S, 335.47; m/z found, 336.2 [M+H]$^+$. $^1$H NMR (500 MHz, DMSO-d$_6$): 12.09-11.07 (br m, 1H), 10.16-9.71 (br m, 2H), 8.03 (d, J=8.0 Hz, 1H), 7.96 (d, J=8.0 Hz, 1H), 7.72-7.70 (m, 2H), 7.50-7.47 (m, 3H), 7.42-7.39 (m, 1H), 4.62-4.59 (br m, 0.5H), 4.52 (br s, 2H), 4.48-4.44 (br m, 2H), 4.37-4.34 (br m, 1.5H), 3.95-3.92 (m, 1H), 3.72-3.70 (m, 1H), 3.34-3.30 (m, 2H), 2.69-2.63 (m, 0.5H), 2.48-2.43 (m, 0.5H), 2.13-2.06 (m, 1H).

Step E: (S,S)-1-[5-(4-Benzothiazol-2-ylmethyl-benzyl)-2,5-diaza-bicyclo[2.2.1]hept-2-yl]-ethanone. This compound was prepared using methods analogous to those outlined in Example 1, Step C. MS (ESI): mass calcd. for C$_{22}$H$_{23}$N$_3$OS, 377.51; m/z found, 378.1 [M+H]$^+$. $^1$H NMR (500 MHz, CDCl$_3$, mixture of rotamers): 8.01 (d, J=8.0 Hz, 1H), 7.80 (d, J=8.0 Hz, 1H), 7.48-7.45 (m, 1H), 7.37-7.33 (m, 5H), 4.78 (br s, 0.5H), 4.44 (d, J=2.0 Hz, 2H), 4.22 (br s, 0.5H), 3.76-3.73 (m, 2.5H), 3.58-3.53 (m, 1.5H), 3.31-3.25 (m, 1H), 3.00 (dd, J=9.8, 2.3 Hz, 0.5H), 2.84 (dd, J=9.8, 2.3 Hz, 0.5H), 2.78-2.76 (br m, 0.5H), 2.57-2.55 (br m, 0.5H), 2.08 (s, 1.5H), 2.00 (s, 1H), 1.99-1.97 (m, 1H), 1.91-1.89 (br d, 0.5H), 1.80-1.78 (br d, 0.5H), 1.66-1.64 (m, 0.5H).

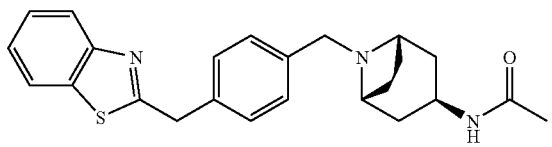

Example 5 meso-endo-N-[8-(4-Benzothiazol-2-ylmethyl-benzyl)-8-aza-bicyclo[3.2.1]oct-3-yl]-acetamide This compound was prepared using methods analogous to those outlined in Example 4. MS (ESI): mass calcd. for C$_{24}$H$_{27}$N$_3$OS, 405.57; m/z found, 406.2 [M+H]$^+$. $^1$H NMR (400 MHz, CDCl$_3$): 7.99 (d, J=7.7 Hz, 1H), 7.79 (d, J=7.7 Hz, 1H), 7.54 (dt, J=7.8, 1.2 Hz, 1H), 7.36-7.30 (m, 6H), 5.81 (br d, J=6.8 Hz, 1H), 4.42 (s, 2H), 4.10 (dd, J=14.2, 7.0 Hz, 1H), 3.52-3.51 (br m, 2H), 3.18 (br s, 2H), 2.23-2.12 (br m, 3H), 1.96 (s, 3H), 1.76-1.70 (br m, 2H), 1.58 (br d, J=14.4 Hz, 2H).

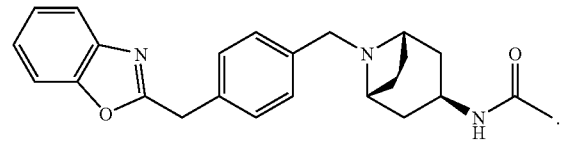

Example 6 meso-endo-N-[8-(4-Benzooxazol-2-ylmethyl-benzyl)-8-aza-bicyclo[3.2.1]oct-3-yl]-acetamide Step A: (4-Benzooxazol-2-ylmethyl-phenyl)-methanol. A mixture of (4-hydroxymethyl-phenyl)-acetic acid (5.0 g, 30.1 mmol) and 2-amino-phenol (6.6 g, 60.2 mmol) was heated at 180° C. for 3 h. The crude residue was cooled and then dissolved in THF (50 mL). The resulting solution was treated with carbonyldiimidazole (3.7 g, 22.5 mmol) and stirred at 80° C. for 72 h. The reaction mixture was then partitioned between EtOAc (200 mL) and water (200 mL). The organic layer was dried (MgSO$_4$), filtered and concentrated. Purification by silica gel flash chromatography (0% to 80% EtOAc in hexanes) followed by a second silica gel flash chromatography (0% to 10% CH$_3$OH in CH$_2$Cl$_2$) afforded a colorless oil. The crude oil was then partitioned between EtOAc (200 mL) and 1 N NaOH (200 mL). The organic layer was dried (MgSO$_4$), filtered and concentrated to afford the title compound as a colorless oil (1.5 g, 20%). MS (ESI): mass calcd. for C$_{15}$H$_{13}$NO$_2$, 239.09; m/z found, 240.1 [M+H]$^+$. $^1$H NMR (500 MHz, CDCl$_3$): 7.70-7.68 (m, 1H), 7.49-7.46 (m, 1H), 7.40-7.35 (m, 4H), 7.33-7.29 (m, 2H), 4.69 (br d, J=4.5. Hz, 2H), 4.28 (s, 2H).

Step B: 2-(4-Chloromethyl-benzyl)-benzooxazole. This compound was prepared using the methods outlined in Example 4, Step B, substituting (4-benzooxazol-2-ylmethyl-phenyl)-methanol for (4-benzothiazol-2-ylmethyl-phenyl)-methanol. MS (ESI): mass calcd. for C$_{15}$H$_{12}$ClNO, 257.06; m/z found, 258.1 [M+H]$^+$.

Step C. meso-endo-[8-(4-Benzooxazol-2-ylmethyl-benzyl)-8-aza-bicyclo[3.2.1]oct-3-yl]-carbamic acid tert-butyl ester. This compound was prepared using the methods outlined in Example 4, Step C, substituting 2-(4-chloromethyl-benzyl)-benzooxazole for 2-(4-chloromethyl-benzyl)-benzothiazole. MS (ESI): mass calcd. for C$_{27}$H$_{33}$N$_3$O, 447.25; m/z found, 448.3 [M+H]$^+$. $^1$H NMR (500 MHz, CDCl$_3$): 7.71-7.69 (m, 1H), 7.49-7.47 (m, 1H), 7.37-7.30 (m, 6H), 4.85 (br s, 1H), 4.27 (s, 2H), 3.82 (br s, 1H), 3.51 (s, 2H), 3.17 (br s, 2H), 2.20-2.10 (m, 4H), 1.81-1.79 (br m, 2H), 1.62-1.45 (br m, 2H), 1.45 (s, 9H).

Step D: meso-endo-8-(4-Benzooxazol-2-ylmethyl-benzyl)-8-aza-bicyclo[3.2.1]oct-3-ylamine dihydrochloride. This compound was prepared using the methods outlined in Example 4, Step D, substituting meso-endo-[8-(4-benzooxazol-2-ylmethyl-benzyl)-8-aza-bicyclo[3.2.1]oct-3-yl]-carbamic acid tert-butyl ester for 5-(4-benzothiazol-2-ylmethyl-benzyl)-2,5-diaza-bicyclo[2.2.1]heptane-2-carboxylic acid tert-butyl ester. MS (ESI): mass calcd. for free amine C$_{22}$H$_{25}$N$_3$O, 347.20; m/z found, 348.2 [M+H]$^+$. $^1$H NMR (500 MHz, DMSO-d$_6$): 11.11 (br s, 1H), 8.36 (br s, 3H), 7.78-7.66 (m, 4H), 7.46 (d, J=8.0 Hz, 2H), 7.38-7.33 (m, 2H), 4.39 (s, 2H), 4.14 (br d, J=6.5 Hz, 2H), 3.75 (br s, 2H), 3.48-3.43 (m, 1H), 2.75-2.72 (m, 2H), 2.39-2.37 (m, 2H), 2.23-2.20 (m, 2H), 2.03 (br d, J=16.0 Hz, 2H).

Step E: meso-endo-N-[8-(4-Benzooxazol-2-ylmethyl-benzyl)-8-aza-bicyclo[3.2.1]oct-3-yl]-acetamide. This compound was prepared using methods analogous to those outlined in Example 4, Step E. MS (ESI): mass calcd. for C$_{24}$H$_{27}$N$_3$O$_2$, 389.50; m/z found, 390.2 [M+H]$^+$. $^1$H NMR (400 MHz, CDCl$_3$): 7.70-7.68 (m, 1H), 7.48-7.46 (m, 1H), 7.36-7.27 (m, 6H), 5.80 (br d, J=6.0 Hz, 1H), 4.26 (s, 2H), 4.10 (dd, J=7.2, 6.8 Hz, 1H), 3.49 (s, 2H), 3.17 (br s, 2H), 2.22-2.11 (m, 4H), 1.96 (s, 3H), 1.76-1.71 (m, 2H), 1.57 (br d, J=14.0 Hz, 2H).

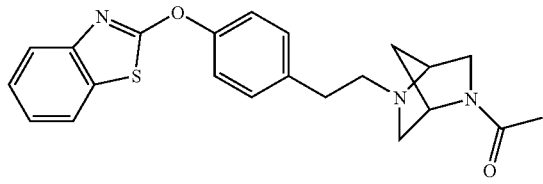

Example 7

(S,S)-1-(5-{2-[4-(Benzothiazol-2-yloxy)-phenyl]-ethyl}-2,5-diaza-bicyclo[2.2.1]hept-2-yl)-ethanone Step A: (S,S)-5-{2-[4-(Benzothiazol-2-yloxy)-phenyl]-ethyl}-2,5-diaza-bicyclo[2.2.1]hep-tane-2-carboxylic acid tert-butyl ester. To a stirred solution of 2-[4-(2-bromo-ethyl)-phenoxy]-benzothiazole (1.5 g, 4.5 mmol) and (S,S)-2,5-diaza-bicyclo[2.2.1]heptane-2-carboxylic acid tert-butyl ester (980 mg, 4.9 mmol) in CH$_3$CN (20 mL) at rt was added Et$_3$N (900 µL, 6.3 mmol). The resulting suspension was stirred at rt for 24 h and then partitioned between CH$_2$Cl$_2$ (200 mL) and satd. aq. NaHCO$_3$ (80 mL). The organic layer was separated, dried (Na$_2$SO$_4$), filtered and concentrated. Purification by silica gel flash chromatography (EtOAc) afforded the title compound as a white foam (1.1 g, 56%). MS (ESI): mass calcd. for C$_{25}$H$_{29}$N$_3$O$_3$S, 451.19; m/z found, 452.2 [M+H]$^+$. $^1$H NMR (500 MHz, CDCl$_3$, mixture of rotamers): 7.73 (d, J=8.4 Hz, 1H), 7.66 (d, J=7.5 Hz, 1H), 7.38 (m, 1H), 7.30-7.24 (m, 5H), 4.38 (br m, 0.5H), 4.24 (br m, 0.5H), 3.53 (br m, 2H), 3.16 (t, J=10.4 Hz, 1H), 3.03 (d, J=8.4 Hz, 0.5H), 2.98 (d, J=9.8 Hz, 0.5H), 2.86-2.74 (br m, 4H), 2.69 (br d, J=9.8 Hz, 0.5H), 2.52 (br d, J=9.4 Hz, 0.5H), 1.84 (br d, J=9.2 Hz, 1H), 1.73 (br d, J=10.0 Hz, 0.5H), 1.69 (br d, J=9.2 Hz, 0.5H), 1.46 (s, 9H).

Step B (Example 7B): (S,S)-2-{4-[2-(2,5-Diaza-bicyclo[2.2.1]hept-2-yl)-ethyl]-phenoxy}-benzothiazole hydrochloride. This compound was prepared using the methods outlined in Example 1, Step B, substituting (S,S)-5-{2-[4-(benzothiazol-2-yloxy)-phenyl]-ethyl}-2,5-diaza-bicyclo[2.2.1]heptane-2-carboxylic acid tert-butyl ester for (S,S)-5-[4-(benzothiazol-2-yloxy)-benzyl]-2,5-diaza-bicyclo[2.2.1]heptane-2-carboxylic acid tert-butyl ester. MS (ESI): mass calcd. for C$_{20}$H$_{21}$N$_3$OS, 351.14; m/z found, 352.2 [M+H]$^+$. $^1$H NMR (500 MHz, CD$_3$OD): 7.80 (d, J=6.5 Hz, 1H), 7.65 (d, J=7.7 Hz, 1H), 7.52 (br d, J=8.3 Hz, 2H), 7.47-7.37 (m, 3H), 7.33 (m, 1H), 4.73 (br m, 1H), 4.65 (br m, 1H), 3.98 (dd, J=13.9, 2.2 Hz, 1H), 3.80-3.45 (br m, 6H), 3.23 (br m, 2H), 2.67 (br m, 1H), 2.33 (br m, 1H).

Step C: (S,S)-1-(5-{2-[4-(Benzothiazol-2-yloxy)-phenyl]-ethyl}-2,5-diaza-bicyclo[2.2.1]hept-2-yl)-ethanone. This compound was prepared using methods analogous to those outlined in Example 1, Step C. MS (ESI): mass calcd. for C$_{22}$H$_{23}$N$_3$O$_2$S, 393.15; m/z found, 394.2 [M+H]$^+$. $^1$H NMR (500 MHz, CDCl$_3$, mixture of rotamers): 7.73 (d, J=8.1 Hz, 1H), 7.66 (d, J=8.0 Hz, 1H), 7.38 (m, 1H), 7.31-7.24 (m, 5H), 4.76 (br m, 0.5H), 4.22 (br m, 0.5H), 3.69 (dd, J=11.5, 2.2 Hz, 0.5H), 3.61 (m, 1H), 3.56 (dd, J=11.4, 2.2 Hz, 0.5H), 3.31 (dd, J=9.4, 2.2 Hz, 0.5H), 3.26 (dd, J=11.5, 2.2 Hz, 0.5H), 3.12 (dd, J=9.8, 2.1 Hz, 0.5H), 2.95 (dd, J=10.0, 2.2 Hz, 0.5H), 2.87-2.75 (br m, 4H), 2.72 (d, J=9.4 Hz, 0.5H), 2.54 (dd, J=9.3, 2.1 Hz, 0.5H), 2.09 (s, 1.5H), 1.98 (s, 1.5H), 1.96 (br m, 0.5H), 1.89 (br m, 0.5H), 1.80 (br m, 0.5H), 1.68 (br m, 0.5H).

Example 8

(S,S)-1-(5-{2-[3-(Benzothiazol-2-yloxy)-phenyl]-ethyl}-2,5-diaza-bicyclo[2.2.1]hept-2-yl)-ethanone This compound was prepared using the methods outlined in Example 7, substituting the appropriate bromoethyl phenoxy-benzothiazole. MS (ESI): mass calcd. for C$_{23}$H$_{23}$N$_3$O$_3$S, 393.15; m/z found, 394.2 [M+H]$^+$. $^1$H NMR (500 MHz, CDCl$_3$, mixture of rotamers): 7.74 (d, J=8.4 Hz, 1H), 7.67 (d, J=7.1 Hz, 1H), 7.42-7.33 (m, 2H), 7.30-7.25 (m, 1H), 7.23-7.18 (br m, 2H), 7.13 (br d, J=7.3 Hz, 1H), 4.75 (br s, 0.6H), 4.20 (br s, 0.4H), 3.66 (br d, J=13.0 Hz, 0.4H), 3.58 (br s, 1H), 3.53 (br d, J=9.4 Hz, 0.6H), 3.29 (dd, J=9.4, 2.2 Hz, 0.6H), 3.24 (dd, J=11.5, 2.1 Hz, 0.4H.), 3.09 (dd, J=9.4, 2.2 Hz, 0.4H), 2.92 (dd, J=9.6, 2.2 Hz, 0.6H), 2.88-2.75 (br m, 4H), 2.70 (br d, J=9.9 Hz, 0.6H), 2.53 (br d, J=9.2 Hz, 0.4H), 2.07 (s, 1H), 1.95 (s, 2H), 1.92 (br d, J=10.6 Hz, 0.4H), 1.85 (br d, J=9.9 Hz, 0.6H), 1.77 (br d, J=9.9 Hz, 0.4H), 1.65 (br d, J=9.9 Hz, 0.6H).

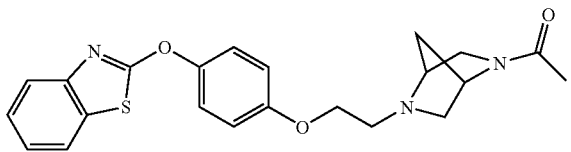

Example 9

(S,S)-1-(5-{2-[4-(Benzothiazol-2-yloxy)-phenoxy]-ethyl}-2,5-diaza-bicyclo[2.2.1]hept-2-yl)-ethanone Step A: (S,S)-5-{2-[4-(Benzothiazol-2-yloxy)-phenoxy]-ethyl}-2,5-diaza-bicyclo[2.2.1]heptane-2-carboxylic acid tert-butyl ester. To a stirred solution of 2-[4-(2-bromo-ethoxy)-phenoxy]-benzothiazole (1.5 g, 4.3 mmol) and (S,S)-2,5-diaza-bicyclo[2.2.1]heptane-2-carboxylic acid tert-butyl ester (1.0 g, 5.1 mmol) in CH$_3$CN (20 mL) at rt was added diisopropylethylamine ((i-Pr)$_2$NEt) (900 μL, 5.1 mmol). The resulting suspension was stirred at rt for 4 h and then heated for 65 h at 60° C. The solution was cooled to rt and then partitioned between CH$_2$Cl$_2$ (200 mL) and satd. aq. NaHCO$_3$ (80 mL). The organic layer was separated, dried (Na$_2$SO$_4$), filtered and concentrated. Purification by silica gel flash chromatography (0% to 5% CH$_3$OH in CH$_2$Cl$_2$) afforded the title compound as a yellow oil (1.8 g, 92%). MS (ESI): mass calcd. for C$_{25}$H$_{29}$N$_3$O$_4$S, 467.19; m/z found, 468.1 [M+H]$^+$. $^1$H NMR (500 MHz, CDCl$_3$): 7.75 (d, J=8.0 Hz, 1H), 7.68-7.66 (m, 1H), 7.42-7.38 (m, 1H), 7.31-7.25 (m, 3H), 6.99-6.95 (m, 2H), 4.40 (br s, 0.5H), 4.27 (br s, 0.5H), 4.13-4.03 (m, 2H), 3.66-3.51 (m, 2H), 3.26-2.97 (m, 4H), 2.78 (d, J=9.5 Hz, 0.5H), 2.63 (d, J=9.7 Hz, 0.5H), 1.92-1.85 (m, 1H), 1.79-1.70 (m, 1H), 1.49 (s, 9H).

Step B: (S,S)-2-{4-[2-(2,5-Diaza-bicyclo[2.2.1]hept-2-yl)-ethoxy]-phenoxy}-benzothiazole trifluoroacetate. To a stirred solution of (S,S)-5-{2-[4-(benzothiazol-2-yloxy)-phenoxy]-ethyl}-2,5-diaza-bicyclo[2.2.1]heptane-2-carboxylic acid tert-butyl ester (1.7 g, 3.6 mmol) in CH$_2$Cl$_2$ (15 mL) was added trifluoroacetic acid (5 mL, 65 mmol). The resulting solution was stirred at rt for 8.5 h. The solution was concentrated to provide the title compound as an oil and used as a crude compound. MS (ESI): mass calcd. for C$_{20}$H$_{21}$N$_3$O$_2$S, 367.14; m/z found, 368.2 [M+H]$^+$. $^1$H NMR (400 MHz, CDCl$_3$, mixture of rotamers): 7.73 (d, J=7.9 Hz, 1H), 7.65 (d, J=7.9 Hz, 1H), 7.38 (t, J=7.7 Hz, 1H), 7.29-7.23 (m, 3H), 6.99-6.91 (m, 2H), 4.13-4.01 (m, 2H), 3.56-3.39 (m, 2H), 3.35-3.32 (m, 1H), 3.20 (d, J=10.4 Hz, 0.5H), 3.09 (dd, J=9.7, 2.4 Hz, 0.5H), 3.06-2.82 (m, 3.5H), 2.76-2.67 (m, 1H), 2.50 (dd, J=9.6, 1.1 Hz, 0.5H), 1.88-1.57 (m, 2H).

Step C: (S,S)-1-(5-{2-[4-(Benzothiazol-2-yloxy)-phenoxy]-ethyl}-2,5-diaza-bicyclo[2.2.1]hept-2-yl)-ethanone. This compound was prepared using methods analogous to those outlined in Example 1, Step C. MS (ESI): mass calcd. for C$_{22}$H$_{23}$N$_3$O$_3$S, 409.15; m/z found, 410.2 [M+H]$^+$. $^1$H NMR (400 MHz, CDCl$_3$, mixture of rotamers): 7.73 (d, J=8.1 Hz, 1H), 7.66 (d, J=8.0 Hz, 1H), 7.40 (d, J=1.2 Hz, 0.25H), 7.38 (s, 0.5H), 7.36 (d, J=1.2 Hz, 0.25H), 7.30-7.24 (m, 3H), 6.97-6.93 (m, 2H), 4.77 (s, 0.5H), 4.23 (s, 0.5H), 4.11-4.02 (m, 2H), 3.75-3.68 (m, 1.5H), 3.61 (dd, J=9.5, 1.2 Hz, 0.5H), 3.32 (ddd, J=13.5, 10.5, 2.1 Hz, 1H), 3.21 (dd, J=9.6, 2.1 Hz, 0.5H), 3.06-2.94 (m, 2.75H), 2.81 (dd, J=9.7, 0.9 Hz, 0.5H), 2.65 (dd, J=9.6, 1.3 Hz, 0.5H), 2.10 (s, 1.25H), 2.00 (s, 1.75H), 1.97 (s, 0.25H), 1.90 (d, J=10.0 Hz, 0.5H), 1.81 (d, J=9.7 Hz, 0.5H), 1.70 (d, J=9.9 Hz, 0.5H).

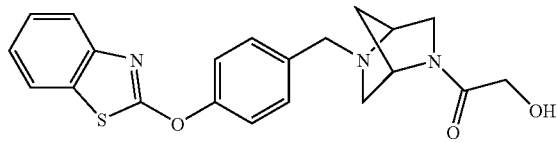

Example 10

(S,S)-1-{5-[4-(Benzothiazol-2-yloxy)-benzyl]-2,5-diaza-bicyclo[2.2.1]hept-2-yl}-2-hydroxy-ethanone To a stirred suspension of (S,S)-2-[4-(2,5-diaza-bicyclo[2.2.1]hept-2-ylmethyl)-phenoxy]-benzothiazole hydrochloride (1.6 g, 3.9 mmol), glycolic acid (600 mg, 7.8 mmol), and 1-(3-dimethylaminopropyl)-3-ethylcarbodiimide hydrochloride (1.5 g, 7.8 mmol) in CH$_2$Cl$_2$ (15 mL) was added Et$_3$N (2.7 mL, 19.5 mmol). The resulting solution was then stirred at rt for 16 h. The resulting white suspension was partitioned between CH$_2$Cl$_2$ (600 mL) and satd. aq. NaHCO$_3$ (100 mL). The organic layer was separated, dried (Na$_2$SO$_4$), filtered and concentrated. Purification by silica gel flash chromatography (0% to 5% CH$_3$OH in CH$_2$Cl$_2$) afforded the title compound as a white solid (853 mg, 55%). MS (ESI): mass calcd. for C$_{21}$H$_{21}$N$_3$O$_3$S, 395.13; m/z found, 396.2 [M+H]$^+$. $^1$H NMR (500 MHz, CDCl$_3$, mixture of rotamers): 7.73 (d, J=8.5 Hz, 1H), 7.67 (d, J=8.0 Hz, 1H), 7.41 (m, 2H), 7.38 (m, 1H), 7.32 (br m, 2H), 7.28 (m, 1H), 4.83 (br m, 0.5H), 4.21 (br d, J=14.5 Hz, 0.5H), 4.10-3.99 (br m, 2H), 3.80 (br d, J=11.7 Hz, 0.5H), 3.76 (d, J=13.8 Hz, 2H), 3.61 (br s, 1H), 3.50 (br s, 0.5H), 3.48-3.45 (m, 0.5H), 3.42 (br s, 0.5H), 3.39-3.35 (m, 0.5H), 3.23 (dd, J=9.2, 2.3 Hz, 0.5H), 3.01 (dd, J=9.7, 2.1 Hz, 0.5H), 2.90 (dd, J=9.8, 2.2 Hz, 0.5H), 2.81-2.77 (m, 0.5H), 2.58 (dd, J=9.7, 1.2 Hz, 0.5H), 2.07-2.01 (m, 0.5H), 2.00-1.96 (m, 0.5H), 1.80 (d, J=9.8 Hz, 0.5H), 1.70 (d, J=10.0 Hz, 0.5H).

Alternative Preparation:

Step A: 5-(2-Acetoxy-acetyl)-2,5-diaza-bicyclo[2.2.1]heptane-2-carboxylic acid tert-butyl ester. A solution of (S,S)-Boc-[2.2.1]diazobicycloheptane (150.6 g, 0.76 mol) in CH$_2$Cl$_2$ (1.5 L) was cooled to 5° C. and Et$_3$N (117 mL, 0.84 mol) was added. Over 50 min was then added acetoxy acetyl chloride (82 mL, 0.76 mol). The ice bath was removed and the heterogeneous mixture was stirred for 16 h. The reaction mixture was then poured over 9 wt % NaHCO$_{3(aq)}$ solution (1.5 L) and the layers were mixed and separated. The organic layer was washed with 26 wt % NaCl(aq) (1.5 L), dried (Na$_2$SO$_4$), filtered, and concentrated to provide the title compound as a white solid (217 g, 96%). $^1$H NMR (600 MHz, DMSO-d$_6$, 100° C.): 4.75-4.41 (m, 4H), 3.50-3.46 (m, 4H), 2.86 (s, 2H), 2.04 (s, 3H), 1.85-1.72 (m, 2H), 1.41 (s, 9H).

Step B: 1-(2,5-Diaza-bicyclo[2.2.1]hept-2-yl)-2-hydroxy-ethanone hydrochloride. To a slurry of 5-(2-acetoxy-acetyl)-2,5-diaza-bicyclo[2.2.1]heptane-2-carboxylic acid tert-butyl ester (1.2 g, 4 mmol) in isopropanol (16 mL) was quickly added 5 M HCl in isopropanyl (3.2 mL, 16 mmol). The mixture was warmed to 51° C. and stirred for 20 h. It was then concentrated to provide the title compound in 97 wt % purity (767 mg, 96%). MS (ESI): mass calcd. for C$_7$H$_{12}$N$_2$O$_2$, 156.1; m/z found, 157.1 [M+H]$^+$. $^1$H NMR (600 MHz, DMSO-d$_6$): 9.9-9.2 (m, 2H), 4.73-4.71 (m, 1H), 4.42-4.37 (m, 1H), 4.1-3.9 (m, 2H), 3.79-3.77 (m, 0.5H), 3.55-3.48 (m, 1H), 3.37-3.35 (m, 0.5H), 3.25-3.07 (m, 2H), 2.00-1.82 (m, 2H).

Step C. A mixture of 4-(benzothiazol-2-yloxy)-benzaldehyde (67 g, 0.26 mol), 1-(2,5-diaza-bicyclo[2.2.1]hept-2-yl)-2-hydroxy-ethanone hydrochloride (40.61 g, 0.26 mol), Et$_3$N (183 mL, 1.31 mol), and N-methylpyrrolidinone (150 mL) in dichloroethane (750 mL) was stirred at rt for 1 h. Sodium triacetoxyborohydride (66.63 g, 0.314 mol) was then added in four equal portions over a 4 h period. After stirring overnight, the mixture was quenched with 3 N HCl$_{(aq)}$ (250 mL) and then 6 N HCl$_{(aq)}$ (3×50 mL) to a final pH of 0.54. The layers were separated and the organic was extracted again with 3 N HCl$_{(aq)}$ (250 mL). The combined aqueous layers were basified with Na$_2$CO$_3$ (50 g) and then 50% NaOH$_{(aq)}$ (130 mL) to a final pH of 13.2. After stirring for 1 h, isopropyl acetate (200 mL) was added and the mixture was stirred for 20 min. After separation of layers, the aqueous was extracted with additional isopropyl acetate (2×200 mL) and the organic layers were combined with an interstitial oil and concentrated. The resulting brown oil was purified by flash chromatography (0-5% MeOH in CH$_2$Cl$_2$) to provide the product as a clear oil (93.84 g, 91%).

The compounds in Examples 11-20 were prepared using methods analogous to those described in Example 10, utilizing the appropriate carboxylic acid in the coupling reaction.

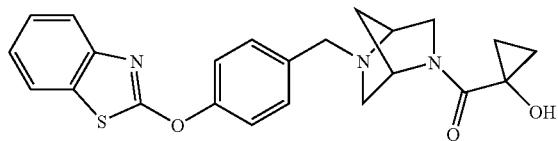

Example 11

(S,S)-{5-[4-(Benzothiazol-2-yloxy)-benzyl]-2,5-diaza-bicyclo[2.2.1]hept-2-yl}-(1-hydroxy-cyclopropyl)-methanone MS (ESI): mass calcd. for $C_{23}H_{23}N_3O_3S$, 421.15; m/z found, 422.2 [M+H]$^+$. $^1$H NMR (400 MHz, CDCl$_3$, mixture of rotamers): 7.73 (d, J=7.9 Hz, 1H), 7.66 (d, J=8.0 Hz, 1H), 7.45-7.35 (m, 3H), 7.33-7.24 (m, 3H), 5.09 (br s, 0.5H), 4.72 (br s, 0.5H), 4.09-4.00 (m, 0.5H), 3.76 (s, 2H), 3.71-3.57 (m, 1H), 3.55 (br s, 1H), 3.35 (d, J=10.8 Hz, 0.5H), 3.06-2.70 (m, 2H), 2.01-1.86 (m, 1H), 1.77-1.65 (m, 1H), 1.27 (br m, 1H), 1.15 (br m, 1H), 1.09-0.81 (br m, 3H).

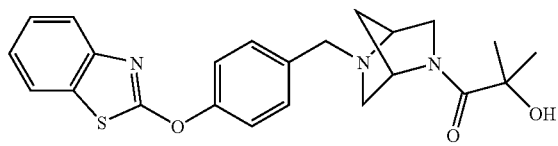

Example 12

(S,S)-1-{5-[4-(Benzothiazol-2-yloxy)-benzyl]-2,5-diaza-bicyclo[2.2.1]hept-2-yl}-2-hydroxy-2-methyl-propan-1-one MS (ESI): mass calcd. for $C_{23}H_{25}N_3O_3S$, 423.16; m/z found, 424.2 [M+H]$^+$. $^1$H NMR (500 MHz, CDCl$_3$, mixture of rotamers): 7.73 (d, J=8.3 Hz, 1H), 7.67 (d, J=8.7 Hz, 1H), 7.43-7.36 (m, 3H), 7.33-7.24 (m, 3H), 4.86 (br m, 0.33H), 4.65 (br m, 0.67H), 4.22 (s, 1H), 3.84 (m, 0.33H), 3.79-3.71 (m, 3H), 3.57 (br m, 1H), 3.48 (br m, 0.33H), 3.37 (br m, 0.67H), 3.02 (br m, 0.67H), 2.90 (br m, 0.33H), 2.73 (m, 0.33H), 2.60 (br m, 0.67H), 2.00 (br m, 0.67H), 1.92 (m, 0.33H), 1.76 (br m, 0.67H), 1.68 (br m, 0.33H), 1.52-1.42 (m, 5.67H).

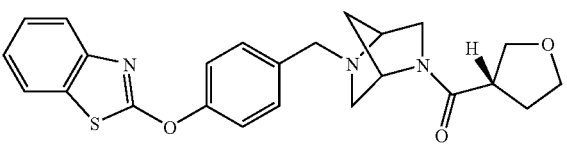

Example 13

(S,S,S)-{5-[4-(Benzothiazol-2-yloxy)-benzyl]-2,5-diaza-bicyclo[2.2.1]hept-2-yl}-(tetrahydro-furan-3-yl)-methanone MS (ESI): mass calcd. for $C_{24}H_{25}N_3O_3S$, 435.16; m/z found, 436.2 [M+H]$^+$. $^1$H NMR (500 MHz, CDCl$_3$, mixture of rotamers): 7.73 (d, J=8.0 Hz, 1H), 7.67 (d, J=7.7 Hz, 1H), 7.44-7.36 (m, 3H), 7.34-7.25 (m, 3H), 4.81 (br m, 0.5H), 4.34 (br m, 0.5H), 4.08 (br m, 1H), 3.93 (m, 1H), 3.86 (m, 2H), 3.78 (s, 1H), 3.74 (m, 1.5H), 3.58 (br m, 1.5H), 3.39 (dd, J=8.5, 2.2 Hz, 0.5H), 3.30 (dd, J=11.5, 2.2 Hz, 0.5H), 3.13 (m, 0.5H), 3.03 (m, 0.5H), 2.86 (dd, J=9.3, 2.2 Hz, 0.5H), 2.74 (d, J=9.9 Hz, 0.5H), 2.57 (d, J=9.3 Hz, 0.5H), 2.29 (m, 0.5H), 2.21 (m, 0.5H), 2.06 (m, 1H), 2.01 (d, J=9.9 Hz, 0.5H), 1.92 (d, J=9.9 Hz, 0.5H), 1.79 (d, J=9.4 Hz, 0.5H), 1.92 (d, J=9.9 Hz, 0.5H), 1.67 (d, J=9.9 Hz, 0.5H).

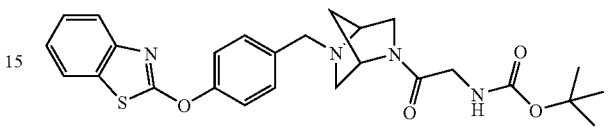

Example 14

(S,S)-(2-{5-[4-(Benzothiazol-2-yloxy)-benzyl]-2,5-diaza-bicyclo[2.2.1]hept-2-yl}-2-oxo-ethyl)-carbamic acid tert-butyl ester MS (ESI): mass calcd. for $C_{26}H_{30}N_4O_4S$, 494.20; m/z found, 495.2 [M+H]$^+$. $^1$H NMR (500 MHz, CDCl$_3$, mixture of rotamers): 7.73 (d, J=8.1 Hz, 1H), 7.67 (d, J=7.9 Hz, 1H), 7.44-7.36 (m, 3H), 7.35-7.24 (m, 3H), 5.46 (br m, 1H), 4.79 (br m, 0.5H), 4.23 (br m, 0.5H), 3.99 (dd, J=12.9, 4.5 Hz, 0.5H), 3.91-3.80 (m, 1.5H), 3.75 (m, 2.5H), 3.58 (br m, 1.5H), 3.30 (m, 1H), 2.98 (br d, J=9.8 Hz, 0.5H), 2.87 (dd, J=9.9, 2.1 Hz, 0.5H), 2.72 (br d, J=9.4 Hz, 0.5H), 2.58 (br d, J=9.7 Hz, 0.5H), 2.01 (br d, J=9.4 Hz, 0.5H), 1.94 (br d, J=9.8 Hz, 0.5H), 1.78 (br d, J=9.8 Hz, 0.5H), 1.67 (br d, J=9.8 Hz, 0.5H), 1.47 (s, 9H).

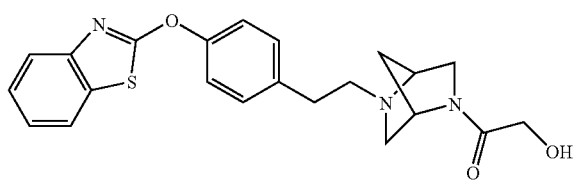

Example 15

(S,S)-1-(5-{2-[4-(Benzothiazol-2-yloxy)-phenyl]-ethyl}-2,5-diaza-bicyclo[2.2.1]hept-2-yl)-2-hydroxy-ethanone MS (ESI): mass calcd. for $C_{22}H_{23}N_3O_3S$, 409.14; m/z found, 410.2 [M+H]$^+$. $^1$H NMR (500 MHz, CDCl$_3$, mixture of rotamers): 7.73 (d, J=8.3 Hz, 1H), 7.66 (d, J=8.8 Hz, 1H), 7.38 (t, J=8.2 Hz, 1H), 7.31-7.23 (m, 5H), 4.81 (br s, 1H), 4.21 (br d, J=14.8 Hz, 0.5H), 4.09-3.96 (br m, 2H), 3.74 (br d, J=11.2 Hz, 0.5H), 3.64 (br s, 1H), 3.43 (br d, J=9.4 Hz, 0.5H), 3.33 (br d, J=11.1 Hz, 0.5H), 3.20 (dd, J=9.3, 2.2 Hz, 0.5H), 3.08 (dd, J=9.4, 2.3 Hz, 0.5H), 2.97 (dd, J=9.7, 2.2 Hz, 1H), 2.89-2.75 (br m, 4H), 2.73 (br d, J=9.8 Hz, 0.5H), 2.54 (br d, J=10.1 Hz, 0.5H), 1.98 (br d, J=9.8 Hz, 0.5H), 1.93 (br d, J=9.8 Hz, 0.5H), 1.77 (br d, J=9.9 Hz, 0.5H), 1.68 (br d, J=10.6 Hz, 0.5H).

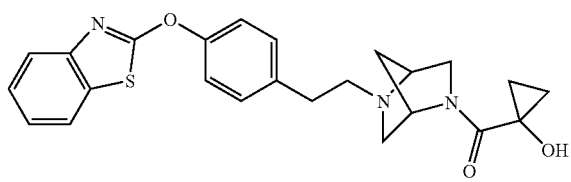

Example 16

(S,S)-(5-{2-[4-(Benzothiazol-2-yloxy)-phenyl]-ethyl}-2,5-diaza-bicyclo[2.2.1]hept-2-yl)-(1-cyclopropyl)-methanone MS (ESI): mass calcd. for $C_{24}H_{25}N_3O_3S$, 435.16; m/z found, 436.2 [M+H]$^+$. $^1$H NMR (500 MHz, CDCl$_3$, mixture of rotamers): 7.72 (d, J=8.1 Hz, 1H), 7.65 (d, J=8.1 Hz, 1H), 7.38 (t, J=7.4 Hz, 1H), 7.30-7.23 (m, 5H), 5.08 (br s, 0.5H), 4.71 (br s, 1.5H), 4.02 (br m, 0.5H), 3.67 (br m, 0.5H), 3.56 (br m, 1.5H), 3.33 (br m, 0.5H), 2.97 (br m, 1H), 2.86-2.67 (br m, 5H), 1.94-1.81 (br m, 1H), 1.76-1.63 (br m, 1H), 1.26 (br s, 1H), 1.15-0.84 (br m, 3H).

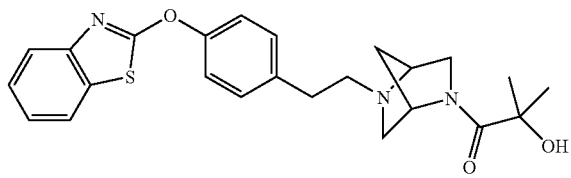

Example 17

(S,S)-1-(5-{2-[4-(Benzothiazol-2-yloxy)-phenyl]-ethyl}-2,5-diaza-bicyclo[2.2.1]hept-2-yl)-2-hydroxy-2-methyl-propan-1-one MS (ESI): mass calcd. for $C_{24}H_{27}N_3O_3S$, 437.17; m/z found, 438.2 [M+H]$^+$. $^1$H NMR (500 MHz, CDCl$_3$, mixture of rotamers): 7.73 (d, J=8.1 Hz, 1H), 7.66 (d, J=8.3 Hz, 1H), 7.38 (t, J=8.8 Hz, 1H), 7.30-7.23 (m, 5H), 4.83 (br s, 0.5H), 4.66 (br s, 0.5H), 4.19 (br s, 1H), 3.81 (br d, J=9.5 Hz, 0.5H), 3.66 (br d, J=11.6 Hz, 0.5H), 3.61-3.56 (br m, 1H), 3.46 (br d, J=9.2 Hz, 0.5H), 3.35 (br d, J=11.6 Hz, 0.5H), 3.09 (br d, J=8.7 Hz, 0.5H), 2.99 (br d, J=9.3 Hz, 0.5H), 2.91-2.74 (br m, 4H), 2.67 (br d, J=9.4 Hz, 0.5H), 2.59 (br d, J=10.0 Hz, 0.5H), 1.98-1.83 (br m, 1H), 1.77-1.64 (br m, 1H), 1.47 (s, 6H).

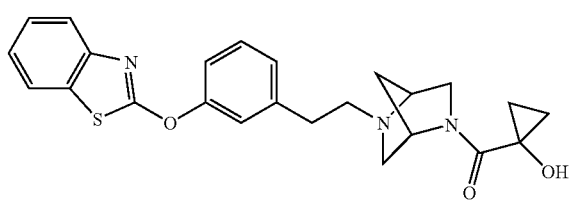

Example 18

(S,S)-(5-{2-[3-(Benzothiazol-2-yloxy)-phenyl]-ethyl}-2,5-diaza-bicyclo[2.2.1]hept-2-yl)-(1-hydroxy-cyclopropyl)-methanone MS (ESI): mass calcd. for $C_{24}H_{25}N_3O_3S$, 435.16; m/z found, 436.2 [M+H]$^+$. $^1$H NMR (500 MHz, CDCl$_3$, mixture of rotamers): 7.74 (d, J=7.7 Hz, 1H), 7.67 (d, J=6.9 Hz, 1H), 7.41-7.32 (m, 2H), 7.29-7.26 (m, 1H), 7.22-7.18 (br m, 2H), 7.13 (br d, J=7.2 Hz, 1H), 5.00 (br s, 0.5H), 4.69 (br s, 0.5H), 3.97 (br s, 0.5H), 3.65-3.54 (br m, 2H), 3.33 (br s, 0.5H), 3.09-2.91 (br m, 1H), 2.89-2.76 (br m, 4H), 2.69 (d, J=9.2 Hz, 1H), 1.88 (br s, 1H), 1.69 (br s, 2H), 1.36-1.28 (br m, 1H), 1.14-0.87 (br m, 3H).

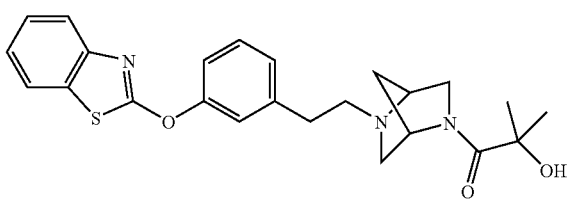

Example 19

(S,S)-1-(5-{2-[3-(Benzothiazol-2-yloxy)-phenyl]-ethyl}-2,5-diaza-bicyclo[2.2.1]hept-2-yl)-2-hydroxy-2-methyl-propan-1-one MS (ESI): mass calcd. for $C_{24}H_{27}N_3O_3S$, 437.17; m/z found, 438.2 [M+H]$^+$. $^1$H NMR (500 MHz, CDCl$_3$, mixture of rotamers): 7.74 (d, J=8.4 Hz, 1H), 7.67 (d, J=8.9 Hz, 1H), 7.41-7.33 (m, 2H), 7.28 (m, 1H), 7.23-7.18 (m, 2H), 7.13 (br d, J=7.0 Hz, 1H), 4.82 (br s, 0.5H), 4.61 (br s, 0.5H), 4.12 (br s, 1H), 3.78 (br d, J=9.4 Hz, 0.5H), 3.65 (br d, J=11.7 Hz, 0.5H), 3.57 (s, 1H), 3.44 (br d, J=9.3 Hz, 0.5H), 3.34 (br d, J=11.4 Hz, 0.5H), 3.08 (br d, J=9.1 Hz, 0.5H), 2.97 (br d, J=9.8 Hz, 0.5H), 2.90-2.74 (br m, 4H), 2.65 (br d, J=9.9 Hz, 0.5H), 2.57 (br d, J=9.3 Hz, 0.5H), 1.93 (br d, J=9.8 Hz, 0.5H), 1.86 (br d, J=9.3 Hz, 0.5H), 1.75-1.69 (m, 1H), 1.49-1.34 (m, 6H).

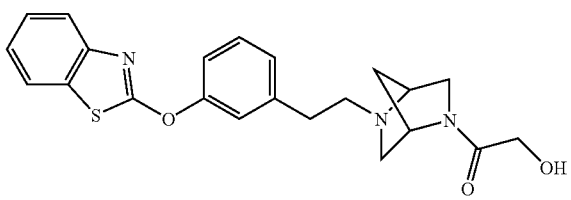

Example 20

(S,S)-1-(5-{2-[3-(Benzothiazol-2-yloxy)-phenyl]-ethyl}-2,5-diaza-bicyclo[2.2.1]hept-2-yl)-2-hydroxy-ethanone MS (ESI): mass calcd. for $C_{22}H_{23}N_3O_3S$, 409.14; m/z found, 410.2 [M+H]$^+$. $^1$H NMR (500 MHz, CDCl$_3$, mixture of rotamers): 7.73 (d, J=7.8 Hz, 1H), 7.67 (d, J=9.1 Hz, 1H), 7.41-7.34 (m, 2H), 7.28 (m, 1H), 7.23-7.18 (m, 2H), 7.13 (d, J=7.7 Hz, 1H), 4.78 (br s, 0.5H), 4.19 (br d, J=14.8 Hz, 0.5H), 4.05-3.94 (br m, 2H), 3.71 (br d, J=11.6 Hz, 0.5H), 3.60 (br s, 1H), 3.39 (dd, J=9.3, 1.1 Hz, 0.5H), 3.31 (dd, J=11.1, 2.4 Hz, 0.5H), 3.17 (dd, J=9.3, 2.2 Hz, 0.5H), 3.05 (dd, J=9.7, 2.2 Hz, 0.5H), 2.94 (dd, J=10.1, 2.2 Hz, 0.5H), 2.89-2.73 (br m, 4H), 2.70 (br d, J=9.8 Hz, 0.5H), 2.51 (dd, J=9.4, 1.2 Hz, 0.5H), 1.95 (br d, J=9.2 Hz, 0.5H), 1.90 (br d, J=9.9 Hz, 0.5H), 1.74 (br d, J=9.4 Hz, 0.5H), 1.65 (br d, J=9.8 Hz, 0.5H), 1.26 (s, 1H).

The compounds in Examples 21-28 were prepared using methods analogous to those described for Example 10, using the appropriate carboxylic acid, by replacing Et$_3$N with (iPr)$_2$NEt and by adding 1-hydroxybenzotriazole (HOBt) as a coupling reagent.

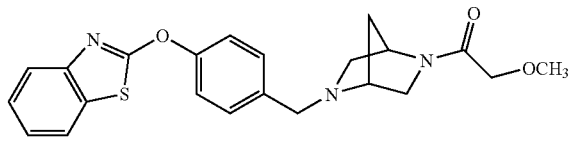

Example 21

(R,R)-1-{5-[4-(Benzothiazol-2-yloxy)-benzyl]-2,5-diaza-bicyclo[2.2.1]hept-2-yl}-2-methoxy-ethanone MS (ESI): mass calcd. for C$_{22}$H$_{23}$N$_3$O$_3$S, 409.15; m/z found, 410.2 [M+H]$^+$. $^1$H NMR (400 MHz, CDCl$_3$, mixture of rotamers): 7.74 (d, J=8.1 Hz, 1H), 7.68 (d, J=8.1 Hz, 1H), 7.45-7.35 (m, 3H), 7.35-7.28 (m, 2.5H), 7.28-7.24 (m, 0.5H), 4.83 (s, 0.5H), 4.46 (s, 0.5H), 4.10-4.04 (m, 1H), 4.03-3.99 (m, 1H), 3.76 (d, J=10.5 Hz, 2.5H), 3.65-3.53 (m, 1.5H), 3.44 (dd, J=11.9, 3.7 Hz, 3H), 3.36-3.31 (m, 1H), 3.01 (dd, J=9.7, 2.2 Hz, 0.5H), 2.87 (dd, J=9.8, 2.2 Hz, 0.5H), 2.78 (d, J=9.7 Hz, 0.5H), 2.57 (dd, J=9.8, 0.9 Hz, 0.5H), 2.00 (d, J=8.0 Hz, 0.5H), 1.94 (d, J=8.0 Hz, 0.5H), 1.77 (d, J=8.0 Hz, 0.5H), 1.67 (d, J=8.0 Hz, 0.5H).

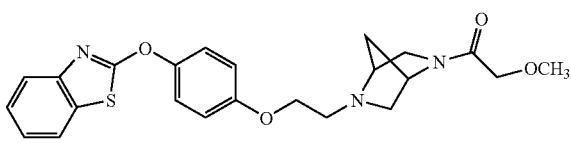

Example 22

(S,S)-1-(5-{2-[4-(Benzothiazol-2-yloxy)-phenoxy]-ethyl}-2,5-diaza-bicyclo[2.2.1]hept-2-yl)-2-methoxy-ethanone MS (ESI): mass calcd. for C$_{23}$H$_{25}$N$_3$O$_4$S, 439.16; m/z found, 440.2 [M+H]$^+$. $^1$H NMR (400 MHz, CDCl$_3$, mixture of rotamers): 7.73 (d, J=7.8 Hz, 1H), 7.66 (d, J=8.5 Hz, 1H), 7.40 (d, J=1.2 Hz, 0.25H), 7.38 (s, 0.5H), 7.36 (d, J=1.2 Hz, 0.25H), 7.30-7.22 (m, 3H), 6.98-6.91 (m, 2H), 4.81 (s, 0.5H), 4.45 (s, 0.5H), 4.12-4.02 (m, 3H), 3.99 (s, 1H), 3.76-3.61 (m, 2H), 3.44 (d, J=2.9 Hz, 3H), 3.38-3.33 (m, 1H), 3.19 (dd, J=9.7, 2.2 Hz, 0.5H), 3.06-2.92 (m, 2.5H), 2.80 (d, J=9.8 Hz, 0.5H), 2.65 (dd, J=9.7, 1.1 Hz, 0.5H), 1.97 (d, J=9.6 Hz, 0.5H), 1.92 (d, J=10.4 Hz, 0.5H), 1.76 (d, J=9.7 Hz, 0.5H), 1.69 (d, J=10.0 Hz, 0.5H).

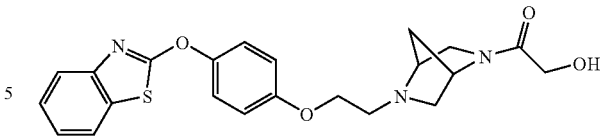

Example 23

(S,S)-1-(5-{2-[4-(Benzothiazol-2-yloxy)-phenoxy]-ethyl}-2,5-diaza-bicyclo[2.2.1]hept-2-yl)-2-hydroxy-ethanone MS (ESI): mass calcd. for C$_{22}$H$_{23}$N$_3$O$_4$S, 425.14; m/z found, 426.1 [M+H]$^+$. $^1$H NMR (500 MHz, CDCl$_3$, mixture of rotamers): 7.74 (d, J=7.7 Hz, 1H), 7.66 (d, J=7.9 Hz, 1H), 7.41 (d, J=1.2 Hz, 0.25H), 7.39 (s, 0.5H), 7.37 (d, J=1.2 Hz, 0.25H), 7.30-7.25 (m, 3H), 6.98-6.92 (m, 2H), 4.81 (s, 0.5H), 4.23 (d, J=14.0 Hz, 0.5H), 4.12-3.97 (m, 4H), 3.82-3.70 (m, 1.5H), 3.55 (s, 0.5H), 3.51-3.43 (m, 1H), 3.38 (dd, J=11.4, 1.9 Hz, 0.5H), 3.24 (dd, J=9.4, 2.2 Hz, 0.5H), 3.19 (dd, J=9.8, 2.1 Hz, 0.5H), 3.09-2.92 (m, 2.5H), 2.82 (d, J=9.8 Hz, 0.5H), 2.64 (dd, J=9.8, 1.2 Hz, 0.5H), 2.00 (d, J=10.0 Hz, 0.5H), 1.94 (d, J=10.0 Hz, 0.5H), 1.79 (d, J=9.8 Hz, 0.5H), 1.71 (d, J=10.0 Hz, 0.5H).

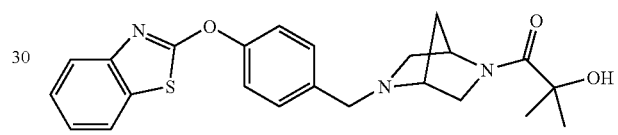

Example 24

(R,R)-1-{5-[4-(Benzothiazol-2-yloxy)-benzyl]-2,5-diaza-bicyclo[2.2.1]hept-2-yl}-2-hydroxy-2-methyl-propan-1-one MS (ESI): mass calcd. for C$_{23}$H$_{25}$N$_3$O$_3$S, 423.16; m/z found, 424.2 [M+H]$^+$. $^1$H NMR (500 MHz, CDCl$_3$, mixture of rotamers): 7.76-7.74 (m, 1H), 7.69 (dd, J=8.0, 0.7 Hz, 1H), 7.46-7.39 (m, 3H), 7.36-7.29 (m, 3H), 4.89 (s, 0.5H), 4.66 (s, 0.5H), 4.22 (s, 1H), 3.89-3.72 (m, 3H), 3.60 (s, 1H), 3.52-3.38 (m, 0.5H), 3.07-3.03 (m, 0.5H), 2.95-2.91 (m, 0.5H), 2.77-2.73 (m, 0.5H), 2.62 (d, J=9.4 Hz, 0.5H), 2.03 (d, J=10.2 Hz, 0.5H), 1.97-1.92 (m, 0.5H), 1.79 (d, J=10.1 Hz, 0.5H), 1.73-1.65 (m, 1H), 1.54-1.45 (m, 6H).

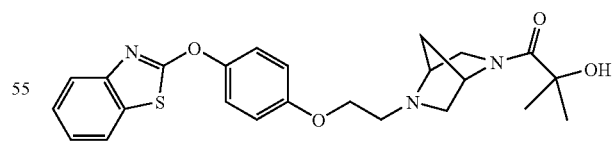

Example 25

(S,S)-1-(5-{2-[4-(Benzothiazol-2-yloxy)-phenoxy]-ethyl}-2,5-diaza-bicyclo[2.2.1]hept-2-yl)-2-hydroxy-2-methyl-propan-1-one MS (ESI): mass calcd. for C$_{24}$H$_{27}$N$_3$O$_4$S, 453.17; m/z found, 454.2 [M+H]$^+$. $^1$H NMR (400 MHz, CDCl$_3$, mixture of rotamers): 7.73 (d, J=8.1 Hz, 1H), 7.66 (d, J=8.0 Hz, 1H), 7.40 (d, J=1.3 Hz, 0.25H), 7.39-7.38 (m, 0.5H), 7.36 (d, J=1.3 Hz, 0.25H), 7.30-7.23 (m, 3H), 6.98-6.92 (m, 2H), 4.85 (s, 0.5H), 4.64 (s, 0.5H), 4.19 (s, 1H), 4.12-4.03 (m, 2H), 3.88 (d, J=9.9 Hz, 0.5H), 3.75-3.65 (m, 1.5H), 3.50 (d, J=8.9 Hz, 0.5H), 3.40 (dd, J=11.8, 1.9 Hz, 0.5H), 3.21 (dd, J=9.8, 2.0 Hz, 0.5H), 3.09 (d, J=8.6 Hz, 0.5H), 3.05-2.95 (m, 2H), 2.74 (d, J=10.0 Hz, 0.5H), 2.68 (d, J=10.0 Hz, 0.5H), 2.03-1.89 (m, 1H), 1.82-1.66 (m, 1H), 1.48-1.44 (m, 6H).

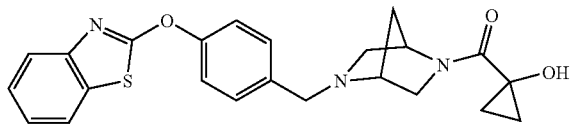

Example 26

(R,R)-{5-[4-(Benzothiazol-2-yloxy)-benzyl]-2,5-diaza-bicyclo[2.2.1]hept-2-yl}-(1-hydroxy-cyclopropyl)-methanone MS (ESI): mass calcd. for $C_{23}H_{23}N_3O_3S$, 421.15; m/z found, 422.2 [M+H]$^+$. $^1$H NMR (500 MHz, CDCl$_3$, mixture of rotamers): 7.75 (d, J=8.1 Hz, 1H), 7.69 (d, J=8.0 Hz, 1H), 7.46-7.38 (m, 3H), 7.35-7.27 (m, 3H), 5.08 (br s, 0.5H), 4.75 (br s, 0.5H), 4.13-3.99 (m, 0.5H), 3.80 (br s, 2H), 3.71-3.63 (m, 1H), 3.57 (br s, 1H), 3.42-3.34 (m, 0.5H), 3.06-2.97 (m, 0.5H), 2.95-2.87 (m, 0.5H), 2.78-2.73 (m, 1H), 2.03-1.89 (m, 1H), 1.81-1.67 (m, 1H), 1.42-1.29 (m, 1H), 1.23-1.09 (m, 1H), 1.08-1.01 (m, 2H), 1.00-0.90 (m, 1H).

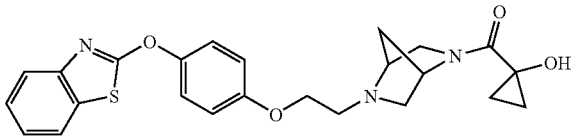

Example 27

(S,S)-(5-{2-[4-(Benzothiazol-2-yloxy)-phenoxy]-ethyl}-2,5-diaza-bicyclo[2.2.1]hept-2-yl)-(1-hydroxy-cyclopropyl)-methanone MS (ESI): mass calcd. for $C_{24}H_{25}N_3O_4S$, 451.16; m/z found, 452.2 [M+H]$^+$. $^1$H NMR (400 MHz, CDCl$_3$, mixture of rotamers): 7.73 (d, J=7.6 Hz, 1H), 7.65 (d, J=7.9 Hz, 1H), 7.40 (d, J=1.3 Hz, 0.25H), 7.38 (s, 0.5H), (d, J=1.3 Hz, 0.25H), 7.29-7.24 (m, 3H), 6.97-6.93 (m, 2H), 5.06 (s, 0.5H), 4.71 (s, 0.5H), 4.11-4.03 (m, 2H), 3.67-3.60 (m, 2H), 3.37 (d, J=11.1 Hz, 0.5H), 3.14 (d, J=8.7 Hz, 0.5H), 3.05-2.95 (m, 2H), 2.86-2.76 (m, 1H), 1.96-1.89 (m, 1H), 1.73 (s, 2H), 1.30 (s, 1H), 1.17-0.87 (m, 3H).

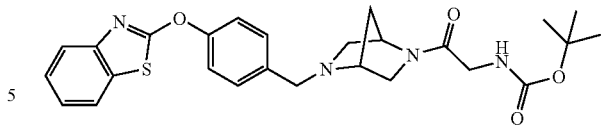

Example 28

(R,R)-(2-{5-[4-(Benzothiazol-2-yloxy)-benzyl]-2,5-diaza-bicyclo[2.2.1]hept-2-yl}-2-oxo-ethyl)-carbamic acid tert-butyl ester MS (ESI): mass calcd. for $C_{26}H_{30}N_4O_4S$, 494.20; m/z found, 495.2 [M+H]$^+$. $^1$H NMR (400 MHz, CDCl$_3$, mixture of rotamers): 7.74 (d, J=7.7 Hz, 1H), 7.68 (d, J=8.0 Hz, 1H), 7.43-7.36 (m, 3H), 7.33-7.25 (m, 3H), 5.50-5.41 (m, 1H), 4.79 (s, 0.54H), 4.24 (s, 0.5H), 4.04-3.80 (m, 2H), 3.72-3.78 (m, 2.5H), 3.62-3.54 (m, 1.5H), 3.34-3.26 (m, 1H), 2.99 (dd, J=9.8, 2.0 Hz, 0.5H), 2.87 (dd, J=9.8, 2.1 Hz, 0.5H), 2.72 (d, J=9.7 Hz, 0.5H), 2.59 (d, J=9.6 Hz, 0.5H), 2.01 (d, J=9.8 Hz, 0.5H), 1.95 (d, J=10.0 Hz, 0.5H), 1.79 (d, J=9.5 Hz, 0.5H), 1.68 (d, J=9.8 Hz, 0.5H), 1.45 (s, 9H).

Example 29

(R,R)-2-Amino-1-{5-[4-(benzothiazol-2-yloxy)-benzyl]-2,5-diaza-bicyclo[2.2.1]hept-2-yl}-ethanone To a mixture of (R,R)-(2-{5-[4-(benzothiazol-2-yloxy)-benzyl]-2,5-diaza-bicyclo[2.2.1]hept-2-yl}-2-oxo-ethyl)-carbamic acid tert-butyl ester (8.2 mg, 0.02 mmol) in CH$_2$Cl$_2$ (0.3 mL) was added HCl (4.0 N in 1,4-dioxane, 0.3 mL). The solution was stirred for 2 h and concentrated under a stream of dry nitrogen. Purification via preparative reverse phase HPLC afforded the title compound (2.7 mg, 38%). MS (ESI): mass calcd. for $C_{21}H_{22}N_4O_2S$, 394.15; m/z found, 395.1 [M+H]$^+$. $^1$H NMR (400 MHz, CDCl$_3$, mixture of rotamers): 7.74 (d, J=8.1 Hz, 1H), 7.67 (d, J=7.9 Hz, 1H), 7.44-7.36 (m, 3H), 7.34-7.28 (m, 2H), 7.28-7.23 (m, 1H), 4.81 (s, 0.5H), 4.21 (s, 0.5H), 3.81-3.72 (m, 2.5H), 3.58 (s, 1H), 3.54-3.46 (m, 1H), 3.39-3.24 (m, 2.5H), 3.00 (dd, J=9.6, 2.0 Hz, 0.5H), 2.86 (dd, J=9.7, 2.1 Hz, 0.5H), 2.76 (d, J=9.8 Hz, 0.5H), 2.67-2.58 (m, 0.25H), 2.54 (d, J=9.6 Hz, 0.5H), 2.00 (d, J=9.6 Hz, 0.5H), 1.93 (d, J=9.9 Hz, 0.5H), 1.86-1.30 (m, 2.75H).

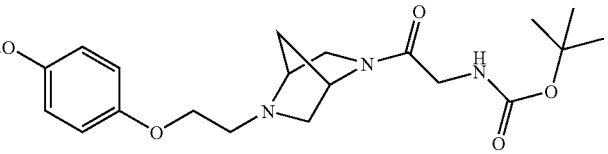

Example 30

(S,S)-[2-(5-{2-[4-(Benzothiazol-2-yloxy)-phenoxy]-ethyl}-2,5-diaza-bicyclo[2.2.1]hept-2-yl)-2-oxo-ethyl]-carbamic acid tert-butyl ester This compound was prepared using methods analogous to those outlined in Example 28. MS (ESI): mass calcd. for $C_{27}H_{32}N_4O_5S$, 524.21; m/z found, 525.3 [M+H]$^+$. $^1$H NMR (400 MHz, CDCl$_3$, mixture of rotamers): 7.73 (d, J=7.6 Hz, 1H), 7.66 (d, J=7.9 Hz, 1H), 7.40 (d, J=1.3 Hz, 0.25H), 7.38 (s, 0.5H), 7.36 (d, J=1.3 Hz, 0.25H), 7.30-7.23 (m, 3H), 6.97-6.91 (m, 2H), 5.46 (d, J=16.9 Hz, 1H), 4.78 (s, 0.5H), 4.22 (s, 0.5H), 4.11-4.00 (m, 2H), 3.98 (d, J=16.9 Hz, 0.25H), 3.90 (d, J=4.6 Hz, 0.25H), 3.87-3.79 (m, 1.25H), 3.77-3.71 (m, 1H), 3.70 (s, 0.5H), 3.59 (d, J=9.5 Hz, 0.5H), 3.49 (s, 0.25H), 3.36-3.28 (m, 1H), 3.17 (dd, J=9.7, 1.6 Hz, 0.5H), 3.07-2.92 (m, 2.5H), 2.77 (d, J=9.7 Hz, 0.5H), 2.66 (dd, J=9.8, 1.0 Hz, 0.5H), 2.03-1.97 (d, J=10.1 Hz, 0.5H), 1.93 (d, J=10.0 Hz, 0.5H), 1.79 (d, J=10.0 Hz, 0.5H), 1.69 (d, J=10.0 Hz, 0.5H), 1.45 (s, 9H).

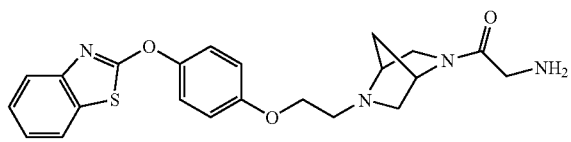

Example 31

(S,S)-2-Amino-1-(5-{2-[4-(benzothiazol-2-yloxy)-phenoxy]-ethyl}-2,5-diaza-bicyclo[2.2.1]hept-2-yl)-ethanone This compound was prepared using methods analogous to those outlined in Example 29. MS (ESI): mass calcd. for $C_{22}H_{24}N_4O_3S$, 424.16; m/z found, 425.2 [M+H]$^+$. $^1$H NMR (400 MHz, CDCl$_3$, mixture of rotamers): 7.73 (d, J=8.1 Hz, 1H), 7.66 (d, J=8.0 Hz, 1H), 7.40 (d, J=1.2 Hz, 0.25H), 7.38 (s, 0.5H), 7.36 (d, J=1.2 Hz, 0.25H), 7.30-7.23 (m, 3H), 6.97-6.92 (m, 2H), 4.79 (s, 0.5H), 4.20 (s, 05H), 4.11-4.01 (m, 2H), 3.80-3.66 (m, 1.5H), 3.56-3.47 (m, 1H), 3.40-3.24 (m, 2.5H), 3.19 (dd, J=9.6, 1.8 Hz, 0.5H), 3.07-2.90 (m, 2.5H), 2.79 (d, J=9.7 Hz, 0.5H), 2.62 (d, J=9.5 Hz, 0.5H), 1.99 (d, J=9.5 Hz, 0.5H), 1.91 (d, J=9.8 Hz, 0.5H), 1.84-1.43 (m, 3H).

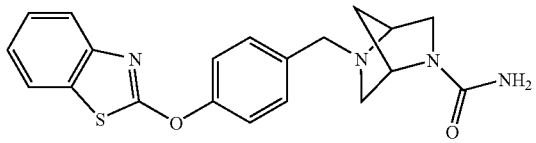

Example 32

(S,S)-5-[4-(Benzothiazol-2-yloxy)-benzyl]-2,5-diaza-bicyclo[2.2.1]heptane-2-carboxylic acid amide To a stirred suspension of (S,S)-2-[4-(2,5-diaza-bicyclo[2.2.1]hept-2-ylmethyl)-phenyl]-benzothiazole hydrochloride (2.8 g, 6.8 mmol) and Et$_3$N (9.1 mL, 68.5 mmol) in CH$_2$Cl$_2$ (50 mL) was added trimethylsilylisocyanate (3.8 mL, 27.4 mmol), and the resulting solution was stirred at rt for 1.5 h. The solution was then partitioned between CH$_2$Cl$_2$ (500 mL) and satd. aq. NaHCO$_3$ (80 mL). The organic layer was separated, dried (Na$_2$SO$_4$), filtered and concentrated. Purification by silica gel flash chromatography (5% to 10% CH$_3$OH in CH$_2$Cl$_2$) afforded the title compound as a white solid (2.2 g, 85%).

Alternative Preparation:

Step A: 4-(Benzothiazol-2-yloxy)-benzaldehyde bisulfite complex. To a solution of 2-chlorobenzothiazole (33.7 g, 199 mmol) in CH$_3$CN (500 mL) was added 4-hydroxy benzaldehyde (24.3 g, 199 mmol) and K$_2$CO$_3$ (28 g, 199 mmol). The heterogeneous mixture was heated at reflux for 72 h and then cooled to rt. The solids were removed by filtration and washed with CH$_3$CN (100 mL). To the filtrate was added an aqueous solution of NaHSO$_3$ (26 g, 199 mmol, 66 mL water). After stirring for 3.5 h, the mixture was filtered and the wet cake was dried under vacuum overnight to afford the bisulfite complex (66 g, 92%) as a white powder. $^1$H NMR (500 MHz, DMSO-d$_6$): 7.93 (d, J=8.0 Hz, 1H), 7.74 (d, J=8.0 Hz, 1H), 7.60-7.55 (m, 2H), 7.44-7.39 (m, 1H), 7.35-7.29 (m, 3H), 6.03 (d, J=5.2 Hz, 1H), 5.04 (d, J=5.2 Hz, 1H).

Step B: 4-(Benzothiazol-2-yloxy)-benzaldehyde. To a solution of the bisulfite complex (66 g, 184 mmol) in CH$_2$Cl$_2$ (600 mL) was added an aqueous solution of NaOH (9.2 g in 644 mL water, 230 mmol). The resulting mixture was vigorously stirred at rt for 2 h. The product was extracted with CH$_2$Cl$_2$ (200 mL), washed with satd. aq. NaCl (200 mL) and dried (MgSO$_4$). After filtration and evaporation of the solvent, the desired aldehyde was obtained as a white solid (38 g, 81%). MS (ESI): mass calcd. for $C_{14}H_9NO_2S$, 255.04; m/z found, 256.2 [M+H]$^+$. $^1$H NMR (500 MHz, CDCl$_3$): 10.05 (s, 1H), 8.01 (d, J=8.7 Hz, 2H), 7.8 (dd, J=8.7, 8.6 Hz, 2H), 7.6 (d, J=8.6 Hz, 2H), 7.4 (td, J=8.6, 1.2 Hz, 1H), 7.3 (td, J=8.6, 1.2 Hz, 1H).

Step C: (S,S)-2,5-Diaza-bicyclo[2.2.1]heptane-2-carboxylic acid amide hydrochloride. To a solution of (S,S)-2,5-diaza-bicyclo[2.2.1]heptane-2-carboxylic acid tert-butyl ester (35.6 g, 179 mmol) in CH$_2$Cl$_2$ (600 mL) was added trimethylsilylisocyanate (82.5 g, 716 mmol). After 2 h at rt, the mixture was concentrated, and the resulting white solid was dissolved in CH$_2$Cl$_2$ (500 mL). The solution was then treated with a solution of HCl (4.0 N in 1,4-dioxane, 135 mL). The resulting heterogeneous suspension was then stirred at rt overnight. Upon evaporation of the solvents, the desired product was isolated as a white solid (33 g), which was used directly in the next step. [Note: the mass balance was found to be 104%, which arose from additional HCl that could not be removed by standard evaporation under vacuum]. $^1$H NMR (500 MHz, CD$_3$OD): 4.77 (s, 1H), 4.55 (s, 1H), 3.69 (d, J=12.1 Hz, 1H), 3.64 (d, J=12.1 Hz, 1H), 3.47 (d, J=11.3 Hz, 1H), 3.40 (d, J=11.3 Hz, 1H), 2.22 (d, J=11.5 Hz, 1H), 2.15 (d, J=11.5 Hz, 1H).

Step D: (S,S)-5-[4-(Benzothiazol-2-yloxy)-benzyl]-2,5-diaza-bicyclo[2.2.1]heptane-2-carboxylic acid amide. To a solution of (S,S)-2,5-diaza-bicyclo[2.2.1]heptane-2-carboxylic acid amide hydrochloride (35.6 g, 200 mmol) in THF (250 mL) was added Et$_3$N (62 mL, 440 mmol), and the resulting suspension was stirred at rt for 5 min. A solution of 4-(benzothiazol-2-yloxy)-benzaldehyde (38 g, 149 mmol) in THF (320 mL) was added. The reaction mixture was allowed to stir at rt for 2 h. Sodium triacetoxyborohydride (37.9 g, 180 mmol) was added in 3 equal portions over 10 min at 0° C. The mixture was then stirred at rt overnight. The reaction was diluted with CH$_2$Cl$_2$ (500 mL) and 1 N NaOH (300 mL). The layers were allowed to separate and the aqueous layer was further extracted with CH$_2$Cl$_2$ (300 mL). The combined organic layers were washed with satd. aq. NaCl (200 mL), dried (MgSO$_4$) and concentrated. The crude material was dissolved in refluxing EtOAc (400 mL) for 5 h. Upon cooling the solution to rt, the product precipitated as a white solid. This solid was purified by silica gel flash chromatography (4:1 CH$_2$Cl$_2$/CH$_3$OH) to afford the desired product (25 g, 44%) as a white powdery solid. The EtOAc solution recovered after filtration of the white solid was concentrated and purified by silica gel flash chromatography (4:1 CH$_2$Cl$_2$/CH$_3$OH) followed by recrystallization to provide additional desired product as a white solid (8 g, 14%). MS (ESI): mass calcd. for C$_{20}$H$_{20}$N$_4$O$_2$S, 380.47; m/z found, 381.1 [M+H]$^+$. $^1$H NMR (500 MHz, CDCl$_3$): 7.75 (d, J=8.1 Hz, 1H), 7.69 (dd, J=8.0, 0.7 Hz, 1H), 7.44 (d, J=8.6 Hz, 2H), 7.42-7.39 (m, 1H), 7.35-7.26 (m, 3H), 4.49-4.32 (m, 3H), 3.79 (s, 2H), 3.62-3.53 (m, 2H), 3.25 (dd, J=8.8, 2.2 Hz, 1H), 2.93 (d, J=9.7 Hz, 1H), 2.77 (d, J=9.7 Hz, 1H), 1.95 (d, J=9.7 Hz, 1H), 1.77 (d, J=9.7 Hz, 1H).

The compounds in Examples 33-40 were prepared using methods analogous to those described in Example 32.

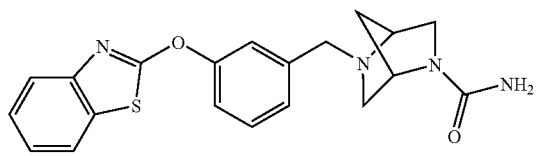

Example 33

(S,S)-5-[3-(Benzothiazol-2-yloxy)-benzyl]-2,5-diaza-bicyclo[2.2.1]heptane-2-carboxylic acid amide MS (ESI): mass calcd. for C$_{20}$H$_{20}$N$_4$O$_2$S, 380.13; m/z found, 381.1 [M+H]$^+$. $^1$H NMR (500 MHz, CDCl$_3$): 7.73 (d, J=7.9 Hz, 1H), 7.67 (d, J=7.9 Hz, 1H), 7.42-7.36 (m, 3H), 7.29-7.22 (m, 3H), 4.57-4.32 (m, 3H), 3.78 (s, 2H), 3.55 (br s, 1H), 3.51 (br s, 1H), 3.21 (dd, J=8.8, 2.2 Hz, 1H), 2.90 (d, J=8.9 Hz, 1H), 2.73 (br d, J=9.2 Hz, 1H), 1.91 (br d, J=10.0 Hz, 1H), 1.73 (br d, J=9.5 Hz, 1H).

Example 34

(R,R)-5-[4-(Benzothiazol-2-yloxy)-benzyl]-2,5-diaza-bicyclo[2.2.1]heptane-2-carboxylic acid amide MS (ESI): mass calcd. for C$_{20}$H$_{20}$N$_4$O$_2$S, 380.13; m/z found, 381.2 [M+H]$^+$. $^1$H NMR (400 MHz, CDCl$_3$): 7.74 (d, J=7.6 Hz, 1H), 7.67 (d, J=8.0 Hz, 1H), 7.45-7.36 (m, 3H), 7.33-7.25 (m, 3H), 4.50-4.25 (m, 3H), 3.77 (s, 2H), 3.52-3.50 (m, 2H), 3.24 (dd, J=8.8, 2.1 Hz, 1H), 2.91 (dd, J=9.5, 1.5 Hz, 1H), 2.76 (d, J=9.5 Hz, 1H), 1.94 (d, J=9.5 Hz, 1H), 1.76 (d, J=9.4 Hz, 1H).

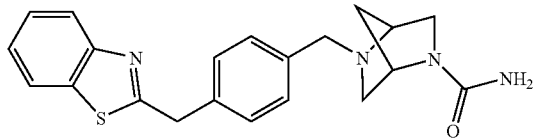

Example 35

(S,S)-5-(4-Benzothiazol-2-ylmethyl-benzyl)-2,5-diaza-bicyclo[2.2.1]heptane-2-carboxylic acid amide MS (ESI): mass calcd. for C$_{21}$H$_{22}$N$_4$OS, 378.50; m/z found, 379.1 [M+H]$^+$. $^1$H NMR (500 MHz, CDCl$_3$): 8.00 (d, J=7.5 Hz, 1H), 7.80 (d, J=7.5 Hz, 1H), 7.48-7.45 (m, 1H), 7.37-7.33 (m, 5H), 4.43-438 (br m, 5H), 3.74 (br s, 2H), 3.53 (br s, 2H), 3.21 (dd, J=9.2, 2.0 Hz, 1H), 2.90 (dd, J=9.2, 2.0 Hz, 1H), 2.74 (d, J=9.2 Hz; 1H), 1.92 (br d, J=9.2 Hz, 1H), 1.73 (br d, J=9.2 Hz, 1H).

Example 36 meso-endo-[8-(4-Benzothiazol-2-ylmethyl-benzyl)-8-aza-bicyclo[3.2.1]oct-3-yl]-urea MS (ESI): mass calcd. for C$_{23}$H$_{26}$N$_4$OS, 406.55; m/z found, 407.2 [M+H]$^+$. $^1$H NMR (400 MHz, CDCl$_3$): 7.99 (d, J=7.8 Hz, 1H), 7.78 (d, J=7.8 Hz, 1H), 7.45 (dt, J=7.8, 1.2 Hz, 1H), 7.37-7.31 (m, 5H), 5.28 (br s, 1H), 4.59 (br s, 2H), 4.42 (s, 2H), 3.84-3.82 (m, 1H), 3.57-3.55 (br m, 2H), 3.20 (br s, 2H), 2.26-2.21 (br m, 2H), 2.10-2.05 (m, 2H), 1.89-1.87 (m, 2H), 1.64 (br d, J=14.0 Hz, 2H).

Example 37 meso-endo-[8-(4-Benzooxazol-2-ylmethyl-benzyl)-8-aza-bicyclo[3.2.1]oct-3-yl]-urea MS (ESI): mass calcd. for C$_{23}$H$_{26}$N$_4$O$_2$, 390.49; m/z found, 391.2 [M+H]$^+$. $^1$H NMR (400 MHz, CDCl$_3$): 7.70-7.67 (m, 1H), 7.48-7.46 (m, 1H), 7.37-7.28 (m, 6H), 5.06 (br s, 1H), 4.44 (br s, 2H), 4.26 (s, 2H), 3.83 (dd, J=6.4, 5.8 Hz, 1H), 3.51 (s, 2H), 3.18 (br s, 2H), 2.24-2.18 (m, 2H), 2.11-2.08 (m, 2H), 1.82 (br d, J=8.4 Hz, 2H), 1.62 (br d, J=14.4 Hz, 2H).

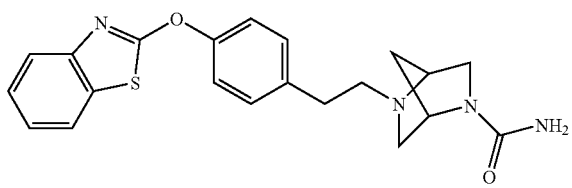

Example 38

(S,S)-5-{2-[4-(Benzothiazol-2-yloxy)-phenyl]-ethyl}-2,5-diaza-bicyclo[2.2.1]heptane-2-carboxylic acid amide MS (ESI): mass calcd. for $C_{21}H_{22}N_4O_2S$, 394.15; m/z found, 395.1 [M+H]$^+$. $^1$H NMR (500 MHz, CD$_3$OD): 7.77 (d, J=8.2 Hz, 1H), 7.65 (d, J=8.3 Hz, 1H), 7.45-7.40 (m, 1H), 7.40-7.36 (m, 2H), 7.33-7.27 (m, 3H), 4.38 (br s, 1H), 3.67 (br s, 1H), 3.60-3.48 (m, 1H), 3.27-3.22 (m, 1H), 3.00-2.94 (m, 1H), 2.90-2.79 (br m, 4H), 2.70 (br d, J=9.9 Hz, 1H), 1.91 (br d, J=10.3 Hz, 1H), 1.79 (br d, J=9.3 Hz, 1H).

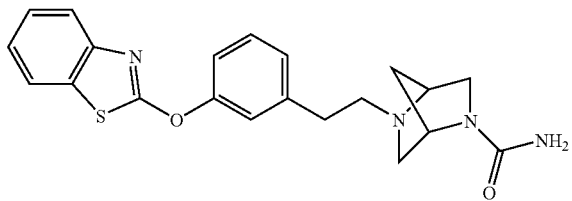

Example 39

(S,S)-5{2-[3-(Benzothiazol-2-yloxy)-phenyl]-ethyl}2,5-diaza-bicyclo[2.2.1]hetpane-2-carboxylic acid amide MS (ESI): mass calcd. for $C_{21}H_{22}N_4O_2S$, 394.14; m/z found, 395.1 [M+H]$^+$. $^1$H NMR (500 MHz, CDCl$_3$): 7.73 (d, J=8.1 Hz, 1H), 7.67 (d, J=7.8 Hz, 1H), 7.42-7.32 (m, 2H), 7.29-7.24 (m, 1H), 7.23-7.18 (br m, 2H), 7.14 (br d, J=7.5 Hz, 1H), 4.41 (br s, 3H), 3.57 (br s, 1H), 3.46 (m, 1H), 3.18 (dd, J=8.8, 2.1 Hz, 1H), 2.98 (dd, J=9.5, 2.3 Hz, 1H), 2.90-2.74 (br m, 4H), 2.69 (br d, J=9.6 Hz, 1H), 1.87 (br d, J=9.8 Hz, 1H), 1.72 (br d, J=9.6 Hz, 1H).

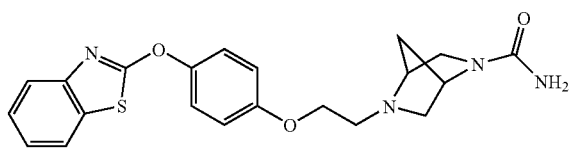

Example 40

(S,S)-5-{2-[4-(Benzothiazol-2-yloxy)-phenoxy]-ethyl}-2,5-diaza-bicyclo[2.2.1]heptane-2-carboxylic acid amide MS (ESI): mass calcd. for $C_{21}H_{22}N_4O_3S$, 410.14; m/z found, 411.2 [M+H]$^+$. $^1$H NMR (400 MHz, CDCl$_3$): 7.73 (d, J=7.7 Hz, 1H), 7.66 (dd, J=7.9, 0.7 Hz, 1H), 7.40 (d, J=1.2 Hz, 0.25H), 7.38 (s, 0.5H), 7.36 (d, J=1.3 Hz, 0.25H), 7.29-7.23 (m, 3H), 6.97-6.92 (m, 2H), 4.39 (s, 3H), 4.12-4.02 (m, 2H), 3.69 (s, 1H), 3.54 (d, J=8.0 Hz, 1H), 3.25 (dd, J=8.9, 2.1 Hz, 1H), 3.11-2.94 (m, 3H), 2.80 (d, J=9.6 Hz, 1H), 1.92 (d, J=9.6 Hz, 1H), 1.82-1.68 (m, 1H).

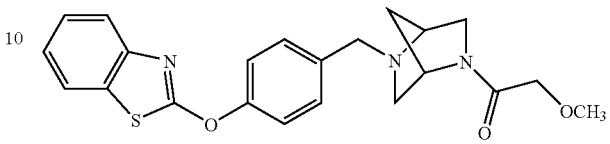

Example 41

(S,S)-1-{5-[4-(Benzothiazol-2-yloxy)-benzyl]-2,5-diaza-bicyclo[2.2.1]hept-2-yl}-2-methoxy-ethanone To a stirred solution of (S,S)-2-[4-(2,5-diaza-bicyclo[2.2.1]hept-2-ylmethyl)-phenoxy]-benzothiazole hydrochloride (144 mg, 0.35 mmol) and Et$_3$N (200 µL, 1.4 mmol) in CH$_2$Cl$_2$ (15 mL) at rt was added methoxyacetyl chloride (50 µL, 0.53 mmol). After 18 h at rt, the reaction mixture was partitioned between CH$_2$Cl$_2$ (150 mL) and satd. aq. NaHCO$_3$ (50 mL). The organic layer was separated, dried (Na$_2$SO$_4$), filtered and concentrated. Purification by silica gel flash chromatography (0% to 5% CH$_3$OH in CH$_2$Cl$_2$) afforded the title compound as a viscous, colorless oil (127 mg, 89%). MS (ESI): mass calcd. for $C_{22}H_{23}N_3O_3S$, 409.15; m/z found, 410.2 [M+H]$^+$. $^1$H NMR (500 MHz, CDCl$_3$, mixture of rotamers): 7.74 (d, J=7.5 Hz, 1H), 7.67 (d, J=7.7 Hz, 1H), 7.40 (m, 3H), 7.30 (m, 3H), 4.83 (br m, 0.5H), 4.46 (br m, 0.5H), 4.06 (m, 1H), 4.01 (s, 1H), 3.76 (m, 2.5H), 3.63 (br d, J=9.3 Hz, 0.5H), 3.58 (br s, 1H), 3.45 (s, 1.5H), 3.43 (s, 1.5H), 3.35 (br d, J=2.1 Hz, 0.5H), 3.33 (m, 0.5H), 3.01 (dd, J=9.9, 2.3 Hz, 0.5H), 2.87 (dd, J=9.8, 2.2 Hz, 0.5H), 2.78 (br d, J=9.9 Hz, 0.5H), 2.58 (d, J=9.5 Hz, 0.5H), 1.99 (br d, J=9.3 Hz, 0.5H), 1.96 (br d, J=9.8 Hz, 0.5H), 1.76 (br d, J=10.0 Hz, 0.5H), 1.66 (br d, J=10.0 Hz, 0.5H).

The compounds in Examples 42-43 were prepared using methods analogous to those described in Example 41.

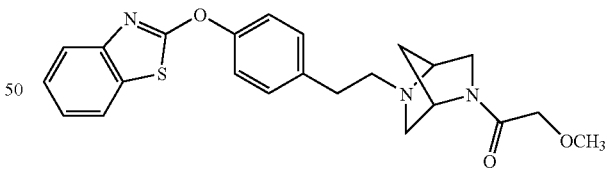

Example 42

(S,S)-1-(5-{2-[4-(Benzothiazol-2-yloxy)-phenyl]-ethyl-2,5-diaza-bicyclo[2.2.1]hept-2-yl)-2-methoxy-ethanone MS (ESI): mass calcd. for $C_{23}H_{25}N_3O_3S$, 423.16; m/z found, 424.2 [M+H]$^+$. $^1$H NMR (500 MHz, CDCl$_3$, mixture of rotamers): 7.73 (d, J=7.8 Hz, 1H), 7.66 (d, J=7.8 Hz, 1H), 7.38 (t, J=7.7 Hz, 1H), 7.29-7.23 (m, 5H), 4.79 (br m, 0.5H), 4.43 (br m, 0.5H), 4.14-4.01 (br m, 1H), 3.97 (br s, 1H), 3.68 (br m, 0.5H), 3.58 (br m, 1.5H), 3.43 (br s, 3H), 3.31 (d, J=11.5 Hz, 1H), 3.07 (d, J=9.2 Hz, 0.5H), 2.95 (d, J=8.7 Hz, 0.5H), 2.88-2.68 (m, 4H), 2.55 (d, J=9.6 Hz, 0.5H), 1.93 (d, J=9.1 Hz, 0.5H), 1.33-1.21 (br m, 1H), 0.92-0.78 (br m, 1H).

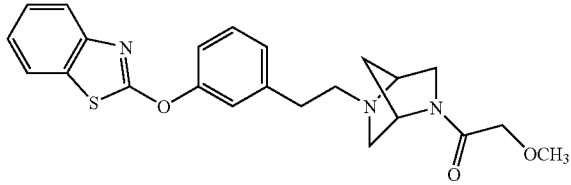

Example 43

(S,S)-1-(5-{2-[3-(Benzothiazol-2-yloxy)-phenyl]-ethyl-2,5-diaza-bicyclo[2.2.1]hept-2-yl)-2-methoxy-ethanone MS (ESI): mass calcd. for $C_{23}H_{25}N_3O_3S$, 423.16; m/z found, 424.2 [M+H]$^+$. $^1$H NMR (500 MHz, CDCl$_3$, mixture of rotamers): 7.74 (d, J=7.6 Hz, 1H), 7.67 (d, J=8.7 Hz, 1H), 7.41-7.33 (m, 2H), 7.30-7.24 (m, 1H), 7.23-7.18 (br m, 2H), 7.13 (br d, J=8.7 Hz, 1H), 4.78 (br s, 0.5H), 4.42 (br s, 0.5H), 4.04 (dd, J=13.8, 6.0 Hz, 1H), 3.94 (dd, J=14.0, 1.0 Hz, 1H), 3.66 (d, J=11.5 Hz, 0.5H), 3.60-3.53 (br m, 1.5H), 3.41 (br s, 3H), 3.33-3.27 (br m, 1H), 3.06 (dd, J=9.9, 2.2 Hz, 0.5H), 2.93 (dd, J=9.8, 2.2 Hz, 0.5H), 2.88-2.74 (br m, 4H), 2.70 (br d, J=9.3 Hz, 0.5H), 2.54 (br d, J=9.5 Hz, 0.5H), 1.91 (br d, J=9.4 Hz, 0.5H), 1.86 (br d, J=9.9 Hz, 0.5H), 1.71 (br d, J=10.0 Hz, 0.5H), 1.64 (br d, J=9.9 Hz, 0.5H).

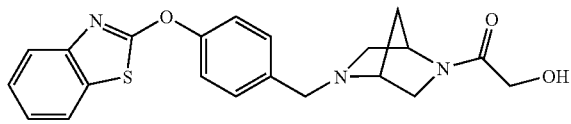

Example 44

(R,R)-1-{5-[4-(Benzothiazol-2-yloxy)-benzyl]-2,5-diaza-bicyclo[2.2.1]hept-2-yl}-2-hydroxy-ethanone Step A. Acetic acid (R,R)-2-{5-[4-(benzothiazol-2-yloxy)-benzyl]-2,5-diaza-bicyclo[2.2.1]hept-2-yl}-2-oxo-ethyl ester. This compound was prepared using the methods outlined in Example 41, substituting acetoxyacetyl chloride for methoxyacetyl chloride. MS (ESI): mass calcd. for $C_{23}H_{23}N_3O_4S$, 437.14; m/z found, 438.1 [M+H]$^+$.

Step B. (R,R)-1-{5-[4-(Benzothiazol-2-yloxy)-benzyl]-2,5-diaza-bicyclo[2.2.1]hept-2-yl}-2-hydroxy-ethanone. To acetic acid (R,R)-2-{5-[4-(benzothiazol-2-yloxy)-benzyl]-2,5-diaza-bicyclo[2.2.1]hept-2-yl}-2-oxo-ethyl ester (161 mg, 0.37 mmol) in methanol (2 mL) was added macroporous polystyrene-supported carbonate (592 mg, 3.11 mmol/g). The mixture was placed on an orbital shaker at 60° C. for 14 h. Filtration of the mixture and purification via preparative reverse phase HPLC afforded the product (91 mg, 62%). MS (ESI): mass calcd. for $C_{21}H_{21}N_3O_3S$, 395.13; m/z found, 396.1 [M+H]$^+$. $^1$H NMR (400 MHz, CDCl$_3$, mixture of rotamers): 7.73 (d, J=8.1 Hz, 1H), 7.66 (d, J=8.0 Hz, 1H), 7.47-7.35 (m, 3H), 7.35-7.23 (m, 3H), 4.82 (s, 0.5H), 4.20 (d, J=14.9 Hz, 0.5H), 4.13-3.96 (m, 2H), 3.86-3.68 (m, 2.5H), 3.67-3.30 (m, 3H), 3.20 (dd, J=9.2, 2.2 Hz, 0.5H), 2.98 (dd, J=9.7, 2.1 Hz, 0.5H), 2.87 (dd, J=9.8, 2.1 Hz, 0.5H), 2.76 (d, J=9.8 Hz, 0.5H), 2.56 (d, J=9.7 Hz, 0.5H), 2.07-1.84 (m, 1H), 1.77 (d, J=9.3 Hz, 0.5H), 1.67 (d, J=9.2 Hz, 0.5H).

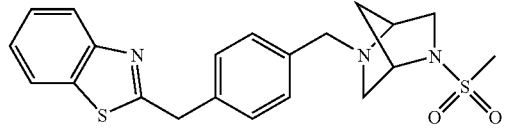

Example 45

(S,S)-2-[4-(5-Methanesulfonyl-2,5-diaza-bicyclo[2.2.1]hept-2-ylmethyl)-benzyl]-benzothiazole To a solution of 1-[5-(4-benzothiazol-2-ylmethyl-benzyl)-2,5-diaza-bicyclo[2.2.1]hept-2-yl]-ethanone (0.2 g, 0.49 mmol) in CH$_2$Cl$_2$ (5 mL) was added Et$_3$N (0.41 mL, 3.0 mmol) and methanesulfonyl chloride (57 µL, 0.74 mmol) and the resulting solution was stirred at rt for 14 h. The reaction mixture was concentrated and the crude residue was partitioned between EtOAc (50 mL) and brine (50 mL). The organic layer was separated, dried (Mg$_2$SO$_4$), filtered and concentrated. Purification by silica gel flash chromatography (0% to 15% CH$_3$OH in CH$_2$Cl$_2$) afforded the title compound as clear oil (0.13 g, 62%). MS (ESI): mass calcd. for $C_{21}H_{23}N_3O_2S_2$, 413.56; m/z found, 414.1 [M+H]$^+$. $^1$H NMR (500 MHz, CDCl$_3$): 8.01 (d, J=7.8 Hz, 1H), 7.81 (dd, J=7.8, 0.5 Hz, 1H), 7.49-7.45 (m, 1H), 7.37-7.34 (m, 5H), 4.44 (d, J=2.0 Hz, 2H), 4.31 (br s, 1H), 3.80 (d, J=13.8 Hz, 1H), 3.75 (d, J=13.8 Hz, 1H), 3.62-3.60 (m, 1H), 3.57 (br s, 1H), 3.24 (dd, J=9.3, 2.3 Hz, 1H), 2.90-2.89 (br m, 4H), 2.85-2.83 (br m, 1H), 1.96-1.94 (m, 1H), 1.74-1.72 (m, 1H).

The compounds in Examples 46-49 were prepared using methods analogous to those described in Example 45.

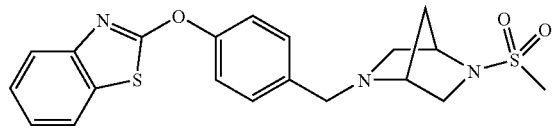

Example 46

(R,R)-2-[4-(5-Methanesulfonyl-2,5-diaza-bicyclo[2.2.1]hept-2-ylmethyl)-phenoxy]-benzothiazole MS (ESI): mass calcd. for $C_{20}H_{21}N_3O_3S_2$, 415.10; m/z found, 416.1 [M+H]$^+$. $^1$H NMR (400 MHz, CDCl$_3$): 7.76-7.71 (m, 1H), 7.69-7.66 (m, 1H), 7.45-7.36 (m, 3H), 7.34-7.25 (m, 3H), 4.32 (br s, 1H), 3.86-3.73 (m, 2H), 3.65-3.58 (m, 2H), 3.25 (dd, J=9.3, 2.2 Hz, 1H), 2.94-2.81 (m, 5H), 1.97 (d, J=9.9 Hz, 1H), 1.75 (d, J=10.0 Hz, 1H).

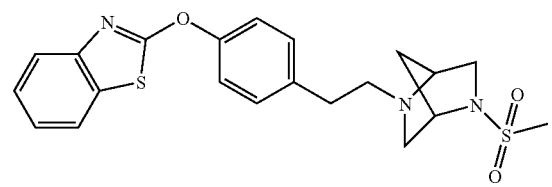

Example 47

(S,S)-2-{4-[2-(5-Methanesulfonyl-2,5-diaza-bicyclo[2.2.1]hept-2-yl)-ethyl]-phenoxy}-benzothiazole MS (ESI): mass calcd. for $C_{21}H_{23}N_3O_3S_2$, 429.11; m/z found, 430.1 [M+H]$^+$. $^1$H NMR (500 MHz, CDCl$_3$): 7.73 (d, J=6.6 Hz, 1H), 7.66 (d, J=6.7 Hz, 1H), 7.38 (m, 1H), 7.30-7.24 (m, 5H), 4.31 (br m, 1H), 3.61 (br m, 1H), 3.56 (br d, J=9.3 Hz, 1H), 3.23 (dd, J=9.4, 2.2 Hz, 1H), 2.98 (dd, J=9.9, 2.2 Hz, 1H), 2.95-2.86 (br m, 4H), 2.85-2.73 (br m, 4H), 1.92 (br d, J=9.9 Hz, 1H), 1.74 (br d, J=9.6 Hz, 1H).

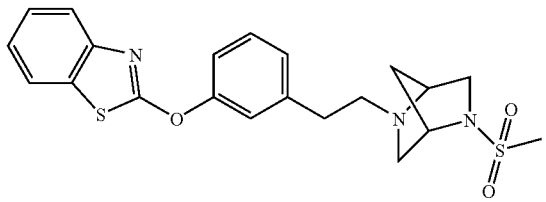

Example 48

(S,S)-2-{3-[2-(5-Methanesulfonyl-2,5-diaza-bicyclo[2.2.1]hept-2-yl)-ethyl]phenoxy}benzothiazole MS (ESI): mass calcd. for $C_{21}H_{23}N_3O_3S_2$, 429.11; m/z found, 430.1 [M+H]$^+$. $^1$H NMR (500 MHz, CDCl$_3$): 7.74 (d, J=7.2 Hz, 1H), 7.67 (d, J=8.6 Hz, 1H), 7.41-7.33 (m, 2H), 7.29-7.26 (m, 1H), 7.23-7.19 (m, 2H), 7.14 (br d, J=7.6 Hz, 1H), 4.28 (br s, 1H), 3.58 (br s, 1H), 3.52 (br d, J=9.4 Hz, 1H), 3.21 (dd, J=9.3, 2.2 Hz, 1H), 2.97-2.87 (br m, 2H), 2.85 (s, 3H), 2.83-2.75 (br m, 4H), 1.89 (br d, J=9.9 Hz, 1H), 1.71 (br d, J=9.9 Hz, 1H).

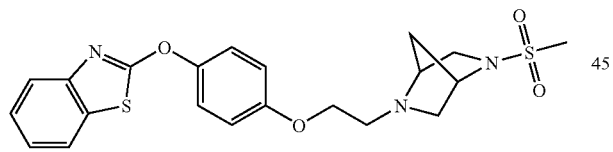

Example 49

(S,S)-2-{4-[2-(5-Methanesulfonyl-2,5-diaza-bicyclo[2.2.1]hept-2-yl)-ethoxy]-phenoxy}-benzothiazole MS (ESI): mass calcd. for $C_{21}H_{23}N_3O_4S_2$, 445.11; m/z found, 446.2 [M+H]$^+$. $^1$H NMR (400 MHz, CDCl$_3$): 7.73 (d, J=7.6 Hz, 1H), 7.66 (d, J=8.0 Hz, 1H), 7.40 (d, J=8.0 Hz, 0.25H), 7.38 (s, 0.5H), 7.36 (d, J=1.3 Hz, 0.25H), 7.29-7.24 (m, 3H), 6.97-6.93 (m, 2H), 4.31 (s, 1H), 4.11-4.04 (m, 2H), 3.72 (s, 1H), 3.63 (dd, J=9.4, 0.9 Hz, 1H), 3.26 (dd, J=9.5, 2.2 Hz, 1H), 3.11-2.98 (m, 3H), 2.91-2.88 (m, 4H), 1.96 (d, J=10.0 Hz, 1H), 1.76 (d, J=10.0 Hz, 1H).

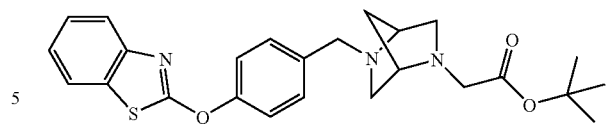

Example 50

(S,S)-{5-[4-(Benzothiazol-2-yloxy)-benzyl]-2,5-diaza-bicyclo[2.2.1]hept-2-yl}-acetic acid tert-butyl ester To a stirred solution of (S,S)-2-[4-(2,5-diaza-bicyclo[2.2.1]hept-2-ylmethyl)-phenoxy]-benzothiazole hydrochloride (257 mg, 0.63 mmol) and bromoacetic acid tert-butyl ester (110 µL, 0.75 mmol) in CH$_3$CN (4.0 mL) at rt was added Et$_3$N (270 µL, 1.9 mmol). After 18 h at rt the suspension was partitioned between CH$_2$Cl$_2$ (200 mL) and satd. aq. NaHCO$_3$ (80 mL). The organic layer was separated, dried (Na$_2$SO$_4$), filtered and concentrated. Purification by silica gel flash chromatography (5% CH$_3$OH in CH$_2$Cl$_2$) afforded the title compound as a viscous, colorless oil (218 mg, 77%). MS (ESI): mass calcd. for $C_{25}H_{29}N_3O_3S$, 451.19; m/z found, 452.2 [M+H]$^+$. $^1$H NMR (500 MHz, CDCl$_3$): 7.75 (d, J=7.7 Hz, 1H), 7.67 (d, J=7.7 Hz, 1H), 7.44 (d, J=8.6 Hz, 2H), 7.39 (m, 1H), 7.34-7.25 (m, 3H), 3.75 (m, 2H), 3.43 (br s, 1H), 3.33 (m, 3H), 2.88 (m, 2H), 2.82 (br d, J=10.0 Hz, 1H), 2.70 (dd, J=10.0, 2.2 Hz, 1H), 1.78 (s, 2H), 1.48 (s, 9H).

The compounds in Examples 51-52 were prepared using methods analogous to those described in Example 1.

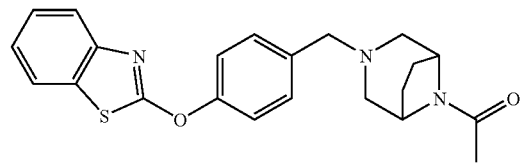

Example 51 meso-1-{3-[4-(Benzothiazol-2-yloxy)-benzyl]-3,8-diaza-bicyclo[3.2.1]oct-8-yl}-ethanone MS (ESI): mass calcd. for $C_{22}H_{23}N_3O_2S$, 393.51; m/z found, 394.1 [M+H]$^+$. $^1$H NMR (400 MHz, CDCl$_3$): 7.74 (d, J=7.6 Hz, 1H), 7.67 (d, J=7.9 Hz, 1H), 7.43-7.35 (m, 3H), 7.34-7.24 (m, 3H), 4.65 (d, J=6.6 Hz, 1H), 4.07-4.01 (m, 1H), 3.51 (q, J=13.4 Hz, 1H), 2.72 (dd, J=10.7, 2.5 Hz, 1H), 2.4 (dd, J=10.7, 1.4 Hz, 2H), 2.25 (dd, J=10.5, 1.5 Hz, 1H), 2.07 (s, 3H), 2.05-1.76 (m, 5H).

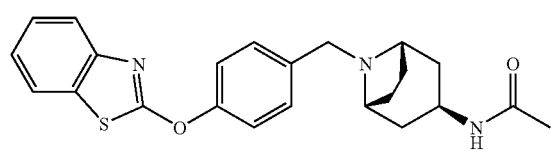

Example 52 meso-endo-N-{8-[4-(Benzothiazol-2-yloxy)-benzyl]-8-aza-bicyclo[3.2.1]oct-3-yl}-acetamide MS (ESI): mass calcd. for $C_{23}H_{25}N_3O_3S$, 407.54; m/z found, 408.2 [M+H]$^+$. $^1$H NMR (500 MHz, CDCl$_3$): 7.76 (d, J=7.6 Hz, 1H), 7.71-7.66 (m, 1H), 7.47 (d, J=8.5 Hz, 1H), 7.43-7.38 (m, 1H), 7.35-7.25 (m, 3H), 5.85-5.76 (m, 1H), 4.20-4.10 (m, 1H), 3.57 (s, 2H), 3.26-3.20 (m, 2H), 2.31-2.12 (m, 4H), 1.99 (s, 3H), 1.83-1.75 (m, 2H), 1.67-1.59 (m, 2H).

The compounds in Examples 53-54 were prepared using methods analogous to those described in Example 10.

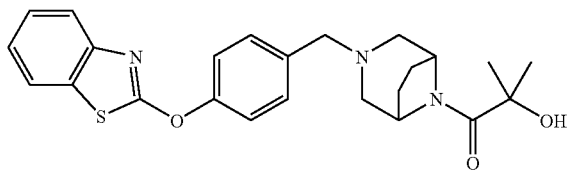

Example 53 meso-1-{3-[4-(Benzothiazol-2-yloxy)-benzyl]-3,8-diaza-bicyclo[3.2.1]oct-8-yl}-2-hydroxy-2-methyl-propan-1-one MS (ESI): mass calcd. for $C_{24}H_{27}N_3O_3S$, 437.57; m/z found, 438.2 [M+H]$^+$. $^1$H NMR (500 MHz, CDCl$_3$): 7.77-7.74 (m, 1H), 7.72-7.68 (m, 1H), 7.45-7.38 (m, 3H), 7.36-7.24 (m, 3H), 4.85-4.67 (m, 1H), 4.55-4.36 (m, 2H), 3.66-3.42 (m, 2H), 2.78 (dd, J=11.2, 3.0 Hz, 1H), 2.44-2.27 (m, 3H), 2.11-1.80 (m, 4H), 1.71-1.37 (m, 5H).

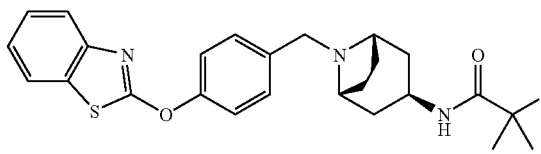

Example 54 meso-endo-N-{8-[4-(Benzothiazol-2-yloxy)-benzyl]-8-aza-bicyclo[3.2.1]oct-3-yl}-2-hydroxy-2-methyl-propionamide MS (ESI): mass calcd. for $C_{25}H_{29}N_3O_3S$, 451.59; m/z found, 452.2 [M+H]$^+$. $^1$H NMR (500 MHz, CDCl$_3$): 7.76 (d, J=8.1 Hz, 1H), 7.72-7.67 (m, 1H), 7.48 (d, J=8.3 Hz, 2H), 7.43-7.38 (m, 1H), 7.33 (d, J=8.3 Hz, 2H), 7.31-7.28 (m, 1H), 7.23-7.16 (m, 1H), 4.18-4.01 (m, 1H), 3.66-3.53 (m, 2H), 3.33-3.17 (m, 2H), 2.35-2.06 (m, 5H), 1.92-1.77 (m, 2H), 1.71-1.52 (m, 7H).

The compounds in Examples 55-56 were prepared using methods analogous to those described in Example 10 and Example 29.

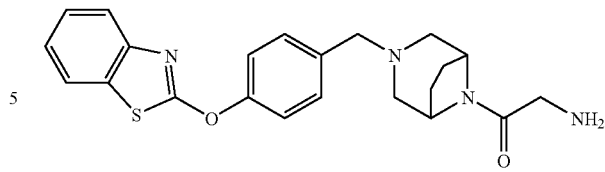

Example 55 meso-2-Amino-1-{3-[4-(benzothiazol-2-yloxy)-benzyl]-3,8-diaza-bicyclo[3.2.1]oct-8-yl}-ethanone MS (ESI): mass calcd. for $C_{22}H_{24}N_4O_2S$, 408.53; m/z found, 409.2 [M+H]$^+$. $^1$H NMR (500 MHz, CDCl$_3$): 7.76 (d, J=8.1 Hz, 1H), 7.70 (d, J=8.0 Hz, 1H), 7.44-7.37 (m, 3H), 7.36-7.28 (m, 3H), 4.69 (d, J=6.6 Hz, 1H), 4.06-4.02 (m, 1H), 3.60-3.36 (m, 4H), 2.81-2.68 (m, 2H), 2.37 (d, J=10.5 Hz, 1H), 2.24 (d, J=9.8 Hz, 1H), 2.10-1.76 (m, 4H).

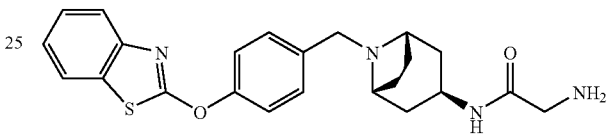

Example 56 meso-endo-2-Amino-N-{8-[4-(benzothiazol-2-yloxy)-benzyl]-8-aza-bicyclo[3.2.1]oct-3-yl}-acetamide MS (ESI): mass calcd. for $C_{23}H_{26}N_4O_2S$, 422.55; m/z found, 423.2 [M+H]$^+$. $^1$H NMR (500 MHz, CDCl$_3$): 8.02-7.93 (m, 1H), 7.76 (d, J=7.7 Hz, 1H), 7.69 (dd, J=8.0, 0.7 Hz, 1H), 7.48 (d, J=8.5 Hz, 2H), 7.43-7.38 (m, 1H), 7.36-7.31 (m, 2H), 7.31-7.26 (m, 1H), 4.22-4.15 (m, 1H), 3.59 (s, 2H), 3.34 (s, 2H), 3.28-3.21 (m, 2H), 2.30-2.21 (m, 2H), 2.20-2.13 (m, 2H), 1.94-1.83 (m, 2H), 1.64 (d, J=14.0 Hz, 2H).

The compounds in Examples 57-58 were prepared using methods analogous to those described in Example 45.

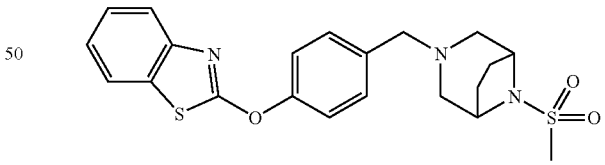

Example 57 meso-2-[4-(8-Methanesulfonyl-3,8-diaza-bicyclo[3.2.1]oct-3-ylmethyl)-phenoxy]-benzothiazole MS (ESI): mass calcd. for $C_{21}H_{23}N_3O_3S_2$, 429.56; m/z found, 430.1 [M+H]$^+$. $^1$H NMR (400 MHz, CDCl$_3$): 7.74 (d, J=7.6 Hz, 1H), 7.67 (d, J=8.0 Hz, 1H), 7.43-7.35 (m, 3H), 7.34-7.24 (m, 3H), 4.17-4.13 (m, 2H), 3.54 (s, 2H), 2.92 (s, 3H), 2.74 (dd, J=10.9, 2.9 Hz, 2H), 2.39 (d, J=10.2 Hz, 2H), 2.03-1.89 (m, 4H).

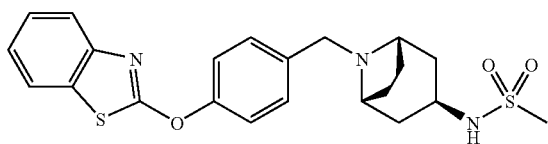

Example 58 meso-endo-N-{8-[4-(Benzothiazol-2-yloxy)-benzyl]-8-aza-bicyclo[3.2.1]oct-3-yl}-methanesulfonamide MS (ESI): mass calcd. for $C_{22}H_{25}N_3O_3S_2$, 443.59; m/z found, 444.1 [M+H]+. 1H NMR (500 MHz, CDCl3): 7.76 (d, J=8.1 Hz, 1H), 7.69 (d, J=7.9 Hz, 1H), 7.49-7.38 (m, 3H), 7.37-7.28 (m, 3H), 4.48 (d, J=6.7 Hz, 1H), 3.80-3.71 (m, 1H), 3.5 (s, 2H), 3.28-3.19 (m, 2H), 2.98 (s, 3H), 2.40-2.22 (m, 2H), 2.22-2.10 (m, 2H), 1.93-1.82 (m, 2H), 1.74 (d, J=14.0 Hz, 2H).

The compounds in Examples 59-60 were prepared using methods analogous to those described in Example 32.

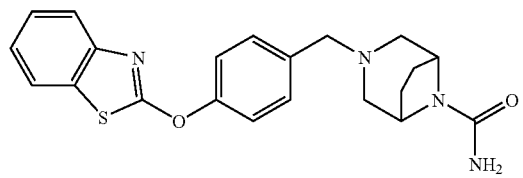

Example 59 meso-3-[4-(Benzothiazol-2-yloxy)-benzyl]-3,8-diaza-bicyclo[3.2.1]octane-8-carboxylic acid amide MS (ESI): mass calcd. for $C_{21}H_{22}N_4O_2S$, 394.50; m/z found, 395.1 [M+H]+. 1H NMR (500 MHz, CDCl3): 7.77-7.74 (m, 1H), 7.71-7.68 (m, 1H), 7.45-7.37 (m, 3H), 7.37-7.28 (m, 3H), 4.45 (s, 2H), 4.18-4.06 (m, 2H), 3.53 (s, 2H), 2.68 (dd, J=10.7, 2.6 Hz, 2H), 2.43-2.39 (m, 2H), 2.03-1.87 (m, 4H).

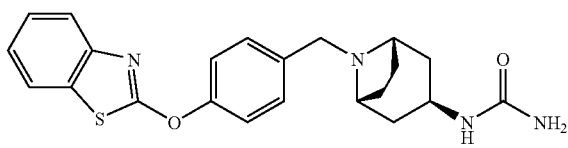

Example 60 meso-endo-{8-[4-(Benzothiazol-2-yloxy)-benzyl]-8-aza-bicyclo[3.2.1]oct-3-yl}-urea MS (ESI): mass calcd. for $C_{22}H_{24}N_4O_2S$, 408.53; m/z found, 409.2 [M+H]+. 1H NMR (500 MHz, CDCl3): 7.79-7.73 (m, 1H), 7.71-7.66 (m, 1H), 7.46 (d, J=8.6 Hz, 2H), 7.43-7.38 (m, 1H), 7.34-7.27 (m, 3H), 4.84 (d, J=7.0 Hz, 1H), 4.36-4.27 (m, 2H), 3.93-3.85 (m, 1H), 3.56 (s, 2H), 3.26-3.19 (m, 2H), 2.30-2.20 (m, 2H), 2.19-2.10 (m, 2H), 1.89-1.79 (m, 2H), 1.66 (d, J=13.9 Hz, 2H).

The compounds in Examples 61-68 were prepared using methods analogous to those described in the preceding examples.

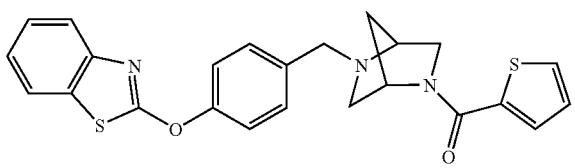

Example 61

(S,S)-{5-[4-(Benzothiazol-2-yloxy)-benzyl]-2,5-diaza-bicyclo[2.2.1]hept-2-yl}-thiophen-2-yl-methanone MS (ESI): mass calcd. for $C_{24}H_{21}N_3O_2S_2$, 447.11; m/z found, 448.1 [M+H]+. 1H NMR (500 MHz, CDCl3, mixture of rotamers): 7.76 (d, J=8.1 Hz, 1H), 7.69 (dd, J=8.0, 0.7 Hz, 1H), 7.60 (s, 0.5H), 7.54-7.26 (m, 7.5H), 7.15-7.06 (m, 1H), 4.97 (s, 0.5H), 4.76 (s, 0.5H), 4.01-3.55 (m, 5H), 3.17-3.07 (m, 0.5H), 2.96 (s, 1H), 2.86-2.76 (m, 0.5H), 2.01 (d, J=9.8 Hz, 1H), 1.89-1.79 (m, 1H).

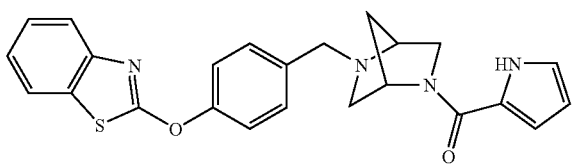

Example 62

(S,S)-{5-[4-(Benzothiazol-2-yloxy)-benzyl]-2,5-diaza-bicyclo[2.2.1]hept-2-yl}-(1H-pyrrol-2-yl)-methanone MS (ESI): mass calcd. for $C_{24}H_{22}N_4O_2S$, 430.15; m/z found, 431.2 [M+H]+. 1H NMR (500 MHz, CDCl3, mixture of rotamers): 9.67-9.43 (m, 1H), 7.76 (d, J=8.1 Hz, 1H), 7.69 (d, J=8.0 Hz, 1H), 7.48-7.38 (m, 3H), 7.36-7.27 (m, 3H), 7.01-8.93 (m, 1H), 6.62 (s, 0.75H), 6.51 (s, 0.25H), 6.35-6.25 (m, 1H), 5.00-4.85 (m, 1H), 4.01-3.76 (m, 3H), 3.72-3.52 (m, 2H), 3.21-3.12 (m, 0.25H), 2.98 (d, J=9.5 Hz, 0.75H), 2.90-2.75 (m, 1H), 2.09-1.96 (m, 1H), 1.91-1.75 (m, 1H).

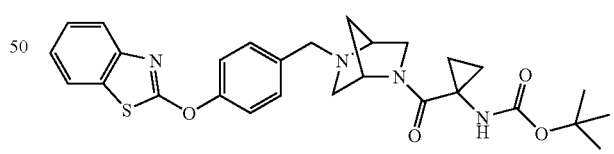

Example 63

(S,S)-(1-{5-[4-(Benzothiazol-2-yloxy)-benzyl]-2,5-diaza-bicyclo[2.2.1]heptane-2-carbonyl}-cyclopropyl)-carbamic acid tert-butyl ester MS (ESI): mass calcd. for $C_{28}H_{32}N_4O_4S$, 520.21; m/z found, 521.2 [M+H]+. 1H NMR (500 MHz, CDCl3, mixture of rotamers): 7.76 (d, J=8.1 Hz, 1H), 7.69 (d, J=7.9 Hz, 1H), 7.47-7.38 (m, 3H), 7.35-7.27 (m, 3H), 5.10 (br s, 1H), 4.74 (br s, 1H), 4.06 (br s, 0.5H), 3.79 (s, 2H), 3.66 (br s, 0.5H), 3.54 (s, 1.5H), 3.40 (br s, 0.5H), 3.10-2.53 (m, 2H), 2.05-1.85 (m, 1H), 1.69 (br s, 2H), 1.52-1.36 (m, 10H), 1.08-0.94 (m, 2H).

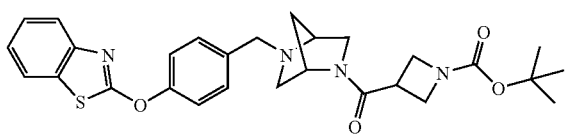

Example 64

(S,S)-3-{5-[4-(Benzothiazol-2-yloxy)-benzyl]-2,5-diaza-bicyclo[2.2.1]heptane-2-carbonyl}-azetidine-1-carboxylic acid tert-butyl ester MS (ESI): mass calcd. for $C_{28}H_{32}N_4O_4S$, 520.21; m/z found, 521.2 [M+H]$^+$. $^1$H NMR (500 MHz, CDCl$_3$, mixture of rotamers): 7.75 (d, J=8.1 Hz, 1H), 7.69 (d, J=7.9 Hz, 1H), 7.46-7.38 (m, 3H), 7.36-7.29 (m, 3H), 4.82 (s, 0.5H), 4.31-3.99 (m, 4H), 3.80-3.76 (m, 1.25H), 3.75 (s, 1.25H), 3.59 (d, J=13.2 Hz, 1H), 3.47-3.29 (m, 2H), 3.22 (dd, J=9.0, 2.2 Hz, 0.5H), 3.04-2.96 (m, 0.5H), 2.88 (dd, J=9.8, 1.7 Hz, 0.5H), 2.78 (d, J=9.8 Hz, 0.5H), 2.51 (dd, J=9.7, 0.9 Hz, 0.5H), 2.01 (d, J=9.5 Hz, 0.5H), 1.94 (d, J=10.0 Hz, 0.5H), 1.76 (d, J=10.0 Hz, 0.5H), 1.66 (d, J=10.0 Hz, 0.5H), 1.51-1.44 (m, 9.5H).

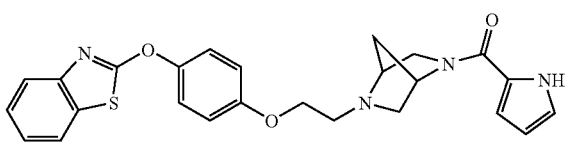

Example 65

(S,S)-(5-{2-[4-(Benzothiazol-2-yloxy)-phenoxy]-ethyl}-2,5-diaza-bicyclo[2.2.1]hept-2-yl)-(1H-pyrrol-2-yl)-methanone MS (ESI): mass calcd. for $C_{25}H_{24}N_4O_3S$, 460.16; m/z found, 461.2 [M+H]$^+$. $^1$H NMR (500 MHz, CDCl$_3$, mixture of rotamers): 9.59-9.38 (m, 1H), 7.75 (d, J=7.7 Hz, 1H), 7.67 (dd, J=8.0, 0.7 Hz, 1H), 7.41 (d, J=1.3 Hz, 0.25H), 7.40-7.39 (m, 0.5H), 7.38 (d, J=1.3 Hz, 0.25H), 7.32-7.25 (m, 3H), 7.00-6.94 (m, 3H), 6.63-6.50 (m, 1H), 6.30 (dd, J=6.4, 2.7 Hz, 1H), 4.99-4.84 (m, 1H), 4.09 (s, 2H), 3.99 (d, J=9.1 Hz, 0.75H), 3.91-3.72 (m, 1.25H), 3.68 (d, J=9.8 Hz, 0.75H), 3.63-3.55 (m, 0.25H), 3.39-3.30 (m, 0.25H), 3.15 (d, J=9.7 Hz, 0.75H), 3.11-2.98 (m, 2H), 2.88 (d, J=9.6 Hz, 1H), 2.08-1.93 (m, 1H), 1.93-1.76 (m, 1H).

Example 66

(S,S)-[1-(5-{2-[4-(Benzothiazol-2-yloxy)-phenoxy]-ethyl}-2,5-diaza-bicyclo[2.2.1]heptane-2-carbonyl)-cyclopropyl]-carbamic acid tert-butyl ester MS (ESI): mass calcd. for $C_{29}H_{34}N_4O_5S$, 550.22; m/z found, 551.2 [M+H]$^+$. $^1$H NMR (500 MHz, CDCl$_3$, mixture of rotamers): 7.75 (d, J=8.1 Hz, 1H), 7.67 (d, J=7.95 Hz, 1H), 7.41 (d, J=1.0 Hz, 0.25H), 7.41-7.39 (m, 0.5H), 7.38 (d, J=1.0 Hz, 0.25H), 7.32-7.25 (m, 3H), 6.99-6.94 (m, 2H), 5.27-4.95 (m, 1H), 4.71 (br s, 1H), 4.12-4.03 (m, 2H), 3.67 (s, 1.25H), 3.64-3.34 (m, 1.25H), 3.30-2.94 (m, 3H), 2.84-2.60 (m, 1H), 1.91 (br s, 1H), 1.78-1.62 (m, 2H), 1.46 (s, 9H), 1.39-0.85 (m, 3.5H).

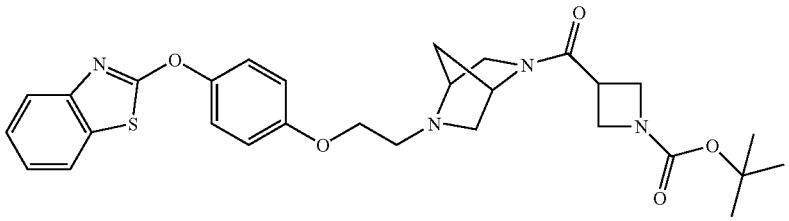

Example 67

(S,S)-3-(5-{2-[4-(Benzothiazol-2-yloxy)-phenoxy]-ethyl}-2,5-diaza-bicyclo[2.2.1]heptane-2-carbonyl)-azetidine-1-carboxylic acid tert-butyl ester MS (ESI): mass calcd. for $C_{29}H_{34}N_4O_5S$, 550.22; m/z found, 551.2 [M+H]$^+$. $^1$H NMR (500 MHz, CDCl$_3$, mixture of rotamers): 7.74 (d, J=7.8 Hz, 1H), 7.67 (d, J=7.9 Hz, 1H), 7.41 (d, J=1.1 Hz, 0.25H), 7.40 (s, 0.5H), 7.38 (d, J=1.1 Hz, 0.25H), 7.32-7.25 (m, 3H), 6.99-6.93 (m, 2H), 4.80 (s, 0.5H), 4.31-4.13 (m, 2H), 4.13-4.00 (m, 4H), 3.76-3.69 (m, 1.5H), 3.50-3.28 (m, 2H), 3.24 (dd, J=9.2, 2.2 Hz, 0.5H), 3.19 (dd, J=9.7, 2.2 Hz, 0.5H), 3.08-2.92 (m, 3H), 2.80 (d, J=9.6 Hz, 0.5H), 2.59 (dd, J=9.6, 0.8 Hz, 0.5H), 1.98 (d, J=9.5 Hz, 0.5H), 1.93 (d, J=0.5 Hz, 0.5H), 1.77 (d, J=9.5 Hz, 0.5H), 1.68 (d, J=10.0 Hz, 0.5H), 1.46 (d, J=1.5 Hz, 9H).

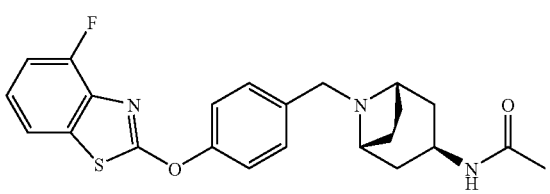

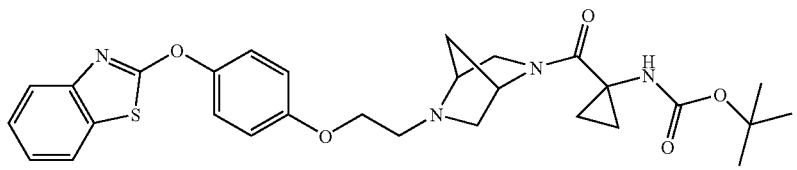

Example 68 meso-endo-N-{8-[4-(4-Fluoro-benzothiazol-2-yloxy)-benzyl]-8-aza-bicyclo[3.2.1]oct-3-yl}-acetamide MS (ESI): mass calcd. for $C_{23}H_{24}FN_3O_2S$, 425.5; m/z found, 426.2 [M+H]$^+$. $^1$H NMR (500 MHz, CDCl$_3$): 7.50-7.42 (m, 3H), 7.36-7.32 (m, 2H), 7.26-7.21 (m, 1H), 7.17-7.10 (m, 1H), 5.85-5.77 (m, 1H), 4.19-4.10 (m, 1H), 3.57 (s, 2H), 3.23 (s, 2H), 2.30-2.11 (m, 4H), 1.99 (s, 3H), 1.83-1.75 (m, 2H), 1.66-1.54 (m, 2H).

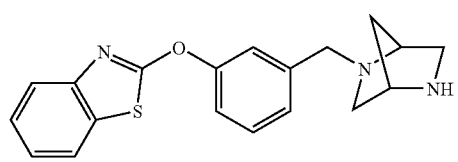

Example 69

(S,S)-2-[3-(2,5-Diaza-bicyclo[2.2.1]hept-2-ylmethyl)-phenoxy]-benzothiazole hydrochloride This compound was prepared using the methods outlined in Example 1, Steps A and B, substituting the appropriate chloromethyl phenoxy-benzothiazole. MS (ESI): mass calcd. for $C_{19}H_{19}N_3OS$, 337.12; m/z found, 338.2 [M+H]$^+$. $^1$H NMR (500 MHz, CD$_3$OD): 7.86-7.78 (m, 2H), 7.74-7.63 (m, 3H), 7.58 (m, 1H), 7.45 (m, 1H), 7.35 (m, 1H), 4.71 (br m, 1H), 4.65 (br m, 1H), 4.56 (br m, 1H), 4.04 (br m, 1H), 3.86 (br d, J=13.2 Hz, 1H), 3.67 (m, 3H), 3.60 (br m, 1H), 2.77 (br m, 1H), 2.33 (br d, J=13.0 Hz, 1H).

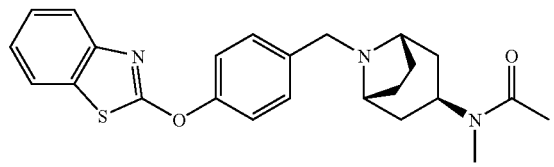

Example 70 meso-endo-N-{8-[4-(Benzothiazol-2-yloxy)-benzyl]-8-aza-bicyclo[3.2.1]oct-3-yl}-N-methyl-acetamide To a stirring suspension of NaH (60% dispersion in mineral oil, 14 mg, 0.34 mmol) in anhydrous DMF (600 µL) was added a solution of meso-endo-N{8-[4-(benzothiazol-2-yloxy)-benzyl]-8-aza-bicyclo[3.2.1]oct-3-yl}-acetamide (100 mg, 0.24 mmol) in DMF (600 µL). After gas evolution ceased, methyl iodide (16 µL, 0.26 mmol) was added via syringe. The reaction was warmed to 50° C. and allowed to stir overnight. The reaction was concentrated under a stream of dry nitrogen and the resultant residue was dissolved in CH$_3$OH (1.5 mL), filtered, and purified via reverse-phase HPLC to afford the title compound as white powder (10 mg, 10%). MS (ESI): mass calcd. for $C_{24}H_{27}N_3O_2S$, 421.6; m/z found, 422.2 [M+H]$^+$. $^1$H NMR (400 MHz, CD$_3$OD): 7.78 (d, J=8.1 Hz, 1H), 7.65 (d, J=7.7 Hz, 1H), 7.54 (d, J=8.6 Hz, 2H), 7.45-7.38 (m, 1H), 7.37-7.25 (m, 3H), 3.95-3.80 (m, 1H), 3.61 (s, 2H), 3.27-3.22 (m, 4H), 3.22-3.13 (m, 2H), 2.25-2.04 (m, 4H), 2.01-1.86 (m, 4H), 1.69-1.65 (m, 2H).

The compounds in Examples 71-80 were prepared using methods analogous to those described in the preceding examples.

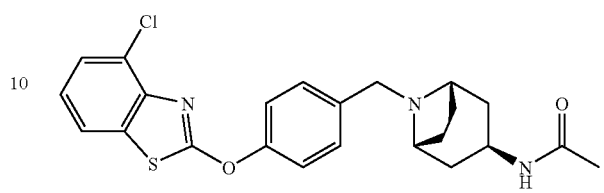

Example 71 meso-endo-N-{8-[4-(4-Chloro-benzothiazol-2-yloxy)-benzyl]-8-aza-bicyclo[3.2.1]oct-3-yl}-acetamide MS (ESI): mass calcd. for $C_{23}H_{24}ClN_3O_2S$, 441.98; m/z found, 442.2 [M+H]$^+$. $^1$H NMR (400 MHz, CDCl$_3$): 7.57-7.51 (m, 1H), 7.49-7.39 (m, 3H), 7.37-7.30 (m, 2H), 7.24-7.16 (m, 1H), 5.85-5.79 (m, 1H), 4.17-4.08 (m, 1H), 3.55 (s, 2H), 3.25-3.16 (m, 2H), 2.28-2.09 (m, 4H), 1.97 (s, 3H), 1.84-1.73 (m, 2H), 1.65-1.57 (m, 2H).

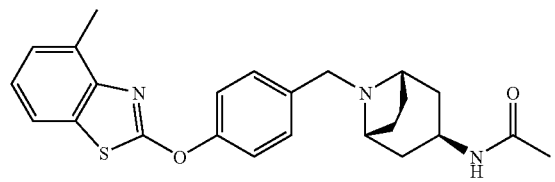

Example 72 meso-endo-N-{8-[4-(4-Methyl-benzothiazol-2-yloxy)-benzyl]-8-aza-bicyclo[3.2.1]oct-3-yl}-acetamide MS (ESI): mass calcd. for $C_{24}H_{27}N_3O_2S$, 421.57; m/z found, 422.2 [M+H]$^+$. $^1$H NMR (400 MHz, CDCl$_3$): 7.52-7.39 (m, 3H), 7.35-7.30 (m, 2H), 7.25-7.13 (m, 2H), 5.86-5.78 (m, 1H), 4.19-4.06 (m, 1H), 3.55 (s, 2H), 3.27-3.17 (m, 2H), 2.61 (s, 3H), 2.31-2.10 (m, 3H), 1.97 (s, 2H), 1.81-1.73 (m, 2H), 1.61-1.57 (m, 4H).

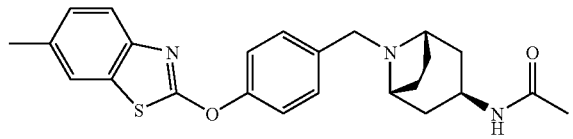

Example 73 meso-endo-N-{8-[4-(6-Methyl-benzothiazol-2-yloxy)-benzyl]-8-aza-bicyclo[3.2.1]oct-3-yl}-acetamide MS (ESI): mass calcd. for $C_{24}H_{27}N_3O_2S$, 421.57; m/z found, 422.2 [M+H]$^+$. $^1$H NMR (400 MHz, CDCl$_3$): 7.64-

7.59 (m, 1H), 7.49-7.39 (m, 3H), 7.34-7.24 (m, 2H), 7.23-7.15 (m, 1H), 5.87-5.72 (m, 1H), 4.16-4.08 (m, 1H), 3.58-3.50 (m, 2H), 3.24-3.18 (m, 2H), 2.48-2.40 (m, 3H), 2.28-2.08 (m, 4H), 1.97 (s, 3H), 1.80-1.69 (m, 2H), 1.60-1.54 (m, 2H).

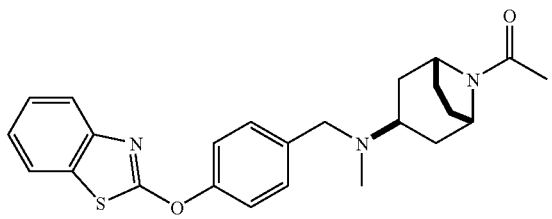

Example 74 meso-endo-1-(3-{[4-(Benzothiazol-2-yloxy)-benzyl]-methyl-amino}-8-aza-bicyclo[3.2.1]oct-8-yl)-ethanone MS (ESI): mass calcd. for $C_{24}H_{27}N_3O_2S$, 421.57; m/z found, 422.2 [M+H]$^+$. $^1$H NMR (400 MHz, CDCl$_3$): 7.75-7.72 (m, 1H), 7.69-7.64 (m, 1H), 7.43-7.18 (m, 5H), 4.72-4.64 (m, 1H), 4.14-4.07 (m, 1H), 3.60-3.50 (m, 2H), 2.60-2.48 (m, 1H), 2.26-1.75 (m, 15H).

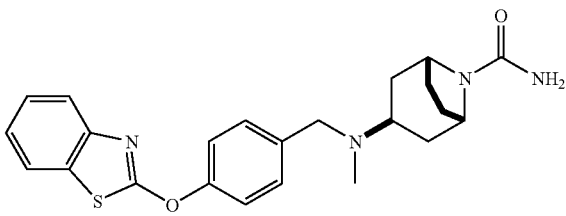

Example 75 meso-endo-3-{[4-(Benzothiazol-2-yloxy)-benzyl]-methyl-amino}-8-aza-bicyclo[3.2.1]octane-8-carboxylic acid amide MS (ESI): mass calcd. for $C_{23}H_{26}N_4O_2S$, 422.55; m/z found, 423.2 [M+H]$^+$. $^1$H NMR (400 MHz, CDCl$_3$): 7.77-7.71 (m, 1H), 7.69-7.64 (m, 1H), 7.42-7.22 (m, 5H), 4.56-4.49 (m, 1H), 4.22-4.07 (m, 1H), 3.58-3.53 (m, 2H), 2.63-2.54 (m, 1H), 2.28-1.72 (m, 12H).

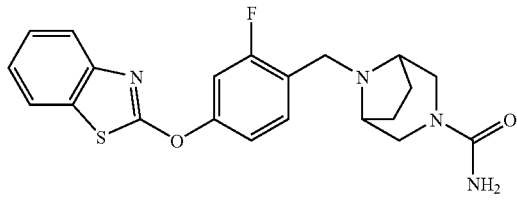

Example 76 meso-8-[4-(Benzothiazol-2-yloxy)-2-fluoro-benzyl]-3,8-diaza-bicyclo[3.2.1]octane-3-carboxylic acid amide Step A: 4-(Benzothiazol-2-yloxy)-2-fluoro-benzoic acid. A solution of 2-fluoro-4-hydroxy-benzoic acid (4.0 g, 25.6 mmol) in DMF (250 mL) was added Cs$_2$CO$_3$ (9.2 g, 28.2 mmol) and the reaction mixture was stirred at 80° C. for 1 h prior to the addition of 2-chloro-benzothiazole (3.3 mL, 25.6 mmol). The reaction mixture was stirred at 100° C. for 50 h, then cooled to rt, and the solid was filtered. The filtrate was diluted with EtOAc (200 mL) and water (100 mL), neutralized with 1 M HCl and the organic layer was separated. The aqueous layer was extracted with EtOAc (2×200 mL). The organic layers were combined, dried (Na$_2$SO$_4$), filtered, and concentrated to afford the title compound as a colorless solid (4.7 g, 63%). MS (ESI): mass calcd. for $C_{14}H_8FNO_3S$, 289.0; m/z found, 290.1 [M+H]$^+$. $^1$H NMR (400 MHz, CD$_3$OD): 8.21 (t, J=8.5 Hz, 1H), 7.99 (d, J=8.5 Hz, 1H), 7.87 (d, J=8.11 Hz, 1H), 7.63-7.45 (m, 4H).

Step B: [4-(Benzothiazol-2-yloxy)-2-fluoro-phenyl]-methanol. To a solution of 4-(benzothiazol-2-yloxy)-2-fluoro-benzoic acid (4.7 g, 16.1 mmol) in THF (100 mL) was added Et$_3$N (2.5 mL, 17.7 mmol). The mixture was cooled to 0° C., and isobutylchloroformate (2.1 mL, 16.1 mmol) was added. The reaction mixture was stirred for 2 h, filtered, and concentrated. The residue was dissolved in THF (50 mL) and cooled to 0° C. Sodium borohydride (1.2 g, 32.2 mmol) was added and immediately followed by water (10 mL). The reaction mixture was then partitioned between EtOAc (50 mL) and brine (20 mL). The organic layer was separated, dried (Mg$_2$SO$_4$), filtered and concentrated. Purification by silica gel flash chromatography (0% to 60% EtOAc in hexanes) afforded the title compound as a colorless solid (3.3 g, 75%). MS (ESI): mass calcd. for $C_{14}H_{10}FNO_2S$, 275.0; m/z found, 276.0 [M+H]$^+$. $^1$H NMR (500 MHz, CDCl$_3$): 7.77 (d, J=8.1 Hz, 1H), 7.72 (dd, J=5.3, 2.7 Hz, 1H), 7.54 (t, J=8.4 Hz, 1H), 7.43 (td, J=7.6, 1.3 Hz, 1H), 7.32 (td, J=7.5, 1.2 Hz, 1H), 7.24-7.16 (m, 2H), 4.81 (d, J=5.8 Hz, 2H), 1.79 (t, J=6.1 Hz, 1H).

Step C: 2-(4-Chloromethyl-3-fluoro-phenoxy)-benzothiazole. This compound was prepared using methods analogous to those described for Example 4, Step B. MS (ESI): mass calcd. for $C_{14}H_9ClFNOS$, 293.0; m/z found, 294.0 [M+H]$^+$. $^1$H NMR (400 MHz, CDCl$_3$): 7.75 (d, J=7.6 Hz, 1H), 7.70 (d, J=8.0 Hz, 1H), 7.49 (t, J=8.2 Hz, 1H), 7.41 (t, J=7.6 Hz, 1H), 7.30 (t, J=7.3 Hz, 1H), 7.24-7.18 (m, 2H), 4.65 (s, 2H).

Step D: 3,8-Diaza-bicyclo[3.2.1]octane-3-carboxylic acid amide hydrochloride. A solution of 3,8-diaza-bicyclo[3.2.1]octane-8-carboxylic acid tert-butyl ester (2.5 g, 11.7 mmol) in CH$_2$Cl$_2$ (50 mL) was treated with trimethylsilyl isocyanate (14 mL, 117 mmol). The resultant mixture was stirred at rt for 4 h., concentrated and redissolved in CH$_2$Cl$_2$ (50 mL). To this solution was added HCl (4.0 N in 1,4-dioxane, 12 mL), and the resultant mixture was stirred at rt for 3 h. Concentration afforded the title compound as a white powder (2.4 g, 99%). MS (ESI): mass calcd. for $C_7H_{13}N_3O$, 155.1; m/z found, 156.2 [M+H]$^+$.

Step E: meso-8-[4-(Benzothiazol-2-yloxy)-2-fluoro-benzyl]-3,8-diaza-bicyclo[3.2.1]octane-3-carboxylic acid amide. This compound was prepared using methods analogous to those described for Example 1, Step A, substituting 3,8-diaza-bicyclo[3.2.1]octane-3-carboxylic acid amide hydrochloride and 2-(4-chloromethyl-3-fluoro-phenoxy)-benzothiazole for 2-(4-chloromethyl-phenoxy)-benzothiazole and (S,S)-2,5-diaza-bicyclo[2.2.1]heptane-2-carboxylic acid tert-butyl ester. MS (ESI): mass calcd. for $C_{21}H_{21}N_4O_2S$, 412.1; m/z found, 413.2 [M+H]$^+$. $^1$H NMR (400 MHz, CDCl$_3$): 7.75 (d, J=8.0 Hz, 1H), 7.70 (d, J=8.0 Hz, 1H), 7.63 (t, J=8.3 Hz, 1H), 7.41 (t, J=7.2 Hz, 1H), 7.30 (t, J=7.2 Hz, 1H), 7.22-7.09 (m, 2H), 4.51 (s, 2H), 3.58 (s, 2H), 3.56-3.46 (m, 1H), 3.23 (s, 2H), 3.17 (d, J=11.3 Hz, 2H), 2.08-2.00 (m, 2H), 1.83 (s, 1H), 1.74 (d, J=7.8 Hz, 2H).

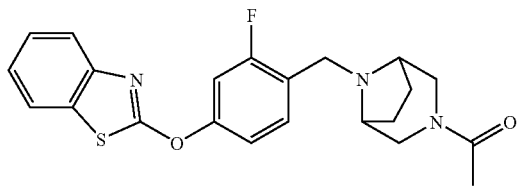

Example 77 meso-1-{8-[4-(Benzothiazol-2-yloxy)-2-fluoro-benzyl]-3,8-diaza-bicyclo[3.2.1]oct-3-yl}-ethanone Step A: 1-(3,8-Diaza-bicyclo[3.2.1]oct-3-yl)-ethanone hydrochloride. This compound was prepared using methods analogous to Example 76, Step D, substituting trimethylsilyl isocyanate with acetic anhydride. MS (ESI): MS (ESI): mass calcd. for $C_8H_{14}N_2O$, 154.1; m/z found, 155.1 [M+H]$^+$.

Step B: meso-1-{8-[4-(Benzothiazol-2-yloxy)-2-fluoro-benzyl]-3,8-diaza-bicyclo[3.2.1]oct-3-yl}-ethanone. This compound was prepared using methods analogous to those described for Example 76, Step E. MS (ESI): mass calcd. for $C_{23}H_{24}N_3O_2S$, 425.1; m/z found, 426.1 [M+H]$^+$. $^1$H NMR (400 MHz, CDCl$_3$): 7.74 (d, J=7.8 Hz, 1H), 7.69 (d, J=7.4 Hz, 1H), 7.64 (t, J=8.4 Hz, 1H), 7.4 (t, J=7.9 Hz, 1H), 7.29 (t, J=6.9 Hz, 1H), 7.14 (m, 2H), 5.96-5.71 (m, 1H), 4.11 (m, 1H), 3.56 (s, 2H), 3.23 (s, 2H), 2.21 (m, 4H), 1.97 (s, 3H), 1.86-1.71 (m, 2H), 1.63 (d, J=14.3 Hz, 2H).

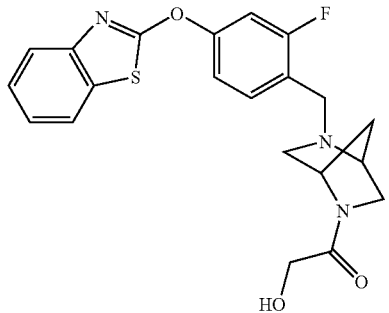

Example 78

(S,S)-1-{5-[4-(Benzothiazol-2-yloxy)-2-fluoro-benzyl]-2,5-diaza-bicyclo[2.2.1]hept-2-yl}-2-hydroxy-ethanone This compound was prepared using methods analogous to those described for Example 76, Step E, substituting (S,S)-2,5-diaza-bicyclo[2.2.1]heptane-2-carboxylic acid tert-butyl ester for 3,8-diaza-bicyclo[3.2.1]octane-3-carboxylic acid amide followed by methods analogous to those described for Example 10. MS (ESI): mass calcd. for $C_{21}H_{20}FN_3O_3S$, 413.1; m/z found, 414.1 [M+H]$^+$. $^1$H NMR (400 MHz, CDCl$_3$, mixture of rotamers): 7.74 (d, J=8.0 Hz, 1H), 7.70 (d, J=8.0 Hz, 1H), 7.50 (td, J=8.5, 2.2 Hz, 1H), 7.41 (t, J=7.7 Hz, 1H), 7.30 (t, J=7.7 Hz, 1H), 7.20-7.12 (m, 2H), 4.83 (s, 0.5H), 4.22 (d, J=14.9 Hz, 0.5H), 4.08 (d, J=15.1 Hz, 1H), 4.01 (d, J=15.4 Hz, 1H), 3.86-3.69 (m, 2.5H), 3.61 (s, 1H), 3.50-3.44 (m, 1.5H), 3.38 (dd, J=11.3, 1.7 Hz, 0.5H), 3.23 (dd, J=9.3, 2.2 Hz, 0.5H), 3.00 (dd, J=9.7, 2.0 Hz, 0.5H), 2.91 (dd, J=9.8, 2.1 Hz, 0.5H), 2.81 (d, J=9.8 Hz, 0.5H), 2.64 (d, J=9.7 Hz, 0.5H), 2.04-1.94 (m, 1.5H), 1.78 (d, J=9.8 Hz, 0.5H), 1.69 (d, J=10.1 Hz, 0.5H).

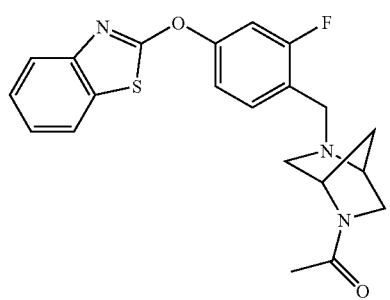

Example 79

(S,S)-1-{5-[4-(Benzothiazol-2-yloxy)-2-fluoro-benzyl]-2,5-diaza-bicyclo[2.2.1]hept-2-yl}-ethanone This compound was prepared using methods analogous to those described for Example 76, Step E, substituting (S,S)-2,5-diaza-bicyclo[2.2.1]heptane-2-carboxylic acid tert-butyl ester for 3,8-diaza-bicyclo[3.2.1]octane-3-carboxylic acid amide followed by methods analogous to those described for Example 1, Steps B and C. MS (ESI): mass calcd. for $C_{21}H_{20}FN_3O_2S$, 397.1; m/z found, 398.1 [M+H]$^+$. $^1$H NMR (400 MHz, CDCl$_3$, mixture of rotamers): 7.74 (d, J=8.1 Hz, 1H), 7.69 (d, J=8.1 Hz, 1H), 7.58-7.47 (m, 1H), 7.40 (t, J=7.7 Hz, 1H), 7.33-7.24 (m, 1H), 7.22-7.07 (m, 2H), 4.79 (s, 0.5H), 4.25 (s, 0.5H), 3.86-3.67 (m, 2.5H), 3.65-3.52 (m, 1.5H), 3.37-3.27 (m, 1H), 3.02 (dd, J=9.6, 2.1 Hz, 0.5H), 2.89 (dd, J=9.7, 2.2 Hz, 1H), 2.81 (d, J=9.8 Hz, 1H), 2.65 (d, J=9.6 Hz, 0.5H), 2.09 (s, 1.0H), 2.01 (s, 1.5H), 1.92 (d, J=10.0 Hz, 0.5H), 1.81 (d, J=9.8 Hz, 0.5H), 1.69 (d, J=10.0 Hz, 0.5H).

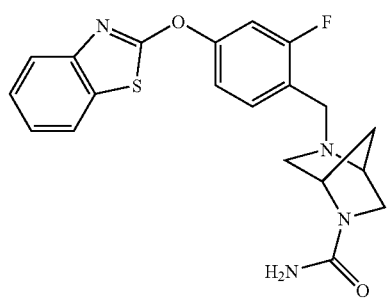

Example 80

(S,S)-5-[4-(Benzothiazol-2-yloxy)-2-fluoro-benzyl]-2,5-diaza-bicyclo[2.2.1]heptane-2-carboxylic acid amide This compound was prepared using methods analogous to those described for Example 76, Step E, substituting (S,S)-2,5-diaza-bicyclo[2.2.1]heptane-2-carboxylic acid tert-butyl ester for 3,8-diaza-bicyclo[3.2.1]octane-3-carboxylic acid amide followed by methods analogous to those described for Example 32. MS (ESI): mass calcd. for $C_{20}H_{19}FN_4O_2S$, 398.1; m/z found, 399.1 [M+H]$^+$. $^1$H NMR (400 MHz, CDCl$_3$): 7.74 (d, J=7.9 Hz, 1H), 7.69 (d, J=7.9 Hz, 1H), 7.52 (t, J=8.3 Hz, 1H), 7.39 (t, J=7.6 Hz, 1H), 7.29 (t, J=7.7 Hz, 1H), 7.20-7.08 (m, 2H), 4.66 (s, 2H), 4.44 (s, 1H), 3.79 (m, 2H), 3.63-3.49 (m, 2H), 3.25 (d, J=7.0 Hz, 1H), 2.94 (d, J=8.0 Hz, 1H), 2.80 (d, J=9.5 Hz, 1H), 1.93 (d, J=9.4 Hz, 1H), 1.76 (d, J=9.4 Hz, 1H).

The compounds in Examples 81-85 were prepared using methods analogous to those described in Example 1, Steps A and B.

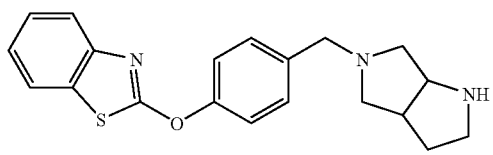

Example 81

2-[4-(Hexahydro-pyrrolo[3,4-b]pyrrol-5-ylmethyl)-phenoxy]-benzothiazole hydrochloride MS (ESI): mass calcd. for $C_{20}H_{21}N_3OS$, 351.4; m/z found, 352.2 [M+H]$^+$. $^1$H NMR (500 MHz, CDCl$_3$): 7.88-7.74 (m, 3H), 7.66 (d, J=8.1 Hz, 1H), 7.55 (d, J=8.4 Hz, 2H), 7.45 (dt, J=8.2, 7.8, 1.3 Hz, 1H), 7.38-7.34 (m, 1H), 4.75-4.42 (m, 3H), 4.13-3.99 (m, 1H), 3.83-3.48 (m, 7H), 2.35-2.00 (m, 1H).

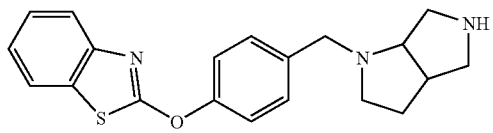

Example 82

2-[4-(Hexahydro-pyrrolo[3,4-b]pyrrol-1-ylmethyl)-phenoxy]-benzothiazole hydrochloride MS (ESI): mass calcd. for $C_{20}H_{21}N_3OS$, 351.4; m/z found, 352.2 [M+H]$^+$. $^1$H NMR (400 MHz, CDCl$_3$) 7.74 (d, J=8.1 Hz, 1H), 7.66 (d, J=7.9 Hz, 1H), 7.42-7.34 (m, 3H), 7.33-7.21 (m, 3H), 3.87 (d, J=13.1 Hz, 1H), 3.70 (s, 1H), 3.46 (d, J=13.1 Hz, 1H), 3.06-2.98 (m, 1H), 2.93-2.62 (m, 4H), 2.50-2.44 (m, 1H), 2.19-2.01 (m, 2H), 1.46-1.29 (m, 1H).

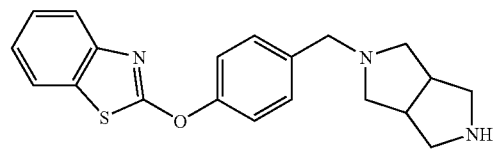

Example 83

2-[4-(Hexahydro-pyrrolo[3,4-c]pyrrol-2-ylmethyl)-phenoxy]-benzothiazole hydrochloride MS (ESI): mass calcd. for $C_{20}H_{21}N_3O_2S$, 351.5; m/z found, 352.2 [M+H]$^+$. $^1$H NMR (500 MHz, CD$_3$OD): 7.87-7.79 (m, 2H), 7.74 (d, J=8.2 Hz, 1H), 7.66 (d, J=8.1 Hz, 1H), 7.57-7.50 (m, 2H), 7.48-7.42 (m, 1H), 7.39-7.32 (m, 1H), 4.61-4.44 (m, 2H), 3.92-3.82 (m, 1H), 3.72-3.35 (m, 9H).

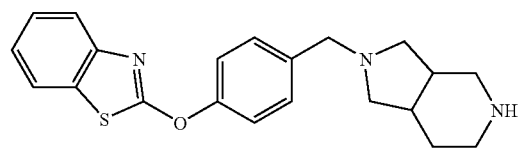

Example 84

2-[3-(Octahydro-pyrrolo[3,4-c]pyridin-2-ylmethyl)-phenoxy]-benzothiazole hydrochloride MS (ESI): mass calcd. for $C_{21}H_{23}N_3OS$, 365.20; m/z found, 366.1 [M+H]$^+$. $^1$H NMR (400 MHz, CD$_3$OD): 7.86-7.74 (m, 3H), 7.61 (d, J=7.6 Hz, 1H), 7.48 (dd, J=8.6 Hz, 3.0, 2H), 7.44-7.37 (m, 1H), 7.34-7.26 (m, 1H), 4.64-4.48 (m, 2H), 3.88-3.64 (m, 1H), 3.61-3.50 (m, 2H), 3.45-3.31 (m, 4H), 3.26-3.07 (m, 2H), 3.04-2.64 (m, 2H), 2.23-1.81 (m, 2H).

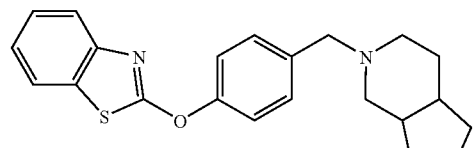

Example 85

2-[4-(Octahydro-pyrrolo[3,4-c]pyridin-5-ylmethyl)-phenoxy]-benzothiazole hydrochloride MS (ESI): mass calcd. for $C_{21}H_{23}N_3OS$, 365.16; m/z found, 366.1 [M+H]$^+$. $^1$H NMR (400 MHz, DMSO-d$_6$): 11.66 (s, 1H), 9.81 (s, 1H), 9.55 (s, 1H), 7.97 (d, J=7.3 Hz, 1H), 7.82 (d, J=8.6 Hz, 2H), 7.71 (d, J=8.1 Hz, 1H), 7.55 (d, J=8.6 Hz, 2H), 7.45 (dt, J=7.8; 1.3 Hz, 1H), 7.35 (dt, J=7.5, 1.2 Hz, 1H), 4.51-4.25 (m, 2H), 3.59-3.31 (m, 4H), 3.12-2.93 (m, 2H), 2.87-2.62 (m, 2H), 2.39-2.16 (m, 1H), 2.14-2.01 (m, 1H), 1.99-1.72 (m, 2H).

The compounds in Examples 86-90 were prepared using methods analogous to those described in Example 1.

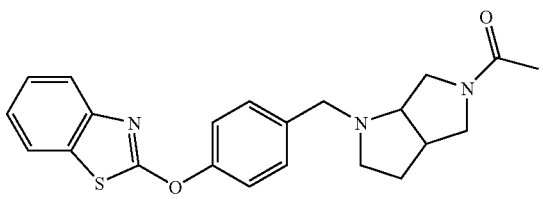

Example 86

1-{1-[4-(Benzothiazol-2-yloxy)-benzyl]-hexahydro-pyrrolo[3,4-b]pyrrol-5-yl}-ethanone MS (ESI): mass calcd. for C$_{22}$H$_{23}$N$_3$O$_2$S, 393.5; m/z found, 394.2 [M+H]$^+$. $^1$H NMR (500 MHz, CDCl$_3$): 7.78-7.71 (m, 1H), 7.71-7.65 (m, 1H), 7.45-7.30 (m, 6H), 3.98 (d, J=13.1 Hz, 0.5H), 3.88-3.77 (m, 1H), 3.75-3.62 (m, 1H), 3.55 (d, J=13.3 Hz, 0.5H), 3.52-3.44 (m, 1H), 3.43-3.29 (m, 2H), 3.22-3.15 (m, 0.5H), 3.15-3.08 (m, 1H), 3.07-3.01 (m, 0.5H), 2.92-2.76 (m, 1H), 2.42-2.28 (m, 1H), 2.03 (s, 3H), 1.70-1.62 (m, 2H).

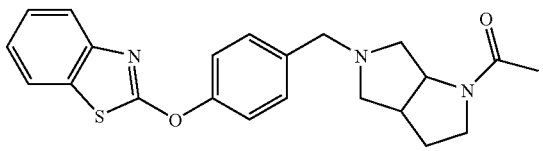

Example 87

1-{5-[4-(Benzothiazol-2-yloxy)-benzyl]-hexahydro-pyrrolo[3,4-b]pyrrol-1-yl}-ethanone MS (ESI): mass calcd. for C$_{22}$H$_{23}$N$_3$O$_2$S, 393.5; m/z found, 394.2 [M+H]$^+$. $^1$H NMR (500 MHz, CDCl$_3$): 7.76 (d, J=8.1 Hz, 1H), 7.71-7.66 (m, 1H), 7.46-7.35 (m, 3H), 7.36-7.28 (m, 3H), 4.49-4.44 (m, 1H), 4.34-4.27 (m, 0.5H), 3.99-3.90 (m, 0.5H), 3.68 (d, J=13.1 Hz, 1H), 3.63-3.52 (m, 2H), 3.48 (d, J=13.2 Hz, 1H), 3.45-3.35 (m, 0.5H), 3.07-2.93 (m, 0.5H), 2.92-2.79 (m, 1H), 2.72-2.63 (m, 1H), 2.63-2.52 (m, 1H), 2.51-2.41 (m, 1H), 2.08 (s, 3H), 1.95-1.83 (m, 1H).

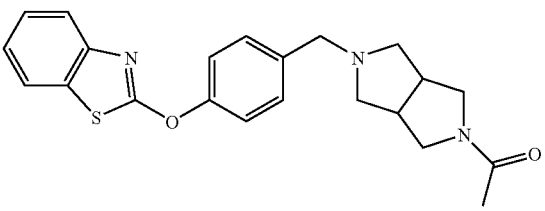

Example 88

1-{5-[4-(Benzothiazol-2-yloxy)-benzyl]-hexahydro-pyrrolo[3,4-c]pyrrol-2-yl}-ethanone MS (ESI): mass calcd. for C$_{22}$H$_{23}$N$_3$O$_2$S, 393.5; m/z found, 394.1 [M+H]$^+$. $^1$H NMR (400 MHz, CDCl$_3$): 7.74 (d, J=7.6 Hz, 1H), 7.67 (d, J=7.3 Hz, 1H), 7.43-7.35 (m, 3H), 7.34-7.23 (m, 3H), 3.76-3.59 (m, 4H), 3.47-3.41 (m, 1H), 3.37-3.28 (m, 1H), 2.98-2.77 (m, 2H), 2.69-2.58 (m, 2H), 2.55-2.44 (m, 2H), 2.06 (s, 3H).

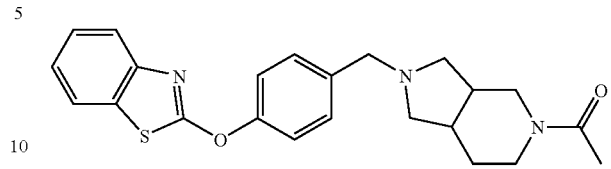

Example 89

1-{2-[4-(Benzothiazol-2-yloxy)-benzyl]-octahydro-pyrrolo[3,4-c]pyridin-5-yl}-ethanone MS (ESI): mass calcd. C$_{23}$H$_{25}$N$_3$O$_2$S, 407.2; m/z found, 408.2 [M+H]$^+$. $^1$H NMR (400 MHz, CDCl$_3$, mixture of rotamers): 7.74 (d, J=8.1 Hz, 1H), 7.67 (d, J=8.0 Hz, 1H), 7.43-7.20 (m, 6H), 3.89 (dd, J=13.4, 5.4 Hz, 0.5H), 3.71-3.46 (m, 3.5H), 3.41-3.20 (m, 2H), 2.80-2.70 (m, 2H), 2.53-2.22 (m, 4H), 2.07 (s, 3H), 1.94-1.61 (m, 2H).

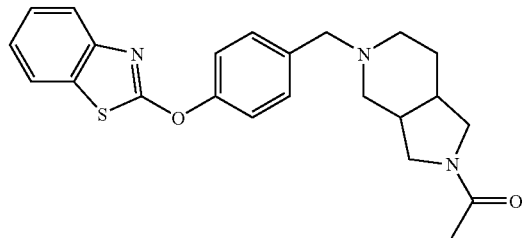

Example 90

1-{5-[4-(Benzothiazol-2-yloxy)-benzyl]-octahydro-pyrrolo[3,4-c]pyridin-2-yl}-ethanone MS (ESI): mass calcd. for C$_{23}$H$_{25}$N$_3$O$_2$S, 407.17; m/z found, 408.2 [M+H]$^+$. $^1$H NMR (400 MHz, CDCl$_3$, mixture of rotamers): 7.74 (d, J=8.1 Hz, 1H), 7.67 (d, J=7.9 Hz, 1H), 7.42-7.35 (m, 3H), 7.35-7.24 (m, 3H), 3.68-3.37 (m, 5.5H), 3.35-3.24 (m, 0.5H), 2.70-2.14 (m, 6H), 2.05 (s, 1.5H), 2.04 (s, 1.5H), 1.83-1.67 (m, 1H), 1.67-1.51 (m, 1H).

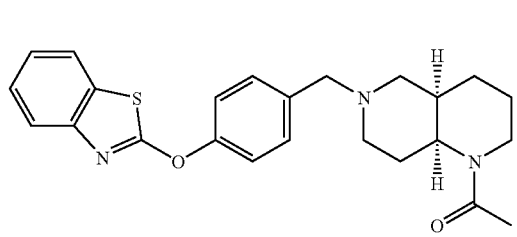

Example 91 cis-1-{7-[4-(Benzothiazol-2-yloxy)-benzyl]-octahydro-[1,7]naphthyridin-1-yl}-ethanone Step A: cis-6-[4-(Benzothiazol-2-yloxy)-benzyl]-decahydro-[1,6]naphthyridine This compound was prepared using methods analogous to those described for Example 81. Separation from the trans-isomer was performed using flash column chromatography. MS (ESI): mass calcd. $C_{22}H_{25}N_3OS$, 379.2; m/z found, 380.2 [M+H]$^+$. $^1$H NMR (400 MHz, CD$_3$OD): 7.82 (d, J=8.0 Hz, 1H), 7.76 (d, J=8.5 Hz, 1H), 7.64 (d, J=8.1 Hz, 1H), 7.57-7.49 (m, 2H), 7.46-7.38 (m, 1H), 7.38-7.29 (m, 1H), 4.50 (s, 2H), 3.92-2.99 (m, 7H), 2.69-2.29 (m, 2H), 2.27-2.01 (m, 2H), 2.06-1.65 (m, 2H), 1.28 (s, 1H), 1.00-0.75 (m, 1H).

Step B: cis-1-{7-[4-(Benzothiazol-2-yloxy)-benzyl]-octahydro-[1,7]naphthyridin-1-yl}-ethanone. This compound was prepared using methods analogous to those described for Example 1, Step C. MS (ESI): mass calcd. for $C_{24}H_{27}N_3O_2S$, 421.18; m/z found, 422.2 [M+H]$^+$. $^1$H NMR (400 MHz, CDCl$_3$, mixture of rotamers): 7.74 (d, J=7.6 Hz, 1H), 7.67 (d, J=7.9 Hz, 1H), 7.44-7.35 (m, 3H), 7.34-7.23 (m, 3H), 4.77-4.60 (m, 0.6H), 4.56-4.47 (m, 0.4H), 3.81-3.69 (m, 0.4H), 3.64-3.55 (m, 0.61H), 3.53-3.36 (m, 2H), 3.20-3.05 (m, 0.6H), 3.03-2.84 (m, 1H), 2.80-2.55 (m, 1.4H), 2.32-1.98 (m, 7H), 1.88-1.66 (m, 2H), 1.55-1.35 (m, 3H).

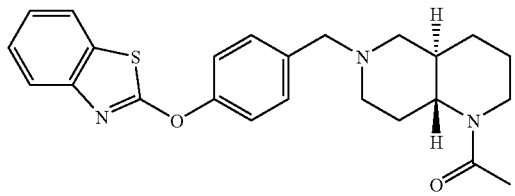

Example 92 trans-1-{7-[4-(Benzothiazol-2-yloxy)-benzyl]-octahydro-[1,7]naphthyridin-1-yl}-ethanone Step A: trans-6-[4-(Benzothiazol-2-yloxy)-benzyl]-decahydro-[1,6]naphthyridine. This compound was prepared using methods analogous to those described for Example 81. Separation from the cis-isomer was performed using flash column chromatography. MS (ESI): mass calcd. $C_{22}H_{25}N_3OS$, 379.2; m/z found, 380.2 [M+H]$^+$. $^1$H NMR (400 MHz, CD$_3$OD): 7.83 (d, J=7.9 Hz, 1H), 7.74 (d, J=8.6 Hz, 2H), 7.64 (d, J=8.1 Hz, 1H), 7.54 (d, J=8.6 Hz, 1H), 7.43 (dt, J=8.2, 7.8, 1.3 Hz, 1H), 7.37-7.31 (m, 1H), 4.42 (s, 2H), 3.81-3.59 (m, 2H), 3.61-3.36 (m, 2H), 3.29-2.96 (m, 4H), 2.37-1.93 (m, 4H), 1.94-1.72 (m, 2H), 1.53-1.27 (m, 1H).

Step B: trans-1-{7-[4-(Benzothiazol-2-yloxy)-benzyl]-octahydro-[1,7]naphthyridin-1-yl}-ethanone. This compound was prepared using methods analogous to those described for Example 1, Step C. MS (ESI): mass calcd. for $C_{24}H_{27}N_3O_2S$, 421.18; m/z found, 422.2 [M+H]$^+$. $^1$H NMR (400 MHz, CDCl$_3$): 7.74 (d, J=8.1 Hz, 1H), 7.67 (d, J=7.9 Hz, 1H), 7.44-7.35 (m, 3H), 7.34-7.24 (m, 3H), 3.66-3.41 (m, 2H), 3.40-3.23 (m, 2H), 3.09-2.77 (m, 2H), 2.30-2.14 (m, 2H), 2.08 (s, 3H), 2.02-1.87 (m, 1H), 1.87-1.52 (m, 6H), 1.22-1.04 (m, 1H).

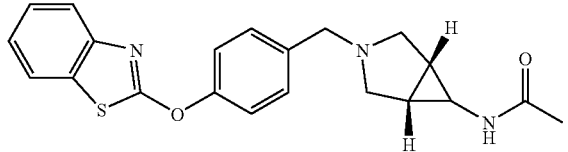

Example 93

(R,S)—N-{3-[4-(Benzothiazol-2-yloxy)-benzyl]-3-aza-bicyclo[3.1.0]hex-6-yl}-acetamide Step A: 3-[4-(Benzothiazol-2-yloxy)-benzyl]-3-aza-bicyclo[3.1.0]hex-6-ylamine. This compound was prepared using methods analogous to those described for Example 81. MS (ESI): mass calcd. $C_{19}H_{19}N_3OS$, 338.1; m/z found, 380.2 [M+H]$^+$. $^1$H NMR (400 MHz, DMSO-d$_6$): 7.93 (d, J=7.2 Hz, 1H), 7.69 (d, J=7.5 Hz, 1H), 7.54-7.25 (m, 6H), 3.56 (s, 2H), 3.35-3.04 (m, 3H), 2.88 (d, J=8.7 Hz, 2H), 2.34 (d, J=8.4 Hz, 2H), 1.32-1.30 (m, 2H).

Step B: (R,S)—N-{3-[4-(Benzothiazol-2-yloxy)-benzyl]-3-aza-bicyclo[3.1.0]hex-6-yl}-acetamide. This compound was prepared using methods analogous to those described for Example 1, Step C. MS (ESI): mass calcd. $C_{21}H_{21}N_3O_2S$, 379.1; m/z found, 380.1 [M+H]$^+$. $^1$H NMR (400 MHz, CD$_3$OD): 7.77 (d, J=7.8 Hz, 1H), 7.65 (d, J=8.0 Hz, 1H), 7.46-7.37 (m, 3H), 7.36-7.25 (m, 3H), 3.62 (s, 2H), 3.09 (d, J=8.9 Hz, 2H), 2.98 (s, 1H), 2.45 (d, J=8.6, 2H), 1.88 (s, 3H), 1.53 (s, 2H).

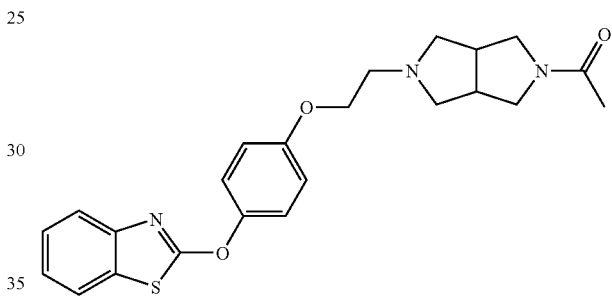

Example 94

1-(5-{2-[4-(Benzothiazol-2-yloxy)-phenoxy]-ethyl}-hexahydro-pyrrolo[3,4-c]pyrrol-2-yl)-ethanone These compounds were prepared using methods analogous to those described for Example 9. MS (ESI): Mass calcd for $C_{23}H_{25}N_3O_3S$, 423.5; m/z found, 424.2 [M+H]$^+$. $^1$H NMR (400 MHz, CD$_3$OD): 7.75 (d, J=8.0 Hz, 1H), 7.65 (d, J=8.1 Hz, 1H), 7.44-7.39 (m, 1H), 7.35-7.21 (m, 3H), 7.09-6.96 (m, 2H), 4.15 (t, J=5.5 Hz, 2H), 3.72 (dd, J=11.1, 8.5 Hz, 1H), 3.61 (dd, J=12.4, 7.9 Hz, 1H), 3.48-3.38 (m, 2H), 3.03-2.91 (m, 1H), 2.91-2.81 (m, 5H), 2.63-2.46 (m, 2H), 2.05 (s, 3H).

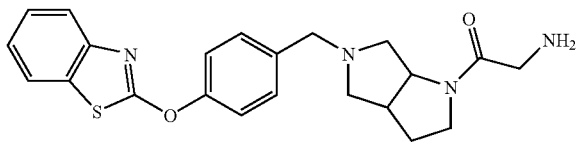

Example 95

2-Amino-1-{5-[4-(benzothiazol-2-yloxy)-benzyl]-hexahydro-pyrrolo[3,4-b]pyrrol-1-yl}-ethanone To a stirred solution of 2-[4-(hexahydro-pyrrolo[3,4-b]pyrrol-5-ylmethyl)-phenoxy]-benzothiazole hydrochloride (100 mg, 0.26 mmol) and Et$_3$N (215 μL, 1.6 mmol) in CH$_2$Cl$_2$ (2 mL) was added N-Boc-glycine (95 mg, 0.5 mmol), and 1-(3-dimethylaminopropyl)-3-ethylcarbodiimide hydrochloride (104 mg, 0.5 mmol). The resulting solution was then stirred at rt for 16 h. The resulting mixture was then treated with trifluoroacetic acid (1 mL) at rt for 3 h. The crude solid was dissolved in CH$_3$OH/DMSO (2:1) and purified via reverse phase preparative HPLC to yield the title compound as a fluffy white solid (37 mg, 35%). MS (ESI): mass calcd. for C$_{22}$H$_{24}$N$_4$O$_2$S, 408.5; m/z found, 409.2 [M+H]$^+$. $^1$H NMR (500 MHz, CDCl$_3$): 7.74 (d, J=8.1 Hz, 1H), 7.68 (d, J=8.0 Hz, 1H), 7.43-7.33 (m, 3H), 7.33-7.26 (m, 3H), 4.51-4.42 (m, 1H), 4.27-4.19 (m, 0.5H), 4.02-3.92 (m, 0.5H), 3.66 (d, J=13.2 Hz, 1H), 3.58 (d, J=5.0 Hz, 0.5H), 3.51-3.37 (m, 3H), 3.28 (d, J=16.7 Hz, 0.5H), 2.91-2.76 (m, 2H), 2.70-2.60 (m, 1H), 2.58-2.50 (m, 1H), 2.50-2.37 (m, 1H), 2.14-1.96 (m, 1H), 1.97-1.80 (m, 1H).

The compounds in Examples 96-97 were prepared using methods analogous to those described in Example 95.

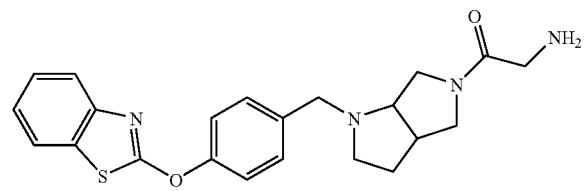

Example 96

2-Amino-1-{1-[4-(benzothiazol-2-yloxy)-benzyl]-hexahydro-pyrrolo[3,4-b]pyrrol-5-yl}-ethanone MS (ESI): mass calcd. for C$_{22}$H$_{24}$N$_4$O$_2$S, 408.5; m/z found, 409.2 [M+H]$^+$. $^1$H NMR (500 MHz, CDCl$_3$): 7.71 (d, J=8.1 Hz, 1H), 7.65 (d, J=8.0 Hz, 1H), 7.40-7.33 (m, 3H), 7.32-7.22 (m, 3H), 4.07-3.93 (m, 0.5H), 3.93-3.70 (m, 2.5H), 3.67-3.58 (m, 1H), 3.54-3.32 (m, 4H), 3.31-3.15 (m, 1H), 3.13-3.01 (m, 1H), 2.96-2.84 (m, 0.5H), 2.81-2.71 (m, 0.5H), 2.46-2.27 (m, 1H), 2.12-1.95 (m, 1H), 1.72-1.53 (m, 1H).

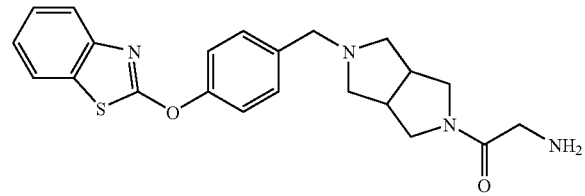

Example 97

2-Amino-1-{5-[4-(benzothiazol-2-yloxy)-benzyl]-hexahydro-pyrrolo[3,4-c]pyrrol-2-yl}-ethanone MS (ESI): mass calcd. for C$_{22}$H$_{24}$N$_4$O$_2$S, 408.5; m/z found, 409.2 [M+H]$^+$. $^1$H NMR (500 MHz, CDCl$_3$): 7.79-7.73 (m, 1H), 7.71-7.67 (m, 1H), 7.43-7.36 (m, 3H), 7.35-7.27 (m, 3H), 3.83-3.73 (m, 1H), 3.67-3.57 (m, 3H), 3.53-3.37 (m, 3H), 3.31-3.23 (m, 1H), 3.00-2.80 (m, 2H), 2.70-2.61 (m, 2H), 2.59-2.48 (m, 2H).

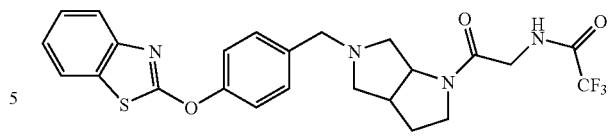

Example 98

N-(2-{5-[4-(Benzothiazol-2-yloxy)-benzyl]-hexahydro-pyrrolo[3,4-b]pyrrol-1-yl}-2-oxo-ethyl)-2,2,2-trifluoro-acetamide To a stirred solution of 2-[4-(hexahydro-pyrrolo[3,4-b]pyrrol-5-ylmethyl)-phenoxy]-benzothiazole hydrochloride (100 mg, 0.26 mmol) and Et$_3$N (215 μL, 1.6 mmol) in CH$_2$Cl$_2$ (2 mL) was added N-Boc-glycine (95 mg, 0.5 mmol), and 1-(3-dimethylaminopropyl)-3-ethylcarbodiimide hydrochloride (104 mg, 0.5 mmol). The resulting solution was then stirred at rt for 16 h. The resulting mixture was then treated with trifluoroacetic acid (1 mL) at rt for 3 h. The crude solid was dissolved in CH$_3$OH/DMSO (2:1) and purified via reverse phase preparative HPLC to yield the title compound as a fluffy white solid (26 mg, 20%). MS (ESI): mass calcd. for C$_{24}$H$_{23}$F$_3$N$_4$O$_3$S, 504.5; m/z found, 505.2 [M+H]$^+$. $^1$H NMR (500 MHz, CDCl$_3$): 7.74 (d, J=7.7 Hz, 1H), 7.68 (d, J=8.0 Hz, 1H), 7.56-7.49 (m, 1H), 7.42-7.26 (m, 6H), 4.55-4.45 (m, 1H), 4.17-3.87 (m, 2H), 3.67 (d, J=13.1 Hz, 1H), 3.60-3.38 (m, 3H), 3.09-2.81 (m, 2H), 2.78-2.54 (m, 2H), 2.52-2.35 (m, 1H), 2.20-2.06 (m, 1H), 2.02-1.87 (m, 1H).

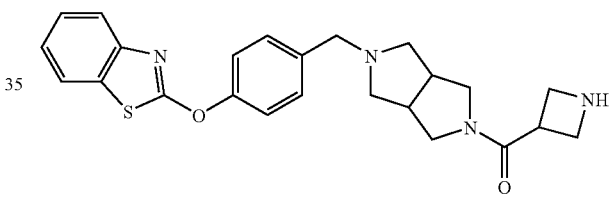

Example 99

Azetidin-3-yl-{5-[4-(benzothiazol-2-yloxy)-benzyl]-hexahydro-pyrrolo[3,4-c]pyrrol-2-yl}-methanone This compound was prepared using methods analogous to Example 95, substituting HCl (4.0 N in dioxane) for trifluoroacetic acid. MS (ESI): Mass calcd for C$_{24}$H$_{26}$N$_4$O$_2$S, 434.6; m/z found, 435.2 [M+H]$^+$; $^1$H NMR (400 MHz, CD$_3$OD): 7.80-7.72 (m, 1H), 7.68-7.57 (m, 1H), 7.53-7.36 (m, 2H), 7.36-7.21 (m, 2H), 7.15-7.03 (m, 2H), 6.77-6.64 (m, 1H), 4.39-4.23 (m, 2H), 4.11-3.94 (m, 0.5H), 3.94-3.82 (m, 1.5H), 3.81-3.66 (m, 1.5H), 3.66-3.38 (m, 4.5H), 3.00-2.73 (m, 2H), 2.73-2.55 (m, 2H), 2.53-2.42 (m, 1H), 2.42-2.26 (m, 1H).

The compounds in Examples 100-103 were prepared using methods analogous to those described in Example 10.

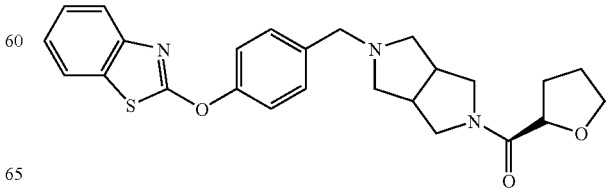

Example 100

(R)-{5-[4-(Benzothiazol-2-yloxy)-benzyl]-hexahydro-pyrrolo[3,4-c]pyrrol-2-yl}-(tetrahydro-furan-2-yl)-methanone MS (ESI): mass calcd. for $C_{25}H_{27}N_3O_3S$, 449.6; m/z found, 450.2 [M+H]⁺; ¹H NMR (400 MHz, CD₃OD): 7.67 (d, J=8.0 Hz, 1H), 7.55 (d, J=8.1 Hz, 1H), 7.38-7.26 (m, 3H), 7.25-7.16 (m, 3H), 4.53-4.43 (m, 1H), 3.90-3.80 (m, 1H), 3.77-3.71 (m, 1H), 3.67 (dd, J=11.3, 8.4 Hz, 1H), 3.59-3.49 (m, 3H), 3.49-3.38 (m, 2H), 3.38-3.29 (m, 1H), 2.89-2.79 (m, 1H), 2.79-2.68 (m, 1H), 2.67-2.48 (m, 2H), 2.40-2.30 (m, 2H), 2.17-1.95 (m, 1H), 1.96-1.68 (m, 3H).

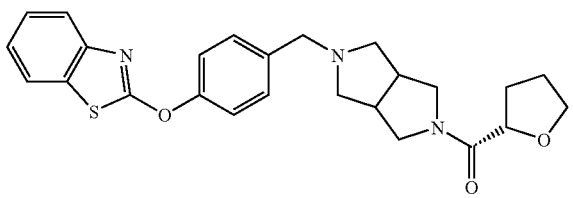

Example 101

(S)-{5-[4-(Benzothiazol-2-yloxy)-benzyl]-hexahydro-pyrrolo[3,4-c]pyrrol-2-yl}-(tetrahydro-furan-2-yl)-methanone MS (ESI): mass calcd. for $C_{25}H_{27}N_3O_3S$, 449.6; m/z found, 450.2 [M+H]⁺; ¹H NMR (400 MHz, CD₃OD): 7.66 (d, J=7.7 Hz, 1H), 7.54 (d, J=8.1 Hz, 1H), 7.39-7.26 (m, 3H), 7.25-7.15 (m, 3H), 4.52-4.43 (m, 1H), 3.90-3.78 (m, 1H), 3.78-3.70 (m, 1H), 3.66 (dd, J=11.3, 8.4 Hz, 1H), 3.58-3.50 (m, 3H), 3.49-3.40 (m, 1H); 2.90-2.77 (m, 1H), 2.78-2.68 (m, 1H), 2.66-2.47 (m, 2H), 2.45-2.28 (m, 2H), 2.18-1.96 (m, 1H), 1.95-1.72 (m, 3H).

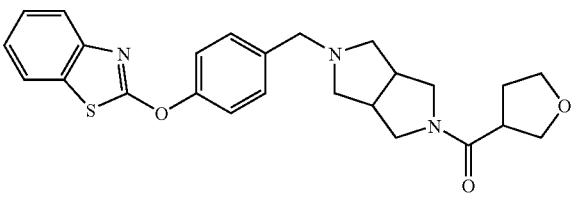

Example 102

{5-[4-(Benzothiazol-2-yloxy)-benzyl]-hexahydro-pyrrolo[3,4-c]pyrrol-2-yl}-(tetrahydro-furan-3-yl)-methanone MS (ESI): mass calcd. for $C_{25}H_{27}N_3O_3S$, 449.6; m/z found, 450.2 [M+H]⁺; ¹H NMR (400 MHz, CD₃OD): 7.66 (d, J=8.0 Hz, 1H), 7.55 (d, J=8.1 Hz, 1H), 7.39-7.26 (m, 3H), 7.25-7.14 (m, 3H), 3.85 (td, J=11.8, 8.2 Hz, 1H), 3.80-3.56 (m, 4H), 3.53 (s, 1H), 3.52-3.45 (m, 1H), 3.45-3.29 (m, 2H), 3.20-3.13 (m, 1H), 2.93-2.68 (m, 2H), 2.65-2.48 (m, 2H), 2.45-2.32 (m, 2H), 2.11-1.88 (m, 2H).

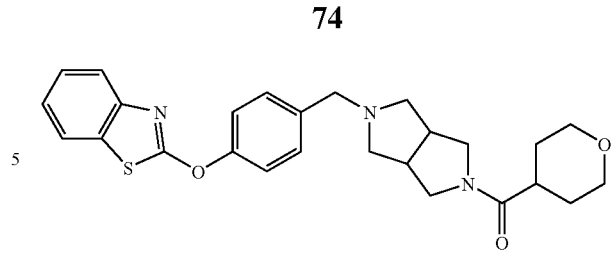

Example 103

{5-[4-(Benzothiazol-2-yloxy)-benzyl]-hexahydro-pyrrolo[3,4-c]pyrrol-2-yl}-(tetrahydro-pyran-4-yl)-methanone MS (ESI): Mass calcd for $C_{26}H_{29}N_3O_3S$, 463.6; m/z found, 464.2 [M+H]⁺; ¹H NMR (400 MHz, CD₃OD): 7.78 (d, J=7.9 Hz, 1H), 7.65 (d, J=8.0 Hz, 1H), 7.49 (d, J=8.5 Hz, 2H), 7.45-7.38 (m, 1H), 7.36 (d, J=8.6 Hz, 2H), 7.34-7.26 (m, 1H), 3.85-3.70 (m, 3H), 3.64-3.51 (m, 2H), 3.09-2.95 (m, 1H), 2.96-2.83 (m, 3H), 2.83-2.70 (m, 1H), 2.70-2.55 (m, 2H), 2.55-2.43 (m, 1H), 1.87-1.53 (m, 8H).

The compounds in Examples 104-115 were prepared using methods analogous to those described in Example 41.

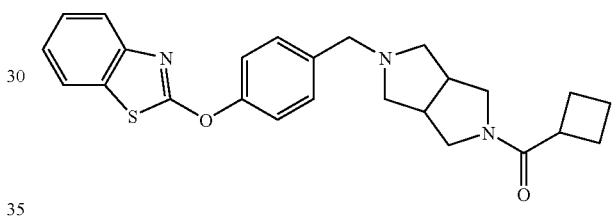

Example 104

{5-[4-(Benzothiazol-2-yloxy)-benzyl]-hexahydro-pyrrolo[3,4-c]pyrrol-2-yl}-cyclobutyl-methanone MS (ESI): mass calcd. for $C_{25}H_{27}N_3O_2S$, 433.6; m/z found, 434.2 [M+H]⁺; ¹H NMR (400 MHz, CD₃OD): 7.67 (d, J=8.0 Hz, 1H), 7.55 (d, J=8.1 Hz, 1H), 7.38-7.26 (m, 3H), 7.25-7.16 (m, 3H), 3.52 (s, 2H), 3.50-3.40 (m, 2H), 3.35 (dd, J=12.4, 3.9 Hz, 1H), 3.26-3.22 (m, 1H), 2.86-2.65 (m, 2H), 2.60 (ddd, J=9.9, 7.2, 3.1 Hz, 2H), 2.36-2.30 (m, 2H), 2.23-1.97 (m, 4H), 1.96-1.79 (m, 1H), 1.77-1.67 (m, 1H).

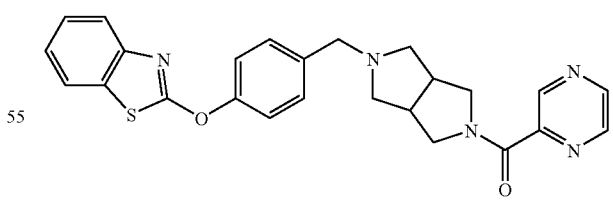

Example 105

{5-[4-(Benzothiazol-2-yloxy)-benzyl]-hexahydro-pyrrolo[3,4-c]pyrrol-2-yl}-pyrazin-2-yl-methanone MS (ESI): mass calcd. for $C_{25}H_{23}N_5O_2S$, 457.6; m/z found, 458.2 [M+H]⁺; ¹H NMR (500 MHz, CD₃OD): 8.97 (d, J=1.4 Hz, 1H), 8.69 (d, J=2.6 Hz, 1H), 8.66 (dd, J=2.5, 1.5 Hz, 1H), 7.79 (d, J=8.5 Hz, 1H), 7.67 (d, J=7.7 Hz, 1H), 7.48 (d, J=8.4 Hz, 2H), 7.45-7.41 (m, 1H), 7.37-7.28 (m, 3H), 3.97-3.85 (m, 2H), 3.79-3.70 (m, 2H), 3.71-3.62 (m, 2H), 3.02-2.89 (m, 2H), 2.76 (dd, J=9.3, 6.6 Hz, 1H), 2.67 (dd, J=9.3, 6.7 Hz, 1H), 2.62 (dd, J=9.5, 2.8 Hz, 1H), 2.51 (dd, J=9.5, 2.8 Hz, 1H).

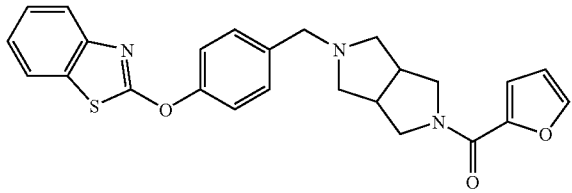

Example 106

{5-[4-(Benzothiazol-2-yloxy)-benzyl]-hexahydro-pyrrolo[3,4-c]pyrrol-2-yl}-furan-2-yl-methanone MS (ESI): mass calcd. for $C_{25}H_{23}N_3O_3S$, 445.5; m/z found, 446.2 [M+H]$^+$; $^1$H NMR (400 MHz, CD$_3$OD) 7.65 (d, J=8.0 Hz, 1H), 7.59 (d, J=1.0 Hz, 1H), 7.53 (d, J=8.1 Hz, 1H), 7.37-7.24 (m, 3H), 7.22-7.14 (m, 3H), 6.99 (d, J=3.5 Hz, 1H), 6.47 (dd, J=3.5, 1.8 Hz, 1H), 4.03-3.82 (m, 1H), 3.80-3.63 (m, 2H), 3.62-3.54 (m, 1H), 3.52 (s, 2H), 2.97-2.68 (m, 2H), 2.66-2.33 (m, 4H).

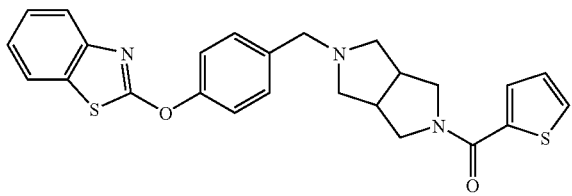

Example 107

{5-[4-(Benzothiazol-2-yloxy)-benzyl]-hexahydro-pyrrolo[3,4-c]pyrrol-2-yl}-thiophen-2-yl-methanone MS (ESI): mass calcd. for $C_{25}H_{23}N_3O_2S_2$, 461.6; m/z found, 462.1 [M+H]$^+$; $^1$H NMR (400 MHz, DMSO-d$_6$): 7.97-7.88 (m, 1H), 7.76 (d, J=5.0 Hz, 1H), 7.69 (d, J=7.5 Hz, 1H), 7.56 (dd, J=3.8, 1.0 Hz, 1H), 7.47-7.28 (m, 6H), 7.14 (dd, J=5.0, 3.7 Hz, 1H), 4.09-3.68 (m, 2H), 3.69-3.42 (m, 4H), 3.07-2.67 (m, 2H), 2.61-2.40 (m, 4H).

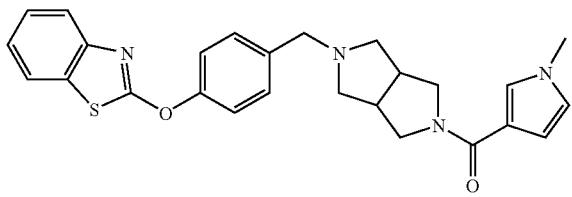

Example 108

{5-[4-(Benzothiazol-2-yloxy)-benzyl]-hexahydro-pyrrolo[3,4-c]pyrrol-2-yl}-(1-methyl-1H-pyrrol-3-yl)-methanone MS (ESI): mass calcd. for $C_{26}H_{26}N_4O_2S$, 458.6; m/z found, 459.2 [M+H]$^+$; $^1$H NMR (500 MHz, CD$_3$OD): 7.80-7.74 (m, 1H), 7.70-7.61 (m, 1H), 7.50-7.38 (m, 3H), 7.37-7.26 (m, 3H), 6.84-6.76 (m, 1H), 6.54-6.45 (m, 1H), 6.12-6.02 (m, 1H), 3.88-3.79 (m, 2H), 3.79 (s, 3H), 3.74-3.67 (m, 2H), 3.65 (d, J=7.6 Hz, 2H), 2.95-2.85 (m, 2H), 2.75-2.68 (m, 2H), 2.54-2.42 (m, 2H).

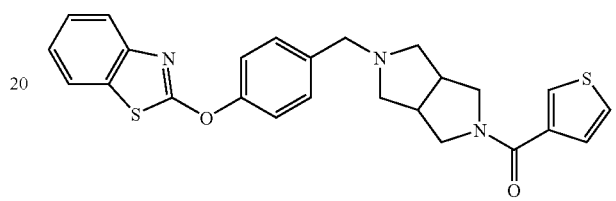

Example 109

{5-[4-(Benzothiazol-2-yloxy)-benzyl]-hexahydro-pyrrolo[3,4-c]pyrrol-2-yl}-thiophen-3-yl-methanone MS (ESI): mass calcd. for $C_{25}H_{23}N_3O_2S_2$, 461.6; m/z found, 462.1 [M+H]$^+$; $^1$H NMR (500 MHz, CD$_3$OD): 7.81 (dd, J=2.9, 1.3 Hz, 1H), 7.79 (dd, J=8.0, 0.5 Hz, 1H), 7.67 (dd, J=8.1, 0.5 Hz, 1H), 7.51-7.45 (m, 3H), 7.45-7.40 (m, 1H), 7.36-7.28 (m, 4H), 3.92-3.77 (m, 2H), 3.76-3.69 (m, 1H), 3.69-3.61 (m, 2H), 3.61-3.50 (m, 1H), 2.99-2.84 (m, 2H), 2.80-2.62 (m, 2H), 2.62-2.37 (m, 2H).

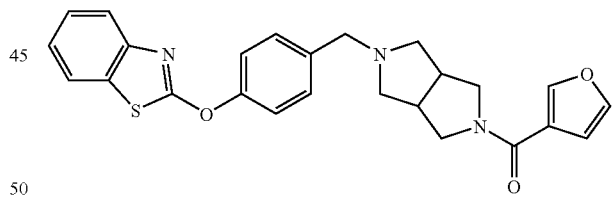

Example 110

{5-[4-(Benzothiazol-2-yloxy)-benzyl]-hexahydro-pyrrolo[3,4-c]pyrrol-2-yl}-furan-3-yl-methanone MS (ESI): mass calcd. for $C_{25}H_{23}N_3O_3S$, 445.5; m/z found, 446.2 [M+H]$^+$; $^1$H NMR (500 MHz, CD$_3$OD): 7.99 (d, J=0.8 Hz, 1H), 7.79 (d, J=8.1 Hz, 1H), 7.67 (d, J=8.2 Hz, 1H), 7.59-7.54 (m, 1H), 7.49-7.46 (m, 2H), 7.46-7.40 (m, 1H), 7.36-7.30 (m, 3H), 6.77-6.75 (m, 1H), 4.00-3.73 (m, 2H), 3.74-3.59 (m, 4H), 3.55-3.41 (m, 1H), 3.06-2.83 (m, 2H), 2.79-2.65 (m, 2H), 2.63-2.46 (m, 2H).

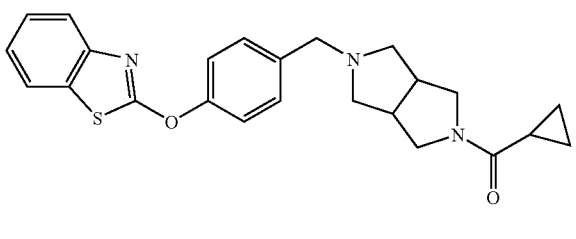

Example 111

{5-[4-(Benzothiazol-2-yloxy)-benzyl]-hexahydro-pyrrolo[3,4-c]pyrrol-2-yl}-cyclopropyl-methanone MS (ESI): mass calcd. for $C_{24}H_{25}N_3O_2S$, 419.6; m/z found, 420.2 [M+H]$^+$; $^1$H NMR (400 MHz, CD$_3$OD): 7.65 (d, J=7.3 Hz, 1H), 7.54 (d, J=8.1 Hz, 1H), 7.40-7.25 (m, 3H), 7.24-7.14 (m, 3H), 3.76 (dd, J=11.0, 8.6 Hz, 1H), 3.60-3.41 (m, 4H), 3.33 (dd, J=12.5, 4.2 Hz, 1H), 2.92-2.79 (m, 1H), 2.79-2.67 (m, 1H), 2.58-2.55 (m, 2H), 2.38 (ddd, J=19.2, 9.4, 4.1 Hz, 2H), 1.72-1.62 (m, 1H), 0.83-0.63 (m, 4H).

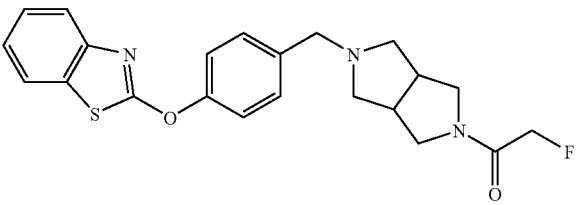

Example 112

1-{5-[4-(Benzothiazol-2-yloxy)-benzyl]-hexahydro-pyrrolo[3,4-c]pyrrol-2-yl}-2-fluoro-ethanone MS (ESI): Mass calcd for $C_{22}H_{22}N_3O_2SF$, 411.5; m/z found, 412.2 [M+H]$^+$; $^1$H NMR (400 MHz, CD$_3$OD): 7.76 (d, J=7.9 Hz, 1H), 7.64 (d, J=8.0 Hz, 1H), 7.46-7.37 (m, 3H), 7.34-7.25 (m, 3H), 5.08-4.99 (m, 1H), 4.97-4.87 (m, 1H), 4.79 (s, 2H), 3.71-3.55 (m, 3H), 3.54-3.41 (m, 1H), 3.03-2.78 (m, 2H), 2.72-2.62 (m, 2H), 2.55-2.46 (m, 2H).

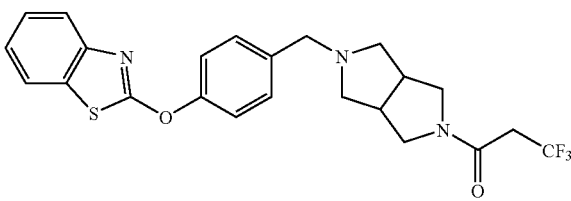

Example 113

1-{5-[4-(Benzothiazol-2-yloxy)-benzyl]-hexahydro-pyrrolo[3,4-c]pyrrol-2-yl}-3,3,3-trifluoro-propan-1-one MS (ESI): Mass calcd for $C_{23}H_{22}N_3O_2SF_3$, 461.5; m/z found, 462.2 [M+H]$^+$; $^1$H NMR (400 MHz, CD$_3$OD): 7.76 (d, J=8.0 Hz, 1H), 7.68-7.60 (m, 1H), 7.48-7.35 (m, 3H), 7.35- 7.23 (m, 3H), 3.80-3.66 (m, 2H), 3.64 (s, 2H), 3.51-3.41 (m, 2H), 3.38 (dd, J=10.2, 2.2 Hz, 2H), 3.01-2.83 (m, 2H), 2.74-2.62 (m, 2H), 2.59-2.45 (m, 2H).

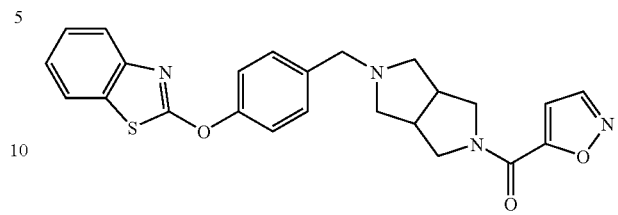

Example 114

{5-[4-(Benzothiazol-2-yloxy)-benzyl]-hexahydro-pyrrolo[3,4-c]pyrrol-2-yl}-isoxazol-5-yl-methanone MS (ESI): Mass calcd for $C_{24}H_{22}N_4O_3S$, 446.5; m/z found, 447.2 [M+H]$^+$; $^1$H NMR (400 MHz, CD$_3$OD): 7.80 (d, J=8.0 Hz, 1H), 7.67 (d, J=8.0 Hz, 1H), 7.56-7.47 (m, 2H), 7.46-7.40 (m, 1H), 7.39-7.34 (m, 2H), 7.34-7.26 (m, 1H), 4.78 (s, 2H), 3.84-3.70 (m, 3H), 3.70-3.58 (m, 2H), 3.57-3.52 (m, 1H), 3.06-2.80 (m, 4H), 2.61-2.36 (m, 2H).

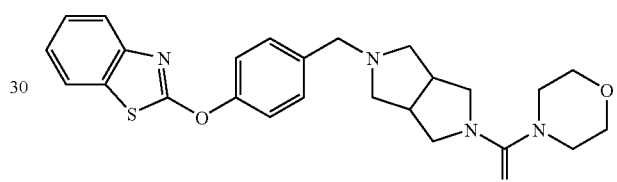

Example 115

{5-[4-(Benzothiazol-2-yloxy)-benzyl]-hexahydro-pyrrolo[3,4-c]pyrrol-2-yl}-morpholin-4-yl-methanone MS (ESI): mass calcd. for $C_{25}H_{28}H_4O_3S$, 464.6; m/z found, 465.2 [M+H]$^+$; $^1$H NMR (400 MHz, CD$_3$OD): 7.72 (d, J=8.0 Hz, 1H), 7.61 (d, J=7.6 Hz, 1H), 7.45-7.32 (m, 3H), 7.32-7.20 (m, 3H), 3.64-3.58 (m, 4H), 3.56 (s, 2H), 3.46 (dd, J=11.3, 7.5 Hz, 2H), 3.33-3.26 (m, 2H), 3.26-3.19 (m, 4H), 2.79-2.68 (m, 2H), 2.65 (dd, J=9.3, 7.0 Hz, 2H), 2.36 (dd, J=9.4, 3.5 Hz, 2H).

The compounds in Examples 116-117 were prepared using methods analogous to those described in Example 21.

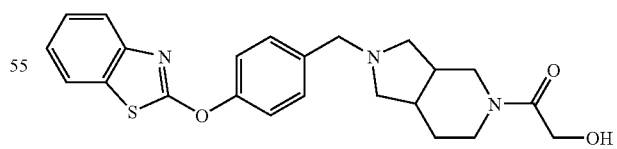

Example 116

1-{2-[4-(Benzothiazol-2-yloxy)-benzyl]-octahydro-pyrrolo[3,4-c]pyridin-5-yl}-2-hydroxy-ethanone MS (ESI): mass calcd. $C_{23}H_{25}N_3O_3S$ 423.2; m/z found, 424.2 [M+H]$^+$. $^1$H NMR (500 MHz, CDCl$_3$, mixture of rotamers): 7.75 (d, J=8.1 Hz, 1H), 7.67 (d, J=7.9 Hz, 1H), 7.40-7.38 (m, 3H), 7.35-7.25 (m, 3H), 4.13-4.12 (m, 2H), 3.91 (dd, J=13.4, 5.4 Hz, 0.5H), 3.77-3.59 (m, 3.5H), 3.48-3.33 (m, 1.5H), 3.28 (dd, J=13.3, 5.3 Hz, 0.5H), 3.21-3.13 (m, 1H), 2.82-2.64 (m, 2H), 2.54-2.30 (m, 4H), 1.94-1.82 (m, 1H), 1.76-1.66 (m, 1H).

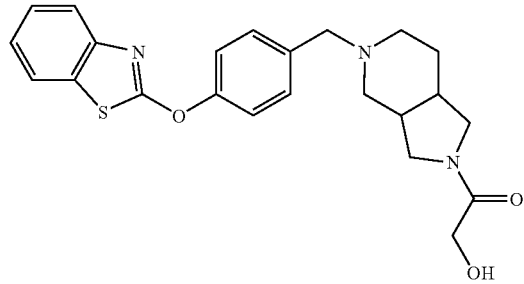

Example 117

1-{5-[4-(Benzothiazol-2-yloxy)-benzyl]-octahydro-pyrrolo[3,4-c]pyridin-2-yl}-2-hydroxy-ethanone MS (ESI): mass calcd. for $C_{23}H_{25}N_3O_3S$, 423.16; m/z found, 424.2 [M+H]+. 1H NMR (400 MHz, CDCl3, mixture of rotamers): 7.74 (d, J=8.1 Hz, 1H), 7.67 (d, J=7.7 Hz, 1H), 7.43-7.34 (m, 3H), 7.35-7.24 (m, 3H), 4.21-3.93 (m, 2H), 3.82-3.27 (m, 6.5H), 3.20-3.06 (m, 0.5H), 2.71-2.12 (m, 6H), 1.88-1.67 (m, 1H), 1.57 (m, J=3.9 Hz, 1H).

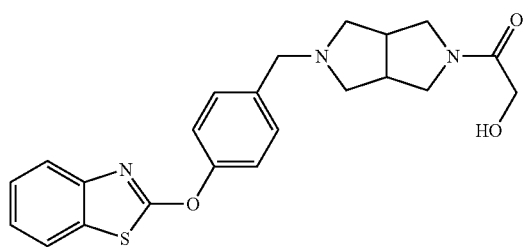

Example 118

1-{5-[4-(Benzothiazol-2-yloxy)-benzyl]-hexahydro-pyrrolo[3,4-c]pyrrol-2-yl}-2-hydroxy-ethanone This compound was prepared using methods analogous to those described for Example 44, substituting macroporous polystyrene-supported carbonate in methanol with lithium hydroxide in THF/water/CH3OH/CH2Cl2. MS (ESI): mass calcd. for $C_{22}H_{23}N_3O_3S$, 409.51; m/z found, 410.2 [M+H]+. 1H NMR (500 MHz, CDCl3): 7.49 (d, J=7.6 Hz, 1H), 7.47 (d, J=8.0 Hz, 1H), 7.40-7.33 (m, 3H), 7.32-7.27 (m, 3H), 4.10 (s, 2H), 3.83-3.82 (m, 1H), 3.63-3.62 (m, 2H), 3.56-3.51 (m, 2H), 3.20-3.17 (m, 1H), 2.64-2.60 (m, 2H), 2.59-2.53 (m, 4H).

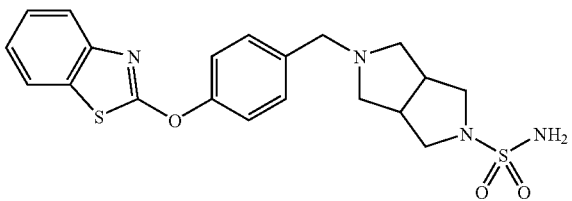

Example 119

5-[4-(Benzothiazol-2-yloxy)-benzyl]-hexahydro-pyrrolo[3,4-c]pyrrole-2-sulfonic acid amide Step A: tert-Butoxy carbonyl-5-[4-(benzothiazol-2-yloxy)-benzyl]-hexahydro-pyrrolo[3,4-c]pyrrole-2-sulfonic acid amide. To a stirred solution of tert-butanol (72 µL, 0.75 mmol) in CH2Cl2 (3 mL) cooled to 0° C. was added chlorosulfonyl isocyanate (65 µL, 0.75 mmol) dropwise via syringe. The resulting solution was allowed to stir at 0° C. for 30 min before being added dropwise to a solution of 2-[4-(hexahydro-pyrrolo[3,4-c]pyrrol-2-ylmethyl)-phenoxy]-benzothiazole dihydrochloride (317 mg, 0.75 mmol) and Et3N (520 µL, 3.75 mmol) in CH2Cl2 (2 mL). The resultant solution was stirred at rt for 2 h. The crude reaction mixture was concentrated to dryness under a stream of dry N2. The crude solid was dissolved in CH3OH/DMSO (2:1) and purified via reverse phase preparative HPLC to yield the title compound as a fluffy white solid (114 mg, 29%). MS (ESI): mass calcd. for $C_{25}H_{30}N_4O_5S_2$, 530.7; m/z found, 531.2 [M+H]+; 1H NMR (400 MHz, CD3OD): 7.69 (d, J=8.0 Hz, 1H), 7.56 (d, J=7.6 Hz, 1H), 7.40 (d, J=8.7 Hz, 2H), 7.35-7.29 (m, 1H), 7.27-7.17 (m, 3H), 3.65 (s, 2H), 3.39 (dd, J=10.3, 7.2 Hz, 2H), 3.15 (dd, J=10.3, 2.9 Hz, 2H), 2.87-2.77 (m, 2H), 2.78-2.67 (m, 2H), 2.42 (dd, J=9.3, 3.5 Hz, 2H), 1.38 (s, 9H).

Step B: 5-[4-(Benzothiazol-2-yloxy)-benzyl]-hexahydro-pyrrolo[3,4-c]pyrrole-2-sulfonic acid amide. To a stirred solution tert-butoxy carbonyl-5-[4-(benzothiazol-2-yloxy)-benzyl]-hexahydro-pyrrolo[3,4-c]pyrrole-2-sulfonic acid amide (108 mg, 0.20 mmol) in CH2Cl2 (5 mL) was added trifluoroacetic acid (1 mL). The homogeneous reaction mixture was allowed to stir overnight at rt. The crude reaction mixture was blown down to dryness and dissolved in CH3OH/DMSO (2:1) and purified via reverse phase preparative HPLC to afford the title compound as fluffy white powder (60 mg, 70%). MS (ESI): mass calcd. for $C_{20}H_{22}N_4O_3S_2$, 430.6; m/z found, 431.1 [M+H]+; 1H NMR (500 MHz, CD3OD): 7.79 (d, J=8.0 Hz, 1H), 7.67 (d, J=8.1 Hz, 1H), 7.52-7.46 (m, 2H), 7.46-7.39 (m, 1H), 7.37-7.27 (m, 3H), 3.68 (s, 2H), 3.24 (dd, J=9.5, 7.0 Hz, 2H), 3.06 (dd, J=9.4, 2.6 Hz, 2H), 2.93-2.87 (m, 2H), 2.87-2.78 (m, 2H), 2.40 (dd, J=8.5, 3.6 Hz, 2H).

The compounds in Examples 120-130 were prepared using methods analogous to those described in Example 45.

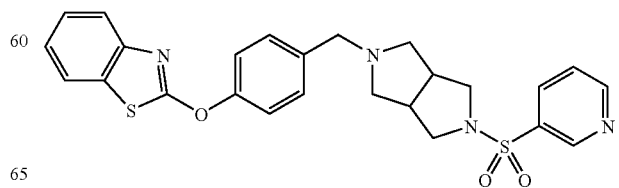

Example 120

2-{4-[5-(Pyridine-3-sulfonyl)-hexahydro-pyrrolo[3,4-c]pyrrol-2-ylmethyl]-phenoxy}-benzothiazole MS (ESI): mass calcd for $C_{25}H_{24}N_4O_3S_2$, 492.6; m/z found, 493.1 [M+H]$^+$; $^1$H NMR (500 MHz, DMSO-d$_6$) 8.96 (dd, J=2.3, 0.6 Hz, 1H), 8.94 (dd, J=4.8, 1.6 Hz, 1H), 8.21 (ddd, J=8.0, 2.3, 1.7 Hz, 1H), 7.94 (dd, J=8.0, 0.7 Hz, 1H), 7.74 (ddd, J=8.80, 4.8, 0.7 Hz, 1H), 7.70 (dd, J=8.1, 0.6 Hz, 1H), 7.46-7.41 (m, 1H), 7.38-7.31 (m, 3H), 7.25-7.21 (m, 2H), 3.51 (s, 2H), 2.81 (dd, J=9.9, 4.3 Hz, 2H), 2.74-2.65 (m, 2H), 2.43 (dd, J=9.2, 6.4 Hz, 2H), 2.30 (dd, J=9.3, 2.4 Hz, 2H).

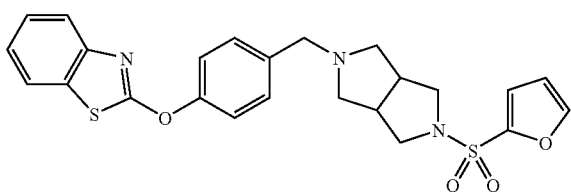

Example 121

2-{4-[5-(Furan-2-sulfonyl)-hexahydro-pyrrolo[3,4-c]pyrrol-2-ylmethyl]-phenoxy}-benzothiazole MS (ESI): mass calcd. for $C_{24}H_{23}N_3O_4S_2$, 481.6; m/z found, 482.1 [M+H]$^+$; $^1$H NMR (400 MHz, DMSO-d$_6$): 8.13-8.08 (m, 1H), 7.98-7.90 (m, 1H), 7.70 (d, J=8.1 Hz, 1H), 7.49-7.37 (m, 3H), 7.36-7.28 (m, 3H), 7.25 (d, J=2.7 Hz, 1H), 6.81 (dd, J=3.5, 1.8 Hz, 1H), 3.55 (s, 2H), 3.48-3.36 (m, 2H), 2.90 (dd, J=10.1, 4.6 Hz, 2H), 2.79-2.66 (m, 2H), 2.42 (dd, J=9.2, 6.2 Hz, 2H), 2.35 (dd, J=9.2, 2.2 Hz, 2H).

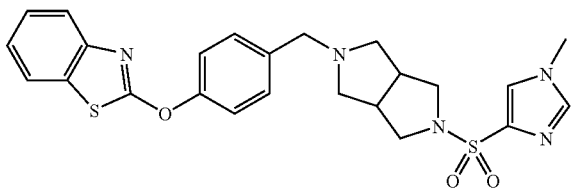

Example 122

2-{4-[5-(1-Methyl-1H-imidazole-4-sulfonyl)-hexahydro-pyrrolo[3,4-c]pyrrol-2-ylmethyl]-phenoxy}-benzothiazole MS (ESI): mass calcd. for $C_{24}H_{25}N_5O_3S_2$, 495.6; m/z found, 496.1 [M+H]$^+$; $^1$H NMR (400 MHz, DMSO-d$_6$): 7.94 (d, J=8.0 Hz, 1H), 7.89-7.81 (m, 2H), 7.70 (d, J=7.5 Hz, 1H), 7.46-7.30 (m, 6H), 3.73 (s, 3H), 3.59-3.51 (m, 2H), 2.91 (dd, J=9.8, 4.2 Hz, 2H), 2.73-2.63 (m, 2H), 2.56-2.40 (m, 4H), 2.37-2.28 (m, 3H).

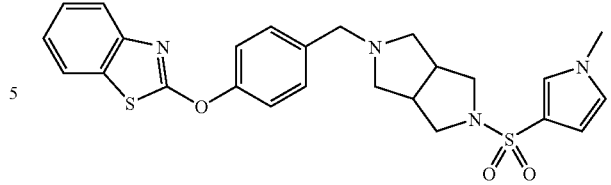

Example 123

2-{4-[5-(1-Methyl-1H-pyrrole-3-sulfonyl)-hexahydro-pyrrolo[3,4-c]pyrrol-2-ylmethyl]-phenoxy}-benzothiazole MS (ESI): mass calcd. for $C_{25}H_{26}N_4O_3S_2$, 494.9; m/z found 496.1 [M+H]$^+$; $^1$H NMR (500 MHz, CD$_3$OD): 7.85-7.76 (m, 2H), 7.76-7.72 (m, 1H), 7.68 (d, J=8.2 Hz, 1H), 7.48-7.39 (m, 3H), 7.38-7.27 (m, 3H), 3.82 (s, 3H), 3.64 (s, 2H), 3.10 (dd, J=9.9, 3.3 Hz, 2H), 2.82-2.70 (m, 4H), 2.38 (dd, J=9.1, 3.7 Hz, 2H).

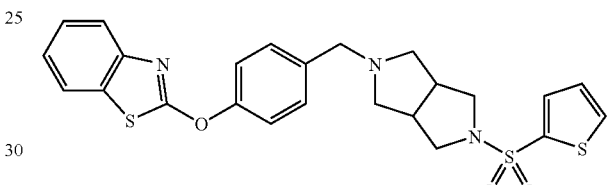

Example 124

2-{4-[5-(Thiophene-2-sulfonyl)-hexahydro-pyrrolo[3,4-c]pyrrol-2-ylmethyl]-phenoxy}-benzothiazole MS (ESI): mass calcd. for $C_{24}H_{23}N_3O_3S_3$, 497.6; m/z found, 498.1 [M+H]$^+$; $^1$H NMR (500 MHz, CD$_3$OD): 7.91 (dd, J=5.0, 1.3 Hz, 1H), 7.80 (d, J=7.6 Hz, 1H), 7.68 (d, J=7.7 Hz, 1H), 7.65 (dd, J=3.8, 1.3 Hz, 1H), 7.47-7.40 (m, 1H), 7.40-7.35 (m, 2H), 7.35-7.30 (m, 3H), 7.29 (dd, J=5.0, 3.8 Hz, 1H), 3.62 (s, 2H), 3.03 (dd, J=9.9, 3.8 Hz, 2H), 2.87-2.77 (m, 2H), 2.70 (dd, J=9.6, 6.9 Hz, 2H), 2.38 (dd, J=9.3, 3.5 Hz, 2H).

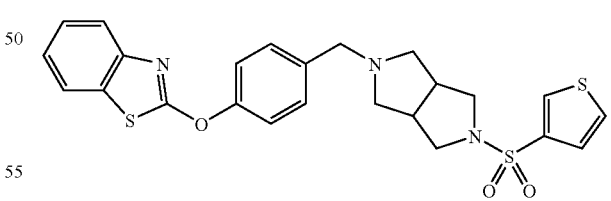

Example 125

2-{4-[5-(Thiophene-3-sulfonyl)-hexahydro-pyrrolo[3,4-c]pyrrol-2-ylmethyl]-phenoxy}-benzothiazole MS (ESI): mass calcd. for $C_{24}H_{23}N_3O_3S_3$, 497.6; m/z found, 498.1 [M+H]$^+$; $^1$H NMR (500 MHz, CD$_3$OD): 8.15 (dd, J=3.0, 1.3 Hz, 1H), 7.80 (d, J=7.6 Hz, 1H), 7.71 (dd, J=5.1, 3.1 Hz, 1H), 7.68 (d, J=8.1 Hz, 1H), 7.46-7.41 (m, 1H), 7.41-7.35 (m, 3H), 7.35-7.30 (m, 3H), 3.62 (s, 2H), 3.26 (dd, J=9.8, 7.5 Hz, 2H), 3.00 (dd, J=9.8, 3.6 Hz, 2H), 2.83-2.74 (m, 2H), 2.69 (dd, J=9.4, 6.8 Hz, 2H), 2.37 (dd, J=9.2, 3.5 Hz, 2H).

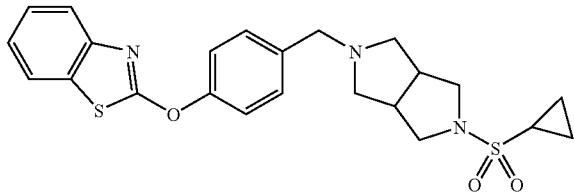

Example 126

2-[4-(5-Cyclopropanesulfonyl-hexahydro-pyrrolo[3,4-c]pyrrol-2-ylmethyl)-phenoxy]-benzothiazole MS (ESI): mass calcd. for $C_{23}H_{25}N_3O_3S_2$, 455.6; m/z found, 456.1 [M+H]$^+$; $^1$H NMR (400 MHz, DMSO-d$_6$): 7.93 (d, J=8.0 Hz, 1H), 7.69 (d, J=7.6 Hz, 1H), 7.48-7.36 (m, 5H), 7.36-7.29 (m, 1H), 3.61 (s, 1H), 3.46 (dd, J=9.9, 7.6 Hz, 2H), 3.02 (dd, J=10.0, 4.0 Hz, 2H), 2.91-2.75 (m, 2H), 2.70-2.61 (m, 1H), 2.57 (dd, J=9.1, 6.6 Hz, 2H), 2.38 (dd, J=9.2, 2.9 Hz, 2H), 1.02-0.88 (m, 4H).

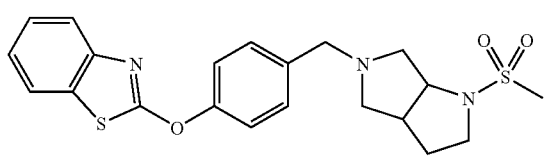

Example 127

2-[4-(1-Methanesulfonyl-hexahydro-pyrrolo[3,4-b]pyrrol-5-ylmethyl)-phenoxy]-benzothiazole MS (ESI): mass calcd. for $C_{21}H_{23}N_3O_3S_2$, 429.5; m/z found, 430.2 [M+H]$^+$. $^1$H NMR (500 MHz, CDCl$_3$): 7.76 (d, J=8.1 Hz, 1H), 7.71-7.68 (m, 1H), 7.44-7.37 (m, 3H), 7.35-7.26 (m, 3H), 4.23-4.16 (m, 1H), 3.69-3.63 (m, 1H), 3.59-3.49 (m, 2H), 3.47-3.38 (m, 1H), 3.03-2.98 (m, 1H), 2.95-2.88 (m, 1H), 2.84 (s, 3H), 2.63-2.53 (m, 2H), 2.49-2.43 (m, 1H), 2.11-2.02 (m, 1H), 1.92-1.84 (m, 1H).

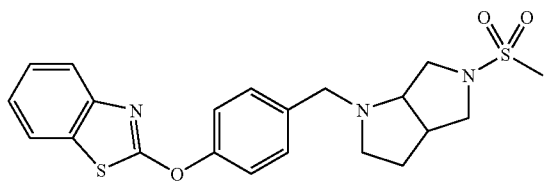

Example 128

2-[4-(5-Methanesulfonyl-hexahydro-pyrrolo[3,4-b]pyrrol-1-ylmethyl)-phenoxy]-benzothiazole MS (ESI): mass calcd. for $C_{21}H_{23}N_3O_3S_2$, 429.5; m/z found, 430.2 [M+H]$^+$. $^1$H NMR (500 MHz, CDCl$_3$): 7.75 (d, J=8.0 Hz, 1H), 7.69 (d, J=7.9 Hz, 1H), 7.44-7.24 (m, 6H), 3.90-3.82 (m, 1H), 3.51 (d, J=13.1 Hz, 1H), 3.48-3.42 (m, 1H), 3.37-3.30 (m, 1H), 3.27-3.18 (m, 3H), 3.10-3.03 (m, 1H), 2.88 (s, 3H), 2.41-2.32 (m, 1H), 2.13-2.05 (m, 1H), 1.76-1.57 (m, 2H).

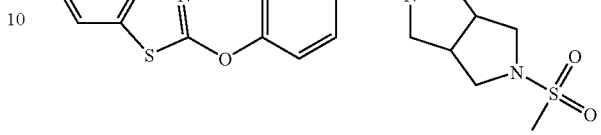

Example 129

2-[4-(5-Methanesulfonyl-hexahydro-pyrrolo[3,4-c]pyrrol-2-ylmethyl)-phenoxy]-benzothiazole MS (ESI): mass calcd. for $C_{21}H_{23}N_3O_3S_2$, 429.5; m/z found, 430.1 [M+H]$^+$. $^1$H NMR (500 MHz, CDCl$_3$): 7.74 (d, J=7.5 Hz, 1H), 7.68 (d, J=8.0 Hz, 1H), 7.43-7.35 (m, 3H), 7.34-7.27 (m, 3H), 3.62 (s, 2H), 3.50-3.44 (m, 2H), 3.16-3.07 (m, 2H), 2.96-2.81 (m, 5H), 2.71-2.60 (m, 2H), 2.51-2.41 (m, 2H).

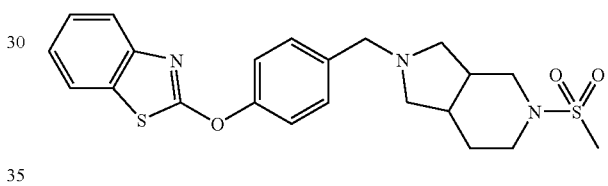

Example 130

2-[4-(5-Methanesulfonyl-octahydro-pyrrolo[3,4-c]pyridin-2-ylmethyl)-phenoxy]-benzothiazole MS (ESI): mass calcd. $C_{22}H_{25}N_3O_3S_2$ 443.1; m/z found, 444.2 [M+H]$^+$. $^1$H NMR (400 MHz, CDCl$_3$): 7.73 (d, J=8.1 Hz, 1H), 7.66 (d, J=7.3 Hz, 1H), 7.42-7.34 (m, 3H), 7.33-7.22 (m, 3H), 3.70 (s, 2H), 3.35-3.32 (m, 2H), 3.25-3.07 (m, 2H), 2.82-2.68 (m, 5H), 2.67-2.50 (m, 2H), 2.49-2.42 (m, 1H), 2.36-2.26 (m, 1H), 1.95-1.73 (m, 2H).

The compounds in Examples 131-143 were prepared using methods analogous to those described in Example 32.

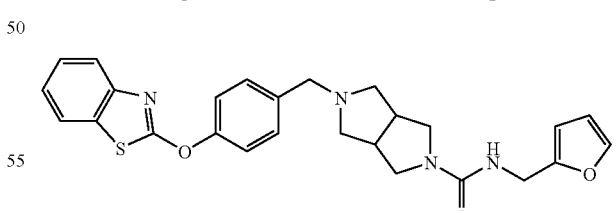

Example 131

5-[4-(Benzothiazol-2-yloxy)-benzyl]-hexahydro-pyrrolo[3,4-c]pyrrole-2-carboxylic acid (furan-2-ylmethyl)-amide MS (ESI): mass calcd for $C_{26}H_{26}N_4O_3S$, 474.6; m/z found, 475.2 [M+H]$^+$; $^1$H NMR (400 MHz, CD$_3$OD) 7.70-7.64 (m, 1H), 7.55 (d, J=8.1 Hz, 1H), 7.39-7.29 (m, 3H), 7.28 (d, J=1.0 Hz, 1H), 7.25-7.17 (m, 3H), 6.21 (dd, J=3.2, 1.9 Hz, 1H), 6.10 (d, J=2.4 Hz, 1H), 4.22 (s, 2H), 3.54 (s, 2H), 3.40 (dd, J=10.6, 8.0 Hz, 2H), 2.85-2.72 (m, 2H), 2.67 (dd, J=9.4, 7.1 Hz, 2H), 2.33 (dd, J=9.5, 3.8 Hz, 2H).

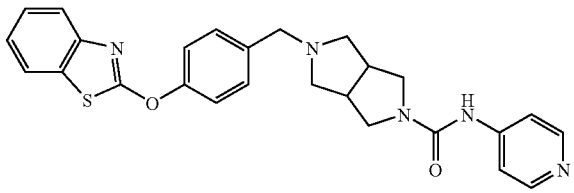

Example 132

5-[4-(Benzothiazol-2-yloxy)-benzyl]-hexahydro-pyrrolo[3,4-c]pyrrole-2-carboxylic acid pyridin-4-yl amide MS (ESI): mass calcd. for $C_{26}H_{25}N_5O_2S$, 471.6; m/z found, 472.2 [M+H]$^+$; $^1$H NMR (400 MHz, CD$_3$OD): 8.18 (dd, J=5.0, 1.6 Hz, 2H), 7.68 (dd, J=8.0, 0.7 Hz, 1H), 7.55 (dd, J=8.1, 0.5 Hz, 1H), 7.47 (dd, J=5.0, 1.6 Hz, 2H), 7.37 (d, J=8.6 Hz, 2H), 7.34-7.29 (m, 1H), 7.25-7.17 (m, 3H), 3.66-3.47 (m, 4H), 3.40 (dd, J=11.0, 3.1 Hz, 2H), 2.93-2.77 (m, 2H), 2.65 (dd, J=9.5, 6.9 Hz, 2H), 2.44 (dd, J=9.5, 3.3 Hz, 2H).

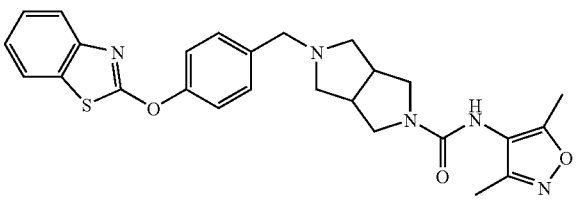

Example 133

5-[4-(Benzothiazol-2-yloxy)-benzyl]-hexahydro-pyrrolo[3,4-c]pyrrole-2-carboxylic acid (3,5-dimethyl-isoxazol-4-yl)-amide MS (ESI): mass calcd. for $C_{26}H_{27}N_5O_3S$, 489.6; m/z found, 490.2 [M+H]$^+$; $^1$H NMR (400 MHz, CD$_3$OD): 7.68 (d, J=8.1 Hz, 1H), 7.55 (d, J=8.1 Hz, 1H), 7.40 (d, J=8.7 Hz, 2H), 7.36-7.28 (m, 1H), 7.28-7.17 (m, 3H), 3.59 (s, 2H), 3.55 (dd, J=10.8, 8.2 Hz, 2H), 3.31 (dd, J=10.8, 3.2 Hz, 2H), 2.92-2.78 (m, 2H), 2.68 (dd, J=9.5, 7.0 Hz, 2H), 2.44 (dd, J=9.6, 3.4 Hz, 2H), 2.19 (s, 3H), 2.06 (s, 3H).

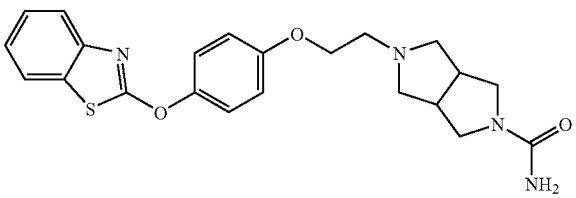

Example 134

5-{2-[4-(Benzothiazol-2-yloxy)-phenoxy]-ethyl}-hexahydro-pyrrolo[3,4-c]pyrrole-2-carboxylic acid amide MS (ESI): Mass calcd for $C_{22}H_{24}N_4O_3S$, 424.5; m/z found, 425.2 [M+H]$^+$; $^1$H NMR (400 MHz, CD$_3$OD): 7.76 (d, J=8.0 Hz, 1H), 7.66 (d, J=8.1 Hz, 1H), 7.44-7.39 (m, 1H), 7.35-7.32 (m, 3H), 7.08-7.03 (m, 2H), 4.20-4.06 (m, 2H), 3.51 (dd, J=10.8, 7.8 Hz, 2H), 3.36-3.33 (m, 2H), 3.03-2.84 (m, 6H), 2.49 (dd, J=9.1, 3.8 Hz, 2H).

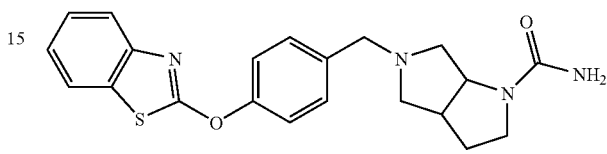

Example 135

5-[4-(Benzothiazol-2-yloxy)-benzyl]-hexahydro-pyrrolo[3,4-b]pyrrole-1-carboxylic acid amide MS (ESI): mass calcd. for $C_{21}H_{22}N_4O_2S$, 394.5; m/z found, 395.2 [M+H]$^+$. $^1$H NMR (500 MHz, CDCl$_3$): 7.76 (d, J=7.6 Hz, 1H), 7.71-7.67 (m, 1H), 7.43-7.36 (m, 3H), 7.34-7.27 (m, 3H), 4.37 (s, 2H), 4.33-4.26 (m, 1H), 3.68 (d, J=13.2 Hz, 1H), 3.56-3.44 (m, 3H), 2.96-2.84 (m, 2H), 2.69-2.62 (m, 1H), 2.57-2.47 (m, 2H), 2.16-2.00 (m, 1H), 1.91-1.83 (m, 1H).

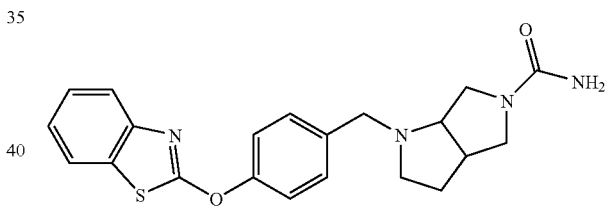

Example 136

1-[4-(Benzothiazol-2-yloxy)-benzyl]-hexahydro-pyrrolo[3,4-b]pyrrole-5-carboxylic acid amide MS (ESI): mass calcd. for $C_{21}H_{22}N_4O_2S$, 394.5; m/z found, 395.2 [M+H]$^+$. $^1$H NMR (500 MHz, CDCl$_3$): 7.74 (d, J=8.1 Hz, 1H), 7.68 (d, J=8.1 Hz, 1H), 7.43-7.38 (m, 3H), 7.35-7.24 (m, 3H), 4.33 (s, 2H), 3.89 (d, J=13.1 Hz, 1H), 3.65-3.55 (m, 1H), 3.51-3.40 (m, 2H), 3.40-3.25 (m, 2H), 3.22-3.14 (m, 1H), 3.13-3.05 (m, 1H), 2.94-2.80 (m, 1H), 2.42-2.33 (m, 1H), 2.12-2.01 (m, 1H), 1.74-1.62 (m, 1H).

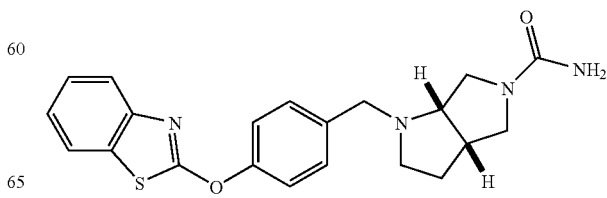

Example 137

(S,S)-1-[4-(Benzothiazol-2-yloxy)-benzyl]-hexahydro-pyrrolo[3,4-b]pyrrole-5-carboxylic acid amide MS (ESI): mass calcd. for $C_{21}H_{22}N_4O_2S$, 394.5; m/z found, 395.2 [M+H]+. $^1$H NMR (500 MHz, CDCl$_3$): 7.73 (d, J=8.1 Hz, 1H), 7.67 (d, J=8.1 Hz, 1H), 7.42-7.35 (m, 3H), 7.35-7.23 (m, 3H), 4.33 (s, 2H), 3.91 (d, J=13.1 Hz, 1H), 3.63-3.55 (m, 1H), 3.51-3.40 (m, 2H), 3.40-3.26 (m, 2H), 3.22-3.12 (m, 1H), 3.13-3.06 (m, 1H), 2.94-2.80 (m, 1H), 2.42-2.33 (m, 1H), 2.12-2.01 (m, 1H), 1.72-1.61 (m, 1H).

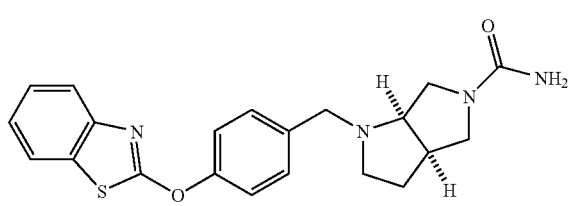

Example 138

(R,R)-1-[4-(Benzothiazol-2-yloxy)-benzyl]-hexahydro-pyrrolo[3,4-b]pyrrole-5-carboxylic acid amide MS (ESI): mass calcd. for $C_{21}H_{22}N_4O_2S$, 394.5; m/z found, 395.2 [M+H]+. $^1$H NMR (500 MHz, CDCl$_3$): 7.74 (d, J=8.1 Hz, 1H), 7.69 (d, J=8.1 Hz, 1H), 7.43-7.38 (m, 3H), 7.34-7.24 (m, 3H), 4.33 (s, 2H), 3.89 (d, J=13.1 Hz, 1H), 3.65-3.55 (m, 1H), 3.51-3.40 (m, 2H), 3.40-3.25 (m, 2H), 3.22-3.14 (m, 1H), 3.14-3.05 (m, 1H), 2.94-2.80 (m, 1H), 2.39-2.33 (m, 1H), 2.14-2.0 (m, 1H), 1.76-1.60 (m, 1H).

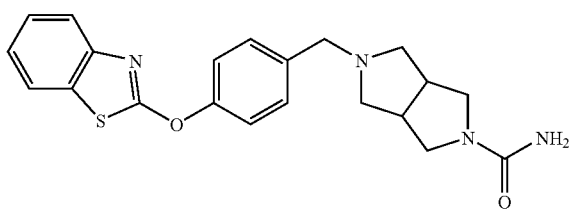

Example 139

5-[4-(Benzothiazol-2-yloxy)-benzyl]-hexahydro-pyrrolo[3,4-c]pyrrole-2-carboxylic acid amide MS (ESI): mass calcd. for $C_{21}H_{22}N_4O_2S$, 394.5; m/z found, 395.1 [M+H]+. $^1$H NMR (400 MHz, CDCl$_3$): 7.74 (d, J=7.5 Hz, 1H), 7.67 (d, J=7.9 Hz, 1H), 7.43-7.35 (m, 3H), 7.34-7.23 (m, 3H), 4.42-4.32 (m, 2H), 3.65-3.55 (m, 4H), 3.33-3.23 (m, 2H), 2.96-2.82 (m, 2H), 2.70-2.63 (m, 2H), 2.55-2.46 (m, 2H).

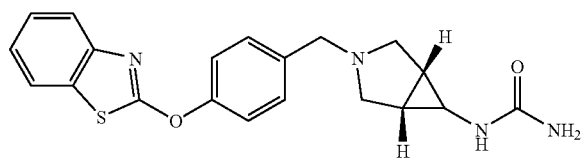

Example 140

(R,S)-{3-[4-(Benzothiazol-2-yloxy)-benzyl]-3-azabicyclo[3.1.0]hex-6-yl}-urea

MS (ESI): mass calcd. $C_{20}H_{20}N_4O_2S_2$ 380.1; m/z found, 381.1 [M+H]+. $^1$H NMR (400 MHz, CDCl$_3$): 7.74 (d, J=7.6 Hz, 1H), 7.67 (d, J=7.3 Hz, 1H), 7.39 (t, J=7.5 Hz, 1H), 7.36-7.25 (m, 5H), 4.74 (s, 2H), 4.70 (s, 1H), 3.59 (s, 2H), 3.09 (d, J=9.0 Hz, 1H), 2.88 (s, 1H), 2.45 (d, J=8.8 Hz, 2H), 1.63 (s, 2H).

Example 141

(±)-5-[4-(Benzothiazol-2-yloxy)-benzyl]-octahydropyrrolo[3,4-c]pyridine-2-carboxylic acid amide MS (ESI): mass calcd. for $C_{22}H_{24}N_4O_2S$, 408.16; m/z found, 409.2 [M+H]+. $^1$H NMR (400 MHz, CDCl$_3$, mixture of rotamers): 7.74 (d, J=8.1 Hz, 1H), 7.67 (d, J=7.9 Hz, 1H), 7.41-7.35 (m, 3H), 7.34-7.22 (m, 3H), 4.38 (s, 2H), 3.65-3.26 (m, 5.5H), 2.73-2.29 (m, 4H), 2.24 (s, 2H), 1.82-1.52 (m, 2.5H).

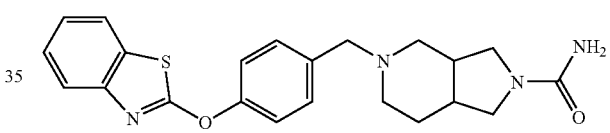

Example 142A and Example 142B (+)-5-[4-(Benzothiazol-2-yloxy)-benzyl]-octahydropyrrolo[3,4-c]pyridine-2-carboxylic acid amide and
(−)-5-[4-(Benzothiazol-2-yloxy)-benzyl]-octahydropyrrolo[3,4-c]pyridine-2-carboxylic acid amide Individual enatiomers were isolated through preparative chiral supercritical fluid chromatography (SFC) using isocratic conditions: 60:40 carbon dioxide (flow rate: 12 g/min)/(1:1 CH$_3$CN/isopropanol with 0.1% triethylamine; flow rate: 8 mL/min) on a Chiralpak AD-H (5 μm, 21×250 mm) column with the back pressure regulator set at 150 bar. Enantiomer 1 (Example 142A): retention time=84 min. MS (ESI): mass calcd. for $C_{22}H_{24}N_4O_2S$, 408.16; m/z found, 409.2 [M+H]+. $^1$H NMR (500 MHz, 1% CD$_3$OD/CDCl$_3$): 7.70 (d, J=8.1 Hz, 1H), 7.65 (d, J=7.4 Hz, 1H), 7.46-7.35 (m, 3H), 7.46-7.35 (m, 2H), 7.28-7.22 (m, 1H), 3.79-3.54 (m, 3H), 3.23-3.03 (m, 2H), 2.99-2.83 (m, 2H), 2.24-1.79 (m, 4H), 1.56 (s, 2H), 1.32-1.18 (m, 2H), 0.92-0.78 (m, 1H). Enantiomer 2 (Example 142B): retention time=125 min. MS (ESI): mass calcd. for $C_{22}H_{24}N_4O_2S$, 408.16; m/z found, 409.2 [M+H]+. $^1$H NMR (500 MHz, 1% CD$_3$OD/CDCl$_3$): 7.72 (d, J=7.7 Hz, 1H), 7.66 (d, J=7.3 Hz, 1H), 7.42-7.36 (m, 3H), 7.33-7.28 (m, 2H), 7.28-7.25 (m, 1H), 3.73-3.51 (m, 2H), 3.16-2.97 (m, 2H), 2.97-2.83 (m, 2H), 2.09 (t, J=10.6 Hz, 1H), 1.96-1.82 (m, 3H), 1.60-1.44 (m, 2H), 1.34-1.25 (m, 1H), 1.24 (br s, 2H), 0.94-0.78 (m, 1H).

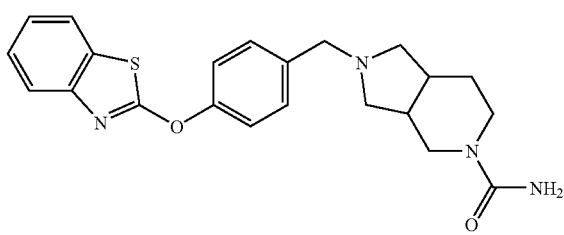

Example 143

2-[4-(Benzothiazol-2-yloxy)-benzyl]-octahydro-pyrrolo[3,4-c]pyridine-5-carboxylic acid amide MS (ESI): mass calcd. for $C_{24}H_{27}N_3O_2S$, 408.16; m/z found, 409.2 [M+H]$^+$. $^1$H NMR (400 MHz, CD$_3$OD): 8.09-7.01 (m, 8H), 4.59-4.06 (m, 8H), 3.80-2.94 (m, 4H), 2.96-2.31 (m, 2H), 2.12-1.36 (m, 2H).

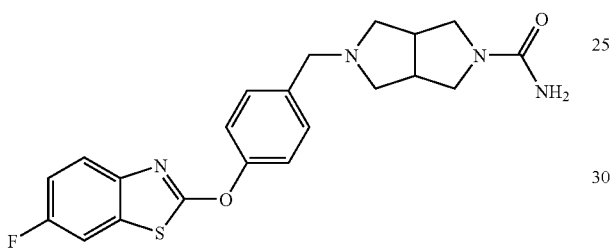

Example 144

5-[4-(6-Fluoro-benzothiazol-2-yloxy)-benzyl]-hexahydro-pyrrolo[3,4-c]pyrrole-2-carboxylic acid amide Step A: [4-(6-Fluoro-benzothiazol-2-yloxy)-phenyl]-methanol. A mixture of 2-chloro-5-fluorobenzthiazole (2.2 g, 12.0 mmol), 4-hydroxybenzyl alcohol (1.48 g, 12.0 mmol) and Cs$_2$CO$_3$ (8.6 g, 26.4 mmol) in DMF (30 mL) was stirred at rt overnight. The reaction was filtered and diluted with CH$_2$Cl$_2$ (200 mL) and concentrated. The crude mixture was purified via silica gel column chromatography (1% to 15% CH$_3$OH/CH$_2$Cl$_2$) to afford the title compound (1.1 g, 34%). MS (ESI): Mass calcd for $C_{14}H_{10}NO_2SF$, 275.0; m/z found, 276.1 [M+H]$^+$ Step B: 2-(4-Chloromethyl-phenoxy)-6-fluoro-benzothiazole. To a solution of [4-(6-fluoro-benzothiazol-2-yloxy)-phenyl]-methanol (1.1 g, 4.0 mmol) in CH$_2$Cl$_2$ (80 mL) at rt under N$_2$ was added SOCl$_2$ (320 µL, 4.4 mmol). The resultant mixture was stirred for 4 h at rt before concentration to afford the title chloride (1.1 g, 92%). MS (ESI): Mass calcd for $C_{14}H_9NOSFCl$, 293.0.1; m/z found, 294.1 [M+H]$^+$.

Step C: Hexahydro-pyrrolo[3,4-c]pyrrole-2-carboxylic acid amide hydrochloride. This compound was prepared using methods analogous to those described for Example 76, Step D. MS (ESI): Mass calcd for $C_7H_{13}N_3O$ (free base), 155.11; m/z found, 156.2 [M+H]$^+$.

Step D: 5-[4-(6-Fluoro-benzothiazol-2-yloxy)-benzyl]-hexahydro-pyrrolo[3,4-c]pyrrole-2-carboxylic acid amide. To a suspension of 2-(4-chloromethyl-phenoxy)-6-fluoro-benzothiazole (152 mg, 0.52 mmol), hexahydro-pyrrolo[3,4-c]pyrrole-2-carboxylic acid amide, hydrochloride (110 mg, 0.57 mmol) and Cs$_2$CO$_3$ (676 mg, 2.08 mmol) in DMF (1 mL) was stirred at rt overnight. The resultant mixture was filtered and the residue purified via preparative reverse phase HPLC to afford the title compound (15 mg, 7%). MS (ESI): Mass calcd for $C_{21}H_{21}N_4O_2SF$, 412.1; m/z found, 413.1 [M+H]$^+$; $^1$H NMR (400 MHz, CD$_3$OD): 7.64 (dd, J=8.9, 4.7 Hz, 1H), 7.58 (dd, J=8.4, 2.6 Hz, 1H), 7.47 (d, J=8.5 Hz, 2H), 7.33 (d, J=8.5 Hz, 2H), 7.19 (dt, J=9.0, 8.9, 2.6 Hz, 1H), 3.66 (s, 2H), 3.59-3.40 (m, 2H), 3.29-3.27 (m, 2H), 2.97-2.83 (m, 2H), 2.77 (d, J=9.3, 6.8 Hz, 2H), 2.46 (d, J=9.3, 3.6 Hz, 2H).

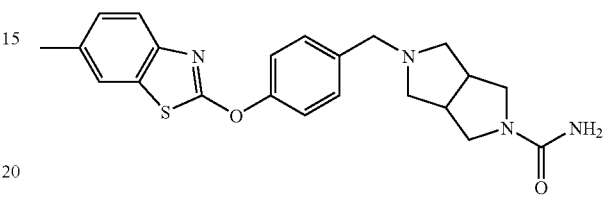

Example 145

5-[4-(6-Methyl-benzothiazol-2-yloxy)-benzyl]-hexahydro-pyrrolo[3,4-c]pyrrole-2-carboxylic acid amide This compound was prepared using methods analogous to those described for Example 144. MS (ESI): Mass calcd for $C_{22}H_{24}N_4O_2S$, 408.5; m/z found, 409.1 [M+H]$^+$; $^1$H NMR (400 MHz, CD$_3$OD): 7.47 (d, J=8.6 Hz, 1H), 7.34-7.28 (m, 2H), 7.17-7.10 (m, 2H), 6.77-6.65 (m, 2H), 5.05 (s, 2H), 3.58-3.41 (m, 2H), 2.96-2.84 (m, 2H), 2.82-2.69 (m, 2H), 2.50-2.38 (m, 4H), 2.34 (s, 3H).

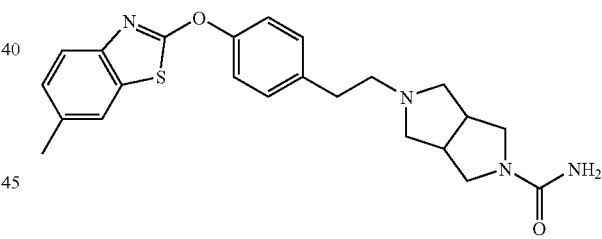

Example 146

5-{2-[4-(4-Methyl-benzothiazol-2-yloxy)-phenyl]-ethyl}-hexahydro-pyrrolo[3,4-c]pyrrole-2-carboxylic acid amide Step A: 2-[4-(6-Methyl-benzothiazol-2-yloxy)-phenyl]-ethanol. To a solution of phenethyl alcohol (3.15 g, 22.86 mmol) and K$_2$CO$_3$ (5.26 g, 38.1 mmol) in CH$_3$CN (35 mL) was added 2-chloro-6-methylbenzthiazole (3.5 g, 19.1 mmol). The reaction mixture was heated at 80° C. for 16 h. To the reaction mixture was added 1 N NaOH (30 mL) and isopropyl acetate (40 mL). The layers were separated and the aqueous layer was extracted with isopropyl acetate (2×30 mL). The combined organic layers were dried (Na$_2$SO$_4$), filtered and concentrated. The resulting residue was purified by silica gel flash chromatography (20% to 90% EtOAc in hexanes) to afford the title compound (3.4 g, 63%). $^1$H NMR (500 MHz, CDCl₃): 7.61 (d, J=8.3 Hz, 1H), 7.47 (s, 1H), 7.33-7.28 (m, 4H), 7.20 (d, J=8.3 Hz, 1H), 3.87 (br s, 2H), 2.90 (t, J=6.6 Hz, 2H), 2.44 (s, 3H).

Step B: 2-[4-(2-Methanesulfonyl-ethyl)-phenoxy]-6-methyl-benzothiazole. To a solution of 2-[4-(6-methyl-benzothiazol-2-yloxy)-phenyl]-ethanol (6.8 g, 23.8 mmol) and dimethylaminopyridine (290 mg, 2.4 mmol) in CH₂Cl₂ (80 mL) was added (i-Pr)₂NEt (4.9 g, 28.6 mmol) followed by the addition of methanesulfonyl chloride (2.2 mL, 28.6 mmol) at 0° C. The reaction was warmed to rt and stirred for 15 min. The reaction was washed with satd. aq. Na₂CO₃ (75 mL), 5% aq. H₂SO₄ (75 mL) and brine. The organic layer was dried (Na₂SO₄), filtered and concentrated to afford the title compound (7.3 g, 85%). ¹H NMR (500 MHz, CDCl₃): 7.61 (d, J=8.3 Hz, 1H), 7.47 (s, 1H), 7.36-7.29 (m, 4H), 7.20 (dd, J=8.3, 1.2 Hz, 1H), 4.45 (t, J=6.8 Hz, 2H), 3.10 (t, J=6.8 Hz, 2H), 2.91 (s, 3H), 2.44 (s, 3H).

Step C: 5-{2-[4-(4-Methyl-benzothiazol-2-yloxy)-phenyl]-ethyl}-hexahydro-pyrrolo[3,4-c]pyrrole-2-carboxylic acid amide. A solution of hexahydro-pyrrolo[3,4-c]pyrrole-2-carboxylic acid amide hydrochloride in 50% CH₂Cl₂/CH₃OH was treated with DOWEX Monosphere 550A (OH) anion-exchange resin to afford the free base. The DOWEX resin was filtered and the resulting solution was concentrated and used without further purification. To a solution of this hexahydro-pyrrolo[3,4-c]pyrrole-2-carboxylic acid amide (85 mg, 0.54 mmol) and K₂CO₃ (116 mg, 0.84 mmol) in tert-amyl alcohol (2.6 mL) was added 2-[4-(2-methanesulfonyl-ethyl)-phenoxy]-6-methyl-benzothiazole (120 mg, 0.34 mmol). The reaction mixture was heated to 80° C. for 16 h. The reaction mixture was filtered and washed with CH₃OH. The resulting liquid was purified by preparative reverse phase HPLC to afford the title compound (11 mg, 5%). MS (ESI): mass calcd. for C₂₃H₂₆N₄O₂S, 422.55; m/z found, 423.2 [M+H]⁺. ¹H NMR (500 MHz, CDCl₃): 7.62 (d, J=8.3 Hz, 1H), 7.48 (s, 1H), 7.28 (s, 4H), 7.20 (dd, J=8.3, 1.1 Hz, 1H), 4.39 (s, 2H), 3.60 (dd, J=10.2, 8.2 Hz, 2H), 3.30 (dd, J=10.0, 1.9 Hz, 2H), 2.98-2.87 (m, 2H), 2.86-2.80 (m, 2H), 2.76 (dd, J=9.3, 6.9 Hz, 2H), 2.74-2.67 (m, 2H), 2.53 (dd, J=9.3, 3.4 Hz, 2H), 2.45 (s, 3H).

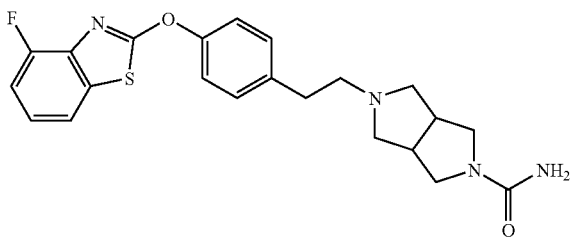

Example 147

5-{2-[4-(4-Fluoro-benzothiazol-2-yloxy)-phenyl]-ethyl}-hexahydro-pyrrolo[3,4-c]pyrrole-2-carboxylic acid amide This compound was prepared using methods analogous to those described for Example 146. MS (ESI): mass calcd. for C₂₂H₂₃FN₄O₂S, 426.52; m/z found, 427.2 [M+H]⁺. ¹H NMR (500 MHz, CDCl₃): 7.46 (dd, J=7.9, 1.0 Hz, 1H), 7.30 (s, 4H), 7.26-7.21 (m, 1H), 7.16-7.11 (m, 1H), 4.37 (s, 2H), 3.61 (dd, J=10.1, 8.2 Hz, 2H), 3.29 (d, J=8.5 Hz, 2H), 2.95-2.88 (m, 2H), 2.86-2.81 (m, 2H), 2.79-2.67 (m, 4H), 2.55 (dd, J=9.2, 3.1 Hz, 2H).

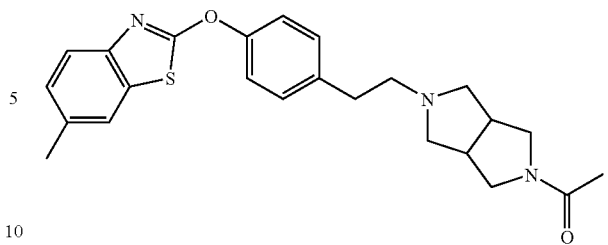

Example 148

1-(5-{2-[4-(6-Methyl-benzothiazol-2-yloxy)-phenyl]-ethyl}-hexahydro-pyrrolo[3,4-c]pyrrol-2-yl)-ethanone This compound was prepared using methods analogous to those described for Example 146, substituting the appropriate amine. MS (ESI): mass calcd. for C₂₄H₂₇N₃O₂S, 421.57; m/z found, 422.2 [M+H]⁺. ¹H NMR (500 MHz, CDCl₃): 7.63 (d, J=8.3 Hz, 1H), 7.48 (s, 1H), 7.28 (s, 4H), 7.21 (dd, J=8.3, 1.5 Hz, 1H), 3.70 (ddd, J=16.1, 11.6, 8.6 Hz, 2H), 3.48 (dd, J=12.5, 4.2 Hz, 1H), 3.35 (dd, J=10.8, 4.5 Hz, 1H), 2.99-2.91 (m, 1H), 2.90-2.80 (m, 3H), 2.79-2.68 (m, 4H), 2.57-2.50 (m, 2H), 2.45 (s, 3H), 2.06 (s, 3H).

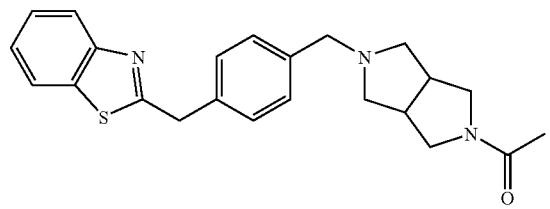

Example 149

1-[5-(4-Benzothiazol-2-ylmethyl-benzyl)-hexahydro-pyrrolo[3,4-c]pyrrol-2-yl]-ethanone This compound was prepared using methods analogous to those described for Example 4. MS (ESI): mass calcd. for C₂₃H₂₅N₃OS, 391.54; m/z found, 392.2 [M+H]⁺. ¹H NMR (500 MHz, CDCl₃): 8.01 (d, J=8.0 Hz, 1H), 7.81 (d, J=8.0 Hz, 1H), 7.48-7.45 (m, 1H), 7.37-7.28 (m, 5H), 4.44 (br s, 2H), 3.73-3.62 (m, 2H), 3.59 (dd, J=16.0, 3.0 Hz, 2H), 3.43 (dd, J=16.0, 3.0 Hz, 1H), 3.32 (dd, J=16.0, 4.5 Hz, 1H), 2.91-2.87 (m, 1H), 2.84-2.80 (m, 1H), 2.65-2.61 (m, 2H), 2.50-2.44 (m, 2H), 2.05 (s, 3H).

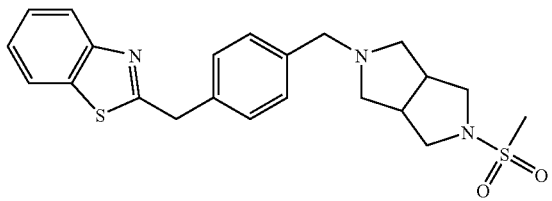

Example 150

2-[4-(5-Methanesulfonyl-hexahydro-pyrrolo[3,4-c]pyrrol-2-ylmethyl)-benzyl]-benzothiazole This compound was prepared using methods analogous to those described for Example 4 and Example 45. MS (ESI): mass calcd. for $C_{22}H_{25}N_3OS_2$, 427.59; m/z found, 428.1 [M+H]$^+$. $^1$H NMR (500 MHz, CDCl$_3$): 8.01 (d, J=8.0 Hz, 1H), 7.82 (d, J=8.0 Hz, 1H), 7.48-7.45 (m, 1H), 7.37-7.28 (m, 5H), 4.44 (s, 2H), 3.59 (s, 2H), 3.49-3.45 (m, 2H), 3.09 (dd, J=9.5, 4.3 Hz, 2H), 2.90-2.86 (m, 2H), 2.85 (s, 3H), 2.63 (dd. J=9.5, 6.5 Hz, 2H), 2.44 (dd, J=9.5, 3.5 Hz, 2H).

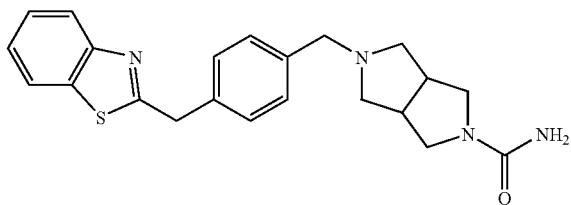

Example 151

1-[5-(4-Benzothiazol-2-ylmethyl-benzyl)-hexahydro-pyrrolo[3,4-c]pyrrol-2-yl]-ethanone This compound was prepared using methods analogous to those described for Example 4 and Example 32. MS (ESI): mass calcd. for $C_{22}H_{24}N_4OS$, 392.53; m/z found, 393.2 [M+H]$^+$. $^1$H NMR (500 MHz, CDCl$_3$): 8.01 (d, J=8.3 Hz, 1H), 7.81 (d, J=8.3 Hz, 1H), 7.48-7.45 (m, 1H), 7.37-7.29 (m, 5H), 4.44 (s, 2H), 4.34 (s, 2H), 3.61-3.58 (m, 4H), 3.27 (dd, J=10.5, 3.5 Hz, 2H), 2.90-2.87 (m, 2H), 2.65 (dd, J=9.5, 6.8 Hz, 2H), 2.48 (dd, J=9.5, 3.0 Hz, 2H).

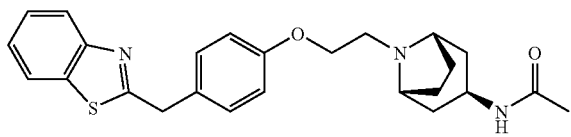

Example 152

N-{8-[2-(4-Benzothiazol-2-ylmethyl-phenoxy)-ethyl]-8-aza-bicyclo[3.2.1]oct-3-yl}-acetamide This compound was prepared using methods analogous to those described for Example 9, Step A. MS (ESI): mass calcd. for $C_{25}H_{29}N_3O_2S$, 435.20; m/z found, 436.2 [M+H]$^+$. $^1$H NMR (400 MHz, CDCl$_3$): 7.98 (d, J=8.0 Hz, 1H), 7.77 (d, J=8.0 Hz, 1H), 7.47-7.40 (m, 1H), 7.35-7.23 (m, 3H), 6.92-6.83 (m, 2H), 5.88 (d, J=6.2 Hz, 1H), 4.36 (s, 2H), 4.11-4.01 (m, 3H), 3.35-3.23 (m, 2H), 2.75 (t, J=6.2 Hz, 2H), 2.25-2.17 (m, 2H), 2.16-2.03 (m, 2H), 1.95 (s, 3H), 1.79-1.71 (m, 2H), 1.62-1.54 (m, 2H)

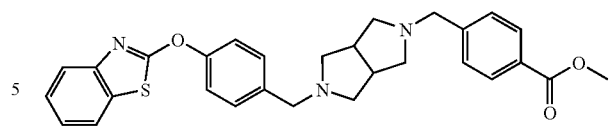

Example 153

4-{5-[4-(Benzothiazol-2-yloxy)-benzyl]-hexahydro-pyrrolo[3,4-c]pyrrol-2-ylmethyl)-benzoic acid methyl ester To a solution of 2-[4-(hexahydro-pyrrolo[3,4-c]pyrrol-2-ylmethyl)-phenoxy]-benzothiazole (200 mg, 0.56 mmol) in CH$_2$Cl$_2$ (22 mL) was added 4-formyl-benzoic acid methyl ester (103 mg, 0.62 mmol) followed by the addition of acetic acid (28 µL, 0.48 mmol) then sodium triacetoxyborohydride (144 mg, 0.68 mmol). The reaction stirred at rt for 16 h. The reaction was then washed with satd. aq. NaHCO$_3$ (2×20 mL). The organic layer was dried, filtered and concentrated. The resulting oil was purified by column chromatography (20% to 60% EtOAc in Hexanes) to afford the title compound (55 mg, 19%). MS (ESI): mass calcd. for $C_{29}H_{29}N_3O_3S$, 499.64; m/z found, 500.2 [M+H]$^+$. $^1$H NMR (500 MHz, CDCl$_3$): 8.01 (d, J=8.3 Hz, 2H), 7.76 (d, J=8.1 Hz, 1H), 7.47-7.38 (m, 1H), 7.35-7.26 (m, 4H), 7.68 (d, J=7.9 Hz, 4H), 3.92 (s, 4H), 3.65 (d, J=12.2 Hz, 4H), 2.71-2.60 (m, 3H), 2.38 (d, J=7.2 Hz, 4H), 1.27 (s, 2H).

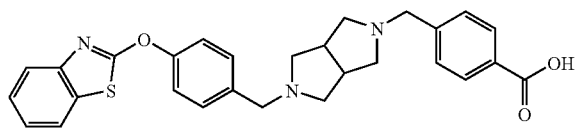

Example 154

4-{5-[4-(Benzothiazol-2-yloxy)-benzyl]-hexahydro-pyrrolo[3,4-c]pyrrol-2-ylmethyl)-benzoic acid To a solution of 4-{5-[4-(benzothiazol-2-yloxy)-benzyl]-hexahydro-pyrrolo[3,4-c]pyrrol-2-ylmethyl)-benzoic acid methyl ester (58.5 mg, 0.12 mmol, 1 equiv) in isopropanol (2.5 mL) was added water (1.1 mL) followed by the addition of aq. KOH (13 mg in 2.5 mL water). The reaction stirred at rt for 16 h. The reaction mixture was acidified to pH 6 with 6 N HCl, and CH$_2$Cl$_2$ was added. The layers were separated and the aqueous layer was extracted with 25% isopropanol/CH$_2$Cl$_2$ (2×10 mL). The combined organics were dried, filtered and concentrated to afford the title compound (32 mg, 56%). MS (ESI): mass calcd. for $C_{28}H_{27}N_3O_3S$, 485.61; m/z found, 486.2 [M+H]$^+$. $^1$H NMR (500 MHz, CDCl$_3$): 8.01 (d, J=8.2 Hz, 2H), 7.71 (m, 2H), 7.52-7.44 (m, 4H), 7.43-7.34 (m, 4H), 3.95 (m, 4H), 3.13 (s, 3H), 2.81 (m, 5H), 2.03 (s, 1H), 1.27 (s, 2H).

The compounds in Examples 155-157 were prepared using methods analogous to those described in Example 50.

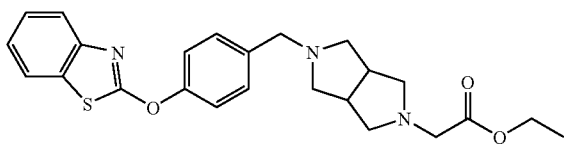

Example 155

{5-[4-(Benzothiazol-2-yloxy)-benzyl]-hexahydro-pyrrolo[3,4-c]pyrrol-2-yl}-acetic acid ethyl ester MS (ESI): Mass calcd for $C_{24}H_{27}N_3O_3S$, 437.6; m/z found, 438.2 [M+H]$^+$; $^1$H NMR (500 MHz, CD$_3$OD): 7.79 (d, J=8.0 Hz, 1H), 7.67 (d, J=8.1 Hz, 1H), 7.52-7.46 (m, 2H), 7.46-7.39 (m, 1H), 7.37-7.29 (m, 3H), 4.19 (q, J=7.1 Hz, 2H), 3.67 (s, 2H), 3.32 (s, 2H), 2.88-2.81 (m, 2H), 2.81-2.71 (m, 2H), 2.71-2.63 (m, 2H), 2.53-2.40 (m, 4H), 1.28 (t, J=7.1 Hz, 3H).

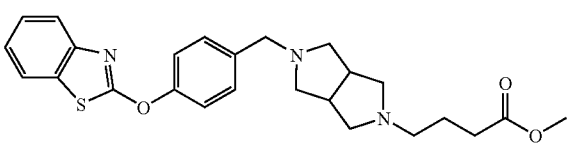

Example 156

4-{5-[4-(Benzothiazol-2-yloxy)-benzyl]-hexahydro-pyrrolo[3,4-c]pyrrol-2-yl}-butyric acid methyl ester MS (ESI): Mass calcd for $C_{25}H_{29}N_3O_3S$, 451.6; m/z found, 452.2 [M+H]$^+$; $^1$H NMR (500 MHz, CD$_3$OD): 7.79 (d, J=8.0 Hz, 1H), 7.67 (d, J=8.2 Hz, 1H), 7.51-7.46 (m, 2H), 7.45-7.39 (m, 1H), 7.37-7.28 (m, 3H), 3.69-3.63 (m, 5H), 2.78-2.70 (m, 4H), 2.69-2.59 (m, 2H), 2.52-2.41 (m, 4H), 2.43-2.30 (m, 4H), 1.90-1.72 (m, 2H).

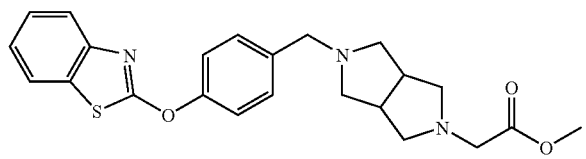

Example 157

{5-[4-(Benzothiazol-2-yloxy)-benzyl]-hexahydro-pyrrolo[3,4-c]pyrrol-2-yl}-acetic acid methyl ester MS (ESI): Mass calcd for $C_{23}H_{25}N_3O_3S$, 423.5; m/z found, 424.2 [M+H]$^+$. $^1$H NMR (CD$_3$OD): 7.81-7.76 (m, 1H), 7.66-7.60 (m, 2H), 7.56-7.49 (m, 2H), 7.45-7.40 (m, 1H), 7.38-7.33 (m, 2H), 4.92 (s, 2H), 4.57 (s, 2H), 4.48-4.36 (m, 2H), 3.77 (s, 3H), 3.57-3.47 (m, 2H), 3.25-3.17 (m, 2H), 2.95-2.86 (m, 2H), 2.47-2.35 (m, 2H).

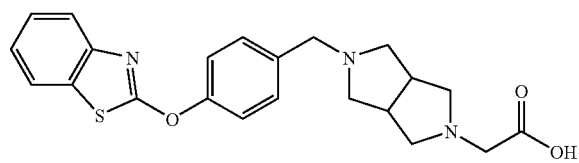

Example 158

{5-[4-(Benzothiazol-2-yloxy)-benzyl]-hexahydro-Pyrrolo[3,4-c]pyrrol-2-yl}-acetic acid A solution of {5-[4-(benzothiazol-2-yloxy)-benzyl]-hexahydro-pyrrolo[3,4-c]pyrrol-2-yl}-acetic acid methyl ester (233 mg, 0.55 mmol) in 1:1 isopropanol/water (2 mL) was treated with KOH (62 mg, 1.1 mmol). The reaction stirred at rt overnight. The reaction was acidified to pH 6.5 and extracted with 25% isopropanol/CHCl$_3$ to afford pure acid as a white powder (67 mg, 30%). MS (ESI): Mass calcd for $C_{22}H_{23}N_3O_3S$, 409.5; m/z found, 410.2 [M+H]$^+$; $^1$H NMR (400 MHz, CD$_3$OD): 7.78 (d, J=8.0 Hz, 1H), 7.65 (d, J=8.1 Hz, 1H), 7.57 (d, J=8.6 Hz, 2H), 7.45-7.35 (m, 3H), 7.34-7.28 (m, 1H), 3.76 (s, 2H), 3.64 (s, 2H), 3.55-3.35 (m, 4H), 3.12-2.97 (m, 2H), 2.94 (d, J=9.9 Hz, 2H), 2.52-2.34 (m, 2H).

The compounds in Examples 159-161 were prepared using methods analogous to those described in Example 76.

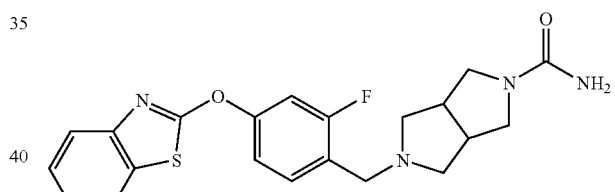

Example 159

5-[4-(Benzothiazol-2-yloxy)-2-fluoro-benzyl]-hexahydro-pyrrolo[3,4-c]pyrrole-2-carboxylic acid amide MS (ESI): mass calcd. for $C_{21}H_{21}FN_4O_2S$, 412.1; m/z found, 413.1 [M+H]$^+$. $^1$H NMR (400 MHz, CDCl$_3$): 7.75 (dd, J=8.1, 0.6 Hz, 1H), 7.70 (dd, J=8.0, 0.7 Hz, 1H), 7.42 (m, 2H), 7.33-7.27 (m, 1H), 7.18-7.10 (m, 2H), 4.31 (s, 2H), 3.68 (s, 2H), 3.65-3.54 (m, 2H), 3.27 (dd, J=10.3, 3.6 Hz, 2H), 2.92-2.85 (m, 2H), 2.77-2.65 (m, 2H), 2.53 (dd, J=9.3, 3.2 Hz, 2H).

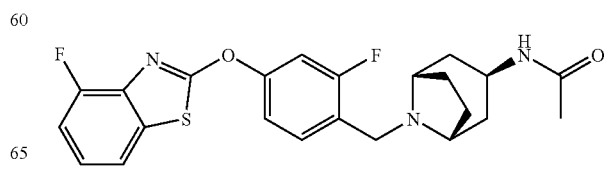

Example 160 meso-endo-N-{8-[2-Fluoro-4-(4-fluoro-benzothiazol-2-yloxy)-benzyl]-8-aza-bicyclo[3.2.1]oct-3-yl}-acetamide MS (ESI): mass calcd. for $C_{20}H_{23}F_2N_3O_2S$, 443.1; m/z found, 444.1 [M+H]$^+$. $^1$H NMR (400 MHz, CDCl$_3$): 7.64 (t, J=8.4 Hz, 1H), 7.46 (d, J=8.0 Hz, 1H), 7.29-7.09 (m, 4H), 5.81-5.73 (m, 1H), 4.17-4.06 (m, 1H), 3.56 (s, 2H), 3.22 (s, 2H), 2.40-2.02 (m, 4H), 1.97 (s, 3H), 1.88-1.70 (m, 2H), 1.62 (d, J=14.8 Hz, 2H).

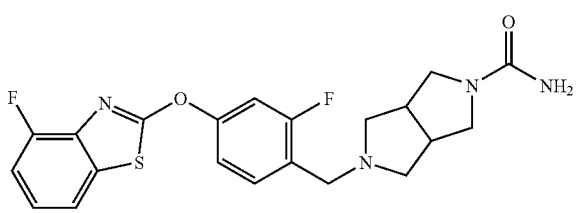

Example 161

5-[2-Fluoro-4-(4-fluoro-benzothiazol-2-yloxy)-benzyl]-hexahydro-pyrrolo[3,4-c]pyrrole-2-carboxylic acid amide MS (ESI): mass calcd. for $C_{21}H_{20}F_2N_4O_2S$, 430.1; m/z found, 431.1 [M+H]$^+$. $^1$H NMR (400 MHz, CDCl$_3$): 7.46 (t, J=8.6 Hz, 1H), 7.21-7.08 (m, 2H), 7.30-7.21 (m, 3H), 4.33 (s, 2H), 3.86 (d, J=6.6 Hz, 1H), 3.66-3.55 (m, 2H), 3.32-3.22 (m, 2H), 3.06-2.84 (m, 2H), 2.78-2.65 (m, 1H), 2.62-2.45 (m, 1H), 0.94 (d, J=6.7 Hz, 3H).

The compounds in examples 162-284 were prepared using methods analogous to those described in the preceding examples, replacing the appropriately substituted 2-[4-(2-bromo-ethyl)-phenoxy]-benzothiazole interned ate with its 2-[4-(2-iodo-ethyl)-phenoxy]-benzothiazole analog where A is an ethylene group.

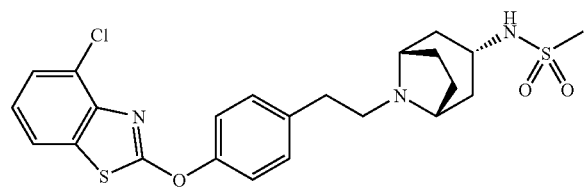

Example 162 meso-exo-N-(8-{2-[4-(4-Chloro-benzothiazol-2-yloxy)-phenyl]-ethyl}-8-aza-bicyclo[3.2.1]oct-3-yl)-methanesulfonamide MS (ESI): mass calcd. for $C_{23}H_{26}ClN_3O_3S_2$, 491.11; m/z found, 492.15 [M+H]$^+$. $^1$H NMR (500 MHz, CDCl$_3$): 7.57-7.53 (m, 1H), 7.44-7.41 (m, 1H), 7.33-7.26 (m, 4H), 7.23-7.17 (m, 1H), 3.60-3.80 (m, 3H), 3.00-3.15 (m, 2H), 3.04 (s, 3H), 2.80-2.94 (m, 2H), 1.96-2.25 (m, 6H), 1.78-1.90 (m, 2H).

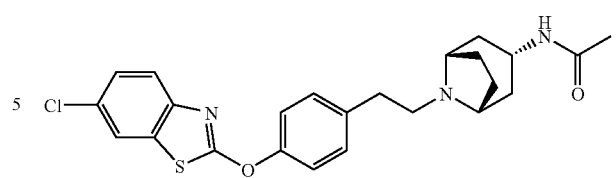

Example 163 meso-exo-N-(8-{2-[4-(6-Chloro-benzothiazol-2-yloxy)-phenyl]-ethyl}-8-aza-bicyclo[3.2.1]oct-3-yl)-acetamide MS (ESI): mass calcd. for $C_{24}H_{26}ClN_3O_2S$, 455.14; m/z found, 456.15 [M+H]$^+$. $^1$H NMR (500 MHz, DMSO-d$_6$, mixture of rotamers): 8.14-8.07 (m, 0.8H), 8.00-7.94 (m, 0.6H), 7.70-7.65 (m, 1H), 7.51-7.31 (m, 4.6H), 4.15-3.90 (m, 2.4H), 3.23-3.05 (m, 3H), 2.32-2.19 (m, 1.6H), 2.04-1.86 (m, 4.6H), 1.85-1.71 (m, 3.3H), 1.64-1.42 (m, 0.6H).

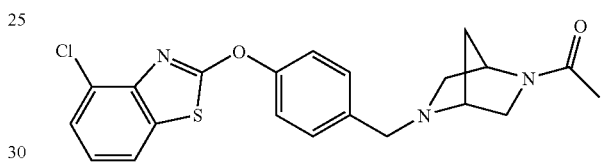

Example 164

(R,R)-1-{5-[4-(4-Chloro-benzothiazol-2-yloxy)-benzyl]-2,5-diaza-bicyclo[2.2.1]hept-2-yl}-ethanone MS (ESI): mass calcd. for $C_{21}H_{20}ClN_3O_2S$, 413.10; m/z found, 414.15 [M+H]$^+$. $^1$H NMR (500 MHz, CDCl$_3$, mixture of rotamers): 7.52-7.61 (m, 1H), 7.30-7.60 (m, 5H), 7.18-7.30 (m, 1H), 4.79 (s, 0.5H), 4.25 (s, 0.5H), 3.74-3.82 (m, 2.5H), 3.55-3.63 (m, 1.5H), 3.24-3.40 (m, 1H), 3.01-3.05 (m, 0.5H), 2.76-2.87 (m, 1H), 2.55-2.58 (m, 0.5H), 1.98-2.05 (m, 3.5H), 1.64-1.97 (m, 1.5H).

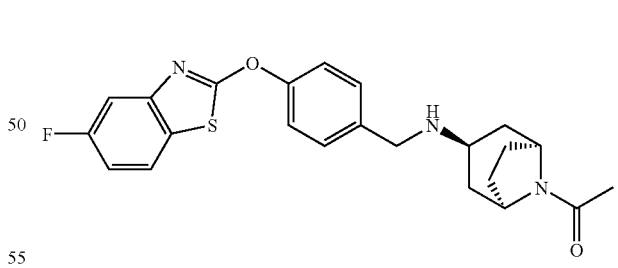

Example 165 meso-exo-1-{3-[4-(5-Fluoro-benzothiazol-2-yloxy)-benzylamino]-8-aza-bicyclo[3.2:1]oct-8-yl}-ethanone MS (ESI): mass calcd. for $C_{23}H_{24}FN_3O_2S$, 425.16; m/z found, 426.15 [M+H]$^+$. $^1$H NMR (500 MHz, 1H NMR (500 MHz, DMSO-d$_6$): 8.03-7.97 (m, 1H), 7.60-7.53 (m, 3H), 7.50-7.44 (m, 2H), 7.28-7.21 (m, 1H), 4.53-4.43 (m, 1H), 4.30-4.24 (m, 1H), 4.06-3.90 (m, 2H), 2.10-2.02 (m, 1H), 2.01-1.89 (m, 6H), 1.88-1.75 (m, 1H), 1.74-1.66 (m, 1H), 1.66-1.46 (m, 3H).

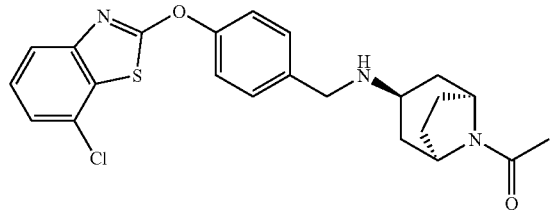

Example 166 meso-exo-1-{3-[4-(7-Chloro-benzothiazol-2-yloxy)-benzylamino]-8-aza-bicyclo[3.2.1]oct-8-yl}-ethanone MS (ESI): mass calcd. for $C_{23}H_{24}ClN_3O_2S$, 441.13; m/z found, 442.05 [M+H]$^+$. $^1$H NMR (500 MHz, DMSO-d$_6$): 7.74-7.66 (m, 1H), 7.52-7.45 (m, 4H), 7.44-7.39 (m, 2H), 4.45-4.41 (m, 1H), 4.21-4.15 (m, 1H), 3.76 (s, 2H), 3.06-2.94 (m, 1H), 2.01-1.88 (m, 5H), 1.88-1.81 (m, 1H), 1.80-1.71 (m, 1H), 1.70-1.62 (m, 1H), 1.62-1.54 (m, 1H), 1.38-1.28 (m, 2H).

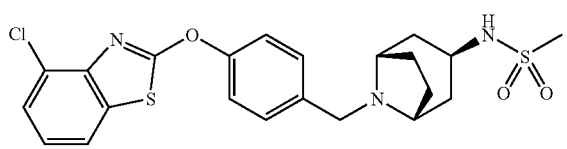

Example 167 meso-endo-N-{8-[4-(4-Chloro-benzothiazol-2-yloxy)-benzyl]-8-aza-bicyclo[3.2.1]oct-3-yl}-methanesulfonamide MS (ESI): mass calcd. for $C_{22}H_{24}ClN_3O_3S_2$, 477.09; m/z found, 478.05 [M+H]$^+$. $^1$H NMR (500 MHz, DMSO-d$_6$): 7.91 (d, J=8.0 Hz, 1H), 7.54 (d, J=7.8 Hz, 1H), 7.50 (d, J=8.3 Hz, 2H), 7.43 (d, J=8.3 Hz, 2H), 7.33 (t, J=8.0 Hz, 1H), 6.71-6.67 (m, 1H), 3.57-3.45 (m, 3H), 3.12-3.00 (m, 2H), 2.91-2.83 (m, 3H), 2.08-1.87 (m, 6H), 1.78-1.70 (m, 2H)

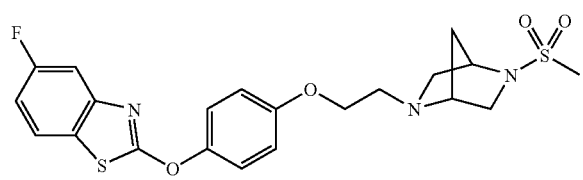

Example 168

(R,R)-5-Fluoro-2-{4-[2-(5-methanesulfonyl-2,5-diaza-bicyclo[2.2.1]hept-2-yl)-ethoxy]-phenoxy}-benzothiazole MS (ESI): mass calcd. for $C_{21}H_{22}FN_3O_4S_2$, 463.10; m/z found, 464.10 [M+H]$^+$. $^1$H NMR (500 MHz, DMSO-d$_6$): 7.98-7.93 (m, 1H), 7.60-7.54 (m, 1H), 7.42-7.36 (m, 2H), 7.24-7.18 (m, 1H), 7.09-7.04 (m, 2H), 4.19-4.14 (m, 2H), 4.10-4.04 (m, 2H), 3.68-3.62 (m, 1H), 3.23-3.16 (m, 1H), 3.00-2.88 (m, 6H), 2.74-2.66 (m, 1H), 1.81-1.74 (m, 1H), 1.70-1.63 (m, 1H).

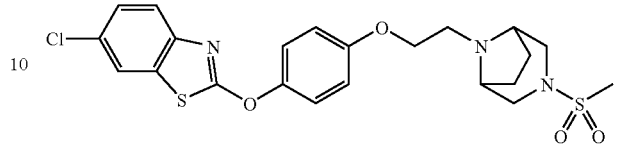

Example 169 meso-6-Chloro-2-{4-[2-(3-methanesulfonyl-3,8-diaza-bicyclo[3.2.1]oct-8-yl)-ethoxy]-phenoxy}-benzothiazole MS (ESI): mass calcd. for $C_{22}H_{24}ClN_3O_4S_2$, 493.09; m/z found, 494.10 [M+H]$^+$. $^1$H NMR (500 MHz, DMSO-d$_6$): 8.09-8.06 (m, 1H), 7.70-7.66 (m, 1H), 7.48-7.43 (m, 1H), 7.41-7.36 (m, 2H), 7.10-7.04 (m, 2H), 4.14-4.03 (m, 2H), 3.46-3.40 (m, 2H), 3.19-3.11 (m, 2H), 2.99-2.90 (m, 2H), 2.84 (s, 3H), 2.75-2.70 (m, 2H), 1.99-1.81 (m, 2H), 1.67-1.59 (m, 2H).

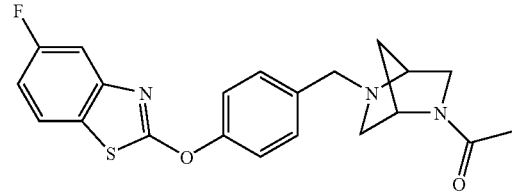

Example 170

(S,S)-1-{5-[4-(5-Fluoro-benzothiazol-2-yloxy)-benzyl]-2,5-diaza-bicyclo[2.2.1]hept-2-yl}-ethanone MS (ESI): mass calcd. for $C_{21}H_{20}FN_3O_2S$, 397.13; m/z found, 398.10 [M+H]$^+$. $^1$H NMR (500 MHz, CDCl$_3$, mixture of rotamers): 7.62-7.55 (m, 1H), 7.55-7.35 (m, 3H), 7.35-7.22 (m, 2H), 7.05-6.96 (m, 1H), 4.81-4.75 (m, 0.5H), 4.20-4.25 (m, 0.5H), 3.82-3.70 (m, 2H), 3.64-3.50 (m, 1.5H), 3.38-3.21 (m, 1H), 3.03-2.98 (m, 0.5H), 2.85-2.75 (m, 1.5H), 2.80-2.52 (m, 0.5H), 2.06-1.96 (m, 3H), 2.00-1.63 (m, 2H).

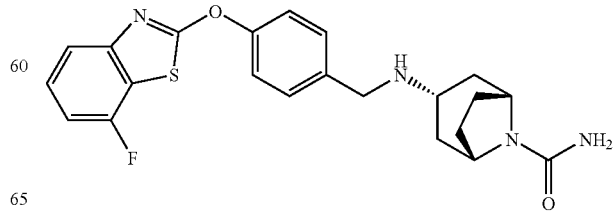

Example 171 meso-endo-3-[4-(7-Fluoro-benzothiazol-2-yloxy)-benzylamino]-8-aza-bicyclo[3.2.1]octane-8-carboxylic acid amide MS (ESI): mass calcd. for $C_{22}H_{23}FN_4O_2S$, 426.15; m/z found, 427.05 [M+H]$^+$. $^1$H NMR (500 MHz, DMSO-d$_6$): 7.72-7.61 (m, 2H), 7.60-7.55 (m, 2H), 7.53-7.47 (m, 1H), 7.33-7.26 (m, 1H), 6.11 (s, 1H), 4.28-4.12 (m, 4H), 3.71-3.54 (m, 1H), 2.02-1.82 (m, 4H), 1.79-1.68 (m, 2H), 1.66-1.59 (m, 2H).

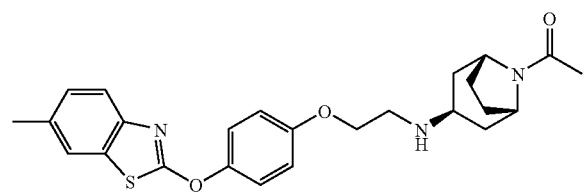

Example 172 meso-exo-1-(3-{2-[4-(6-Methyl-benzothiazol-2-yloxy)-phenoxy]-ethylamino}-8-aza-bicyclo[3.2.1]oct-8-yl)-ethanone MS (ESI): mass calcd. for $C_{25}H_{29}N_3O_3S$, 451.19; m/z found, 452.10 [M+H]$^+$. $^1$H NMR (500 MHz, DMSO-d$_6$): 7.71-7.69 (m, 1H), 7.55 (d, J=8.2 Hz, 1H), 7.36 (d, J=8.9 Hz, 2H), 7.25-7.21 (m, 1H), 7.06 (d, J=9.0 Hz, 2H), 4.42-4.32 (m, 1H), 4.14-4.00 (m, 3H), 3.02-2.80 (m, 3H), 2.38 (s, 3H), 2.20-2.03 (m, 2H), 1.94 (s, 3H), 1.91-1.59 (m, 7H),

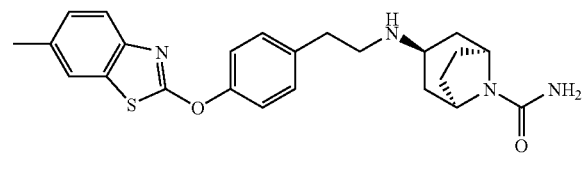

Example 173 meso-exo-3-{2-[4-(6-Methyl-benzothiazol-2-yloxy)-phenyl]-ethylamino}-8-aza-bicyclo[3.2.1]octane-8-carboxylic acid amide MS (ESI): mass calcd. for $C_{24}H_{28}N_4O_2S$, 436.19; m/z found, 437.25 [M+H]$^+$. $^1$H NMR (500 MHz, DMSO-d$_6$): 7.76-7.70 (m, 1H), 7.58-7.53 (m, 1H), 7.42-7.36 (m, 4H), 7.27-7.22 (m, 1H), 6.03 (br s, 2H), 4.17 (br s, 2H), 3.14-2.96 (m, 2H), 2.93-2.84 (m, 2H), 2.39 (s, 3H), 1.91-1.79 (m, 4H), 1.66-1.50 (m, 4H).

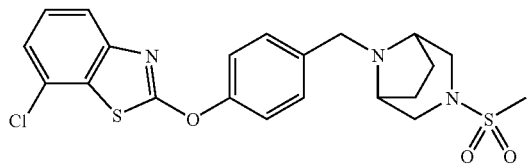

Example 174 meso-7-Chloro-2-[4-(3-methanesulfonyl-3,8-diaza-bicyclo[3.2.1]oct-8-ylmethyl)-phenoxy]-benzothiazole MS (ESI): mass calcd. for $C_{21}H_{22}ClN_3O_3S_2$, 463.08; m/z found, 464.10 [M+H]$^+$. $^1$H NMR (500 MHz, DMSO-d$_6$): 7.73-7.68 (m, 1H), 7.56-7.42 (m, 6H), 3.57 (s, 2H), 3.28-3.23 (m, 2H), 3.22-3.18 (m, 2H), 2.99-2.93 (m, 2H), 2.87-2.85 (m, 3H), 2.03-1.95 (m, 2H), 1.70-1.62 (m, 2H).

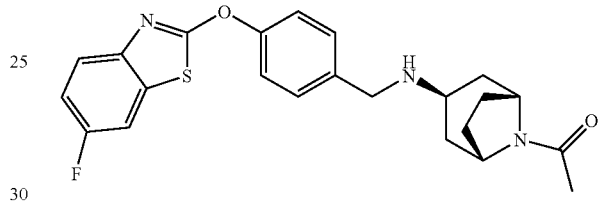

Example 175 meso-endo-1-{3-[4-(6-Fluoro-benzothiazol-2-yloxy)-benzylamino]-8-aza-bicyclo[3.2.1]oct-8-yl}-ethanone MS (ESI): mass calcd. for $C_{23}H_{24}FN_3O_2S$, 425.16; m/z found, 426.1 [M+H]$^+$. $^1$H NMR (600 MHz, DMSO-d$_6$): 7.86 (dd, J=8.7, 2.7 Hz, 1H), 7.70 (dd, J=8.9, 4.9 Hz, 1H), 7.48-7.45 (m, 2H), 7.40-7.37 (m, 2H), 7.31-7.26 (m, 1H), 4.40-4.34 (m, 1H), 4.15-4.07 (m, 1H), 3.77-3.72 (m, 2H), 2.94-2.86 (m, 1H), 2.31-2.13 (m, 3H), 1.94 (s, 3H), 1.86-1.67 (m, 5H).

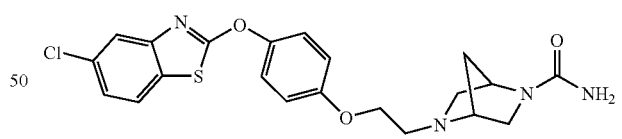

Example 176

(R,R)-5-{2-[4-(5-Chloro-benzothiazol-2-yloxy)-phenoxy]-ethyl}-2,5-diaza-bicyclo[2.2.1]heptane-2-carboxylic acid amide MS (ESI): mass calcd. for $C_{21}H_{21}ClN_4O_3S$, 444.10; m/z found, 445.0 [M+H]$^+$. $^1$H NMR (600 MHz, DMSO-d$_6$): 7.95 (d, J=8.6 Hz, 1H), 7.77 (d, J=2.1 Hz, 1H), 7.40-7.35 (m, 3H), 7.09-7.03 (m, 2H), 5.80-5.70 (m, 2H), 4.27-4.20 (m, 1H), 4.10-4.00 (m, 2H), 3.60-3.52 (m, 1H), 3.30-3.24 (m, 1H), 3.10-3.03 (m, 1H), 2.94-2.85 (m, 3H), 2.57-2.52 (m, 1H), 1.77-1.57 (m, 2H).

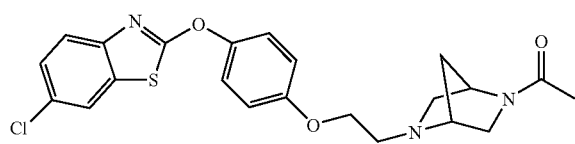

Example 177

(R,R)-1-(5-{2-[4-(6-Chloro-benzothiazol-2-yloxy)-phenoxy]-ethyl}-2,5-diaza-bicyclo[2.2.1]hept-2-yl)-ethanone MS (ESI): mass calcd. for $C_{22}H_{22}ClN_3O_3S$, 443.11; m/z found, 444.1 [M+H]$^+$. $^1$H NMR (600 MHz, DMSO-d$_6$): 8.32-8.30 (m, 1H), 8.07 (d, J=2.2 Hz, 1H), 7.70-7.65 (m, 1H), 7.47-7.43 (m, 1H), 7.39-7.36 (m, 1.5H), 7.07-7.04 (m, 1.5H), 4.53-4.31 (m, 1H), 4.13-3.99 (m, 2H), 3.71-3.55 (m, 1H), 3.55-3.39 (m, 1H), 3.15-2.84 (m, 3H), 2.52-2.50 (m, 3H), 1.97 (s, 1H), 1.86 (s, 1H), 1.83-1.55 (m, 2H).

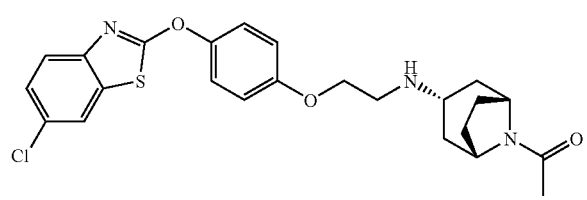

Example 178 meso-exo-1-(3-{2-[4-(6-Chloro-benzothiazol-2-yloxy)-phenoxy]-ethylamino}-8-aza-bicyclo[3.2.1]oct-8-yl)-ethanone MS (ESI): mass calcd. for $C_{24}H_{26}ClN_3O_3S$, 471.14; m/z found, 472.0 [M+H]$^+$. $^1$H NMR (600 MHz, DMSO-d$_6$): 8.09-8.05 (m, 1H), 7.68 (d, J=8.7 Hz, 1H), 7.45 (dd, J=8.7, 2.3 Hz, 1H), 7.40-7.35 (m, 2H), 7.07-7.03 (m, 2H), 5.75 (s, 1H), 4.46-4.40 (m, 1H), 4.22-4.15 (m, 1H), 4.07-3.98 (m, 2H), 3.09-2.97 (m, 1H), 2.94-2.87 (m, 2H), 1.98-1.93 (m, 4H), 1.89-1.61 (m, 5H), 1.33-1.22 (m, 2H).

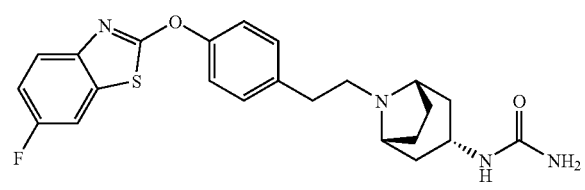

Example 179 meso-exo-(8-{2-[4-(6-Fluoro-benzothiazol-2-yloxy)-phenyl]-ethyl}-8-aza-bicyclo[3.2.1]oct-3-yl)-urea MS (ESI): mass calcd. for $C_{23}H_{25}FN_4O_2S$, 440.17; m/z found, 441.1 [M+H]$^+$. $^1$H NMR (600 MHz, DMSO-d$_6$): 7.86 (dd, J=8.7, 2.7 Hz, 1H), 7.70 (dd, J=8.9, 4.8 Hz, 1H), 7.40-7.36 (m, 2H), 7.36-7.32 (m, 2H), 7.31-7.26 (m, 1H), 5.80-5.71 (m, 1H), 5.27 (s, 2H), 3.72-3.60 (m, 1H), 3.29-3.18 (m, 2H), 2.79-2.70 (m, 2H), 2.61-2.53 (m, 2H), 1.93-1.82 (m, 2H), 1.63-1.49 (m, 4H), 1.44-1.33 (m, 2H).

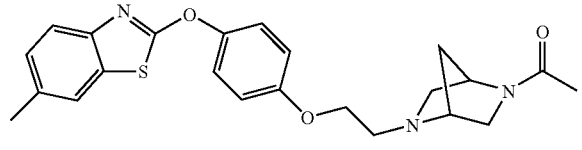

Example 180

(R,R)-1-(5-{2-[4-(6-Methyl-benzothiazol-2-yloxy)-phenoxy]-ethyl}-2,5-diaza-bicyclo[2.2.1]hept-2-yl)-ethanone MS (ESI): mass calcd. for $C_{23}H_{25}N_3O_3S$, 423.16; m/z found, 424.2 [M+H]$^+$. $^1$H NMR (600 MHz, DMSO-d$_6$): 7.72-7.68 (m, 1H), 7.55 (d, J=8.3 Hz, 1H), 7.37-7.34 (m, 2H), 7.26-7.21 (m, 1H), 7.06-7.02 (m, 2H), 4.54-4.31 (m, 1H), 4.12-4.00 (m, 2H), 3.71-3.40 (m, 3H), 3.12-2.85 (m, 3H), 2.66-2.53 (m, 1H), 2.38 (s, 3H), 2.00-1.85 (m, 3H), 1.84-1.57 (m, 2H).

Example 181

(R,R)-5-Chloro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}ClN_3O_3S_2$, 449.06; m/z found, 450.0 [M+H]$^+$. $^1$H NMR (600 MHz, DMSO-d$_6$): 7.97 (d, J=8.6 Hz, 1H), 7.80-7.78 (m, 1H), 7.50-7.47 (m, 2H), 7.42-7.37 (m, 3H), 4.21-4.16 (m, 1H), 3.83-3.74 (m, 2H), 3.57-3.50 (m, 1H), 3.45-3.41 (m, 1H), 3.24-3.19 (m, 1H), 2.95 (s, 3H), 2.82-2.77 (m, 1H), 2.65-2.60 (m, 1H), 2.55-2.51 (m, 2H).

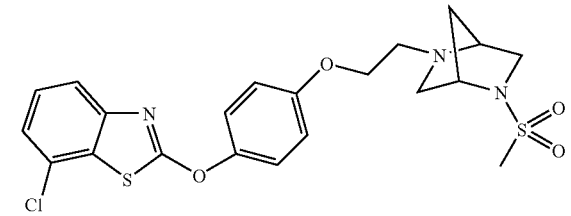

Example 182

(S,S)-7-Chloro-2-{4-[2-(5-methanesulfonyl-2,5-diaza-bicyclo[2.2.1]hept-2-yl)-ethoxy]-phenoxy}-benzothiazole MS (ESI): mass calcd. for $C_{21}H_{22}ClN_3O_4S_2$, 479.07; m/z found, 480.0 [M+H]$^+$. $^1$H NMR (600 MHz, DMSO-d$_6$): 7.69

(dd, J=7.8, 1.2 Hz, 1H), 7.51-7.43 (m, 2H), 7.43-7.39 (m, 2H), 7.10-7.05 (m, 2H), 4.17-4.15 (m, 1H), 4.09-4.05 (m, 2H), 3.66-3.63 (m, 1H), 3.21-3.16 (m, 1H), 2.94-2.91 (m, 4H), 2.73-2.68 (m, 1H), 2.51-2.50 (m, 3H), 1.81-1.73 (m, 1H), 1.69-1.62 (m, 1H).

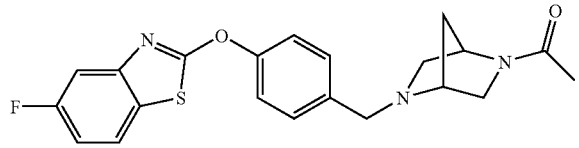

Example 183

(R,R)-1-{5-[4-(5-Fluoro-benzothiazol-2-yloxy)-benzyl]-2,5-diaza-bicyclo[2.2.1]hept-2-yl}-ethanone MS (ESI): mass calcd. for $C_{21}H_{20}FN_3O_2S$, 397.13; m/z found, 398.1 [M+H]$^+$. $^1$H NMR (600 MHz, DMSO-d$_6$): 7.97 (dd, J=8.8, 5.5 Hz, 1H), 7.59-7.55 (m, 1H), 7.50-7.45 (m, 2H), 7.41-7.37 (m, 2H), 7.25-7.19 (m, 1H), 4.57-4.33 (m, 1H), 3.82-3.73 (m, 2H), 3.63-3.43 (m, 3H), 3.18-3.07 (m, 1H), 2.87-2.76 (m, 1H), 1.97 (s, 1H), 1.92-1.86 (m, 2H), 1.86-1.59 (m, 2H).

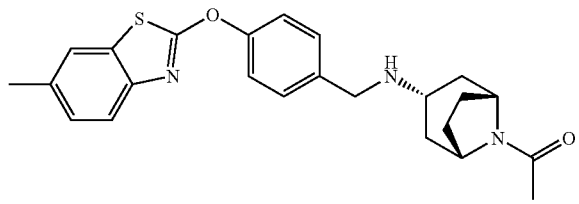

Example 184 meso-exo-1-{3-[4-(6-Methyl-benzothiazol-2-yloxy)-benzylamino]-8-aza-bicyclo[3.2.1]oct-8-yl}-ethanone MS (ESI): mass calcd. for $C_{24}H_{27}N_3O_2S$, 421.18; m/z found, 422.2 [M+H]$^+$. $^1$H NMR (600 MHz, DMSO-d$_6$): 7.73-7.70 (m, 1H), 7.56 (d, J=8.2 Hz, 1H), 7.47-7.43 (m, 2H), 7.38-7.34 (m, 2H), 7.26-7.22 (m, 1H), 4.46-4.39 (m, 1H), 4.21-4.17 (m, 1H), 3.80-3.71 (m, 2H), 3.09-2.97 (m, 1H), 2.39 (s, 3H), 1.98-1.94 (m, 4H), 1.93-1.71 (m, 3H), 1.70-1.54 (m, 2H), 1.37-1.28 (m, 2H).

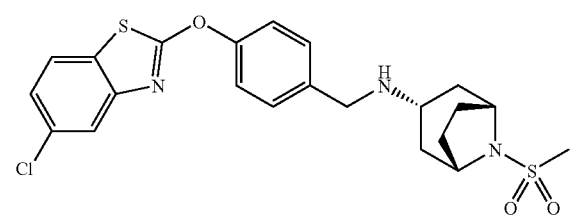

Example 185 meso-exo-[4-(5-Chloro-benzothiazol-2-yloxy)-benzyl]-(8-methanesulfonyl-8-aza-bicyclo[3.2.1]oct-3-yl)-amine MS (ESI): mass calcd. for $C_{22}H_{24}ClN_3O_3S_2$, 477.09; m/z found, 478.0 [M+H]$^+$. $^1$H NMR (600 MHz, DMSO-d$_6$): 7.97 (d, J=8.6 Hz, 1H), 7.79-7.77 (m, 1H), 7.50-7.45 (m, 2H), 7.41-7.37 (m, 3H), 4.17-4.07 (m, 2H), 3.80-3.73 (m, 2H), 2.99-2.87 (m, 4H), 2.00-1.93 (m, 4H), 1.68-1.61 (m, 2H), 1.49-1.39 (m, 2H).

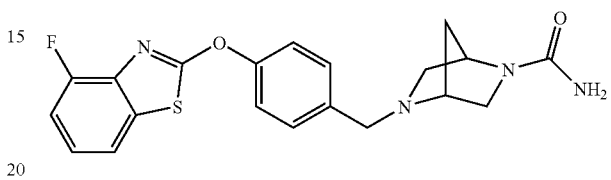

Example 186

(R,R)-5-[4-(4-Fluoro-benzothiazol-2-yloxy)-benzyl]-2,5-diaza-bicyclo[2.2.1]heptane-2-carboxylic acid amide MS (ESI): mass calcd. for $C_{20}H_{19}FN_4O_2S$, 398.12; m/z found, 399.1 [M+H]$^+$. $^1$H NMR (600 MHz, DMSO-d$_6$): 7.79-7.75 (m, 1H), 7.51-7.46 (m, 2H), 7.44-7.39 (m, 2H), 7.37-7.28 (m, 2H), 5.77 (s, 2H), 4.30-4.23 (m, 1H), 3.77-3.70 (m, 2H), 3.49-3.45 (m, 1H), 3.13-3.06 (m, 1H), 2.82-2.73 (m, 1H), 1.95-1.89 (m, 1H), 1.84-1.76 (m, 1H), 1.66-1.59 (m, 1H), 1.29-1.19 (m, 1H).

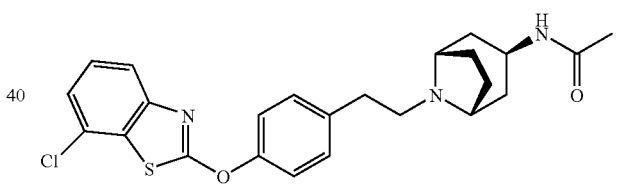

Example 187 meso-endo-N-(8-{2-[4-(7-Chloro-benzothiazol-2-yloxy)-phenyl]-ethyl}-8-aza-bicyclo[3.2.1]oct-3-yl)-acetamide MS (ESI): mass calcd. for $C_{24}H_{26}ClN_3O_2S$, 456.01; m/z found, 457.1 [M+H]$^+$. $^1$H NMR (500 MHz, DMSO-d$_6$): 7.69 (d, J=7.7 Hz, 1H), 7.49-7.39 (m, 6H), 4.28 (br s, 1H), 4.10 (br s, 1H), 2.90-2.78 (m, 5H), 2.07-1.92 (m, 6H), 1.85-1.78 (br m, 3H), 1.68-1.55 (m, 3H).

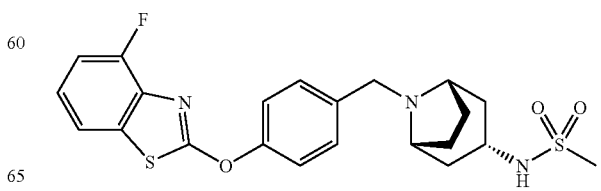

Example 188 meso-exo-N-{8-[4-(4-Fluoro-benzothiazol-2-yloxy)-benzyl]-8-aza-bicyclo[3.2.1]oct-3-yl}-methane-sulfonamide MS (ESI): mass calcd. for $C_{22}H_{24}FN_3O_3S_2$, 461.58; m/z found, 462.2 [M+H]$^+$. $^1$H NMR (500 MHz, DMSO-d$_6$): 7.80 (d, J=7.8 Hz, 1H), 7.50-7.26 (m, 5H), 7.00 (br s, 1H), 3.59 (br s, 2H), 3.17 (br s, 2H), 2.91 (br s, 3H), 2.00 (br s, 3H), 1.73-1.62 (br m, 5H).

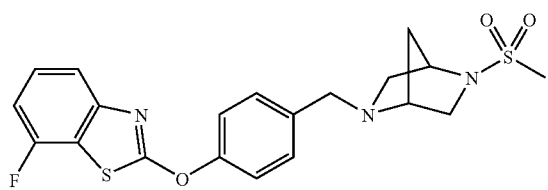

Example 189

(R,R)-7-Fluoro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}FN_3O_3S_2$, 433.53; m/z found, 434.1 [M+H]$^+$. $^1$H NMR (500 MHz, DMSO-d$_6$): 7.59 (d, J=8.1 Hz, 1H), 7.51-7.47 (m, 3H), 7.44-7.43 (m, 2H), 7.29-7.25 (m, 1H), 4.19 (br s, 1H), 3.82-3.76 (m, 2H), 3.55 (br s, 1H), 3.43 (d, J=9.1 Hz, 1H), 3.23-3.21 (m, 1H), 2.95 (s, 3H), 2.82-2.80 (m, 1H), 2.65-2.62 (m, 1H), 1.86-1.84 (m, 1H), 1.70-1.68 (m, 1H).

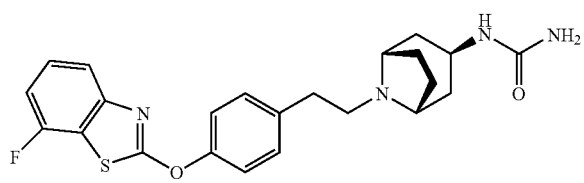

Example 190 meso-endo-(8-{2-[4-(7-Fluoro-benzothiazol-2-yloxy)-phenyl]-ethyl}-8-aza-bicyclo[3.2.1]oct-3-yl)-urea MS (ESI): mass calcd. for $C_{23}H_{25}FN_4O_2S$, 440.54; m/z found, 441.2 [M+H]$^+$. $^1$H NMR (500 MHz, DMSO-d$_6$): 7.59 (d, J=8.1 Hz, 1H), 7.50-7.46 (m, 1H), 7.39-7.36 (m, 4H), 7.28-7.24 (m, 1H), 5.90 (d, J=6.6 Hz, 1H), 5.40 (s, 2H), 3.68-3.66 (m, 1H), 3.18 (br s, 2H), 2.76-2.73 (m, 2H), 2.00-1.82 (m, 6H), 1.48-1.44 (m, 2H).

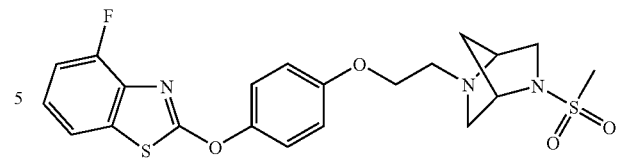

Example 191

(S,S)-4-Fluoro-2-{4-[2-(5-methanesulfonyl-2,5-diaza-bicyclo[2.2.1]hept-2-yl)-ethoxy]-phenoxy}-benzothiazole MS (ESI): mass calcd. for $C_{21}H_{22}FN_3O_4S_2$, 463.55; m/z found, 464.1 [M+H]$^+$. $^1$H NMR (500 MHz, DMSO-d$_6$): 7.75 (d, J=7.7 Hz, 1H), 7.42-7.38 (m, 2H), 7.34-7.29 (m, 2H), 7.09-7.05 (m, 2H), 4.16 (brs, 1H), 4.08-4.06 (m, 2H), 3.65 (brs, 1H), 3.20-3.18 (m, 1H), 2.95-2.90 (m, 6H), 2.72-2.70 (m, 1H), 1.78-1.76 (m, 1H), 1.67-1.65 (m, 1H).

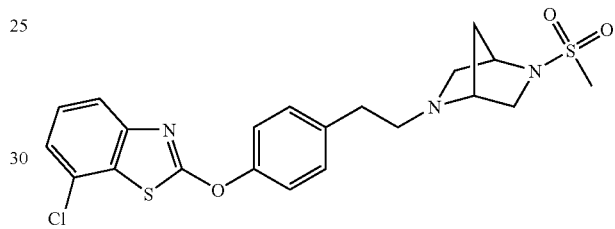

Example 192

(R,R)-7-Chloro-2-{4-[2-(5-methanesulfonyl-2,5-diaza-bicyclo[2.2.1]hept-2-yl)-ethyl]-phenoxy}-benzothiazole MS (ESI): mass calcd. for $C_{21}H_{22}ClN_3O_3S_2$, 464.01; m/z found, 465.0 [M+H]$^+$. $^1$H NMR (500 MHz, DMSO-d$_6$): 7.71-7.69 (m, 1H), 7.50-7.45 (m, 2H), 7.42-7.38 (m, 4H), 4.16 (brs, 1H), 3.58 (brs, 1H), 3.18-3.15 (m, 1H), 2.92 (s, 3H), 2.86-2.80 (m, 3H), 2.78-2.70 (m, 3H), 2.67-2.65 (m, 1H), 2.76-2.74 (m, 1H), 1.65-1.63 (m, 1H).

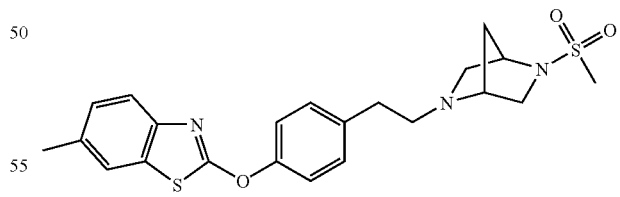

Example 193

(R,R)-2-{4-[2-(5-Methanesulfonyl-2,5-diaza-bicyclo[2.2.1]hept-2-yl)-ethyl]-phenoxy}-6-methyl-benzothiazole MS (ESI): mass calcd. for $C_{22}H_{25}N_3O_3S_2$, 443.59; m/z found, 444.2 [M+H]$^+$. $^1$H NMR (500 MHz, DMSO-d$_6$): 7.71 (br s, 1H), 7.56 (d, J=8.1 Hz, 1H), 7.38-7.32 (m, 4H), 7.25-

7.23 (m, 1H), 4.16 (brs, 1H), 3.58 (brs, 1H), 3.17-3.15 (m, 1H), 2.92 (s, 3H), 2.92-2.65 (m, 6H), 2.39 (s, 3H), 1.76-1.74 (m, 1H), 1.65-1.63 (m, 1H).

(d, J=7.2 Hz, 1H), 7.50-7.44 (m, 6H), 5.80 (br s, 2H), 4.28 (br s, 1H), 3.75 (br s, 2H), 3.11 (br s, 1H), 2.79 br s, 1H), 1.82 (br s, 1H), 1.65 (br s, 1H).

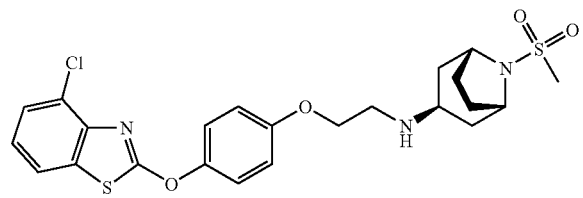

Example 194 meso-endo-{2-[4-(4-Chloro-benzothiazol-2-yloxy)-phenoxy]-ethyl}-(8-methanesulfonyl-8-aza-bicyclo[3.2.1]oct-3-yl)-amine MS (ESI): mass calcd. for $C_{23}H_{26}ClN_3O_4S_2$, 508.06; m/z found, 509.1 [M+H]$^+$. $^1$H NMR (500 MHz, DMSO-d$_6$): 7.89 (d, J=7.7 Hz, 1H), 7.53 (d, J=7.7 Hz, 1H), 7.42 (d, J=8.2 Hz, 2H), 7.34-7.28 (m, 1H), 7.08 (d, J=8.2 Hz, 2H), 4.07 (br s, 4H), 2.91 (br s, 6H), 2.15 (br s, 2H), 1.90-1.76 (br m, 7H).

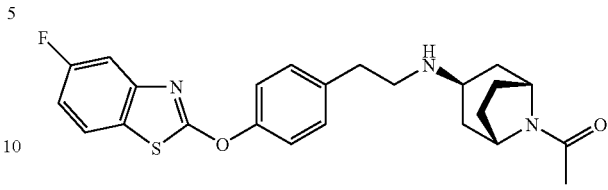

Example 197 meso-endo-1-(3-{2-[4-(5-Fluoro-benzothiazol-2-yloxy)-phenyl]-ethylamino}-8-aza-bicyclo[3.2.1]oct-8-yl)-ethanone MS (ESI): mass calcd. for $C_{24}H_{26}FN_3O_2S$, 439.56; m/z found, 440.1 [M+H]$^+$. $^1$H NMR (500 MHz, DMSO-d$_6$): 7.98-7.94 (m, 1H), 7.58-7.55 (m, 1H), 7.43-7.35 (m, 4H), 7.24-7.21 (m, 1H), 4.32 (br s, 1H), 4.07 (br s, 1H), 2.89 (br s, 1H), 2.79 (br s, 3H), 2.00-1.84 (m, 7H), 1.68-1.57 (m, 3H).

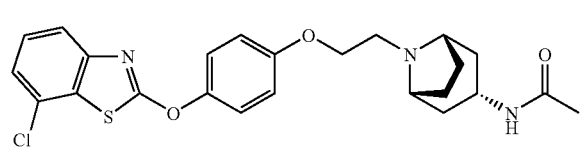

Example 195 meso-exo-N-(8-{2-[4-(7-Chloro-benzothiazol-2-yloxy)-phenoxy]-ethyl}-8-aza-bicyclo[3.2.1]oct-3-yl)-acetamide MS (ESI): mass calcd. for $C_{24}H_{26}ClN_3O_3S$, 472.01; m/z found, 473.1 [M+H]$^+$. $^1$H NMR (500 MHz, DMSO-d$_6$): 7.70-7.65 (m, 2H), 7.50-7.46 (m, 2H), 7.44-7.41 (m, 2H), 7.09-7.07 (m, 2H), 4.10-4.08 (m, 2H), 3.92-3.88 (m, 1H), 2.78-2.75 (m, 2H), 1.91-1.88 (m, 2H), 1.75 (s, 3H), 1.56-1.50 (m, 6H).

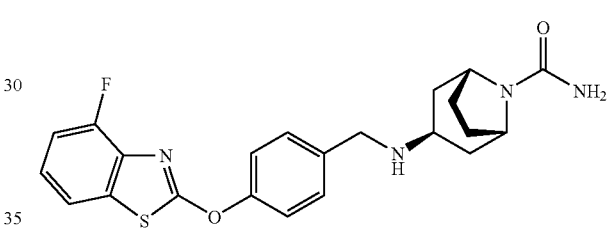

Example 198 meso-endo-3-[4-(4-Fluoro-benzothiazol-2-yloxy)-benzylamino]-8-aza-bicyclo[3.2.1]octane-8-carboxylic acid amide MS (ESI): mass calcd. for $C_{22}H_{23}FN_4O_2S$, 426.52; m/z found, 427.0 [M+H]$^+$. $^1$H NMR (500 MHz, DMSO-d$_6$): 7.77 (d, J=7.8 Hz, 1H), 7.50-7.29 (m, 6H), 5.85 (br s, 2H), 4.08 (br s, 2H), 3.77 (br s, 1H), 2.90 (br s, 1H), 2.20-1.79 (br m, 7H), 1.62-1.59 (m, 2H).

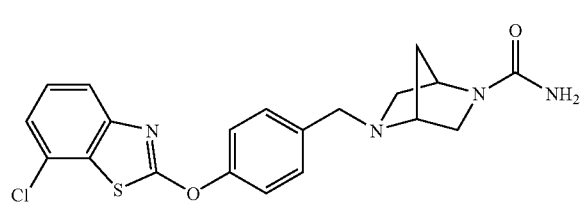

Example 196

(R,R)-5-[4-(7-Chloro-benzothiazol-2-yloxy)-benzyl]-2,5-diaza-bicyclo[2.2.1]heptane-2-carboxylic acid amide MS (ESI): mass calcd. for $C_{20}H_{19}ClN_4O_2S$, 414.92; m/z found, 415.1 [M+H]$^+$. $^1$H NMR (500 MHz, DMSO-d$_6$): 7.70

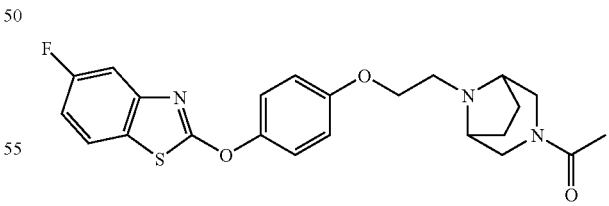

Example 199 meso-1-(8-{2-[4-(5-Fluoro-benzothiazol-2-yloxy)-phenoxy]-ethyl}-3,8-diaza-bicyclo[3.2.1]oct-3-yl)-ethanone MS (ESI): mass calcd. for $C_{23}H_{24}FN_3O_3S$, 441.53; m/z found, 442.0 [M+H]$^+$. $^1$H NMR (500 MHz, DMSO-d$_6$): 7.95

(dd, J=8.9, 5.5 Hz, 1H), 7.56 (dd, J=9.9, 2.5 Hz, 1H), 7.39-7.36 (m, 2H), 7.23-7.19 (m, 1H), 7.08-7.06 (m, 2H), 4.13-4.11 (m, 2H), 3.97-3.94 (m, 1H), 3.46-3.43 (m, 1H), 3.24-3.22 (m, 1H), 2.72-2.70 (m, 3H), 1.96 (s, 3H), 1.88-1.83 (m, 2H), 1.58-1.54 (m, 1H), 1.41-1.37 (m, 1H).

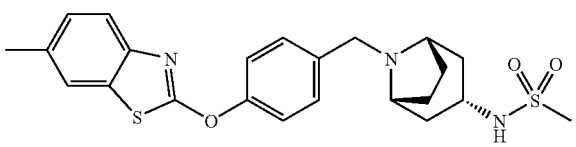

Example 200 meso-exo-N-{8-[4-(6-Methyl-benzothiazol-2-yloxy)-benzyl]-8-aza-bicyclo[3.2.1]oct-3-yl}-methanesulfonamide MS (ESI): mass calcd. for $C_{23}H_{27}N_3O_3S_2$, 457.15; m/z found, 458.1 [M+H]$^+$. $^1$H NMR (500 MHz, CDCl$_3$): 7.61 (d, J=8.3 Hz, 1H), 7.52 (d, J=8.5 Hz, 2H), 7.47 (s, 1H), 7.33 (d, J=8.6 Hz, 2H), 7.20 (dd, J=8.3, 1.1 Hz, 1H), 3.66 (s, 3H), 3.37 (s, 2H), 2.97 (s, 3H), 2.43 (s, 3H), 2.17-2.06 (m, 2H), 2.03-1.84 (m, 4H), 1.82-1.68 (m, 2H).

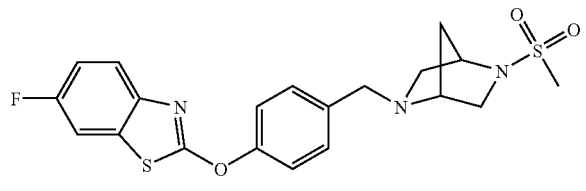

Example 201

(R,R)-6-Fluoro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}FN_3O_3S_2$, 433.09; m/z found, 434.1 [M+H]$^+$. $^1$H NMR (500 MHz, DMSO-d$_6$): 7.87 (d, J=8.7 Hz, 1H), 7.74-7.65 (m, 1H), 7.48 (d, J=7.9 Hz, 2H), 7.39 (d, J=7.3 Hz, 2H), 7.29 (t, J=9.1 Hz, 1H), 4.18 (s, 1H), 3.85-3.69 (m, 2H), 3.54 (s, 1H), 3.43 (d, J=9.4 Hz, 1H), 3.27-3.17 (m, 1H), 2.95 (s, 3H), 2.80 (d, J=9.5 Hz, 1H), 2.62 (d, J=9.5 Hz, 1H), 1.84 (d, J=9.7 Hz, 1H), 1.68 (d, J=9.9 Hz, 1H).

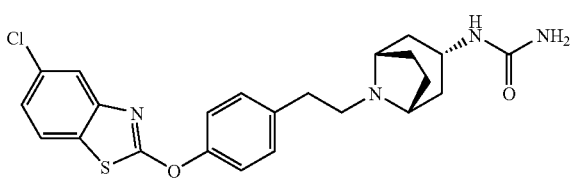

Example 202 meso-exo-(8-{2-[4-(5-Chloro-benzothiazol-2-yloxy)-phenyl]-ethyl}-8-aza-bicyclo[3.2.1]oct-3-yl)-urea MS (ESI): mass calcd. for $C_{23}H_{25}ClN_4O_2S$, 456.14; m/z found, 457.0 [M+H]$^+$. $^1$H NMR (500 MHz, DMSO-d$_6$): 7.98

(d, J=8.6 Hz, 1H), 7.78 (d, J=2.0 Hz, 1H), 7.49-7.18 (m, 5H), 5.97 (s, 1H), 5.37 (s, 2H), 3.66 (s, 1H), 3.24 (s, 2H), 2.82-2.69 (m, 2H), 2.60-2.53 (m, 2H), 1.87 (s, 2H), 1.64-1.47 (m, 4H), 1.48-1.29 (m, 2H).

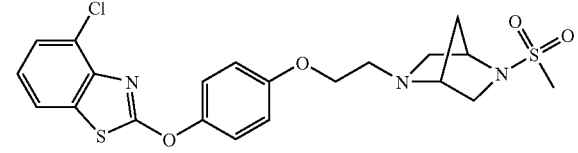

Example 203

(R,R)-4-Chloro-2-{4-[2-(5-methanesulfonyl-2,5-diaza-bicyclo[2.2.1]hept-2-yl)-ethoxy]-phenoxy}-benzothiazole MS (ESI): mass calcd. for $C_{21}H_{22}ClN_3O_4S_2$, 479.07; m/z found, 480.1 [M+H]$^+$. $^1$H NMR (500 MHz, DMSO-d$_6$): 7.89 (dd, J=8.0, 1.1 Hz, 1H), 7.53 (dd, J=7.9, 1.1 Hz, 1H), 7.46-7.39 (m, 2H), 7.31 (t, J=8.0 Hz, 1H), 7.12-7.04 (m, 2H), 4.16 (s, 1H), 4.11-4.04 (m, 2H), 3.64 (s, 1H), 3.36 (d, J=9.3 Hz, 1H), 3.19 (dd, J=9.4, 2.1 Hz, 1H), 3.02-2.86 (m, 6H), 2.71 (d, J=9.8 Hz, 1H), 1.77 (d, J=9.9 Hz, 1H), 1.66 (d, J=9.9 Hz, 1H).

Example 204 meso-exo-(8-{2-[4-(4-Fluoro-benzothiazol-2-yloxy)-phenoxy]-ethyl}-8-aza-bicyclo[3.2.1]oct-3-yl)-urea MS (ESI): mass calcd. for $C_{23}H_{25}FN_4O_3S$, 456.16; m/z found, 457.0 [M+H]$^+$. $^1$H NMR (500 MHz, DMSO-d$_6$): 7.79-7.71 (m, 1H), 7.45-7.36 (m, 2H), 7.36-7.25 (m, 2H), 7.10-7.02 (m, 2H), 5.90 (d, J=6.8 Hz, 1H), 5.39 (s, 2H), 4.07 (t, J=6.1 Hz, 2H), 3.65 (d, J=7.0 Hz, 1H), 3.21 (s, 2H), 2.68 (t, J=6.2 Hz, 2H), 2.05-1.73 (m, 6H), 1.46 (d, J=13.8 Hz, 2H).

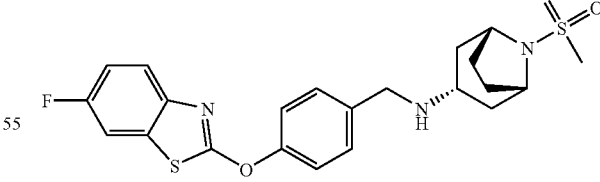

Example 205 meso-exo-[4-(6-Fluoro-benzothiazol-2-yloxy)-benzyl]-(8-methanesulfonyl-8-aza-bicyclo[3.2.1]oct-3-yl)-amine MS (ESI): mass calcd. for $C_{22}H_{24}FN_3O_3S_2$, 461.12; m/z found, 462.1 [M+H]$^+$. $^1$H NMR (500 MHz, DMSO-d$_6$): 7.87

(dd, J=8.7, 2.7 Hz, 1H), 7.70 (dd, J=8.9, 4.9 Hz, 1H), 7.46 (d, J=8.5 Hz, 2H), 7.37 (d, J=8.6 Hz, 2H), 7.29 (td, J=9.1, 2.8 Hz, 1H), 4.13 (s, 2H), 3.74 (s, 2H), 3.41-3.21 (m, 1H), 2.93 (s, 3H), 2.03-1.86 (m, 5H), 1.64 (d, J=7.8 Hz, 2H), 1.41 (s, 2H).

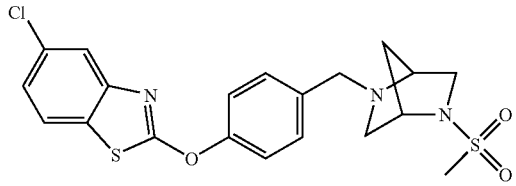

Example 206

(S,S)-5-Chloro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}ClN_3O_3S_2$, 449.06; m/z found, 450.0 [M+H]$^+$. $^1$H NMR (500 MHz, DMSO-d$_6$): 7.97 (d, J=8.5 Hz, 1H), 7.79 (s, 1H), 7.48 (d, J=8.2 Hz, 2H), 7.44-7.32 (m, 3H), 4.18 (s, 1H), 3.87-3.71 (m, 2H), 3.54 (s, 1H), 3.41 (t, J=17.4 Hz, 1H), 3.22 (d, J=8.8 Hz, 1H), 2.94 (s, 3H), 2.80 (d, J=8.6 Hz, 1H), 2.62 (d, J=9.5 Hz, 1H), 1.84 (d, J=9.9 Hz, 1H), 1.68 (d, J=9.7 Hz, 1H).

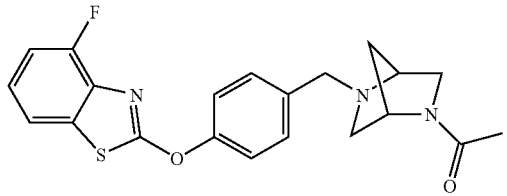

Example 207

(S,S)-1-{5-[4-(4-Fluoro-benzothiazol-2-yloxy)-benzyl]-2,5-diaza-bicyclo[2.2.1]hept-2-yl}-ethanone MS (ESI): mass calcd. for $C_{21}H_{20}FN_3O_2S$, 397.13; m/z found, 398.1 [M+H]$^+$. $^1$H NMR (500 MHz, DMSO-d$_6$, mixture of rotamers): 7.77 (dd, J=7.8, 1.2 Hz, 1H), 7.53-7.45 (m, 2H), 7.44-7.39 (m, 2H), 7.40-7.23 (m, 2H), 4.52 (s, 0.5H), 4.37 (s, 0.5H), 4.09 (s, 0.5H), 3.78 (d, J=4.4 Hz, 1H), 3.62-3.42 (m, 2H), 3.17 (s, 1H), 3.12 (d, J=9.0 Hz, 0.5H), 2.90-2.73 (m, 1H), 2.52 (d, J=14.2 Hz, 0.5H), 2.46 (d, J=9.5 Hz, 0.5H), 1.97 (s, 1.5H), 1.87 (d, J=18.5 Hz, 2H), 1.82 (d, J=9.7 Hz, 0.5H), 1.72 (d, J=9.6 Hz, 0.5H), 1.62 (d, J=9.6 Hz, 0.5H).

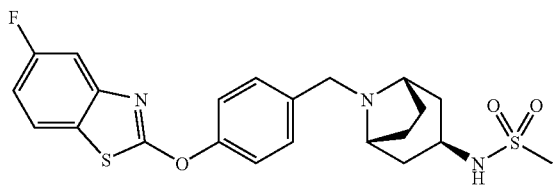

Example 208 meso-endo-N-{8-[4-(5-Fluoro-benzothiazol-2-yloxy)-benzyl]-8-aza-bicyclo[3.2.1]oct-3-yl}-methanesulfonamide MS (ESI): mass calcd. for $C_{22}H_{24}FN_3O_3S_2$, 461.12; m/z found, 462.1 [M+H]$^+$. $^1$H NMR (500 MHz, CDCl$_3$): 7.61 (d, J=8.3 Hz, 1H), 7.52 (d, J=8.5 Hz, 2H), 7.47 (s, 1H), 7.33 (d, J=8.6 Hz, 2H), 7.20 (dd, J=8.3, 1.1 Hz, 1H), 3.66 (s, 3H), 2.97 (s, 3H), 2.43 (s, 3H), 2.16-2.06 (m, 2H), 1.91 (dd, J=14.4, 8.1 Hz, 4H), 1.76 (d, J=8.4 Hz, 2H).

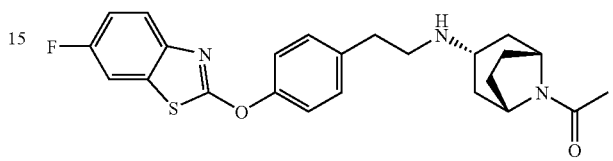

Example 209 meso-exo-1-(3-{2-[4-(6-Fluoro-benzothiazol-2-yloxy)-phenyl]-ethylamino}-8-aza-bicyclo[3.2.1]oct-8-yl)-ethanone MS (ESI): mass calcd. for $C_{24}H_{26}FN_3O_2S$, 439.17; m/z found, 440.1 [M+H]$^+$. $^1$H NMR (500 MHz, DMSO-d$_6$): 7.88 (d, J=6.0 Hz, 1H), 7.70 (dd, J=8.9, 4.9 Hz, 1H), 7.38 (s, 4H), 7.29 (s, 1H), 4.43 (s, 1H), 4.20 (s, 1H), 2.94 (s, 2H), 2.83 (s, 2H), 1.96 (s, 3H), 1.93-1.52 (m, 6H), 1.40 (s, 2H).

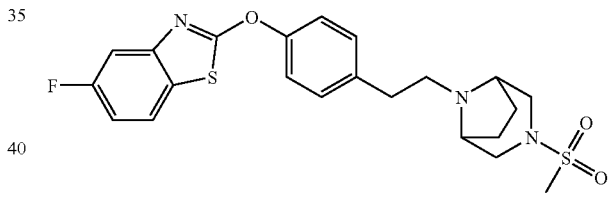

Example 210 meso-5-Fluoro-2-{4-[2-(3-methanesulfonyl-3,8-diaza-bicyclo[3.2.1]oct-8-yl)-ethyl]-phenoxy}-benzothiazole MS (ESI): mass calcd. for $C_{22}H_{24}FN_3O_3S_2$, 461.12; m/z found, 462.1 [M+H]$^+$. $^1$H NMR (500 MHz, DMSO-d$_6$): 8.32 (s, 1H), 7.96 (dd, J=8.8, 5.5 Hz, 1H), 7.56 (dd, J=9.9, 2.6 Hz, 1H), 7.43-7.32 (m, 3H), 7.22 (td, J=9.1, 2.6 Hz, 1H), 3.38 (s, 2H), 3.16 (s, 2H), 3.01-2.68 (m, 7H), 2.62-2.50 (m, 2H), 1.91-1.86 (m, 2H), 1.68-1.56 (m, 2H).

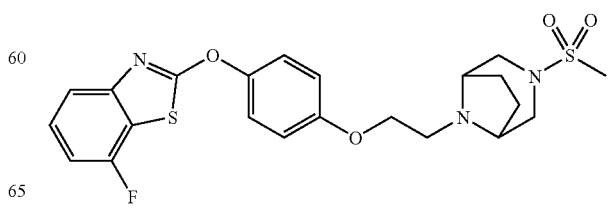

Example 211 meso-7-Fluoro-2-{4-[2-(3-methanesulfonyl-3,8-diaza-bicyclo[3.2.1]oct-8-yl)-ethoxy]-phenoxy}-benzothiazole MS (ESI): mass calcd. for $C_{22}H_{24}FN_3O_4S_2$, 477.12; m/z found, 478.0 [M+H]+. 1H NMR (500 MHz, DMSO-$d_6$): 7.58 (d, J=8.1 Hz, 1H), 7.52-7.46 (m, 1H), 7.46-7.38 (m, 2H), 7.29-7.21 (m, 1H), 7.08 (d, J=9.0 Hz, 2H), 4.11 (t, J=5.8 Hz, 2H), 3.43 (s, 2H), 3.16 (d, J=8.5 Hz, 2H), 2.94 (d, J=11.2 Hz, 3H), 2.84 (s, 2H), 2.73 (t, J=5.8 Hz, 2H), 1.89 (s, 2H), 1.63 (d, J=7.4 Hz, 2H).

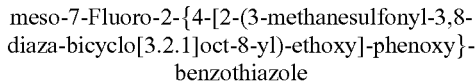

Example 212 meso-exo-3-{2-[4-(4-Fluoro-benzothiazol-2-yloxy)-phenyl]-ethylamino}-8-aza-bicyclo[3.2.1]octane-8-carboxylic acid amide MS (ESI): mass calcd. for $C_{23}H_{25}N_4O_2SF$, 440.2; m/z found, 441.1 [M+H]+. 1H NMR (500 MHz, DMSO-$d_6$): 7.59 (d, J=8.1 Hz, 1H), 7.52-7.45 (m, 3H), 7.45-7.40 (m, 2H), 7.29-7.23 (m, 1H), 4.07 (s, 2H), 3.76-3.70 (m, 2H), 2.91 (s, 3H), 2.26-2.21 (m, 2H), 2.21-2.14 (m, 1H), 1.95-1.88 (m, 2H), 1.88-1.80 (m, 4H).

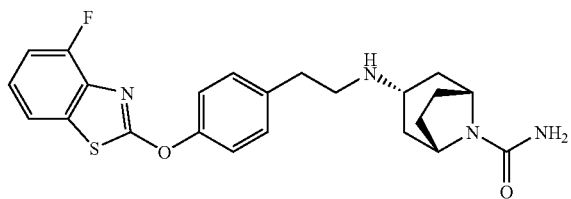

Example 213 meso-exo-{2-[4-(4-Fluoro-benzothiazol-2-yloxy)-phenoxy]-ethyl}-(8-methanesulfonyl-8-aza-bicyclo[3.2.1]oct-3-yl)-amine MS (ESI): mass calcd. for $C_{23}H_{26}N_3O_4S_2F$, 491.1; m/z found, 492.1 [M+H]+. 1H NMR (500 MHz, DMSO-$d_6$): 7.75 (d, J=7.3 Hz, 1H), 7.45-7.36 (m, 2H), 7.36-7.26 (m, 2H), 7.13-7.01 (m, 2H), 4.43-4.26 (m, 1H), 4.11-4.04 (m, 3H), 2.96-2.83 (m, 3H), 2.22-2.02 (m, 2H), 1.94 (s, 3H), 1.90-1.77 (m, 4H), 1.75-1.59 (m, 3H).

Example 214

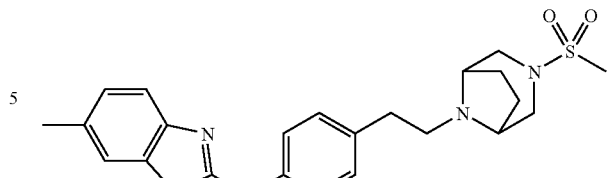

meso-2-{4-[2-(3-Methanesulfonyl-3,8-diaza-bicyclo[3.2.1]oct-8-yl)-ethyl]-phenoxy}-6-methyl-benzothiazole MS (ESI): mass calcd. for $C_{23}H_{27}N_3O_3S_2$, 457.2; m/z found, 458.1 [M+H]+. 1H NMR (500 MHz, DMSO-$d_6$): 7.71 (s, 1H), 7.60-7.50 (m, 1H), 7.41-7.35 (m, 2H), 7.35-7.30 (m, 2H), 7.26-7.21 (m, 1H), 3.41-3.33 (m, 2H), 3.19-3.11 (m, 2H), 2.98-2.89 (m, 2H), 2.88-2.81 (m, 2H), 2.81-2.70 (m, 2H), 2.60-2.51 (m, 2H), 2.38 (s, 3H), 1.96-1.77 (m, 2H), 1.67-1.55 (m, 2H).

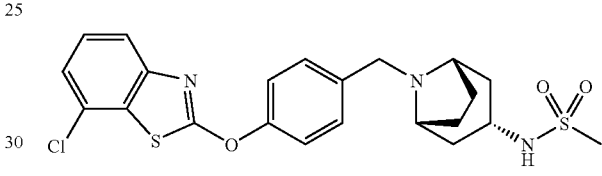

Example 215 meso-exo-N-{8-[4-(7-Chloro-benzothiazol-2-yloxy)-benzyl]-8-aza-bicyclo[3.2.1]oct-3-yl}-methane-sulfonamide MS (ESI): mass calcd. for $C_{22}H_{24}N_3O_3S_2Cl$, 477.1; m/z found, 478.1 [M+H]+. 1H NMR (500 MHz, DMSO-$d_6$): 7.74-7.67 (m, 1H), 7.53-7.37 (m, 5H), 7.01-6.92 (m, 1H), 3.60-3.50 (m, 2H), 3.20-3.08 (m, 2H), 2.89 (s, 3H), 2.02-1.90 (m, 2H), 1.75-1.66 (m, 2H), 1.65-1.50 (m, 2H).

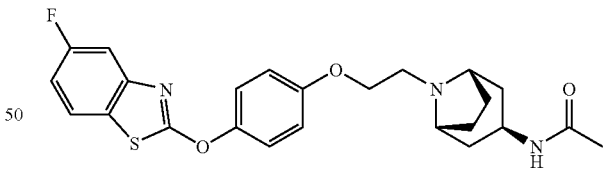

Example 216 meso-endo-N-(8-{2-[4-(5-Fluoro-benzothiazol-2-yloxy)-phenoxy]-ethyl}-8-aza-bicyclo[3.2.1]oct-3-yl)-acetamide MS (ESI): mass calcd. for $C_{24}H_{26}N_3O_3SF$, 455.2; m/z found, 456.1 [M+H]+. 1H NMR (500 MHz, DMSO-$d_6$): 7.85 (dd, J=8.7, 2.7 Hz, 1H), 7.70 (dd, J=8.9, 4.9 Hz, 1H), 7.40-7.34 (m, 2H), 7.28 (dt, J=9.1, 2.8 Hz, 1H), 7.11-7.01 (m, 2H), 4.39-4.30 (m, 1H), 4.13-4.04 (m, 3H), 2.94-2.86 (m, 3H), 2.21-2.08 (m, 2H), 1.94 (s, 3H), 1.92-1.78 (m, 3H), 1.76-1.60 (m, 3H).

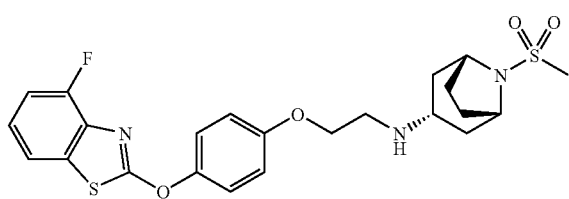

Example 217 meso-exo-{2-[4-(4-Fluoro-benzothiazol-2-yloxy)-phenoxy]-ethyl}-(8-methanesulfonyl-8-aza-bicyclo[3.2.1]oct-3-yl)-amine MS (ESI): mass calcd. for $C_{23}H_{26}N_3O_4S_2F$, 491.1; m/z found, 492.1 [M+H]$^+$. $^1$H NMR (500 MHz, DMSO-d$_6$): 7.75 (dd, J=7.6, 1.4 Hz, 1H), 7.43-7.36 (m, 2H), 7.38-7.25 (m, 2H), 7.10-7.02 (m, 2H), 4.19-4.08 (m, 2H), 4.02 (t, J=5.7 Hz, 2H), 2.93 (s, 3H), 2.91-2.86 (m, 2H), 2.00-1.87 (m, 4H), 1.74-1.64 (m, 3H), 1.40-1.29 (m, 2H).

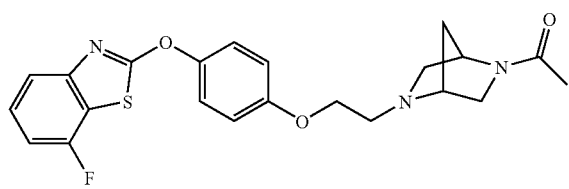

Example 218

(R,R)-1-(5-{2-[4-(7-Fluoro-benzothiazol-2-yloxy)-phenoxy]-ethyl}-2,5-diaza-bicyclo[2.2.1]hept-2-yl)-ethanone MS (ESI): mass calcd. for $C_{22}H_{22}N_3O_3SF$, 427.1; m/z found, 428.2 [M+H]$^+$. $^1$H NMR (500 MHz, DMSO-d$_6$, mixture of rotamers): 7.58 (d, J=8.1 Hz, 1H), 7.48 (dt, J=8.2, 5.6 Hz, 1H), 7.44-7.37 (m, 2H), 7.28-7.22 (m, 2H), 7.10-7.02 (m, 2H), 4.50-4.48 (m, 0.5H), 4.37-4.32 (m, 0.5H), 4.09-4.01 (m, 2H), 3.66-3.63 (m, 0.5H), 3.60-3.57 (m, 0.5H), 3.55-3.50 (m, 0.5H), 3.42-3.37 (m, 0.5H), 3.11-3.05 (m, 0.5H), 3.00-2.86 (m, 3H), 3.64-2.59 (m, 0.5H), 2.57-2.52 (m, 0.5H), 2.49-2.42 (m, 0.5H), 1.97 (s, 1.5H), 1.86 (s, 1.5H), 1.84-1.79 (m, 0.5H), 1.77-1.72 (m, 0.5H), 1.72-1.66 (m, 0.5H), 1.62-1.57 (m, 0.5H).

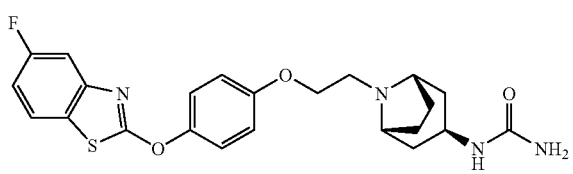

Example 219 meso-endo-(8-{2-[4-(5-Fluoro-benzothiazol-2-yloxy)-phenoxy]-ethyl}-8-aza-bicyclo[3.2.1]oct-3-yl)-urea MS (ESI): mass calcd. for $C_{23}H_{25}N_4O_3SF$, 456.2; m/z found, 457.1 [M+H]$^+$. $^1$H NMR (500 MHz, DMSO-d$_6$): 7.45 (dd, J=8.8, 5.5 Hz, 1H), 7.56 (dd, J=9.9, 2.6 Hz, 1H), 7.40-7.32 (m, 2H), 7.21 (dt, J=9.1, 2.6 Hz, 1H), 7.09-7.02 (m, 2H), 5.90 (d, J=6.0 Hz, 1H), 5.43-5.35 (m, 2H), 4.12-4.01 (m, 2H), 3.70-3.59 (m, 1H), 3.25-3.14 (m, 2H), 2.72-2.63 (m, 2H), 3.02-1.94 (m, 2H), 1.95-1.87 (m, 2H), 1.87-1.81 (m, 2H), 1.51-1.38 (m, 2H).

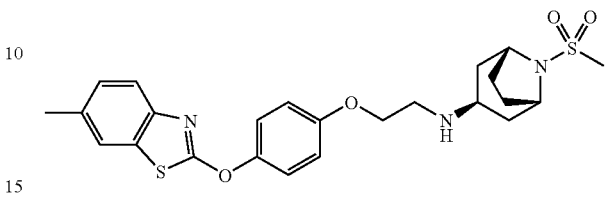

Example 220 meso-endo-(8-Methanesulfonyl-8-aza-bicyclo[3.2.1]oct-3-yl)-{2-[4-(6-methyl-benzothiazol-2-yloxy)-phenoxy]-ethyl}-amine MS (ESI): mass calcd. for $C_{24}H_{29}N_3O_4S_2$, 487.2; m/z found, 488.1 [M+H]$^+$. $^1$H NMR (500 MHz, DMSO-d$_6$): 7.72 (s, 1H), 7.58-7.49 (m, 1H), 7.43-7.36 (m, 2H), 7.26-7.19 (m, 1H), 7.12-7.02 (m, 2H), 4.28-4.10 (m, 4H), 3.29-3.12 (m, 2H), 2.97 (s, 3H), 2.66-2.53 (m, 2H), 2.38 (s, 3H), 2.11-1.92 (m, 4H), 1.75-1.68 (m, 2H), 1.67-1.53 (m, 2H).

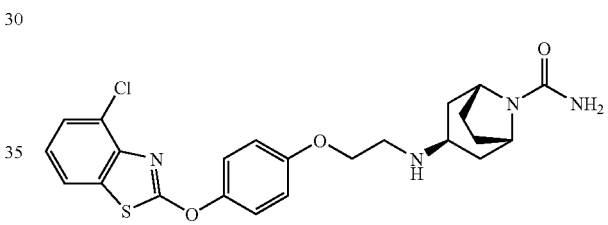

Example 221 meso-endo-3-{2-[4-(4-Chloro-benzothiazol-2-yloxy)-phenoxy]-ethylamino}-8-aza-bicyclo[3.2.1]octane-8-carboxylic acid amide MS (ESI): mass calcd. for $C_{23}H_{25}N_4O_3SCl$, 472.1; m/z found, 473.1 [M+H]$^+$. $^1$H NMR (500 MHz, DMSO-d$_6$): 7.95-7.88 (m, 1H), 7.56-7.53 (m, 1H), 7.52-7.38 (m, 4H), 7.37-7.29 (m, 1H), 6.08-6.01 (m, 1H), 4.28-4.14 (m, 1H), 3.28-3.18 (m, 2H), 3.06-2.87 (m, 2H), 2.01-1.42 (m, 6H).

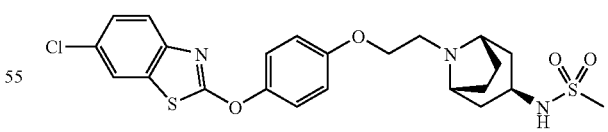

Example 222 meso-endo-N-(8-{2-[4-(6-Chloro-benzothiazol-2-yloxy)-phenoxy]-ethyl}-8-aza-bicyclo[3.2.1]oct-3-yl)-methanesulfonamide MS (ESI): mass calcd. for $C_{23}H_{26}N_3O_4S_2Cl$, 507.1; m/z found, 508.1 [M+H]$^+$. $^1$H NMR (500 MHz, DMSO-d$_6$): 8.07

(d, J=1.7 Hz, 1H), 7.68 (d, J=8.6 Hz, 1H), 7.46 (dd, J=8.6, 2.2 Hz, 1H), 7.42-7.32 (m, 2H), 7.10-6.99 (m, 2H), 4.14-3.95 (m, 2H), 3.50-3.39 (m, 1H), 3.24-3.12 (m, 2H), 3.03-2.79 (m, 3H), 2.71-2.58 (m, 2H), 2.07-1.75 (m, 6H), 1.76-1.64 (m, 2H).

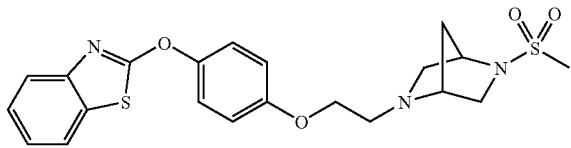

Example 223

(R,R)-2-{4-[2-(5-Methanesulfonyl-2,5-diaza-bicyclo[2.2.1]hept-2-yl)-ethoxy]-phenoxy}-benzothiazole MS (ESI): mass calcd. for $C_{21}H_{23}N_3O_4S_2$, 445.12; m/z found, 446.1 [M+H]$^+$. $^1$H NMR (400 MHz, DMSO-d$_6$): 7.90 (dd, J=8.0, 0.8 Hz, 1H), 7.67 (d, J=7.4 Hz, 1H), 7.45-7.39 (m, 1H), 7.39-7.34 (m, 2H), 7.34-7.28 (m, 1H), 7.08-7.02 (m, 2H), 4.16 (s, 1H), 4.06 (t, J=5.8 Hz, 2H), 3.64 (s, 1H), 3.35 (dd, J=10.0, 8.6 Hz, 1H), 3.22-3.15 (m, 1H), 2.99-2.89 (m, 6H), 2.71 (d, J=9.6 Hz, 1H), 1.77 (d, J=9.8 Hz, 1H), 1.66 (d, J=10.0 Hz, 1H).

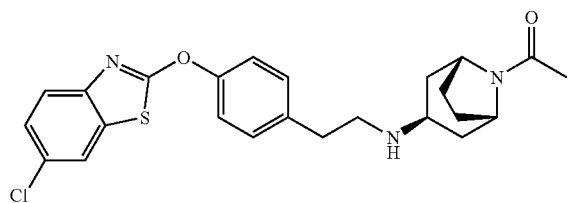

Example 224 meso-endo-1-(3-{2-[4-(6-Chloro-benzothiazol-2-yloxy)-phenyl]-ethylamino}-8-aza-bicyclo[3.2.1]oct-8-yl)-ethanone MS (ESI): mass calcd. for $C_{24}H_{26}ClN_3O_2S$, 455.14; m/z found, 456.2 [M+H]$^+$. $^1$H NMR (400 MHz, DMSO-d$_6$, mixture of rotamers): 7.96 (d, J=8.6 Hz, 1H), 7.77 (d, J=2.0 Hz, 1H), 7.36-7.42 (m, 5H), 4.70-4.61 (m, 0.5H), 4.50-4.43 (m, 0.5H), 4.33-4.38 (m, 1H), 4.05-4.10 (m, 1H), 2.91 (s, 1H), 2.82 (s, 3H), 2.24-2.28 (m, 1H), 1.90-1.96 (m, 7H), 1.60-1.64 (m, 3H).

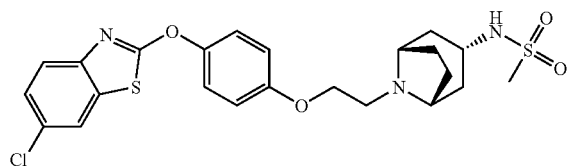

Example 225 meso-exo-N-(8-{2-[4-(6-Chloro-benzothiazol-2-yloxy)-phenoxy]-ethyl}-8-aza-bicyclo[3.2.1]oct-3-yl)-methanesulfonamide MS (ESI): mass calcd. for $C_{23}H_{26}ClN_3O_4S_2$, 507.11; m/z found, 508.1 [M+H]$^+$. $^1$H NMR (400 MHz, DMSO-d$_6$): 7.59 (dd, J=8.1, 0.8 Hz, 1H), 7.48 (td, J=8.2, 5.8 Hz, 1H), 7.43-7.36 (m, 4H), 7.29-7.22 (m, 1H), 4.16 (m, 1H), 3.59 (m, 1H), 3.17 (d, J=7.4 Hz, 1H), 2.92 (s, 3H), 2.88-2.63 (m, 6H), 1.67-1.73 (m, 2H).

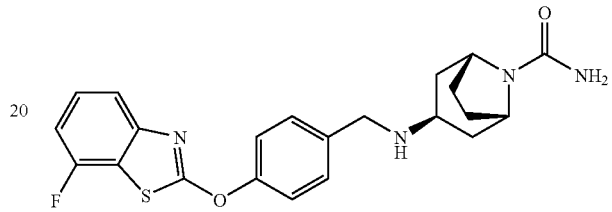

Example 226 meso-endo-3-[4-(7-Fluoro-benzothiazol-2-yloxy)-benzylamino]-8-aza-bicyclo[3.2.1]octane-8-carboxylic acid amide MS (ESI): mass calcd. for $C_{22}H_{23}FN_4O_2S$, 426.15; m/z found, 427.1 [M+H]$^+$. $^1$H NMR (400 MHz, DMSO-d$_6$, mixture of rotamers): 7.61-7.57 (m, 1H), 7.52-7.44 (m, 3H), 7.43-7.39 (m, 2H), 7.29-7.23 (m, 1H), 5.78 (s, 2H), 4.06 (m, 2H), 3.74 (s, 2H), 2.85-2.90 (m, 1H), 2.67 (s, 0.5H), 2.33 (s, 0.5H), 2.15 (d, J=7.0 Hz, 2H), 1.88-1.83 (m, 2H), 1.78-1.73 (m, 2H), 1.61 (d, J=13.8 Hz, 2H).

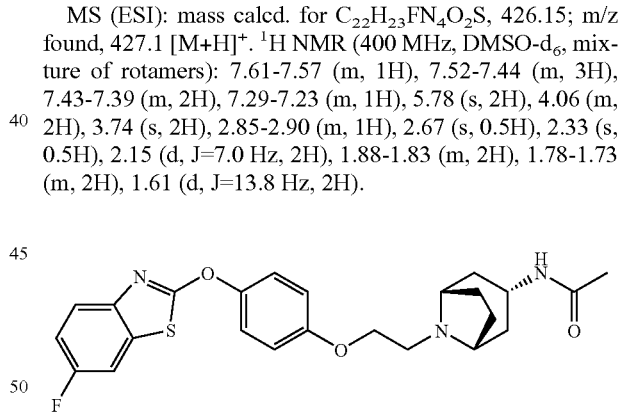

Example 227 meso-exo-N-(8-{2-[4-(6-Fluoro-benzothiazol-2-yloxy)-phenoxy]-ethyl}-8-aza-bicyclo[3.2.1]oct-3-yl)-acetamide MS (ESI): mass calcd. for $C_{24}H_{26}FN_3O_3S$, 455.17; m/z found, 456.2 [M+H]$^+$. $^1$H NMR (400 MHz, DMSO-d$_6$): 7.95 (dd, J=8.8, 5.5 Hz, 1H), 7.55 (dd, J=9.9, 2.6 Hz, 1H), 7.38 (d, J=8.9 Hz, 2H), 7.21 (td, J=9.1, 2.6 Hz, 1H), 7.07 (d, J=8.9 Hz, 2H), 4.23-4.02 (m, 2H), 3.98-3.83 (m, 1H), 2.90-2.67 (m, 2H), 2.01-1.85 (m, 2H), 1.76 (s, 3H), 1.56 (m, 5H).

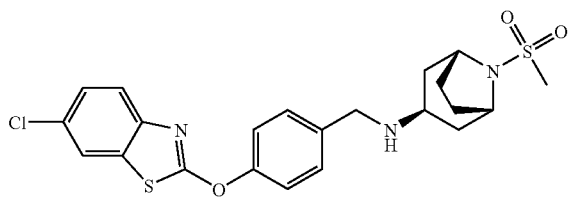

Example 228 meso-endo-[4-(6-Chloro-benzothiazol-2-yloxy)-benzyl]-(8-methanesulfonyl-8-aza-bicyclo[3.2.1]oct-3-yl)-amine MS (ESI): mass calcd. for $C_{22}H_{24}ClN_3O_3S_2$, 477.09; m/z found, 478.1 [M+H]$^+$. $^1$H NMR (400 MHz, DMSO-d$_6$): 8.07 (d, J=2.2 Hz, 1H), 7.68 (d, J=8.6 Hz, 1H), 7.45 (dd, J=8.7, 2.2 Hz, 1H), 7.40-7.33 (m, 2H), 7.09-7.03 (m, 2H), 5.76 (d, J=8.3 Hz, 1H), 5.28 (br s, 2H), 4.07 (t, J=6.1 Hz, 2H), 3.70-3.65 (m, 1H), 3.30-3.23 (m, 2H), 2.74 (t, J=6.1 Hz, 2H), 1.93-1.82 (m, 2H), 1.58-1.53 (m, 3H), 1.45-1.35 (m, 2H).

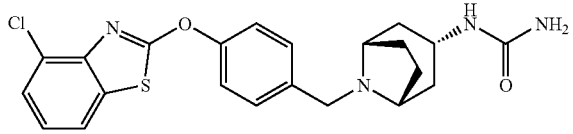

Example 229 meso-exo-{8-[4-(4-Chloro-benzothiazol-2-yloxy)-benzyl]-8-aza-bicyclo[3.2.1]oct-3-yl}-urea MS (ESI): mass calcd. for $C_{22}H_{23}ClN_4O_2S$, 442.17; m/z found, 443.2 [M+H]$^+$. $^1$H NMR (400 MHz, DMSO-d$_6$): 7.98-7.93 (m, 3H), 7.60 (d, J=8.1 Hz, 2H), 7.55 (m, 1H), 7.35 (t, J=8.0 Hz, 1H), 6.05-6.00 (m, 1H), 5.51 (br s, 2H), 4.19 (m, 2H), 3.77 (m, 3H), 2.33 (m, 2H), 2.13-1.83 (m, 6H).

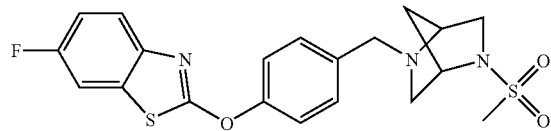

Example 230

(S,S)-6-Fluoro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}FN_3O_3S_2$, 433.09; m/z found, 434.1 [M+H]$^+$. $^1$H NMR (400 MHz, DMSO-d$_6$): 7.86 (dd, J=8.7, 2.7 Hz, 1H), 7.71 (dd, J=8.9, 4.9 Hz, 1H), 7.50-7.45 (m, 2H), 7.41-7.36 (m, 2H), 7.28 (td, J=9.1, 2.8 Hz, 1H), 4.19 (s, 1H), 3.85-3.72 (m, 1H), 3.54 (s, 1H), 3.43 (dd, J=9.5, 2.3 Hz, 1H), 3.22 (dd, J=9.4, 2.2 Hz, 1H), 2.94 (s, 3H), 2.79 (dd, J=9.6, 2.3 Hz, 1H), 2.63 (d, J=9.6 Hz, 1H), 1.85 (d, J=9.9 Hz, 1H), 1.68 (d, J=9.9 Hz, 1H).

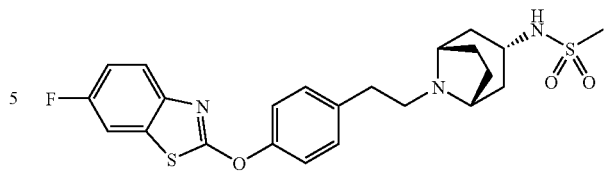

Example 231 meso-exo-N-(8-{2-[4-(6-Fluoro-benzothiazol-2-yloxy)-phenyl]-ethyl}-8-aza-bicyclo[3.2.1]oct-3-yl)-methanesulfonamide MS (ESI): mass calcd. for $C_{23}H_{26}FN_3O_3S_2$, 475.14; m/z found, 476.1 [M+H]$^+$. $^1$H NMR (400 MHz, DMSO-d$_6$): 7.96 (dd, J=8.8, 5.5 Hz, 1H), 7.55 (dd, J=9.9, 2.6 Hz, 1H), 7.43-7.35 (m, 4H), 7.22 (td, J=9.1, 2.6 Hz, 1H), 3.50-3.35 (m, 3H), 2.95-2.80 (m, 6H), 2.05-1.60 (m, 8H).

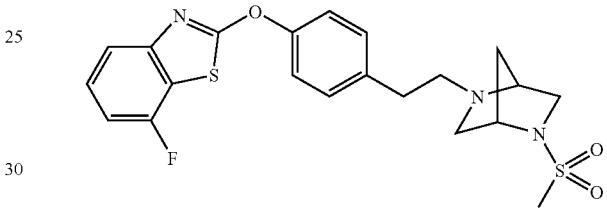

Example 232

(S,S)-7-Fluoro-2-{4-[2-(5-methanesulfonyl-2,5-diaza-bicyclo[2.2.1]hept-2-yl)-ethyl]-phenoxy}-benzothiazole MS (ESI): mass calcd. for $C_{21}H_{22}FN_3O_3S_2$, 447.11; m/z found, 448.1 [M+H]$^+$. $^1$H NMR (400 MHz, DMSO-d$_6$): 7.59 (dd, J=8.1, 0.8 Hz, 1H), 7.48 (td, J=8.2, 5.8 Hz, 1H), 7.43-7.35 (m, 4H), 7.29-7.22 (m, 1H), 4.16 (br s, 1H), 3.59 (br s, 1H), 3.20-3.15 (m, 1H), 2.92 (s, 3H), 2.89-2.63 (m, 6H), 1.76 (d, J=9.7 Hz, 1H), 1.65 (d, J=9.8 Hz, 1H).

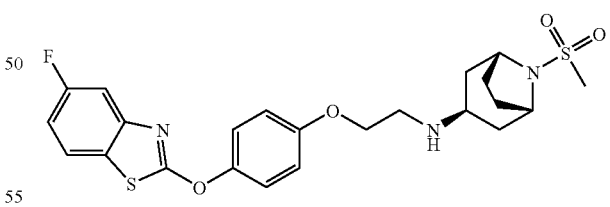

Example 233 meso-endo-{2-[4-(5-Fluoro-benzothiazol-2-yloxy)-phenoxy]-ethyl}-(8-methanesulfonyl-8-aza-bicyclo[3.2.1]oct-3-yl)-amine MS (ESI): mass calcd. for $C_{23}H_{26}FN_3O_4S_2$, 491.13; m/z found, 492.0 [M+H]$^+$. $^1$H NMR (400 MHz, DMSO-d$_6$): 7.94 (dd, J=8.8, 5.5 Hz, 1H), 7.55 (dd, J=10.0, 2.5 Hz, 1H), 7.38 (d, J=9.0 Hz, 2H), 7.21 (td, J=9.1, 2.6 Hz, 1H), 7.07 (d, J=9.0 Hz, 2H), 4.07 (br s, 4H), 3.00-2.90 (m, 6H), 2.14 (br s, 2H), 1.95-1.85 (m, 4H), 1.76 (d, J=13.9 Hz, 2H).

1H), 3.46-3.40 (m, 1H), 3.25-3.19 (m, 1H), 2.95 (s, 3H), 2.83-2.78 (m, 1H), 2.66-2.60 (m, 1H), 1.85 (d, J=9.9 Hz, 1H), 1.69 (d, J=10.0 Hz, 1H).

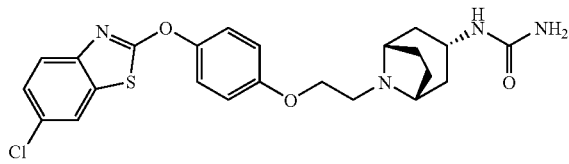

Example 234 meso-exo-(8-{2-[4-(6-Chloro-benzothiazol-2-yloxy)-phenoxy]-ethyl}-8-aza-bicyclo[3.2.1]oct-3-yl)-urea MS (ESI): mass calcd. for $C_{23}H_{25}ClN_4O_3S$, 472.13; m/z found, 473.1 [M+H]$^+$. $^1$H NMR (400 MHz, DMSO-d$_6$): 8.08 (d, J=2.2 Hz, 1H), 7.68 (d, J=8.6 Hz, 1H), 7.48-7.43 (m, 3H), 7.42-7.37 (m, 2H), 4.07 (br s, 2H), 3.73 (br s, 2H), 2.91 (s, 5H), 2.25-2.20 (m, 2H), 2.16 (br s, 1H), 1.95-1.81 (m, 6H).

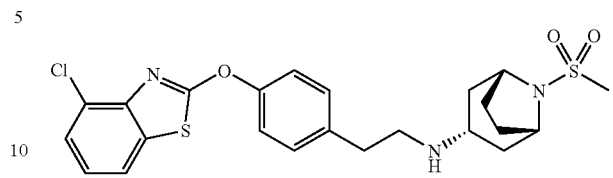

Example 237 meso-exo-{2-[4-(4-Chloro-benzothiazol-2-yloxy)-phenyl]-ethyl}-(8-methanesulfonyl-8-aza-bicyclo[3.2.1]oct-3-yl)-amine MS (ESI): mass calcd. for $C_{23}H_{26}ClN_3O_3S_2$, 491.11; m/z found, 492.15 [M+H]$^+$. $^1$H NMR (500 MHz, DMSO-d$_6$): 7.91 (d, J=8.0 Hz, 1H), 7.54 (d, J=7.9 Hz, 1H), 7.44-7.36 (m, 4H), 7.35-7.29 (m, 1H), 4.13 (s, 2H), 3.05-2.95 (m, 1H), 2.93 (s, 3H), 2.90-2.83 (m, 2H), 2.81-2.73 (m, 2H), 2.00-1.89 (m, 4H), 1.72-1.64 (m, 2H), 1.46-1.36 (m, 2H).

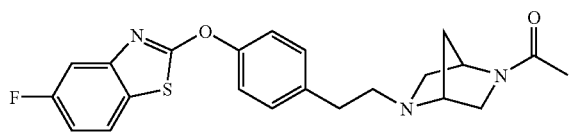

Example 235

(R,R)-1-(5-{2-[4-(5-Fluoro-benzothiazol-2-yloxy)-phenyl]-ethyl}-2,5-diaza-bicyclo[2.2.1]hept-2-yl)-ethanone MS (ESI): mass calcd. for $C_{22}H_{22}FN_3O_2S$, 411.14; m/z found, 412.2 [M+H]$^+$. $^1$H NMR (400 MHz, DMSO-d$_6$, mixture of rotamers): 7.86 (dd, J=8.7, 2.2 Hz, 1H), 7.70 (dd, J=8.9, 4.8 Hz, 1H), 7.42-7.32 (m, 4H), 7.28 (td, J=9.1, 2.8 Hz, 1H), 4.51, (m, 0.5H), 4.37 (m, 0.5H), 3.70-3.50 (m, 2H), 3.14-3.04 (m, 1H), 2.95-2.70 (m, 5H), 1.97 (s, 2H), 1.86 (s, 2H), 1.84-1.56 (m, 2H).

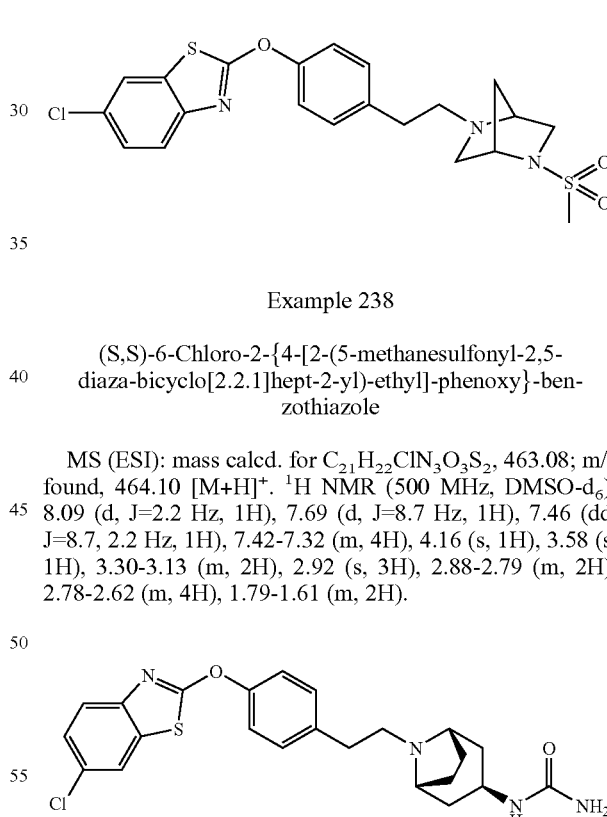

Example 238

(S,S)-6-Chloro-2-{4-[2-(5-methanesulfonyl-2,5-diaza-bicyclo[2.2.1]hept-2-yl)-ethyl]-phenoxy}-benzothiazole MS (ESI): mass calcd. for $C_{21}H_{22}ClN_3O_3S_2$, 463.08; m/z found, 464.10 [M+H]$^+$. $^1$H NMR (500 MHz, DMSO-d$_6$): 8.09 (d, J=2.2 Hz, 1H), 7.69 (d, J=8.7 Hz, 1H), 7.46 (dd, J=8.7, 2.2 Hz, 1H), 7.42-7.32 (m, 4H), 4.16 (s, 1H), 3.58 (s, 1H), 3.30-3.13 (m, 2H), 2.92 (s, 3H), 2.88-2.79 (m, 2H), 2.78-2.62 (m, 4H), 1.79-1.61 (m, 2H).

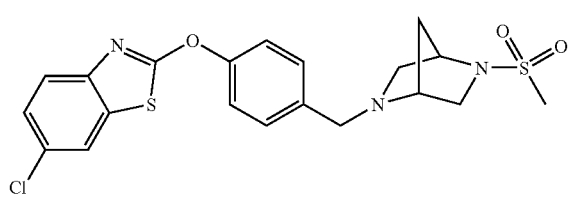

Example 236

(R,R)-6-Chloro-2-[4-(5-methanesulfonyl-2,5-diaza-bicyclo[2.2.1]hept-2-ylmethyl)-phenoxy]-benzothiazole MS (ESI): mass calcd. for $C_{20}H_{20}ClN_3O_3S_2$, 449.06; m/z found, 450.00 [M+H]$^+$. $^1$H NMR (500 MHz, DMSO-d$_6$): 8.13-8.06 (m, 1H), 7.69 (d, J=8.6 Hz, 1H), 7.52-7.44 (m, 3H), 7.43-7.37 (m, 2H), 4.19 (s, 1H), 3.83-3.74 (m, 2H), 3.54 (s,

Example 239 meso-endo-(8-{2-[4-(6-Chloro-benzothiazol-2-yloxy)-phenyl]-ethyl}-8-aza-bicyclo[3.2.1]oct-3-yl)-urea MS (ESI): mass calcd. for $C_{23}H_{25}ClN_4O_2S$, 456.14; m/z found, 457.05 [M+H]$^+$. $^1$H NMR (500 MHz, DMSO-d$_6$):

8.08 (s, 1H), 7.69 (d, J=8.7 Hz, 1H), 7.51-7.42 (m, 1H), 7.40-7.26 (m, 4H), 5.96-5.81 (m, 1H), 5.39 (s, 2H), 3.72-3.57 (m, 1H), 3.17 (s, 2H), 2.82-2.67 (m, 2H), 2.06-1.73 (m, 6H), 1.46 (d, J=13.8, 2H).

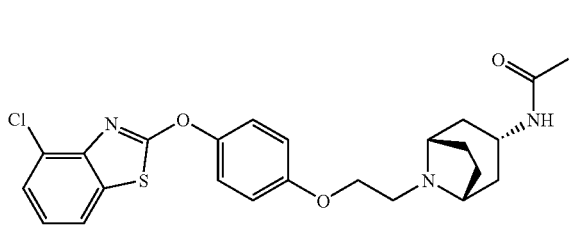

Example 240 meso-exo-N-(8-{2-[4-(4-Chloro-benzothiazol-2-yloxy)-phenoxy]-ethyl}-8-aza-bicyclo[3.2.1]oct-3-yl)-acetamide MS (ESI): mass calcd. for $C_{24}H_{26}ClN_3O_3S$, 471.14; m/z found, 472.05 [M+H]+. 1H NMR (500 MHz, DMSO-$d_6$, mixture of rotamers): 7.89 (d, J=8.0 Hz, 1H), 7.53 (d, J=7.9 Hz, 1H), 7.47-7.38 (m, 2H), 7.31 (t, J=8.0 Hz, 1H), 7.15-7.01 (m, 2H), 4.41-4.29 (m, 1H), 4.16-4.02 (m, 3H), 2.98-2.81 (m, 3H), 2.23-2.03 (m, 2H), 1.94 (m, 3H), 1.91-1.78 (m, 4H), 1.78-1.58 (m, 3H).

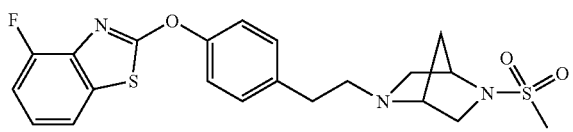

Example 241

(R,R)-4-Fluoro-2-{4-[2-(5-methanesulfonyl-2,5-diaza-bicyclo[2.2.1]hept-2-yl)-ethyl]-phenoxy}-benzothiazole MS (ESI): mass calcd. for $C_{21}H_{22}FN_3O_3S_2$, 447.11; m/z found, 448.05 [M+H]+. 1H NMR (500 MHz, DMSO-$d_6$, mixture of rotamers): 7.79-7.74 (m, 1H), 7.43-7.27 (m, 6H), 4.15 (s, 1H), 3.58 (s, 1H), 3.20-3.12 (m, 1H), 2.92 (d, J=2.7 Hz, 3H), 2.87-2.62 (m, 7H), 1.75 (d, J=9.8 Hz, 1H), 1.63 (d, J=9.8 Hz, 1H).

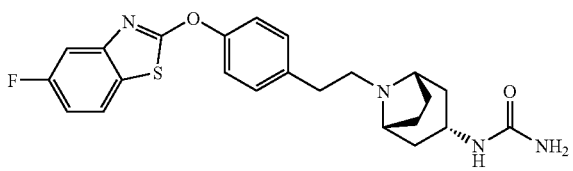

Example 242 meso-exo-(8-{2-[4-(5-Fluoro-benzothiazol-2-yloxy)-phenyl]-ethyl}-8-aza-bicyclo[3.2.1]oct-3-yl)-urea MS (ESI): mass calcd. for $C_{23}H_{25}FN_4O_2S$, 440.17; m/z found, 441.15 [M+H]+. 1H NMR (500 MHz, DMSO-$d_6$):
7.79 (d, J=7.7 Hz, 1H), 7.56-7.24 (m, 6H), 4.20-3.92 (m, 3H), 3.25-3.05 (m, 4H), 2.33-2.14 (m, 2H), 1.87 (d, 9H).

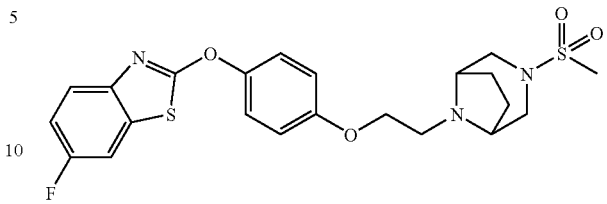

Example 243 meso-6-Fluoro-2-{4-[2-(3-methanesulfonyl-3,8-diaza-bicyclo[3.2.1]oct-8-yl)-ethoxy]-phenoxy}-benzothiazole MS (ESI): mass calcd. for $C_{22}H_{24}FN_3O_4S_2$, 477.12; m/z found, 478.05 [M+H]+. 1H NMR (500 MHz, DMSO-$d_6$): 7.89-7.83 (m, 1H), 7.69 (dd, J=8.8, 4.8 Hz, 1H), 7.41-7.35 (m, 2H), 7.32-7.24 (m, 1H), 7.10-7.03 (m, 2H), 4.16-4.03 (m, 2H), 3.43 (s, 2H), 3.16 (d, J=10.5 Hz, 2H), 2.99-2.90 (m, 3H), 2.84 (s, 2H), 2.78-2.68 (m, 2H), 1.94-1.86 (m, 2H), 1.66-1.60 (m, 2H).

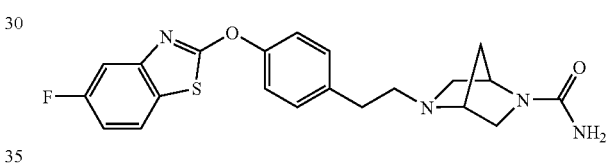

Example 244

(R,R)-5-{2-[4-(5-Fluoro-benzothiazol-2-yloxy)-phenyl]-ethyl}-2,5-diaza-bicyclo[2.2.1]heptane-2-carboxylic acid amide MS (ESI): mass calcd. for $C_{21}H_{21}FN_4O_2S$, 412.14; m/z found, 413.10 [M+H]+. 1H NMR (500 MHz, DMSO-$d_6$): 7.96 (dd, J=8.8, 5.5 Hz, 1H), 7.64-7.52 (m, 1H), 7.44-7.28 (m, 4H), 7.28-7.16 (m, 1H), 5.75 (s, 2H), 4.24 (s, 1H), 3.59-3.46 (m, 1H), 3.05 (s, 1H), 2.92-2.62 (m, 5H), 1.77-1.66 (m, 1H), 1.66-1.55 (m, 1H).

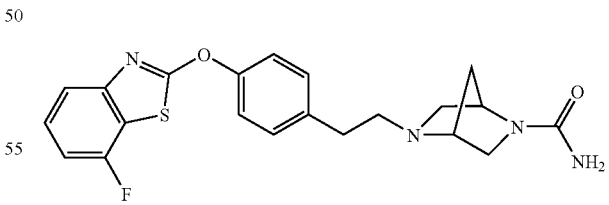

Example 245

(R,R)-5-{2-[4-(7-Fluoro-benzothiazol-2-yloxy)-phenyl]-ethyl}-2,5-diaza-bicyclo[2.2.1]heptane-2-carboxylic acid amide MS (ESI): mass calcd. for $C_{21}H_{21}FN_4O_2S$, 412.14; m/z found, 413.10 [M+H]+. 1H NMR (500 MHz, DMSO-$d_6$):

7.60 (d, J=8.1 Hz, 1H), 7.55-7.44 (m, 1H), 7.39 (s, 4H), 7.32-7.21 (m, 1H), 5.75 (s, 2H), 4.24 (s, 1H), 3.52 (s, 1H), 3.12-2.99 (m, 1H), 2.91-2.80 (m, 1H), 2.73 (s, 4H), 1.78-1.66 (m, 1H), 1.65-1.52 (m, 1H).

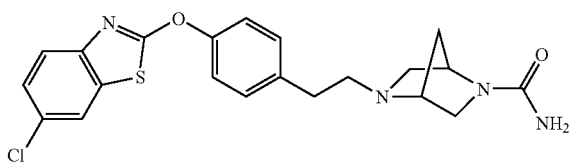

Example 246

(R,R)-5-{2-[4-(6-Chloro-benzothiazol-2-yloxy)-phenyl]-ethyl}-2,5-diaza-bicyclo[2.2.1]heptane-2-carboxylic acid amide MS (ESI): mass calcd. for $C_{21}H_{21}ClN_4O_2S$, 428.11; m/z found, 429.15 [M+H]+. $^1$H NMR (500 MHz, DMSO-d$_6$): 8.10-8.06 (m, 1H), 7.72-7.65 (m, 1H), 7.47-7.43 (m, 1H), 7.40-7.31 (m, 4H), 5.75 (s, 2H), 4.23 (s, 1H), 3.51 (s, 1H), 3.29-3.20 (m, 1H), 3.04 (d, J=9.3 Hz, 1H), 2.84 (d, J=9.1 Hz, 1H), 2.72 (s, 4H), 1.73-1.67 (m, 1H), 1.62-1.55 (m, 1H).

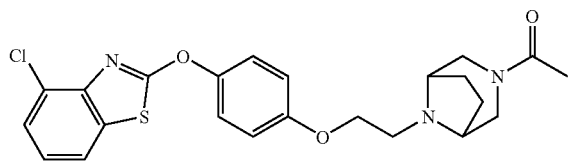

Example 247 meso-5-{2-[4-(5-Fluoro-benzothiazol-2-yloxy)-phenyl]-ethyl}-2,5-diaza-bicyclo[2.2.1]heptane-2-carboxylic acid amide MS (ESI): mass calcd. for $C_{23}H_{24}ClN_3O_3S$, 457.12; m/z found, 458.10 [M+H]+. $^1$H NMR (500 MHz, DMSO-d$_6$): 7.89 (d, J=8.0 Hz, 1H), 7.53 (d, J=7.9 Hz, 1H), 7.42 (d, J=9.0 Hz, 2H), 7.31 (t, J=8.0 Hz, 1H), 7.09 (d, J=9.1 Hz, 2H), 4.12 (t, J=5.9 Hz, 2H), 3.94 (d, J=11.9 Hz, 1H), 3.45 (d, J=11.7 Hz, 1H), 3.23 (d, J=12.1 Hz, 1H), 2.80-2.61 (m, 3H), 1.96 (s, 3H), 1.92-1.75 (m, 2H), 1.64-1.49 (m, 1H), 1.45-1.31 (m, 1H).

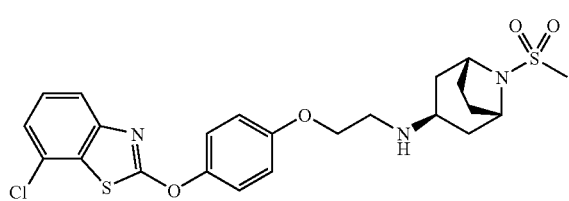

Example 248 meso-endo-{2-[4-(7-Chloro-benzothiazol-2-yloxy)-phenoxy]-ethyl}-(8-methanesulfonyl-8-aza-bicyclo[3.2.1]oct-3-yl)-amine MS (ESI): mass calcd. for $C_{23}H_{26}ClN_3O_4S_2$, 507.11; m/z found, 508.2 [M+H]+. $^1$H NMR (600 MHz, DMSO-d$_6$): 7.71-

7.67 (m, 1H), 7.51-7.39 (m, 4H), 7.10-7.06 (m, 2H), 4.11-4.01 (m, 4H), 2.96-2.84 (m, 6H), 2.20-2.10 (m, 2H), 1.94-1.84 (m, 4H), 1.81-1.74 (m, 2H).

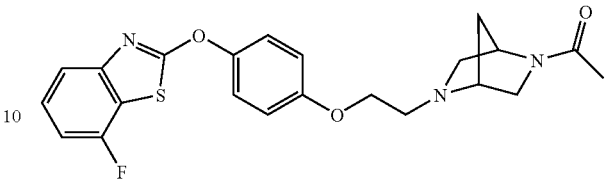

Example 249

(R,R)-1-(5-{2-[4-(7-Fluoro-benzothiazol-2-yloxy)-phenoxy]-ethyl}-2,5-diaza-bicyclo[2.2.1]hept-2-yl)-ethanone MS (ESI): mass calcd. for $C_{22}H_{22}FN_3O_3S$, 427.14; m/z found, 428.2 [M+H]+. $^1$H NMR (600 MHz, DMSO-d$_6$, mixture of rotamers): 7.75 (d, J=7.8 Hz, 1H), 7.41-7.39 (m, 2H), 7.35-7.27 (m, 2H), 7.09-7.04 (m, 2H), 4.49 (s, 0.5H), 4.34 (s, 0.5H), 4.08-4.04 (m, 2H), 3.65 (s, 0.5H), 3.59 (s, 0.5H), 3.53 (d, J=7.8 Hz, 0.5H), 3.40 (d, J=7.8 Hz, 0.5H), 3.09 (d, J=7.8 Hz, 0.5H), 2.99-2.86 (m, 3.5H), 2.62 (d, J=7.8 Hz, 0.5H), 2.53 (d, J=7.8 Hz, 0.5H), 1.97 (s, 1.5H), 1.87 (s, 1.5H), 1.83-1.79 (m, 0.5H), 1.77-1.72 (m, 0.5H), 1.72-1.67 (m, 0.5H), 1.62-1.57 (m, 0.5H).

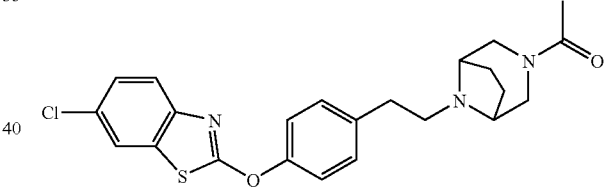

Example 250 meso-1-(8-{2-[4-(6-Chloro-benzothiazol-2-yloxy)-phenyl]-ethyl}-3,8-diaza-bicyclo[3.2.1]oct-3-yl)-ethanone MS (ESI): mass calcd. for $C_{23}H_{24}ClN_3O_2S$, 441.13; m/z found, 442.2 [M+H]+. $^1$H NMR (600 MHz, DMSO-d$_6$): 8.09 (d, J=7.8 Hz, 1H), 7.68 (d, J=7.8 Hz, 1H), 7.48-7.33 (m, 5H), 4.07-3.87 (m, 1H), 3.59-3.42 (m, 1H), 3.41-3.19 (m, 2H), 2.94-2.45 (m, 6H), 1.98 (s, 3H), 1.95-1.77 (m, 2H), 1.65-1.30 (m, 2H).

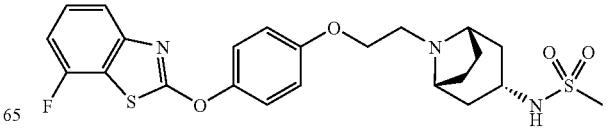

Example 251 meso-exo-N-(8-{2-[4-(7-Fluoro-benzothiazol-2-yloxy)-phenoxy]-ethyl}-8-aza-bicyclo[3.2.1]oct-3-yl)-methanesulfonamide MS (ESI): mass calcd. for $C_{23}H_{26}FN_3O_4S_2$, 491.13; m/z found, 492.2 [M+H]$^+$. $^1$H NMR (600 MHz, DMSO-d$_6$): 7.60-7.56 (m, 1H), 7.52-7.45 (m, 1H), 7.44-7.40 (m, 1H), 7.28-7.22 (m, 1H), 7.13-7.05 (m, 2H), 4.26-3.98 (m, 2H), 3.56-3.44 (m, 1H), 3.38-3.11 (m, 4H), 2.89 (s, 3H), 2.80-2.57 (m, 1H), 2.25-1.61 (m, 7H).

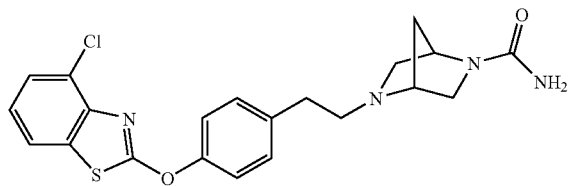

Example 252

(R,R)-5-{2-[4-(4-Chloro-benzothiazol-2-yloxy)-phenyl]-ethyl}-2,5-diaza-bicyclo[2.2.1]heptane-2-carboxylic acid amide MS (ESI): mass calcd. for $C_{21}H_{21}ClN_4O_2S$, 428.11; m/z found, 429.2 [M+H]$^+$. $^1$H NMR (600 MHz, DMSO-d$_6$): 7.97-7.81 (m, 2H), 7.54-7.52 (m, 2H), 7.41-7.38 (m, 1H), 7.32 (d, J=7.8 Hz, 2H), 4.23 (s, 1H), 3.54-3.48 (m, 2H), 3.08-3.00 (m, 2H), 3.89-2.81 (m, 2H), 1.77-1.65 (m, 2H), 1.63-1.53 (m, 2H).

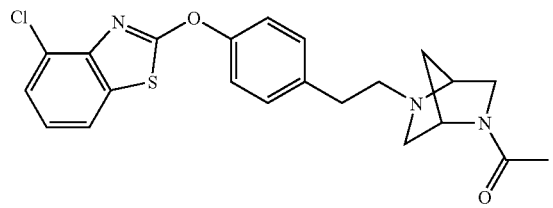

Example 253

(S,S)-1-(5-{2-[4-(4-Chloro-benzothiazol-2-yloxy)-phenyl]-ethyl}-2,5-diaza-bicyclo[2.2.1]hept-2-yl)-ethanone MS (ESI): mass calcd. for $C_{22}H_{22}ClN_3O_2S$, 427.11; m/z found, 428.2 [M+H]$^+$. $^1$H NMR (600 MHz, DMSO-d$_6$): 7.92-7.88 (m, 2H), 7.55-7.52 (m, 2H), 7.44-7.37 (m, 1H), 7.32-7.29 (m, 2H), 3.78-3.47 (m, 3H), 3.15-3.01 (m, 1H), 3.00-2.63 (m, 3H), 1.86 (s, 3H), 1.79-1.53 (m, 3H).

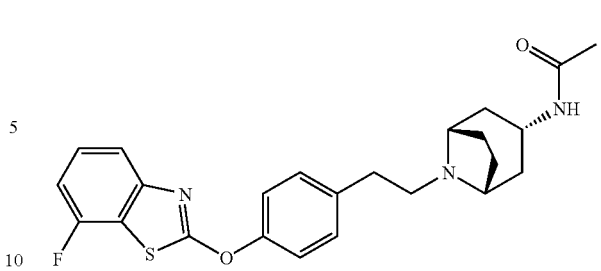

Example 254 meso-exo-N-(8-{2-[4-(7-Fluoro-benzothiazol-2-yloxy)-phenyl]-ethyl}-8-aza-bicyclo[3.2.1]oct-3-yl)-acetamide MS (ESI): mass calcd. for $C_{24}H_{26}FN_3O_2S$, 439.17; m/z found, 440.2 [M+H]$^+$. $^1$H NMR (600 MHz, DMSO-d$_6$): 7.60-7.56 (m, 1H), 7.53-7.42 (m, 5H), 7.31-7.24 (m, 1H), 4.14-3.93 (m, 3H), 3.21-3.06 (m, 3H), 2.54-2.47 (m, 3H), 2.34-2.18 (m, 1H), 2.06-1.87 (m, 4H), 1.86-1.76 (m, 4H).

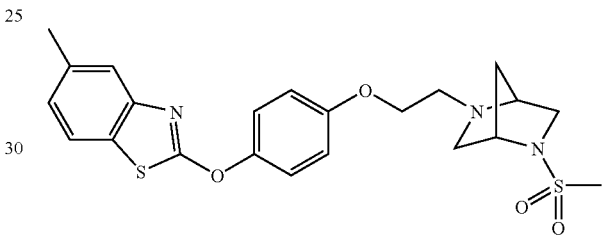

Example 255

(S,S)-2-{4-[2-(5-Methanesulfonyl-2,5-diaza-bicyclo[2.2.1]hept-2-yl)-ethoxy]-phenoxy}-5-methyl-benzothiazole MS (ESI): mass calcd. for $C_{22}H_{25}N_3O_4S_2$, 459.13; m/z found, 460.2 [M+H]$^+$. $^1$H NMR (600 MHz, DMSO-d$_6$): 7.69 (s, 1H), 7.55 (d, J=7.8 Hz, 1H), 7.40-7.30 (m, 2H), 7.26-7.20 (m, 1H), 7.09-7.01 (m, 2H), 4.18-4.03 (m, 3H), 3.69-3.61 (m, 1H), 3.41-3.29 (m, 1H), 3.24-3.13 (m, 1H), 3.02-2.86 (m, 3H), 2.75-2.68 (m, 1H), 2.38 (s, 3H), 1.81-1.62 (m, 2H).

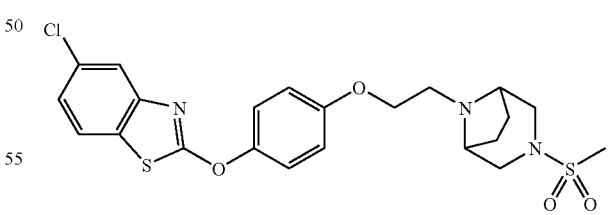

Example 256 meso-5-Chloro-2-{4-[2-(3-methanesulfonyl-3,8-diaza-bicyclo[3.2.1]oct-8-yl)-ethoxy]-Phenoxy}-benzothiazole MS (ESI): mass calcd. for $C_{22}H_{24}ClN_3O_4S_2$, 493.09; m/z found, 494.2 [M+H]$^+$. $^1$H NMR (600 MHz, DMSO-d$_6$): 7.95

(d, J=7.8 Hz, 1H), 7.77 (d, J=7.8 Hz, 1H), 7.41-7.34 (m, 3H), 7.09-7.04 (m, 2H), 4.14-4.09 (m, 2H), 3.44-3.39 (m, 2H), 3.21-3.12 (m, 2H), 2.97-2.92 (m, 2H), 2.84 (s, 3H), 2.76-2.69 (m, 2H), 1.93-1.87 (m, 2H), 1.66-1.60 (m, 2H).

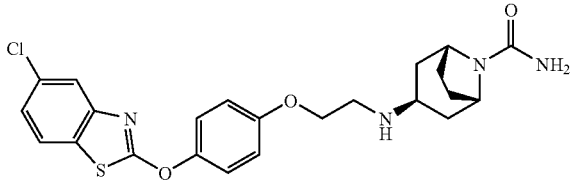

Example 257 meso-endo-3-{2-[4-(5-Chloro-benzothiazol-2-yloxy)-phenoxy]-ethylamino}-8-aza-bicyclo[3.2.1]octane-8-carboxylic acid amide MS (ESI): mass calcd. for $C_{23}H_{25}ClN_4O_3S$, 472.13; m/z found, 473.2 [M+H]$^+$. $^1$H NMR (600 MHz, DMSO-d$_6$): 7.95 (d, J=7.8 Hz, 1H), 7.77 (d, J=7.8 Hz, 1H), 7.40-7.35 (m, 3H), 7.08-7.04 (m, 2H), 4.11-4.01 (m, 4H), 2.94-2.85 (m, 3H), 2.10-2.03 (m, 2H), 1.96-1.87 (m, 2H), 1.77-1.70 (m, 2H), 1.56-1.49 (m, 2H).

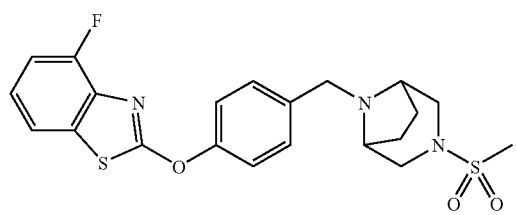

Example 258 meso-4-Fluoro-2-[4-(3-methanesulfonyl-3,8-diaza-bicyclo[3.2.1]oct-8-ylmethyl)-phenoxy]-benzothiazole MS (ESI): mass calcd. for $C_{21}H_{22}FN_3O_3S_2$, 447.11; m/z found, 448.2 [M+H]+. $^1$H NMR (600 MHz, DMSO-d$_6$): 7.78 (d, J=7.8 Hz, 1H), 7.54 (d, J=7.8 Hz, 2H), 7.46-7.42 (m, 2H), 7.37-7.27 (m, 2H), 3.57 (s, 1H), 3.29-3.24 (m, 2H), 3.23-3.17 (m, 2H), 3.00-2.92 (m, 2H), 2.90-2.80 (m, 3H), 2.05-1.93 (m, 2H), 1.70-1.62 (m, 2H).

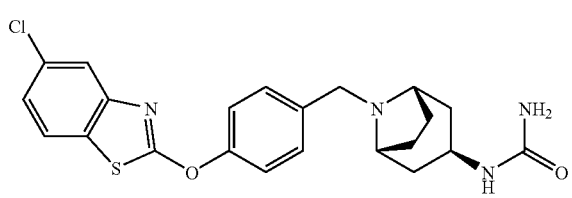

Example 259 meso-endo-{8-[4-(5-Chloro-benzothiazol-2-yloxy)-benzyl]-8-aza-bicyclo[3.2.1]oct-3-yl}-urea MS (ESI): mass calcd. for $C_{22}H_{23}ClN_4O_2S$, 442.12; m/z found, 443.2 [M+H]$^+$. $^1$H NMR (600 MHz, DMSO-d$_6$): 8.00-

7.95 (m, 1H), 7.79 (d, J=7.8 Hz, 1H), 7.53-7.35 (m, 5H), 5.44-5.36 (m, 2H), 3.74-3.67 (m, 1H), 3.57-3.48 (m, 2H), 3.10-3.02 (m, 2H), 2.08-1.82 (m, 4H), 1.54-1.45 (m, 2H).

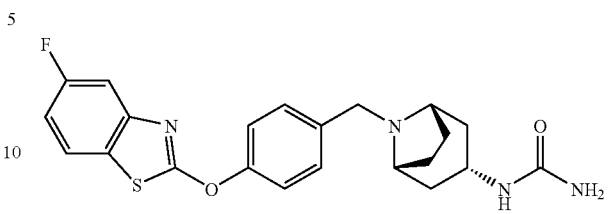

Example 260 meso-exo-{8-[4-(5-Fluoro-benzothiazol-2-yloxy)-benzyl]-8-aza-bicylclo[3.2.1]oct-3-yl}-urea MS (ESI): mass calcd. for $C_{22}H_{23}FN_4OS$, 426.51; m/z found, 427.3 [M+H]$^+$. $^1$H NMR (500 MHz, DMSO-d$_6$): 10.26-10.10 (m, 1H), 8.06-7.92 (m, 1H), 7.81 (s, 1H), 7.58 (s, 4H), 7.31-7.14 (m, 1H), 6.00-5.88 (m, 1H), 5.51 (s, 1H), 4.20 (s, 1H), 3.83 (s, 3H), 3.61-3.50 (m, 1H), 2.44-2.27 (m, 1H), 2.05-1.79 (m, 5H).

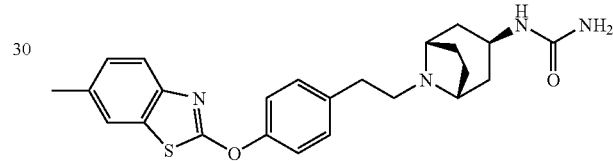

Example 261 meso-endo-(8-{2-[4-(6-Methyl-benzothiazol-2-yloxy)-phenyl]-ethyl}-8-aza-bicyclo[3.2.1]oct-3-yl)-urea MS (ESI): mass calcd. for $C_{24}H_{28}N_4O_2S$, 436.57; m/z found, 437.1 [M+H]$^+$. $^1$H NMR (500 MHz, DMSO-d$_6$): 7.72 (s, 1H), 7.56 (d, J=8.2 Hz, 1H), 7.39 (s, 4H), 7.24 (d, J=8.2 Hz, 1H), 6.16-5.66 (m, 2H), 5.66-5.08 (m, 2H), 4.16-3.44 (m, 2H), 2.87-2.53 (m, 2H), 2.39 (s, 4H), 2.07-1.74 (m, 4H), 1.73-1.20 (m, 5H).

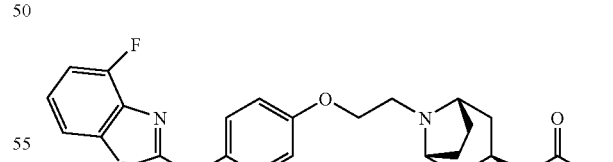

Example 262 meso-endo-(8-{2-[4-(4-Fluro-benzothiazole-2-yloxy)-phenoxy]-ethyl}-8-aza-bicyclo[3.2.1]oct-3-yl)-urea MS (ESI): mass calcd. for $C_{23}H_{25}FN_4O_3S$, 456.53; m/z found, 457.0 [M+H]$^+$. $^1$H NMR (500 MHz, DMSO-d$_6$): 8.32

(s, 1H), 7.76 (d, J=7.7 Hz, 1H), 7.43 (s, 2H), 7.38-7.26 (m, 2H), 7.11 (s, 2H), 6.15-5.14 (m, 4H), 4.65-3.53 (m, 3H), 2.37-1.12 (m, 10H).

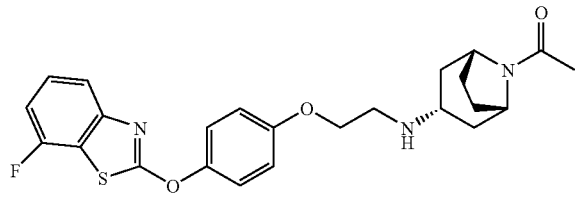

Example 263 meso-exo-1-(3-{2[4-(7-Fluro-benzothiazole-2-yloxy)-phenoxy]-ethylamino}8-aza-bicyclo[3.2.1]oct-8-yl)-ethanone MS (ESI): mass calcd. for $C_{24}H_{26}FN_3O_3S$, 455.55; m/z found, 456.1 [M+H]$^+$. $^1$H NMR (500 MHz, DMSO-d$_6$): 8.32 (s, 1H), 7.58 (d, J=7.4 Hz, 1H), 7.50-7.46 (m, 1H), 7.44-7.37 (m, 2H), 7.30-7.20 (m, 1H), 7.09-7.03 (m, 2H), 4.43 (s, 1H), 4.18 (s, 1H), 4.03 (t, J=5.7 Hz, 2H), 3.04 (s, 1H), 2.91 (t, J=5.6 Hz, 2H), 1.95 (s, 6H), 1.87-1.57 (m, 5H).

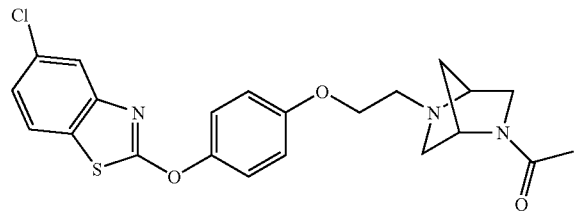

Example 264

(S,S)-1-(5-{2-[4-(5-Chloro-benzothiazole-2-yloxy)-phenoxy]-ethyl}-2,5-diaza-bicyclo[2.2.1]hept-2-yl)-ethanone MS (ESI): mass calcd. for $C_{22}H_{22}ClN_3O_3S$, 443.95; m/z found, 444.1 [M+H]$^+$. $^1$H NMR (500 MHz, DMSO-d$_6$, mixture of rotamers): 8.32 (s, 1H), 7.95 (d, J=8.6 Hz, 1H), 7.77 (d, J=1.9 Hz, 1H), 7.42-7.34 (m, 3H), 7.09-7.02 (m, 2H), 4.49 (s, 0.5H), 4.34 (s, 0.5H), 4.05 (t, J=5.8 Hz, 2H), 3.64 (s, 0.5H), 3.58 (s, 0.5H), 3.52 (d, J=9.5 Hz, 0.5H), 3.39 (d, J=12.2 Hz, 0.5H), 3.08 (d, J=9.1 Hz, 0.5H), 3.01-2.83 (m, 3H), 2.62 (d, J=9.6 Hz, 0.5H), 1.97 (s, 1.5H), 1.86 (s, 1.5H), 1.84-1.71 (m, 1H), 1.71-1.57 (m, 1H).

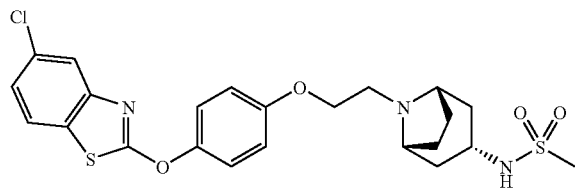

Example 265 meso-exo-N-(8-{2-[4-(5-Chloro-benzothiazol-2-yloxy)-phenoxy]-ethyl}-8-aza-bicyclo[3.2.1]oct-3-yl)-methanesulfonamide MS (ESI): mass calcd. for $C_{23}H_{26}ClN_3O_4S_2$, 508.06; m/z found, 509.1 [M+H]$^+$. $^1$H NMR (500 MHz, DMSO-d$_6$): 7.96 (d, J=8.5 Hz, 1H), 7.77 (d, J=2.0 Hz, 1H), 7.38 (d, J=8.5 Hz, 3H), 7.07 (s, 2H), 4.52-4.32 (m, 1H), 4.16-3.93 (m, 2H), 3.54-3.35 (m, 2H), 3.29-3.10 (m, 2H), 2.87 (s, 3H), 2.74-2.55 (m, 2H), 2.18-1.59 (m, 7H).

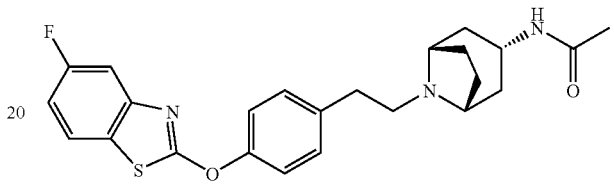

Example 266 meso-exo-N-(8-{2-[4-(5-Fluro-benzothiazol-2-yloxy)-phenyl]-ethyl}-8-aza-bicyclo[3.2.1]oct-3-yl)-acetamide MS (ESI): mass calcd. for $C_{24}H_{26}FN_3O_2S$, 439.55; m/z found, 440.1 [M+H]$^+$. $^1$H NMR (500 MHz, DMSO-d$_6$): 8.32 (s, 1H), 7.97 (dd, J=8.8, 5.5 Hz, 1H), 7.56 (dd, J=9.9, 2.6 Hz, 1H), 7.44-7.32 (m, 4H), 7.24-7.20 (m, 1H), 4.34 (s, 1H), 4.08 (s, 1H), 2.93-2.72 (m, 5H), 2.08 (s, 1H), 1.93 (s, 8H), 1.70-1.51 (m, 3H).

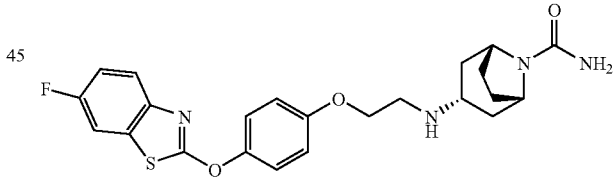

Example 267 meso-exo-3-{2-[4.(6-Fluoro-benzothiazol-2-yloxy)-phenoxy]-ethylamino}-8-aza-bicyclo[3.2.1]octane-8-carboxylic acid amide MS (ESI): mass calcd. for $C_{23}H_{25}FN_4O_3S$, 456.53; m/z found, 457.2 [M+H]$^+$. $^1$H NMR (500 MHz, DMSO-d$_6$): 7.39 (dd, J=8.7, 2.7 Hz, 1H), 7.24 (dd, J=8.9, 4.9 Hz, 1H), 6.92 (d, J=9.0 Hz, 2H), 6.82 (dd, J=10.4, 7.7 Hz, 1H), 6.61 (d, J=9.1 Hz, 2H), 5.38 (s, 2H), 3.67-3.50 (m, 4H), 2.04 (s, 4H), 1.68-1.20 (m, 6H), 1.07 (d, J=14.1 Hz, 2H).

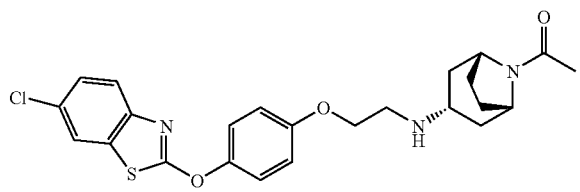

Example 268 meso-exo-1-(3-{2-[4-(6-Chloro-benzothiazol-2-yloxy)-phenoxy]-ethylamino}-8-aza-bicyclo[3.2.1]oct-8-yl)-ethanone MS (ESI): mass calcd. for $C_{24}H_{26}ClN_3O_2S$, 472.0; m/z found, 473.1 [M+H]$^+$. $^1$H NMR (500 MHz, DMSO-d$_6$): 8.07 (d, J=2.2 Hz, 1H), 7.68 (d, J=8.6 Hz, 1H), 7.45 (dd, J=8.7, 2.2 Hz, 1H), 7.38 (d, J=9.0 Hz, 2H), 7.07 (d, J=9.0 Hz, 2H), 4.35 (s, 1H), 4.07 (t, J=5.6 Hz, 3H), 2.89 (t, J=5.7 Hz, 3H), 2.27-2.04 (m, 3H), 1.94 (s, 3H), 1.90-1.80 (m, 3H), 1.77-1.56 (m, 3H).

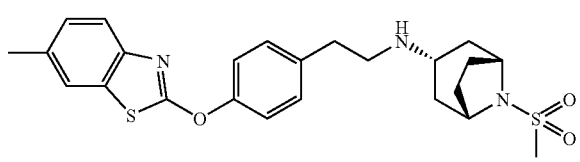

Example 269 meso-exo-(8-Methanesulfonyl-8-aza-bicyclo[3.2.1]oct-3-yl)-{2-[4-(6-methyl-benxothiazol-2-yloxy)-phenyl]-ethyl}-amine MS (ESI): mass calcd. for $C_{24}H_{29}N_3O_3S_2$, 471.64; m/z found, 472.0 [M+H]$^+$. $^1$H NMR (500 MHz, DMSO-d$_6$): 7.71 (s, 1H), 7.56 (d, J=8.2 Hz, 1H), 7.39-7.30 (m, 4H), 7.23 (d, J=8.0 Hz, 1H), 4.02 (s, 2H), 2.88 (s, 4H), 2.76 (s, 4H), 2.38 (s, 3H), 1.99 (br s, 2H), 1.83 (br s, 4H), 1.77-1.66 (m, 3H).

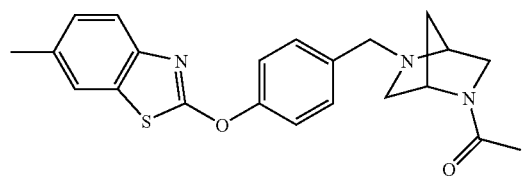

Example 270

(S,S)-1-{5-[4-(6-Methyl-benzothiazol-2-yloxy)-benzyl]-2,5-diaza-bicyclo[2.2.1]hept-2-yl}-ethanone MS (ESI): mass calcd. for $C_{22}H_{23}N_3O_2S$, 393.50; m/z found, 394.2 [M+H]$^+$. $^1$H NMR (500 MHz, DMSO-d$_6$, mixture of rotamers): 7.72 (s, 1H), 7.57 (d, J=8.2 Hz, 1H), 7.46 (s, 2H), 7.37 (d, J=6.9 Hz, 2H), 7.24 (d, J=8.3 Hz, 1H), 4.53 (s, 0.5H), 4.37 (s, 0.5H), 3.75 (s, 2H), 3.63-3.43 (s, 2H), 3.33 (s, 3H), 2.83 (s, 1H), 2.61-2.43 (m, 2H), 1.97 (s, 1H), 1.89 (s, 3H), 1.73 (s, 1H).

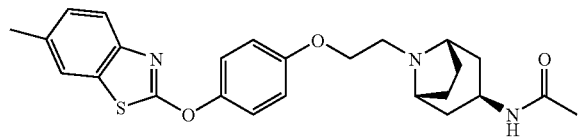

Example 271 meso-endo-N-(8-{2-[4-(6-Methyl-benzothiazol-2-yloxy)-phenoxy-ethyl}-8-aza-bicyclo[3.2.1]oct-3-yl)-acetamide MS (ESI): mass calcd. for $C_{25}H_{29}N_3O_3S$, 451.58; m/z found, 452.1 [M+H]$^+$. $^1$H NMR (500 MHz, DMSO-d$_6$): 7.98-7.87 (m, 1H), 7.71 (s, 1H), 7.55 (d, J=8.2 Hz, 1H), 7.41 (s, 2H), 7.24 (d, J=8.4 Hz, 1H), 7.12 (s, 2H), 4.46 (s, 2H), 4.16-3.92 (m, 3H), 3.46-3.34 (m, 2H), 2.39 (s, 3H), 2.26 (br s, 1H), 1.96 (br s, 6H), 1.81 (s, 4H).

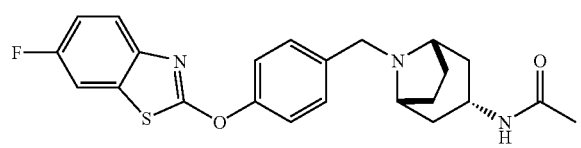

Example 272 meso-exo-N-{8-[4-(6-Fluoro-benzothiazol-2-yloxy)-benzyl]-8-aza-bicyclo[3.2.1]oct-3-yl}-acetamide MS (ESI): mass calcd. for $C_{23}H_{24}FN_3O_2S$, 425.16; m/z found, 426.10 [M+H]$^+$. $^1$H NMR (400 MHz, CDCl$_3$): 7.67 (dd, J=8.9, 4.8 Hz, 1H), 7.60 (d, J=8.4 Hz, 2H), 7.41-7.34 (m, 3H), 7.12 (td, J=9.0, 2.7 Hz, 1H), 5.68-5.53 (m, 1H), 4.31-4.15 (m, 1H), 3.73 (s, 2H), 3.43 (s, 2H), 2.25-1.70 (m, 11H).

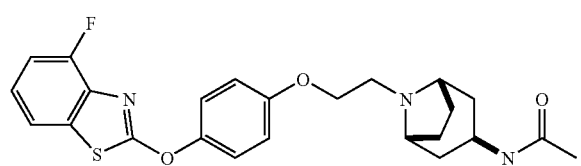

Example 273 meso-endo-N-(8-{2-[4-(4-Fluoro-benzothiazol-2-yloxy)-phenoxy]-ethyl}-8-aza-bicyclo[3.2.1]oct-3-yl)-acetamide MS (ESI): mass calcd. for $C_{24}H_{26}FN_3O_3S$, 455.17; m/z found, 456.10 [M+H]$^+$. $^1$H NMR (400 MHz, DMSO-d$_6$): 7.76 (dd, J=7.5, 1.6 Hz, 1H), 7.44-7.37 (m, 2H), 7.37-7.26 (m, 2H), 7.11-7.05 (m, 2H), 4.39-4.30 (m, 1H), 4.13-4.03 (m, 3H), 2.94-2.86 (m, 3H), 2.21-2.06 (m, 2H), 1.94 (s, 3H), 1.91-1.77 (m, 4H), 1.77-1.60 (m, 3H).

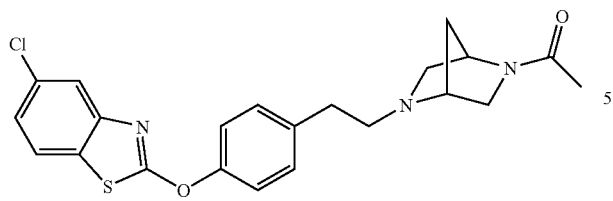

Example 274

(R,R)-1-(5-{2-[4-(5-Chloro-benzothiazol-2-yloxy)-phenyl]-ethyl}-2,5-diaza-bicyclo[2.2.1]hept-2-yl)-ethanone MS (ESI): mass calcd. for $C_{22}H_{22}ClN_3O_2S$, 427.11; m/z found, 428.10 [M+H]$^+$. $^1$H NMR (400 MHz, DMSO-d$_6$, mixture of rotamers): 7.97 (d, J=8.6 Hz, 1H), 7.80-7.78 (m, 1H), 7.42-7.33 (m, 5H), 4.49 (s, 0.5H), 4.34 (s, 0.5H), 3.63-3.46 (m, 1.5H), 3.29 (dd, J=9.5, 2.2 Hz, 1H), 3.06 (dd, J=11.0, 1.9 Hz, 0.5H), 2.88 (ddd, J=14.9, 9.4, 2.1 Hz, 1H), 2.82-2.66 (m, 4H), 2.56 (d, J=9.5 Hz, 0.5H), 2.45 (d, J=9.2 Hz, 0.5H), 1.96 (s, 1.5H), 1.85 (s, 1.5H), 1.79 (d, J=9.8 Hz, 0.5H), 1.72 (d, J=9.7 Hz, 0.5H), 1.67 (d, J=9.3 Hz, 0.5H), 1.58 (d, J=9.6 Hz, 0.5H).

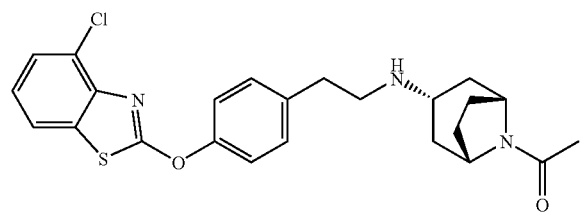

Example 275 meso-exo-1-(3-{2-[4-(4-Chloro-benzothiazol-2-yloxy)-phenyl]-ethylamino}-8-aza-bicyclo[3.2.1]oct-8-yl)-ethanone MS (ESI): mass calcd. for $C_{24}H_{26}ClN_3O_2S$, 455.14; m/z found, 456.10 [M+H]$^+$. $^1$H NMR (400 MHz, DMSO-d$_6$): 7.92 (dd, J=8.0, 1.1 Hz, 1H), 7.54 (dd, J=7.9, 1.1 Hz, 1H), 7.46-7.37 (m, 4H), 7.33 (t, J=8.0 Hz, 1H), 4.47-4.40 (m, 1H), 4.23-4.17 (m, 1H), 3.29-3.07 (m, 2H), 2.98-2.87 (m, 2H), 2.85-2.77 (m, 2H), 2.01-1.89 (m, 5H), 1.89-1.57 (m, 4H), 1.43-1.30 (m, 2H).

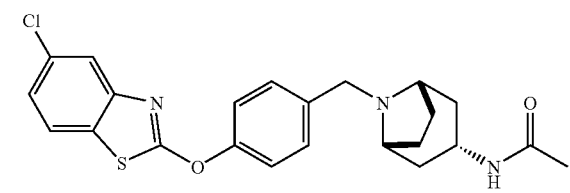

Example 276 meso-exo-N-{8-[4-(5-Chloro-benzothiazol-2-yloxy)-benzyl]-8-aza-bicyclo[3.2.1]oct-3-yl}-acetamide MS (ESI): mass calcd. for $C_{23}H_{24}ClN_3O_2S$, 441.13; m/z found, 442.10 [M+H]$^+$. $^1$H NMR (400 MHz, CDCl$_3$): 7.76-7.70 (m, 3H), 7.60 (d, J=8.4 Hz, 1H), 7.41 (d, J=8.6 Hz, 2H), 7.29 (d, J=2.0 Hz, 0.5H), 7.27-7.26 (m, 0.5H), 5.95-5.82 (m, 1H), 4.40-4.22 (m, 1H), 3.88 (s, 2H), 3.58 (s, 2H), 2.35-1.83 (m, 11H).

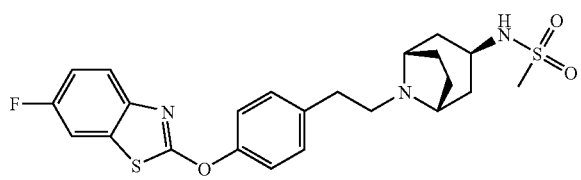

Example 277 meso-endo-N-(8-{2-[4-(6-Fluoro-benzothiazol-2-yloxy)-phenyl]-ethyl}-8-aza-bicyclo[3.2.1]oct-3-yl)-methanesulfonamide MS (ESI): mass calcd. for $C_{23}H_{26}FN_3O_3S_2$, 475.14; m/z found, 476.10 [M+H]$^+$. $^1$H NMR (400 MHz, CDCl$_3$): 7.66 (dd, J=8.9, 4.8 Hz, 1H), 7.37 (dd, J=8.0, 2.6 Hz, 1H), 7.32-7.24 (m, 4H), 7.11 (dd, J=10.3, 7.7 Hz, 1H), 4.51 (d, J=6.3 Hz, 1H), 3.77-3.68 (m, 1H), 3.48-3.26 (m, 2H), 2.97 (s, 3H), 2.93-2.76 (m, 2H), 2.75-2.56 (m, 2H), 2.54-2.20 (m, 2H), 2.18-2.00 (m, 2H), 2.00-1.72 (m, 4H).

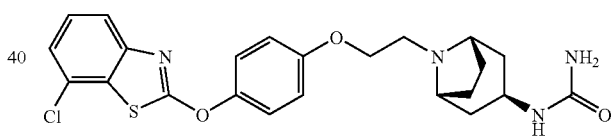

Example 278 meso-endo-(8-{2-[4-(7-Chloro-benzothiazol-2-yloxy)-phenoxy]-ethyl}-8-aza-bicyclo[3.2.1]oct-3-yl)-urea MS (ESI): mass calcd. for $C_{23}H_{25}ClN_4O_3S$, 472.13; m/z found, 473.10 [M+H]$^+$. $^1$H NMR (300 MHz, CDCl$_3$): 7.60-7.50 (m, 1H), 7.30-7.10 (m, 4H), 6.90-7.00 (m, 2H), 5.80-5.60 (m, 1H), 4.60-4.40 (m, 2H), 4.20-4.00 (m, 2H), 3.90-3.80 (m, 1H), 3.50-3.30 (m, 2H), 2.90-2.40 (m, 4H), 2.40-2.20 (m, 2H), 2.20-2.00 (m, 2H), 1.90-1.60 (m, 2H),

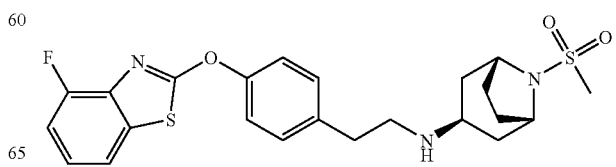

Example 279 meso-endo-{2-[4-(4-Fluoro-benzothiazol-2-yloxy)-phenyl]-ethyl}-(8-methanesulfonyl-8-aza-bicyclo[3.2.1]oct-3-yl)-amine MS (ESI): mass calcd. for $C_{23}H_{26}FN_3O_3S_2$, 475.14; m/z found, 476.10+. $^1$H NMR (400 MHz, CDCl$_3$): 7.44 (dd, J=8.0, 0.9 Hz, 1H), 7.34-7.29 (m, 4H), 7.25-7.19 (m, 1H), 7.15-7.08 (m, 1H), 4.20 (s, 2H), 3.20-2.89 (m, 5H), 2.87 (s, 3H), 2.47-2.08 (m, 2H), 2.02 (s, 4H), 1.90-1.68 (m, 3H).

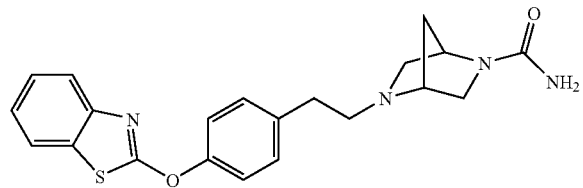

Example 280

(R,R)-5-{2-[4-(Benzothiazol-2-yloxy)-phenyl]-ethyl}-2,5-diaza-bicyclo[2.2.1]heptane-2-carboxylic acid amide MS (ESI): mass calcd. for $C_{21}H_{22}N_4O_2S$, 394.15; m/z found, 395.10 [M+H]+. $^1$H NMR (300 MHz, CDCl$_3$): 7.80-7.60 (m, 2H), 7.40-7.10 (m, 6H), 4.90-4.20 (m, 3H), 3.70-3.40 (m, 2H), 3.30-3.10 (m, 1H), 3.10-2.90 (m, 1H), 2.90-2.60 (m, 5H), 2.00-1.60 (m, 2H).

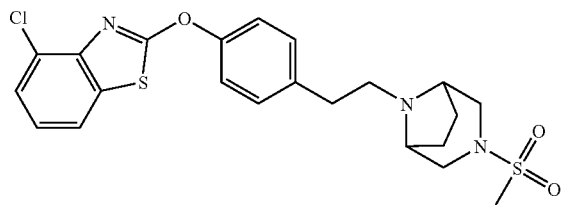

Example 281 meso-4-Chloro-2-{4-[2-(3-methanesulfonyl-3,8-diaza-bicyclo[3.2.1]oct-8-yl)-ethyl]-phenoxy}-benzothiazole MS (ESI): mass calcd. for $C_{22}H_{24}ClN_3O_3S_2$, 477.09; m/z found, 478.00 [M+H]+. $^1$H NMR (400 MHz, DMSO-d$_6$): 7.91 (dd, J=8.0, 1.1 Hz, 1H), 7.54 (dd, J=8.0, 1.1 Hz, 1H), 7.44-7.38 (m, 4H), 7.32 (t, J=8.0 Hz, 1H), 3.41-3.34 (m, 2H), 3.18-3.13 (m, 2H), 2.96-2.89 (m, 2H), 2.85 (s, 3H), 2.82-2.74 (m, 2H), 2.60-2.53 (m, 2H), 1.94-1.83 (m, 2H), 1.65-1.56 (m, 2H).

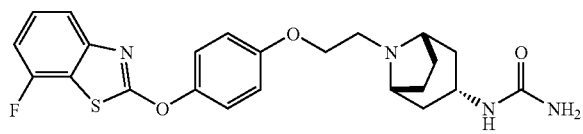

Example 282 meso-exo-(8-{2-[4-(7-Fluoro-benzothiazol-2-yloxy)-phenoxy]-ethyl}-8-aza-bicyclo[3.2.1]oct-3-yl)-urea MS (ESI): mass calcd. for $C_{23}H_{25}FN_4O_3S$, 456.16; m/z found, 457.20 [M+H]+. $^1$H NMR (600 MHz, CDCl$_3$): 7.53 (d, J=8.1 Hz, 1H), 7.36-7.31 (m, 1H), 7.31-7.28 (m, 2H), 7.03-6.95 (m, 3H), 5.22 (s, 1H), 4.59 (s, 2H), 4.40 (t, J=4.7 Hz, 2H), 4.13-3.98 (m, 1H), 3.78 (s, 2H), 3.21-3.03 (m, 2H), 2.24-2.12 (m, 2H), 2.12-2.02 (m, 2H), 2.01-1.93 (m, 4H).

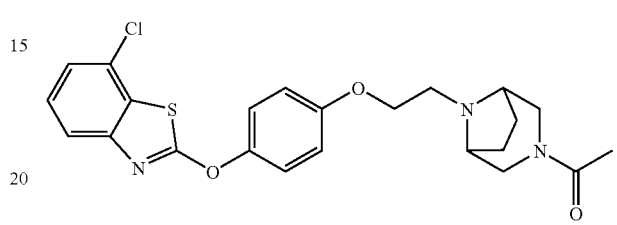

Example 283 meso-1-(8-{2-[4-(7-Chloro-benzothiazol-2-yloxy)-phenoxy]-ethyl}-3,8-diaza-bicyclo[3.2.1]oct-3-yl)-ethanone MS (ESI): mass calcd. for $C_{23}H_{24}ClN_3O_3S$, 457.12; m/z found, 458.10 [M+H]+. $^1$H NMR (400 MHz, DMSO-d$_6$): 7.70 (dd, J=7.5, 1.5 Hz, 1H), 7.52-7.39 (m, 4H), 7.13-7.06 (m, 2H), 4.13 (t, J=6.0 Hz, 2H), 3.95 (d, J=11.3 Hz, 1H), 3.49-3.41 (m, 1H), 3.39-3.31 (m, 2H), 3.23 (d, J=11.1 Hz, 1H), 2.76-2.67 (m, 3H), 1.96 (s, 3H), 1.91-1.79 (m, 2H), 1.60-1.50 (m, 1H), 1.45-1.34 (m, 1H).

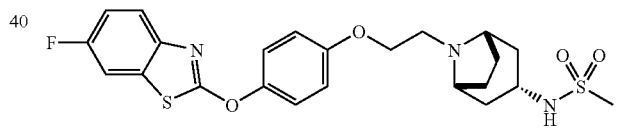

Example 284 meso-exo-N-(8-{2-[4-(6-Fluoro-benzothiazol-2-yloxy)-phenoxy]-ethyl}-8-aza-bicyclo[3.2.1]oct-3-yl)-methanesulfonamide MS (ESI): mass calcd. for $C_{23}H_{26}FN_3O_4S_2$, 491.13; m/z found, 492.10 [M+H]+. $^1$H NMR (400 MHz, DMSO-d$_6$): 7.86 (dd, J=8.7, 2.7 Hz, 1H), 7.70 (dd, J=8.9, 4.9 Hz, 1H), 7.42-7.35 (m, 2H), 7.29 (td, J=9.2, 2.8 Hz, 1H), 7.10-7.04 (m, 2H), 6.97 (d, J=8.3 Hz, 1H), 4.07 (t, J=6.0 Hz, 2H), 3.33-3.27 (m, 3H), 2.90 (s, 3H), 2.80-2.71 (m, 2H), 1.96-1.83 (m, 2H), 1.72-1.52 (m, 6H).

Biological Methods: Recombinant Human LTA$_4$ Hydrolase Assay for LTA$_4$ Hydrolase Inhibitor Activity Compounds of the present invention were tested for LTA$_4$ hydrolase inhibitor activity against recombinant human LTA$_4$ hydrolase (rhLTA$_4$H). Vectors were prepared and used to express rhLTA$_4$H essentially as follows: LTA$_4$ hydrolase encoding DNA was amplified by polymerase chain reaction (PCR) using a human placental cDNA library as a template.

Oligonucleotide primers for the PCR reaction were based on the 5'-end, and the complement of the 3'-end, of the published nucleotide sequence for the coding region of the human $LTA_4$ hydrolase gene (C. D. Funk et al., Proc. Natl. Acad. Sci. USA 1987, 84:6677-6681). The amplified 1.9 kb DNA fragment encoding $LTA_4$ hydrolase was isolated and cloned into the pFastBac1 vector (Invitrogen). Recombinant baculovirus was generated as described by the manufacturer, and used to infect Spodoptera frugiperda (Sf-9) cells. Recombinant $LTA_4$ hydrolase enzyme was purified from the infected Sf-9 cells essentially as described by J. K. Gierse et al. (Protein Expression and Purification 1993, 4:358-366). The purified enzyme solution was adjusted to contain 0.29 mg/mL $LTA_4$ hydrolase, 50 mM Tris (pH 8.0), 150 mM NaCl, 5 mM dithiothreitol, 50% glycerol, and EDTA-free Complete protease inhibitor cocktail (Roche). The specific activity of the enzyme was about 3.8 μmol/min/mg.

$LTA_4$ substrate was prepared from the methyl ester of $LTA_4$ (Cayman Chemical) by treatment with 67 equiv of NaOH under nitrogen at rt for 40 min. The $LTA_4$ substrate in its free acid form was kept frozen at −80° C. until needed. Each compound was diluted to different concentrations in assay buffer (0.1 M potassium phosphate (pH 7.4), 5 mg/mL fatty acid free BSA) containing 10% DMSO. A 25-uL aliquot of each compound dilution was incubated for 10 min at rt with an equal volume of assay buffer containing 36 ng of recombinant human $LTA_4H$. The solution was then adjusted to 200 μL with assay buffer. $LTA_4$ (free acid) was thawed and diluted in assay buffer to a concentration of 357 ng/mL, and 25 μL (9 ng) of $LTA_4$ substrate was added to the reaction mixture (total volume=225 μL) at time zero. Each reaction was carried out at rt for 10 min. The reaction was stopped by diluting 10 μL of the reaction mixture with 200 μL of assay buffer. $LTB_4$ was quantified in the diluted sample by a commercially available enzyme-linked immunoassay (Cayman Chemical Co.), as recommended by the manufacturer. Positive controls, under essentially identical conditions but without addition of an inhibitor compound, and negative controls, containing all assay components except enzyme, were routinely run in each experiment. $IC_{50}$ values were determined by fitting the activity data at different compound concentrations to a 4-parameter equation using the Grafit program (Erithacus software).

Results for the compounds tested in this assay are presented in Table 1 as an average of results obtained.

TABLE 1

| Ex. | Ki (μM) |
| --- | --- |
| 1 | 0.006 |
| 1B | 0.054 |
| 2 | 0.508 |
| 3 | 0.007 |
| 4 | 0.163 |
| 4D | 0.260 |
| 5 | 0.035 |
| 6 | 0.050 |
| 7 | 0.013 |
| 7B | 0.010 |
| 8 | 0.206 |
| 9 | 0.003 |
| 9B | 0.043 |
| 10 | 0.010 |
| 11 | 0.013 |
| 12 | 0.031 |
| 13 | 0.034 |
| 14 | 0.009 |
| 15 | 0.018 |
| 16 | 0.011 |
| 17 | 0.011 |
| 18 | 0.066 |
| 19 | 0.163 |
| 20 | 0.073 |
| 21 | 0.013 |
| 22 | 0.010 |
| 23 | 0.026 |
| 24 | 0.052 |
| 25 | 0.008 |
| 26 | 0.037 |
| 27 | 0.001 |
| 28 | 0.088 |
| 29 | 0.077 |
| 30 | 0.016 |
| 31 | 0.076 |
| 32 | 0.003 |
| 33 | 0.164 |
| 34 | 0.007 |
| 35 | 0.093 |
| 36 | 0.094 |
| 37 | 0.044 |
| 38 | 0.003 |
| 39 | 0.100 |
| 40 | 0.038 |
| 41 | 0.015 |
| 42 | 0.034 |
| 43 | 0.442 |
| 44 | 0.038 |
| 45 | 0.190 |
| 46 | 0.032 |
| 47 | 0.057 |
| 48 | 1.167 |
| 49 | 0.020 |
| 50 | 0.009 |
| 51 | 0.092 |
| 52 | 0.002 |
| 53 | 0.117 |
| 54 | 0.004 |
| 55 | 0.116 |
| 56 | 0.030 |
| 57 | 0.173 |
| 58 | 0.0002 |
| 59 | 0.174 |
| 60 | 0.002 |
| 61 | 0.027 |
| 62 | 0.036 |
| 63 | 0.021 |
| 64 | 0.058 |
| 65 | 0.064 |
| 66 | 0.191 |
| 67 | 0.201 |
| 68 | 0.002 |
| 69 | 0.450 |
| 70 | 0.004 |
| 71 | 0.025 |
| 72 | 0.098 |
| 73 | 0.033 |
| 74 | 0.240 |
| 75 | 0.095 |
| 76 | 0.195 |
| 77 | 0.012 |
| 78 | 0.039 |
| 79 | 0.059 |
| 80 | 0.060 |
| 81 | 0.162 |
| 82 | 0.097 |
| 83 | 0.055 |
| 84 | 0.084 |
| 85 | 0.450 |
| 86 | 0.055 |
| 87 | 0.036 |
| 88 | 0.003 |
| 89 | 0.006 |
| 90 | 0.021 |
| 91 | 0.050 |
| 92 | 0.230 |
| 93 | 0.034 |
| 94 | 0.012 |
| 95 | 0.036 |
| 96 | 0.026 |

TABLE 1-continued

| Ex. | Ki (µM) |
|---|---|
| 97 | 0.033 |
| 98 | 0.040 |
| 99 | 0.221 |
| 100 | 0.168 |
| 101 | 0.108 |
| 102 | 0.046 |
| 103 | 0.051 |
| 104 | 0.062 |
| 105 | 0.069 |
| 106 | 0.003 |
| 107 | 0.020 |
| 108 | 0.097 |
| 109 | 0.135 |
| 110 | 0.088 |
| 111 | 0.010 |
| 112 | 0.002 |
| 113 | 0.100 |
| 114 | 0.033 |
| 115 | 0.010 |
| 116 | 0.013 |
| 117 | 0.020 |
| 118 | 0.023 |
| 119 | 0.072 |
| 120 | 0.205 |
| 121 | 0.631 |
| 122 | 0.139 |
| 123 | 0.097 |
| 124 | 2.285 |
| 125 | 3.618 |
| 126 | 0.017 |
| 127 | 0.273 |
| 128 | 0.120 |
| 129 | 0.035 |
| 130 | 0.021 |
| 131 | 0.013 |
| 132 | 0.018 |
| 133 | 0.020 |
| 134 | 0.032 |
| 135 | 0.057 |
| 136 | 0.024 |
| 137 | 0.018 |
| 138 | 0.029 |
| 139 | 0.003 |
| 140 | 0.019 |
| 141 | 0.035 |
| 142A | 0.053 |
| 142B | 0.095 |
| 143 | 0.033 |
| 144 | 0.101 |
| 145 | 0.597 |
| 146 | 0.078 |
| 147 | 0.005 |
| 148 | 0.229 |
| 149 | 0.079 |
| 150 | 0.193 |
| 151 | 0.154 |
| 152 | 0.075 |
| 153 | 0.167 |
| 154 | 0.032 |
| 155 | 0.170 |
| 156 | 0.047 |
| 157 | 0.057 |
| 158 | 0.048 |
| 159 | 0.110 |
| 160 | 0.001 |
| 161 | 0.043 |
| 162 | 0.188 |
| 163 | 0.086 |
| 164 | 0.417 |
| 165 | 0.414 |
| 166 | 1.900 |
| 167 | 0.033 |
| 168 | 0.128 |
| 169 | 0.693 |
| 170 | 0.090 |
| 171 | 0.224 |
| 172 | 1.055 |
| 173 | 0.973 |
| 174 | 0.196 |
| 175 | 0.053 |
| 176 | 0.431 |
| 177 | 0.094 |
| 178 | 0.900 |
| 179 | 0.047 |
| 180 | 0.124 |
| 181 | 1.467 |
| 182 | 1.590 |
| 183 | 0.383 |
| 184 | 0.406 |
| 185 | 0.965 |
| 186 | 0.010 |
| 187 | 0.975 |
| 188 | 0.004 |
| 189 | 0.375 |
| 190 | 0.016 |
| 191 | 0.032 |
| 192 | >10 |
| 193 | 0.612 |
| 194 | 3.139 |
| 195 | 1.663 |
| 196 | 0.793 |
| 197 | 0.085 |
| 198 | 0.009 |
| 199 | 0.020 |
| 200 | 0.065 |
| 201 | 0.145 |
| 202 | 0.127 |
| 203 | 0.293 |
| 204 | 0.005 |
| 205 | 0.394 |
| 206 | 1.101 |
| 207 | 0.006 |
| 208 | 0.022 |
| 209 | 0.069 |
| 210 | 0.163 |
| 211 | 0.159 |
| 212 | 0.248 |
| 213 | 0.020 |
| 214 | 0.543 |
| 215 | 0.090 |
| 216 | 0.100 |
| 217 | 0.030 |
| 218 | 0.020 |
| 219 | 0.015 |
| 220 | 0.445 |
| 221 | 0.802 |
| 222 | 0.130 |
| 223 | 0.064 |
| 224 | 0.033 |
| 225 | 0.116 |
| 226 | 0.090 |
| 227 | 0.008 |
| 228 | 1.592 |
| 229 | 0.020 |
| 230 | 0.397 |
| 231 | 0.017 |
| 232 | 0.072 |
| 233 | 0.225 |
| 234 | 0.072 |
| 235 | 0.023 |
| 236 | 0.169 |
| 237 | 0.244 |
| 238 | 0.651 |
| 239 | 0.130 |
| 240 | 0.510 |
| 241 | 0.281 |
| 242 | 0.398 |
| 243 | 0.061 |
| 244 | 0.012 |
| 245 | 0.012 |
| 246 | 0.040 |
| 247 | 0.167 |
| 248 | 3.127 |
| 249 | 0.011 |
| 250 | 0.232 |
| 251 | 0.033 |

TABLE 1-continued

| Ex. | Ki (μM) |
|---|---|
| 252 | 0.108 |
| 253 | 2.600 |
| 254 | 0.115 |
| 255 | 0.277 |
| 256 | 1.709 |
| 257 | 0.490 |
| 258 | 0.008 |
| 259 | 0.058 |
| 260 | 0.026 |
| 261 | 0.100 |
| 262 | 0.012 |
| 263 | 0.190 |
| 264 | 0.212 |
| 265 | 0.310 |
| 266 | 0.064 |
| 267 | 0.296 |
| 268 | 0.360 |
| 269 | 0.630 |
| 270 | 0.072 |
| 271 | 0.079 |
| 272 | 0.006 |
| 273 | 0.016 |
| 274 | 0.121 |
| 275 | 0.264 |
| 276 | 0.038 |
| 277 | 0.017 |
| 278 | 1.739 |
| 279 | 0.021 |
| 280 | 0.011 |
| 281 | 2.041 |
| 282 | 0.008 |
| 283 | 0.338 |
| 284 | 0.029 |

While the invention has been illustrated by reference to examples, it is understood that the invention is intended not to be limited to the foregoing detailed description.

What is claimed is:

1. A chemical entity selected from compounds of Formula (I), pharmaceutically acceptable salts of compounds of Formula (I), and pharmaceutically acceptable prodrugs of compounds of Formula (I):

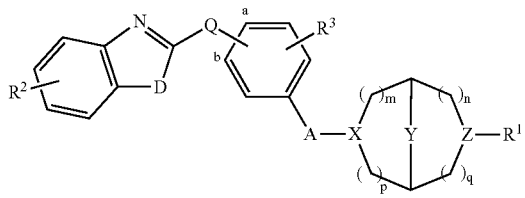
(I)

wherein

Q is O or $CH_2$, and said Q is linked at the "a" or "b" position of the phenyl ring;

D is S;

$R^2$ is H, $CH_3$, $OCH_3$, halo, OH, $NH_2$, or CN;

$R^3$ is H or F; and

A is $-CH_2-$, $-CH_2CH_2-$, or $-OCH_2CH_2-$; and wherein

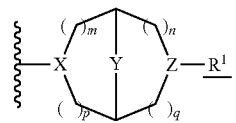

is octahydro-pyrrolo[3,4-b]pyrrole, octahydro-pyrrolo[3,4-c]pyrrole, octahydro-pyrrolo[3,4-c]pyridine, decahydro-[1,6]naphthyridine, or 3-aza-bicyclo[3.1.0]hex-6-ylamine.

2. A chemical entity as in claim 1, wherein $R^2$ is H, $CH_3$, OH, $OCH_3$, CN, $NH_2$, fluoro, or chloro.

3. A chemical entity selected from the group consisting of:
2-[4-(Hexahydro-pyrrolo[3,4-b]pyrrol-5-ylmethyl)-phenoxy]-benzothiazole hydrochloride;
2-[4-(Hexahydro-pyrrolo[3,4-b]pyrrol-1-ylmethyl)-phenoxy]-benzothiazole hydrochloride;
2-[4-(Hexahydro-pyrrolo[3,4-c]pyrrol-2-ylmethyl)-phenoxy]-benzothiazole hydrochloride;
2-[3-(Octahydro-pyrrolo[3,4-c]pyridin-2-ylmethyl)-phenoxy]-benzothiazole hydrochloride;
2-[4-(Octahydro-pyrrolo[3,4-c]pyridin-5-ylmethyl)-phenoxy]-benzothiazole hydrochloride;
1-{1-[4-(Benzothiazol-2-yloxy)-benzyl]-hexahydro-pyrrolo[3,4-b]pyrrol-5-yl}-ethanone;
1-{5-[4-(Benzothiazol-2-yloxy)-benzyl]-hexahydro-pyrrolo[3,4-b]pyrrol-1-yl}-ethanone;
1-{5-[4-(Benzothiazol-2-yloxy)-benzyl]-hexahydro-pyrrolo[3,4-c]pyrrol-2-yl}-ethanone;
1-{2-[4-(Benzothiazol-2-yloxy)-benzyl]-octahydro-pyrrolo[3,4-c]pyridin-5-yl}-ethanone;
1-{5-[4-(Benzothiazol-2-yloxy)-benzyl]-octahydro-pyrrolo[3,4-c]pyridin-2-yl}-ethanone;
cis-1-{7-[4-(Benzothiazol-2-yloxy)-benzyl]-octahydro-[1,7]naphthyridin-1-yl}-ethanone;
trans-1-{7-[4-(Benzothiazol-2-yloxy)-benzyl]-octahydro-[1,7]naphthyridin-1-yl}-ethanone;
(R,S)—N-{3-[4-(Benzothiazol-2-yloxy)-benzyl]-3-aza-bicyclo[3.1.0]hex-6-yl}-acetamide;
1-(5-{2-[4-(Benzothiazol-2-yloxy)-phenoxy]-ethyl}-hexahydro-pyrrolo[3,4-c]pyrrol-2-yl)-ethanone;
2-Amino-1-{5-[4-(benzothiazol-2-yloxy)-benzyl]-hexahydro-pyrrolo[3,4-b]pyrrol-1-yl}-ethanone;
2-Amino-1-{1-[4-(benzothiazol-2-yloxy)-benzyl]-hexahydro-pyrrolo[3,4-b]pyrrol-5-yl}-ethanone;
2-Amino-1-{5-[4-(benzothiazol-2-yloxy)-benzyl]-hexahydro-pyrrolo[3,4-c]pyrrol-2-yl}-ethanone;
N-(2-{5-[4-(Benzothiazol-2-yloxy)-benzyl]-hexahydro-pyrrolo[3,4-b]pyrrol-1-yl}-2-oxo-ethyl)-2,2,2-trifluoro-acetamide;
Azetidin-3-yl-{5-[4-(benzothiazol-2-yloxy)-benzyl]-hexahydro-pyrrolo[3,4-c]pyrrol-2-yl}-methanone;
(R)-{5-[4-(Benzothiazol-2-yloxy)-benzyl]-hexahydro-pyrrolo[3,4-c]pyrrol-2-yl}-(tetrahydro-furan-2-yl)-methanone;
(S)-{5-[4-(Benzothiazol-2-yloxy)-benzyl]-hexahydro-pyrrolo[3,4-c]pyrrol-2-yl}-(tetrahydro-furan-2-yl)-methanone;
{5-[4-(Benzothiazol-2-yloxy)-benzyl]-hexahydro-pyrrolo[3,4-c]pyrrol-2-yl}-(tetrahydro-furan-3-yl)-methanone;
{5-[4-(Benzothiazol-2-yloxy)-benzyl]-hexahydro-pyrrolo[3,4-c]pyrrol-2-yl}-(tetrahydro-pyran-4-yl)-methanone;
{5-[4-(Benzothiazol-2-yloxy)-benzyl]-hexahydro-pyrrolo[3,4-c]pyrrol-2-yl}-cyclobutyl-methanone;

{5-[4-(Benzothiazol-2-yloxy)-benzyl]-hexahydro-pyrrolo[3,4-c]pyrrol-2-yl}-pyrazin-2-yl-methanone;
{5-[4-(Benzothiazol-2-yloxy)-benzyl]-hexahydro-pyrrolo[3,4-c]pyrrol-2-yl}-furan-2-yl-methanone;
{5-[4-(Benzothiazol-2-yloxy)-benzyl]-hexahydro-pyrrolo[3,4-c]pyrrol-2-yl}-thiophen-2-yl-methanone;
{5-[4-(Benzothiazol-2-yloxy)-benzyl]-hexahydro-pyrrolo[3,4-c]pyrrol-2-yl}-(1-methyl-1H-pyrrol-3-yl)-methanone;
{5-[4-(Benzothiazol-2-yloxy)-benzyl]-hexahydro-pyrrolo[3,4-c]pyrrol-2-yl}-thiophen-3-yl-methanone;
{5-[4-(Benzothiazol-2-yloxy)-benzyl]-hexahydro-pyrrolo[3,4-c]pyrrol-2-yl}-furan-3-yl-methanone;
{5-[4-(Benzothiazol-2-yloxy)-benzyl]-hexahydro-pyrrolo[3,4-c]pyrrol-2-yl}-cyclopropyl-methanone;
1-{5-[4-(Benzothiazol-2-yloxy)-benzyl]-hexahydro-pyrrolo[3,4-c]pyrrol-2-yl}-2-fluoro-ethanone;
1-{5-[4-(Benzothiazol-2-yloxy)-benzyl]-hexahydro-pyrrolo[3,4-c]pyrrol-2-yl}-3,3,3-trifluoro-propan-1-one;
{5-[4-(Benzothiazol-2-yloxy)-benzyl]-hexahydro-pyrrolo[3,4-c]pyrrol-2-yl}-isoxazol-5-yl-methanone;
{5-[4-(Benzothiazol-2-yloxy)-benzyl]-hexahydro-pyrrolo[3,4-c]pyrrol-2-yl}-morpholin-4-yl-methanone;
1-{2-[4-(Benzothiazol-2-yloxy)-benzyl]-octahydro-pyrrolo[3,4-c]pyridin-5-yl}-2-hydroxy-ethanone;
1-{5-[4-(Benzothiazol-2-yloxy)-benzyl]-octahydro-pyrrolo[3,4-c]pyridin-2-yl}-2-hydroxy-ethanone;
1-{5-[4-(Benzothiazol-2-yloxy)-benzyl]-hexahydro-pyrrolo[3,4-c]pyrrol-2-yl}-2-hydroxy-ethanone;
5-[4-(Benzothiazol-2-yloxy)-benzyl]-hexahydro-pyrrolo[3,4-c]pyrrole-2-sulfonic acid amide,
2-{4-[5-(Pyridine-3-sulfonyl)-hexahydro-pyrrolo[3,4-c]pyrrol-2-ylmethyl]-phenoxy}-benzothiazole;
2-{4-[5-(Furan-2-sulfonyl)-hexahydro-pyrrolo[3,4-c]pyrrol-2-ylmethyl]-phenoxy}-benzothiazole;
2-{4-[5-(1-Methyl-1H-imidazole-4-sulfonyl)-hexahydro-pyrrolo[3,4-c]pyrrol-2-ylmethyl]-phenoxy}-benzothiazole;
2-{4-[5-(1-Methyl-1H-pyrrole-3-sulfonyl)-hexahydro-pyrrolo[3,4-c]pyrrol-2-ylmethyl]-phenoxy}-benzothiazole;
2-{4-[5-(Thiophene-2-sulfonyl)-hexahydro-pyrrolo[3,4-c]pyrrol-2-ylmethyl]-phenoxy}-benzothiazole;
2-{4-[5-(Thiophene-3-sulfonyl)-hexahydro-pyrrolo[3,4-c]pyrrol-2-ylmethyl]-phenoxy}-benzothiazole;
2-[4-(5-Cyclopropanesulfonyl-hexahydro-pyrrolo[3,4-c]pyrrol-2-ylmethyl)-phenoxy]-benzothiazole;
2-[4-(1-Methanesulfonyl-hexahydro-pyrrolo[3,4-b]pyrrol-5-ylmethyl)-phenoxy]-benzothiazole;
2-[4-(5-Methanesulfonyl-hexahydro-pyrrolo[3,4-b]pyrrol-1-ylmethyl)-phenoxy]-benzothiazole;
2-[4-(5-Methanesulfonyl-hexahydro-pyrrolo[3,4-c]pyrrol-2-ylmethyl)-phenoxy]-benzothiazole;
2-[4-(5-Methanesulfonyl-octahydro-pyrrolo[3,4-c]pyridin-2-ylmethyl)-phenoxy]-benzothiazole;
5-[4-(Benzothiazol-2-yloxy)-benzyl]-hexahydro-pyrrolo[3,4-c]pyrrole-2-carboxylic acid (furan-2-ylmethyl)-amide;
5-[4-(Benzothiazol-2-yloxy)-benzyl]-hexahydro-pyrrolo[3,4-c]pyrrole-2-carboxylic acid pyridin-4-yl amide;
5-[4-(Benzothiazol-2-yloxy)-benzyl]-hexahydro-pyrrolo[3,4-c]pyrrole-2-carboxylic acid (3,5-dimethyl-isoxazol-4-yl)-amide;
5-{2-[4-(Benzothiazol-2-yloxy)-phenoxy]-ethyl}-hexahydro-pyrrolo[3,4-c]pyrrole-2-carboxylic acid amide;
5-[4-(Benzothiazol-2-yloxy)-benzyl]-hexahydro-pyrrolo[3,4-b]pyrrole-1-carboxylic acid amide;
1-[4-(Benzothiazol-2-yloxy)-benzyl]-hexahydro-pyrrolo[3,4-b]pyrrole-5-carboxylic acid amide;
(S,S)-1-[4-(Benzothiazol-2-yloxy)-benzyl]-hexahydro-pyrrolo[3,4-b]pyrrole-5-carboxylic acid amide;
(R,R)-1-[4-(Benzothiazol-2-yloxy)-benzyl]-hexahydro-pyrrolo[3,4-b]pyrrole-5-carboxylic acid amide;
5-[4-(Benzothiazol-2-yloxy)-benzyl]-hexahydro-pyrrolo[3,4-c]pyrrole-2-carboxylic acid amide;
(R,S)-{3-[4-(Benzothiazol-2-yloxy)-benzyl]-3-aza-bicyclo[3.1.0]hex-6-yl}-urea;
(±)-5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
2-[4-(Benzothiazol-2-yloxy)-benzyl]-octahydro-pyrrolo[3,4-c]pyridine-5-carboxylic acid amide;
5-[4-(6-Fluoro-benzothiazol-2-yloxy)-benzyl]-hexahydro-pyrrolo[3,4-c]pyrrole-2-carboxylic acid amide;
5-[4-(6-Methyl-benzothiazol-2-yloxy)-benzyl]-hexahydro-pyrrolo[3,4-c]pyrrole-2-carboxylic acid amide;
5-{2-[4-(4-Methyl-benzothiazol-2-yloxy)-phenyl]-ethyl}-hexahydro-pyrrolo[3,4-c]pyrrole-2-carboxylic acid amide;
5-{2-[4-(4-Fluoro-benzothiazol-2-yloxy)-phenyl]-ethyl}-hexahydro-pyrrolo[3,4-c]pyrrole-2-carboxylic acid amide;
1-(5-{2-[4-(6-Methyl-benzothiazol-2-yloxy)-phenyl]-ethyl}-hexahydro-pyrrolo[3,4-c]pyrrol-2-yl)-ethanone;
1-[5-(4-Benzothiazol-2-ylmethyl-benzyl)-hexahydro-pyrrolo[3,4-c]pyrrol-2-yl]-ethanone;
2-[4-(5-Methanesulfonyl-hexahydro-pyrrolo[3,4-c]pyrrol-2-ylmethyl)-benzyl]-benzothiazole;
1-[5-(4-Benzothiazol-2-ylmethyl-benzyl)-hexahydro-pyrrolo[3,4-c]pyrrol-2-yl]-ethanone;
4-{5-[4-(Benzothiazol-2-yloxy)-benzyl]-hexahydro-pyrrolo[3,4-c]pyrrol-2-ylmethyl)-benzoic acid methyl ester;
4-{5-[4-(Benzothiazol-2-yloxy)-benzyl]-hexahydro-pyrrolo[3,4-c]pyrrol-2-ylmethyl)-benzoic acid;
{5-[4-(Benzothiazol-2-yloxy)-benzyl]-hexahydro-pyrrolo[3,4-c]pyrrol-2-yl}-acetic acid ethyl ester;
4-{5-[4-(Benzothiazol-2-yloxy)-benzyl]-hexahydro-pyrrolo[3,4-c]pyrrol-2-yl}-butyric acid methyl ester;
{5-[4-(Benzothiazol-2-yloxy)-benzyl]-hexahydro-pyrrolo[3,4-c]pyrrol-2-yl}-acetic acid methyl ester;
{5-[4-(Benzothiazol-2-yloxy)-benzyl]-hexahydro-pyrrolo[3,4-c]pyrrol-2-yl}-acetic acid;
5-[4-(Benzothiazol-2-yloxy)-2-fluoro-benzyl]-hexahydro-pyrrolo[3,4-c]pyrrole-2-carboxylic acid amide;
5-[2-Fluoro-4-(4-fluoro-benzothiazol-2-yloxy)-benzyl]-hexahydro-pyrrolo[3,4-c]pyrrole-2-carboxylic acid amide;

pharmaceutically acceptable salts, and pharmaceutically acceptable prodrugs thereof.

4. A chemical entity as in claim 3, selected from the group consisting of:
2-[4-(Hexahydro-pyrrolo[3,4-b]pyrrol-5-ylmethyl)-phenoxy]-benzothiazole hydrochloride;
2-[4-(Hexahydro-pyrrolo[3,4-b]pyrrol-1-ylmethyl)-phenoxy]-benzothiazole hydrochloride;
2-[4-(Hexahydro-pyrrolo[3,4-c]pyrrol-2-ylmethyl)-phenoxy]-benzothiazole hydrochloride;

2-[3-(Octahydro-pyrrolo[3,4-c]pyridin-2-ylmethyl)-phenoxy]-benzothiazole hydrochloride;
2-[4-(Octahydro-pyrrolo[3,4-c]pyridin-5-ylmethyl)-phenoxy]-benzothiazole hydrochloride;
1-{1-[4-(Benzothiazol-2-yloxy)-benzyl]-hexahydro-pyrrolo[3,4-b]pyrrol-5-yl}-ethanone;
1-{5-[4-(Benzothiazol-2-yloxy)-benzyl]-hexahydro-pyrrolo[3,4-b]pyrrol-1-yl}-ethanone;
1-{5-[4-(Benzothiazol-2-yloxy)-benzyl]-hexahydro-pyrrolo[3,4-c]pyrrol-2-yl}-ethanone;
1-{2-[4-(Benzothiazol-2-yloxy)-benzyl]-octahydro-pyrrolo[3,4-c]pyridin-5-yl}-ethanone;
1-{5-[4-(Benzothiazol-2-yloxy)-benzyl]-octahydro-pyrrolo[3,4-c]pyridin-2-yl}-ethanone;
cis-1-{7-[4-(Benzothiazol-2-yloxy)-benzyl]-octahydro-[1,7]naphthyridin-1-yl}-ethanone;
trans-1-{7-[4-(Benzothiazol-2-yloxy)-benzyl]-octahydro-[1,7]naphthyridin-1-yl}-ethanone;
(R,S)—N-{3-[4-(Benzothiazol-2-yloxy)-benzyl]-3-azabicyclo[3.1.0]hex-6-yl}-acetamide;
1-(5-{2-[4-(Benzothiazol-2-yloxy)-phenoxy]-ethyl}-hexahydro-pyrrolo[3,4-c]pyrrol-2-yl)-ethanone;
2-Amino-1-{5-[4-(benzothiazol-2-yloxy)-benzyl]-hexahydro-pyrrolo[3,4-b]pyrrol-1-yl}-ethanone;
2-Amino-1-{1-[4-(benzothiazol-2-yloxy)-benzyl]-hexahydro-pyrrolo[3,4-b]pyrrol-5-yl}-ethanone;
2-Amino-1-{5-[4-(benzothiazol-2-yloxy)-benzyl]-hexahydro-pyrrolo[3,4-c]pyrrol-2-yl}-ethanone;
N-(2-{5-[4-(Benzothiazol-2-yloxy)-benzyl]-hexahydro-pyrrolo[3,4-b]pyrrol-1-yl}-2-oxo-ethyl)-2,2,2-trifluoro-acetamide;
Azetidin-3-yl-{5-[4-(benzothiazol-2-yloxy)-benzyl]-hexahydro-pyrrolo[3,4-c]pyrrol-2-yl}-methanone;
(R)-{5-[4-(Benzothiazol-2-yloxy)-benzyl]-hexahydro-pyrrolo[3,4-c]pyrrol-2-yl}-(tetrahydro-furan-2-yl)-methanone;
(S)-{5-[4-(Benzothiazol-2-yloxy)-benzyl]-hexahydro-pyrrolo[3,4-c]pyrrol-2-yl}-(tetrahydro-furan-2-yl)-methanone;
{5-[4-(Benzothiazol-2-yloxy)-benzyl]-hexahydro-pyrrolo[3,4-c]pyrrol-2-yl}-(tetrahydro-furan-3-yl)-methanone;
{5-[4-(Benzothiazol-2-yloxy)-benzyl]-hexahydro-pyrrolo[3,4-c]pyrrol-2-yl}-(tetrahydro-pyran-4-yl)-methanone;
{5-[4-(Benzothiazol-2-yloxy)-benzyl]-hexahydro-pyrrolo[3,4-c]pyrrol-2-yl}-cyclobutyl-methanone;
{5-[4-(Benzothiazol-2-yloxy)-benzyl]-hexahydro-pyrrolo[3,4-c]pyrrol-2-yl}-pyrazin-2-yl-methanone;
{5-[4-(Benzothiazol-2-yloxy)-benzyl]-hexahydro-pyrrolo[3,4-c]pyrrol-2-yl}-furan-2-yl-methanone;
{5-[4-(Benzothiazol-2-yloxy)-benzyl]-hexahydro-pyrrolo[3,4-c]pyrrol-2-yl}-thiophen-2-yl-methanone;
{5-[4-(Benzothiazol-2-yloxy)-benzyl]-hexahydro-pyrrolo[3,4-c]pyrrol-2-yl}-(1-methyl-1H-pyrrol-3-yl)-methanone;
{5-[4-(Benzothiazol-2-yloxy)-benzyl]-hexahydro-pyrrolo[3,4-c]pyrrol-2-yl}-thiophen-3-yl-methanone;
{5-[4-(Benzothiazol-2-yloxy)-benzyl]-hexahydro-pyrrolo[3,4-c]pyrrol-2-yl}-furan-3-yl-methanone;
{5-[4-(Benzothiazol-2-yloxy)-benzyl]-hexahydro-pyrrolo[3,4-c]pyrrol-2-yl}-cyclopropyl-methanone;
1-{5-[4-(Benzothiazol-2-yloxy)-benzyl]-hexahydro-pyrrolo[3,4-c]pyrrol-2-yl}-2-fluoro-ethanone;
1-{5-[4-(Benzothiazol-2-yloxy)-benzyl]-hexahydro-pyrrolo[3,4-c]pyrrol-2-yl}-3,3,3-trifluoro-propan-1-one;
{5-[4-(Benzothiazol-2-yloxy)-benzyl]-hexahydro-pyrrolo[3,4-c]pyrrol-2-yl}-isoxazol-5-yl-methanone;
{5-[4-(Benzothiazol-2-yloxy)-benzyl]-hexahydro-pyrrolo[3,4-c]pyrrol-2-yl}-morpholin-4-yl-methanone;
1-{2-[4-(Benzothiazol-2-yloxy)-benzyl]-octahydro-pyrrolo[3,4-c]pyridin-5-yl}-2-hydroxy-ethanone;
1-{5-[4-(Benzothiazol-2-yloxy)-benzyl]-octahydro-pyrrolo[3,4-c]pyridin-2-yl}-2-hydroxy-ethanone;
1-{5-[4-(Benzothiazol-2-yloxy)-benzyl]-hexahydro-pyrrolo[3,4-c]pyrrol-2-yl}-2-hydroxy-ethanone;
5-[4-(Benzothiazol-2-yloxy)-benzyl]-hexahydro-pyrrolo[3,4-c]pyrrole-2-sulfonic acid amide;
2-{4-[5-(Pyridine-3-sulfonyl)-hexahydro-pyrrolo[3,4-c]pyrrol-2-ylmethyl]-phenoxy}-benzothiazole;
2-{4-[5-(Furan-2-sulfonyl)-hexahydro-pyrrolo[3,4-c]pyrrol-2-ylmethyl]-phenoxy}-benzothiazole;
2-{4-[5-(1-Methyl-1H-imidazole-4-sulfonyl)-hexahydro-pyrrolo[3,4-c]pyrrol-2-ylmethyl]-phenoxy}-benzothiazole;
2-{4-[5-(1-Methyl-1H-pyrrole-3-sulfonyl)-hexahydro-pyrrolo[3,4-c]pyrrol-2-ylmethyl]-phenoxy}-benzothiazole;
2-{4-[5-(Thiophene-2-sulfonyl)-hexahydro-pyrrolo[3,4-c]pyrrol-2-ylmethyl]-phenoxy}-benzothiazole;
2-{4-[5-(Thiophene-3-sulfonyl)-hexahydro-pyrrolo[3,4-c]pyrrol-2-ylmethyl]-phenoxy}-benzothiazole;
2-[4-(5-Cyclopropanesulfonyl-hexahydro-pyrrolo[3,4-c]pyrrol-2-ylmethyl)-phenoxy]-benzothiazole;
2-[4-(1-Methanesulfonyl-hexahydro-pyrrolo[3,4-b]pyrrol-5-ylmethyl)-phenoxy]-benzothiazole;
2-[4-(5-Methanesulfonyl-hexahydro-pyrrolo[3,4-b]pyrrol-1-ylmethyl)-phenoxy]-benzothiazole;
2-[4-(5-Methanesulfonyl-hexahydro-pyrrolo[3,4-c]pyrrol-2-ylmethyl)-phenoxy]-benzothiazole;
2-[4-(5-Methanesulfonyl-octahydro-pyrrolo[3,4-c]pyridin-2-ylmethyl)-phenoxy]-benzothiazole;
5-{2-[4-(Benzothiazol-2-yloxy)-phenoxy]-ethyl}-hexahydro-pyrrolo[3,4-c]pyrrole-2-carboxylic acid amide;
5-[4-(Benzothiazol-2-yloxy)-benzyl]-hexahydro-pyrrolo[3,4-b]pyrrole-1-carboxylic acid amide;
1-[4-(Benzothiazol-2-yloxy)-benzyl]-hexahydro-pyrrolo[3,4-b]pyrrole-5-carboxylic acid amide;
(S,S)-1-[4-(Benzothiazol-2-yloxy)-benzyl]-hexahydro-pyrrolo[3,4-b]pyrrole-5-carboxylic acid amide;
(R,R)-1-[4-(Benzothiazol-2-yloxy)-benzyl]-hexahydro-pyrrolo[3,4-b]pyrrole-5-carboxylic acid amide;
5-[4-(Benzothiazol-2-yloxy)-benzyl]-hexahydro-pyrrolo[3,4-c]pyrrole-2-carboxylic acid amide;
(R,S)-{3-[4-(Benzothiazol-2-yloxy)-benzyl]-3-aza-bicyclo[3.1.0]hex-6-yl}-urea;
(±)-5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
2-[4-(Benzothiazol-2-yloxy)-benzyl]-octahydro-pyrrolo[3,4-c]pyridine-5-carboxylic acid amide;
5-[4-(6-Fluoro-benzothiazol-2-yloxy)-benzyl]-hexahydro-pyrrolo[3,4-c]pyrrole-2-carboxylic acid amide;
5-[4-(6-Methyl-benzothiazol-2-yloxy)-benzyl]-hexahydro-pyrrolo[3,4-c]pyrrole-2-carboxylic acid amide;
5-{2-[4-(4-Methyl-benzothiazol-2-yloxy)-phenyl]-ethyl}-hexahydro-pyrrolo[3,4-c]pyrrole-2-carboxylic acid amide;

5-{2-[4-(4-Fluoro-benzothiazol-2-yloxy)-phenyl]-ethyl}-hexahydro-pyrrolo[3,4-c]pyrrole-2-carboxylic acid amide;
1-(5-{2-[4-(6-Methyl-benzothiazol-2-yloxy)-phenyl]-ethyl}-hexahydro-pyrrolo[3,4-c]pyrrol-2-yl)-ethanone;
4-{5-[4-(Benzothiazol-2-yloxy)-benzyl]-hexahydro-pyrrolo[3,4-c]pyrrol-2-ylmethyl)-benzoic acid methyl ester;
4-{5-[4-(Benzothiazol-2-yloxy)-benzyl]-hexahydro-pyrrolo[3,4-c]pyrrol-2-ylmethyl)-benzoic acid;
{5-[4-(Benzothiazol-2-yloxy)-benzyl]-hexahydro-pyrrolo[3,4-c]pyrrol-2-yl}-acetic acid ethyl ester;
4-{5-[4-(Benzothiazol-2-yloxy)-benzyl]-hexahydro-pyrrolo[3,4-c]pyrrol-2-yl}-butyric acid methyl ester;
{5-[4-(Benzothiazol-2-yloxy)-benzyl]-hexahydro-pyrrolo[3,4-c]pyrrol-2-yl}-acetic acid methyl ester;
{5-[4-(Benzothiazol-2-yloxy)-benzyl]-hexahydro-pyrrolo[3,4-c]pyrrol-2-yl}-acetic acid;
5-[4-(Benzothiazol-2-yloxy)-2-fluoro-benzyl]-hexahydro-pyrrolo[3,4-c]pyrrole-2-carboxylic acid amide;
5-[2-Fluoro-4-(4-fluoro-benzothiazol-2-yloxy)-benzyl]-hexahydro-pyrrolo[3,4-c]pyrrole-2-carboxylic acid amide;
pharmaceutically acceptable salts, and pharmaceutically acceptable prodrugs thereof.

5. A chemical entity as in claim 3, selected from the group consisting of:
1-[5-(4-Benzothiazol-2-ylmethyl-benzyl)-hexahydro-pyrrolo[3,4-c]pyrrol-2-yl]-ethanone;
2-[4-(5-Methanesulfonyl-hexahydro-pyrrolo[3,4-c]pyrrol-2-ylmethyl)-benzyl]-benzothiazole;
1-[5-(4-Benzothiazol-2-ylmethyl-benzyl)-hexahydro-pyrrolo[3,4-c]pyrrol-2-yl]-ethanone;
pharmaceutically acceptable salts, and pharmaceutically acceptable prodrugs thereof.

6. A chemical entity as in claim 1, wherein Q is O and is linked at the a or b position and A is —$CH_2$—.

7. A chemical entity as in claim 1, wherein Q is O and is linked at the a or b position and A is —$OCH_2CH_2$—.

8. A chemical entity as in claim 1, wherein Q is O and is linked at the a or b position and A is —$CH_2CH_2$—.

9. A chemical entity as in claim 1, wherein Q is —$CH_2$— and is linked at the a or b position and A is —$CH_2$—.

10. A chemical entity as in claim 1, wherein Q is —$CH_2$— and is linked at the a or b position and A is —$OCH_2CH_2$—.

11. A chemical entity as in claim 1, wherein Q is —$CH_2$— and is linked at the a or b position and A is —$CH_2CH_2$—.

12. A pharmaceutical composition comprising an effective amount of at least one chemical entity selected from the group consisting of compounds of Formula (I), pharmaceutically acceptable salts of compounds of Formula (I), and pharmaceutically acceptable prodrugs of compounds of Formula (I),

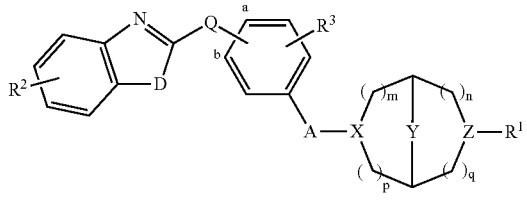

(I)

wherein
Q is O or $CH_2$, and said Q is linked at the "a" or "b" position of the phenyl ring;
D is S;
$R^2$ is H, $CH_3$, $OCH_3$, halo, OH, $NH_2$, or CN;
$R^3$ is H or F; and
A is —$CH_2$—, —$CH_2CH_2$—, or —$OCH_2CH_2$—; and
wherein

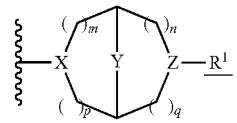

is octahydro-pyrrolo[3,4-b]pyrrole, octahydro-pyrrolo[3,4-c]pyrrole, octahydro-pyrrolo[3,4-c]pyridine, decahydro-[1,6]naphthyridine, or 3-aza-bicyclo[3.1.0]hex-6-ylamine.

13. A pharmaceutical composition comprising an effective amount of at least one chemical entity selected from the group consisting of:
2-[4-(Hexahydro-pyrrolo[3,4-b]pyrrol-5-ylmethyl)-phenoxy]-benzothiazole hydrochloride;
2-[4-(Hexahydro-pyrrolo[3,4-b]pyrrol-1-ylmethyl)-phenoxy]-benzothiazole hydrochloride;
2-[4-(Hexahydro-pyrrolo[3,4-c]pyrrol-2-ylmethyl)-phenoxy]-benzothiazole hydrochloride;
2-[3-(Octahydro-pyrrolo[3,4-c]pyridin-2-ylmethyl)-phenoxy]-benzothiazole hydrochloride;
2-[4-(Octahydro-pyrrolo[3,4-c]pyridin-5-ylmethyl)-phenoxy]-benzothiazole hydrochloride;
1-{1-[4-(Benzothiazol-2-yloxy)-benzyl]-hexahydro-pyrrolo[3,4-b]pyrrol-5-yl}-ethanone;
1-{5-[4-(Benzothiazol-2-yloxy)-benzyl]-hexahydro-pyrrolo[3,4-b]pyrrol-1-yl}-ethanone;
1-{5-[4-(Benzothiazol-2-yloxy)-benzyl]-hexahydro-pyrrolo[3,4-c]pyrrol-2-yl}-ethanone;
1-{2-[4-(Benzothiazol-2-yloxy)-benzyl]-octahydro-pyrrolo[3,4-c]pyridin-5-yl}-ethanone;
1-{5-[4-(Benzothiazol-2-yloxy)-benzyl]-octahydro-pyrrolo[3,4-c]pyridin-2-yl}-ethanone;
cis-1-{7-[4-(Benzothiazol-2-yloxy)-benzyl]-octahydro-[1,7]naphthyridin-1-yl}-ethanone;
trans-1-{7-[4-(Benzothiazol-2-yloxy)-benzyl]-octahydro-[1,7]naphthyridin-1-yl}-ethanone;
(R,S)—N-{3-[4-(Benzothiazol-2-yloxy)-benzyl]-3-aza-bicyclo[3.1.0]hex-6-yl}-acetamide;
1-(5-{2-[4-(Benzothiazol-2-yloxy)-phenoxy]-ethyl}-hexahydro-pyrrolo[3,4-c]pyrrol-2-yl)-ethanone;
2-Amino-1-{5-[4-(benzothiazol-2-yloxy)-benzyl]-hexahydro-pyrrolo[3,4-b]pyrrol-1-yl}-ethanone;
2-Amino-1-{1-[4-(benzothiazol-2-yloxy)-benzyl]-hexahydro-pyrrolo[3,4-b]pyrrol-5-yl}-ethanone;
2-Amino-1-{5-[4-(benzothiazol-2-yloxy)-benzyl]-hexahydro-pyrrolo[3,4-c]pyrrol-2-yl}-ethanone;
N-(2-{5-[4-(Benzothiazol-2-yloxy)-benzyl]-hexahydro-pyrrolo[3,4-b]pyrrol-1-yl}-2-oxo-ethyl)-2,2,2-trifluoro-acetamide;
Azetidin-3-yl-{5-[4-(benzothiazol-2-yloxy)-benzyl]-hexahydro-pyrrolo[3,4-c]pyrrol-2-yl}-methanone;
(R)-{5-[4-(Benzothiazol-2-yloxy)-benzyl]-hexahydro-pyrrolo[3,4-c]pyrrol-2-yl}-(tetrahydro-furan-2-yl)-methanone;
(S)-{5-[4-(Benzothiazol-2-yloxy)-benzyl]-hexahydro-pyrrolo[3,4-c]pyrrol-2-yl}-(tetrahydro-furan-2-yl)-methanone;

{5-[4-(Benzothiazol-2-yloxy)-benzyl]-hexahydro-pyrrolo[3,4-c]pyrrol-2-yl}-(tetrahydro-furan-3-yl)-methanone;
{5-[4-(Benzothiazol-2-yloxy)-benzyl]-hexahydro-pyrrolo[3,4-c]pyrrol-2-yl}-(tetrahydro-pyran-4-yl)-methanone;
{5-[4-(Benzothiazol-2-yloxy)-benzyl]-hexahydro-pyrrolo[3,4-c]pyrrol-2-yl}-cyclobutyl-methanone;
{5-[4-(Benzothiazol-2-yloxy)-benzyl]-hexahydro-pyrrolo[3,4-c]pyrrol-2-yl}-pyrazin-2-yl-methanone;
{5-[4-(Benzothiazol-2-yloxy)-benzyl]-hexahydro-pyrrolo[3,4-c]pyrrol-2-yl}-furan-2-yl-methanone;
{5-[4-(Benzothiazol-2-yloxy)-benzyl]-hexahydro-pyrrolo[3,4-c]pyrrol-2-yl}-thiophen-2-yl-methanone;
{5-[4-(Benzothiazol-2-yloxy)-benzyl]-hexahydro-pyrrolo[3,4-c]pyrrol-2-yl}-(1-methyl-1H-pyrrol-3-yl)-methanone;
{5-[4-(Benzothiazol-2-yloxy)-benzyl]-hexahydro-pyrrolo[3,4-c]pyrrol-2-yl}-thiophen-3-yl-methanone;
{5-[4-(Benzothiazol-2-yloxy)-benzyl]-hexahydro-pyrrolo[3,4-c]pyrrol-2-yl}-furan-3-yl-methanone;
{5-[4-(Benzothiazol-2-yloxy)-benzyl]-hexahydro-pyrrolo[3,4-c]pyrrol-2-yl}-cyclopropyl-methanone;
1-{5-[4-(Benzothiazol-2-yloxy)-benzyl]-hexahydro-pyrrolo[3,4-c]pyrrol-2-yl}-2-fluoro-ethanone;
1-{5-[4-(Benzothiazol-2-yloxy)-benzyl]-hexahydro-pyrrolo[3,4-c]pyrrol-2-yl}-3,3,3-trifluoro-propan-1-one;
{5-[4-(Benzothiazol-2-yloxy)-benzyl]-hexahydro-pyrrolo[3,4-c]pyrrol-2-yl}-isoxazol-5-yl-methanone;
{5-[4-(Benzothiazol-2-yloxy)-benzyl]-hexahydro-pyrrolo[3,4-c]pyrrol-2-yl}-morpholin-4-yl-methanone;
1-{2-[4-(Benzothiazol-2-yloxy)-benzyl]-octahydro-pyrrolo[3,4-c]pyridin-5-yl}-2-hydroxy-ethanone;
1-{5-[4-(Benzothiazol-2-yloxy)-benzyl]-octahydro-pyrrolo[3,4-c]pyridin-2-yl}-2-hydroxy-ethanone;
1-{5-[4-(Benzothiazol-2-yloxy)-benzyl]-hexahydro-pyrrolo[3,4-c]pyrrol-2-yl}-2-hydroxy-ethanone;
5-[4-(Benzothiazol-2-yloxy)-benzyl]-hexahydro-pyrrolo[3,4-c]pyrrole-2-sulfonic acid amide;
2-{4-[5-(Pyridine-3-sulfonyl)-hexahydro-pyrrolo[3,4-c]pyrrol-2-ylmethyl]-phenoxy}-benzothiazole;
2-{4-[5-(Furan-2-sulfonyl)-hexahydro-pyrrolo[3,4-c]pyrrol-2-ylmethyl]-phenoxy}-benzothiazole;
2-{4-[5-(1-Methyl-1H-imidazole-4-sulfonyl)-hexahydro-pyrrolo[3,4-c]pyrrol-2-ylmethyl]-phenoxy}-benzothiazole;
2-{4-[5-(1-Methyl-1H-pyrrole-3-sulfonyl)-hexahydro-pyrrolo[3,4-c]pyrrol-2-ylmethyl]-phenoxy}-benzothiazole;
2-{4-[5-(Thiophene-2-sulfonyl)-hexahydro-pyrrolo[3,4-c]pyrrol-2-ylmethyl]-phenoxy}-benzothiazole;
2-{4-[5-(Thiophene-3-sulfonyl)-hexahydro-pyrrolo[3,4-c]pyrrol-2-ylmethyl]-phenoxy}-benzothiazole;
2-[4-(5-Cyclopropanesulfonyl-hexahydro-pyrrolo[3,4-c]pyrrol-2-ylmethyl)-phenoxy]-benzothiazole;
2-[4-(1-Methanesulfonyl-hexahydro-pyrrolo[3,4-b]pyrrol-5-ylmethyl)-phenoxy]-benzothiazole;
2-[4-(5-Methanesulfonyl-hexahydro-pyrrolo[3,4-b]pyrrol-1-ylmethyl)-phenoxy]-benzothiazole;
2-[4-(5-Methanesulfonyl-hexahydro-pyrrolo[3,4-c]pyrrol-2-ylmethyl)-phenoxy]-benzothiazole;
2-[4-(5-Methanesulfonyl-octahydro-pyrrolo[3,4-c]pyridin-2-ylmethyl)-phenoxy]-benzothiazole;
5-[4-(Benzothiazol-2-yloxy)-benzyl]-hexahydro-pyrrolo[3,4-c]pyrrole-2-carboxylic acid (furan-2-ylmethyl)-amide;
5-[4-(Benzothiazol-2-yloxy)-benzyl]-hexahydro-pyrrolo[3,4-c]pyrrole-2-carboxylic acid pyridin-4-yl amide;
5-[4-(Benzothiazol-2-yloxy)-benzyl]-hexahydro-pyrrolo[3,4-c]pyrrole-2-carboxylic acid (3,5-dimethyl-isoxazol-4-yl)-amide;
5-{2-[4-(Benzothiazol-2-yloxy)-phenoxy]-ethyl}-hexahydro-pyrrolo[3,4-c]pyrrole-2-carboxylic acid amide;
5-[4-(Benzothiazol-2-yloxy)-benzyl]-hexahydro-pyrrolo[3,4-b]pyrrole-1-carboxylic acid amide;
1-[4-(Benzothiazol-2-yloxy)-benzyl]-hexahydro-pyrrolo[3,4-b]pyrrole-5-carboxylic acid amide;
(S,S)-1-[4-(Benzothiazol-2-yloxy)-benzyl]-hexahydro-pyrrolo[3,4-b]pyrrole-5-carboxylic acid amide;
(R,R)-1-[4-(Benzothiazol-2-yloxy)-benzyl]-hexahydro-pyrrolo[3,4-b]pyrrole-5-carboxylic acid amide;
5-[4-(Benzothiazol-2-yloxy)-benzyl]-hexahydro-pyrrolo[3,4-c]pyrrole-2-carboxylic acid amide;
(R,S)-{3-[4-(Benzothiazol-2-yloxy)-benzyl]-3-aza-bicyclo[3.1.0]hex-6-yl}-urea;
(±)-5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
5-[4-(Benzothiazol-2-yloxy)-benzyl]-octahydro-pyrrolo[3,4-c]pyridine-2-carboxylic acid amide;
2-[4-(Benzothiazol-2-yloxy)-benzyl]-octahydro-pyrrolo[3,4-c]pyridine-5-carboxylic acid amide;
5-[4-(6-Fluoro-benzothiazol-2-yloxy)-benzyl]-hexahydro-pyrrolo[3,4-c]pyrrole-2-carboxylic acid amide;
5-[4-(6-Methyl-benzothiazol-2-yloxy)-benzyl]-hexahydro-pyrrolo[3,4-c]pyrrole-2-carboxylic acid amide;
5-{2-[4-(4-Methyl-benzothiazol-2-yloxy)-phenyl]-ethyl}-hexahydro-pyrrolo[3,4-c]pyrrole-2-carboxylic acid amide;
5-{2-[4-(4-Fluoro-benzothiazol-2-yloxy)-phenyl]-ethyl}-hexahydro-pyrrolo[3,4-c]pyrrole-2-carboxylic acid amide;
1-(5-{2-[4-(6-Methyl-benzothiazol-2-yloxy)-phenyl]-ethyl}-hexahydro-pyrrolo[3,4-c]pyrrol-2-yl)-ethanone;
1-[5-(4-Benzothiazol-2-ylmethyl-benzyl)-hexahydro-pyrrolo[3,4-c]pyrrol-2-yl]-ethanone;
2-[4-(5-Methanesulfonyl-hexahydro-pyrrolo[3,4-c]pyrrol-2-ylmethyl)-benzyl]-benzothiazole;
1-[5-(4-Benzothiazol-2-ylmethyl-benzyl)-hexahydro-pyrrolo[3,4-c]pyrrol-2-yl]-ethanone;
4-{5-[4-(Benzothiazol-2-yloxy)-benzyl]-hexahydro-pyrrolo[3,4-c]pyrrol-2-ylmethyl)-benzoic acid methyl ester;
4-{5-[4-(Benzothiazol-2-yloxy)-benzyl]-hexahydro-pyrrolo[3,4-c]pyrrol-2-ylmethyl)-benzoic acid;
{5-[4-(Benzothiazol-2-yloxy)-benzyl]-hexahydro-pyrrolo[3,4-c]pyrrol-2-yl}-acetic acid ethyl ester;
4-{5-[4-(Benzothiazol-2-yloxy)-benzyl]-hexahydro-pyrrolo[3,4-c]pyrrol-2-yl}-butyric acid methyl ester;
{5-[4-(Benzothiazol-2-yloxy)-benzyl]-hexahydro-pyrrolo[3,4-c]pyrrol-2-yl}-acetic acid methyl ester;
{5-[4-(Benzothiazol-2-yloxy)-benzyl]-hexahydro-pyrrolo[3,4-c]pyrrol-2-yl}-acetic acid;
5-[4-(Benzothiazol-2-yloxy)-2-fluoro-benzyl]-hexahydro-pyrrolo[3,4-c]pyrrole-2-carboxylic acid amide;
5-[2-Fluoro-4-(4-fluoro-benzothiazol-2-yloxy)-benzyl]-hexahydro-pyrrolo[3,4-c]pyrrole-2-carboxylic acid amide;

pharmaceutically acceptable salts, and pharmaceutically acceptable prodrugs thereof.

14. A method for modulating leukotriene A4 hydrolase activity, comprising exposing leukotriene A4 hydrolase to an effective amount of at least one chemical entity as claimed in claim 1.

15. A method as in claim 14, wherein the LTA4H is in a subject with a disease, disorder, or medical condition mediated by LTA4H activity.

16. A method for modulating leukotriene A4 hydrolase activity, wherein the leukotriene A4 hydrolase is in a subject with a disease, disorder, or medical condition mediated by LTA4H activity, comprising exposing leukotriene A4 hydrolase to at least one chemical entity as claimed in claim 3.

* * * * *